US012173082B2

(12) United States Patent
Dahlén et al.

(10) Patent No.: US 12,173,082 B2
(45) Date of Patent: Dec. 24, 2024

(54) BISPECIFIC POLYPEPTIDES AGAINST CD137

(71) Applicant: ALLIGATOR BIOSCIENCE AB, Lund (SE)

(72) Inventors: Eva Dahlén, Lund (SE); Peter Ellmark, Lund (SE); Christina Furebring, Lund (SE); Per Norlén, Lund (SE); Anna Säll, Lund (SE); Laura von Schantz, Lund (SE); Niina Veitonmäki, Lund (SE); Laura Varas, Lund (SE); Jessica Petersson, Lund (SE); Sara Fritzell, Lund (SE)

(73) Assignee: Alligator Bioscience AB, Lund (SE)

( * ) Notice: Subject to any disclaimer, the term of this patent is extended or adjusted under 35 U.S.C. 154(b) by 345 days.

(21) Appl. No.: 17/482,708

(22) Filed: Sep. 23, 2021

(65) Prior Publication Data

US 2022/0213213 A1 Jul. 7, 2022

Related U.S. Application Data

(63) Continuation of application No. 16/094,127, filed as application No. PCT/EP2017/059656 on Apr. 24, 2017, now abandoned.

(30) Foreign Application Priority Data

Apr. 22, 2016 (GB) ..................................... 1607046

(51) Int. Cl.

| | |
|---|---|
| ***C07K 16/30*** | (2006.01) |
| ***A61K 39/395*** | (2006.01) |
| ***C07K 16/28*** | (2006.01) |
| *A61K 39/00* | (2006.01) |

(52) U.S. Cl.

CPC .......... *C07K 16/30* (2013.01); *A61K 39/3955* (2013.01); *A61K 39/39558* (2013.01); *C07K 16/2878* (2013.01); *A61K 2039/505* (2013.01); *C07K 2317/21* (2013.01); *C07K 2317/31* (2013.01); *C07K 2317/52* (2013.01); *C07K 2317/56* (2013.01); *C07K 2317/622* (2013.01); *C07K 2317/71* (2013.01); *C07K 2317/74* (2013.01); *C07K 2317/75* (2013.01); *C07K 2317/76* (2013.01); *C07K 2317/92* (2013.01); *C07K 2317/94* (2013.01)

(58) Field of Classification Search

CPC ................ C07K 16/30; C07K 16/2878; C07K 2317/31; C07K 2317/56; C07K 2317/622; C07K 2317/75; C07K 2317/76; C07K 2317/92; A61K 39/3955; A61K 39/39558; A61K 2039/505

USPC ...................................................... 424/136.1

See application file for complete search history.

(56) References Cited

U.S. PATENT DOCUMENTS

| | | | |
|---|---|---|---|
| 4,235,871 | A | 11/1980 | Papahadjopoulos et al. |
| 4,816,567 | A | 3/1989 | Cabilly et al. |
| 5,851,451 | A | 12/1998 | Takechi et al. |
| 10,239,949 | B2 | 3/2019 | Bienvenue et al. |
| 2007/0071675 | A1 | 3/2007 | Wu et al. |
| 2007/0161080 | A1 | 7/2007 | Kingsman et al. |
| 2010/0021483 | A1 | 1/2010 | Boghaert et al. |
| 2012/0251531 | A1 | 10/2012 | Baehner et al. |
| 2015/0307620 | A1 | 10/2015 | Vella et al. |

FOREIGN PATENT DOCUMENTS

| | | | |
|---|---|---|---|
| EP | 0213303 | B1 | 9/1991 |
| EP | 3130606 | A1 | 2/2017 |
| WO | 2001/056603 | A1 | 8/2001 |
| WO | 2001/077342 | A1 | 10/2001 |
| WO | 2012/095412 | A1 | 7/2012 |
| WO | 2012/130831 | A1 | 10/2012 |
| WO | 2013/026839 | A1 | 2/2013 |
| WO | 2013/041687 | A1 | 3/2013 |
| WO | 2014/116846 | A2 | 7/2014 |
| WO | 2015/156268 | A1 | 10/2015 |
| WO | 2016/004875 | A1 | 1/2016 |
| WO | 2016/110584 | A1 | 7/2016 |
| WO | 2016/115274 | A1 | 7/2016 |
| WO | 2016/185016 | A1 | 11/2016 |
| WO | 2018/156740 | A1 | 8/2018 |

OTHER PUBLICATIONS

Harmsen and Haard (Appl Microbiol Biotechnol 2007, 77:13-22).*
Li, et al., “Research progress of CD137 and tumor immunotherapy” (2013) Int. J. Immunol., 36(2):101-105 [Abstract].
Makkouk, A., et al., “Rationale for anti-CD137 cancer immunotherapy” Eur. J. Cancer (2016) 54:112-119.
Arndt, C., et al., “Costimulation improves the killing capability of T cells redirected to tumor cells expressing low levels of CD33: description of a novel modular targeting system” Leukemia (2014) 28(1):59-69.
Hinner, M.J., et al., “Costimulatory T cell engagement via a novel bispecific anti-CD137 /anti-HER2 protein” J. Immuno Therapy of Cancer (2015) 3(Suppl 2):P187.
Hinner, M.J., et al., “Costimulatory T cell engagement via a novel bispecific anti-CD137 /anti-HER2 protein” CRI, New York (2015), available at http://c.eqcdn.com/pierisag/db/164/1975/pdf/150914%20CRI%20Poster%20postFinal.pdf.
Vezys, V., et al., “4-1BB signaling synergizes with programmed death ligand 1 blockade to augment CD8 T cell responses during chronic viral infection” J. Immunol. (2011) 187(4):1634-42.

(Continued)

*Primary Examiner* — Yan Xiao
(74) *Attorney, Agent, or Firm* — Robert C. Netter, Jr.; Dann, Dorfman, Herrell & Skillman

(57) ABSTRACT

The invention provides bispecific polypeptides comprising a first binding domain, designated B1, which is capable of binding specifically to CD137, and a second binding domain, designated B2, which is capable of specifically binding to a tumour cell-associated antigen. Also provided are pharmaceutical compositions of such bispecific polypeptides and uses of the same in medicine.

17 Claims, 30 Drawing Sheets

Specification includes a Sequence Listing.

(56) References Cited

OTHER PUBLICATIONS

Imura, A., et al., "OX40 expressed on fresh leukemic cells from adult T-cell leukemia patients mediates cell adhesion to vascular endothelial cells: implication for the possible involvement of OX40 in leukemic cell infiltration" Blood (1997) 89(8):2951-8.
Yamauchi, N., et al., "The glypican 3 oncofetal protein is a promising diagnostic marker for hepatocellular carcinoma" Mod. Pathol. (2005) 18(12):1591-8.
Forsberg, G., et al., "Naptumomab estafenatox, an engineered antibody-superantigen fusion protein with low toxicity and reduced antigenicity" J. Immunother. (2010) 33(5):492-9.
Akhmetzyanova, I., et al., "CD137 Agonist Therapy Can Reprogram Regulatory T Cells into Cytotoxic CD4+ T Cells with Antitumor Activity" J. Immunol. (2016) 196:484-492.
Angov, E., "Codon usage: Nature's roadmap to expression and folding of proteins" Biotechnol. J. (2011) 6:650-659.
Ascierto, P.A., et al., "Clinical experiences with anti-CD137 and anti-PD1 therapeutic antibodies" Semin. Oncol. (2010) 37:508-516.
Bartkowiak, T., et al., "4-1BB Agonists: Multi-Potent Potentiators of Tumor Immunity" Front. Oncol. (2015) 5:117.
Boghaert, E.R., et al., "The oncofetal protein, 5T4, is a suitable target for antibody-guided anticancer chemotherapy with calicheamicin" Int. J. Oncol. (2008) 32:221-234.
Bruhns, P., "Properties of mouse and human IgG receptors and their contribution to disease models" Blood (2012) 119(24):5640-5649.
Castro, F.V., et al., "5T4 oncofetal antigen is expressed in high risk of relapse childhood pre-B acute lymphoblastic leukemia and is associated with a more invasive and chemotactic phenotype" Leukemia (2012) 26(7):1487-1498.
Cheever, M.A., et al., "The prioritization of cancer antigens: a national cancer institute pilot project for the acceleration of translational research" Clin. Cancer Res. (2009) 15:5323-5337.
Cole, S.P.C., et al., "Human Monoclonal Antibodies" Mol. Cell. Biol. (1984) 62:109-120.
Cote, R.J., et al., "Generation of human monoclonal antibodies reactive with cellular antigens" Proc. Natl. Acad. Sci. (1983) 80:2026-2030.
Curran, M.A., et al., "Combination CTLA-4 blockade and 4-1 BB activation enhances tumor rejection by increasing T-cell infiltration, proliferation, and cytokine production" PLoS ONE (2011) 6:e19499.
Damelin, M., et al., "Delineation of a cellular hierarchy in lung cancer reveals an oncofetal antigen expressed on tumor-initiating cells" Cancer Res. (2011) 71:4236-4246.
Dubrot, J., et al., "Treatment with anti-CD137 mAbs causes intense accumulations of liver T cells without selective antitumor immunotherapeutic effects in this organ" Cancer Immunol. Immunother. (2010) 59:1223-1233.
Elkord, E., et al., "5T4 as a target for immunotherapy in renal cell carcinoma" Expert Rev. Anticancer Ther. (2009) 9:1705-1709.
Forsberg, G., et al., "Therapy of human non-small-cell lung carcinoma using antibody targeting of a modified superantigen" Br. J. Cancer (2001) 85:129-136.
Garber, K., "Beyond ipilimumab: new approaches target the immunological synapse" J. Natl. Cancer Inst. (2011) 103:1079-1082.
Gauttier, V., et al., "Agonistic anti-CD137 antibody treatment leads to antitumor response in mice with liver cancer" Int. J. Cancer (2014) 135:2857-2867.
Gebauer, M., et al., "Engineered protein scaffolds as next-generation antibody therapeutics" Curr. Opin. Chem. Biol. (2009) 13(3):245-255.
Gray, J.C., et al., "Optimising anti-tumour CDS T-cell responses using combinations of immunomodulatory antibodies" Eur. J. Immunol. (2008) 38:2499-2511.
Guo, Z., et al., "Combined TIM-3 blockade and CD137 activation affords the long-term protection in a murine model of ovarian cancer" J. Transl. Med. (2013) 11:215.
Hezareh, M., et al., "Effector Function Activities of a Panel of Mutants of a Broadly Neutralizing Antibody against Human Immunodeficiency Virus Type 1" J. Virol. (2001) 75(24):12161-8.
Hinton, P.R., et al., Engineered Human IgG Antibodies with Longer Serum Half-lives in Primates J. Biol. Chem. (2004) 279(8):6213-6.
Hogarth, P.M., et al., "Fc receptor-targeted therapies for the treatment of inflammation, cancer and beyond" Nat. Rev. Drug Discov. (2012) 11:311-331.
Hole, N., et al., "A 72 kD trophoblast glycoprotein defined by a monoclonal antibody" Br. J. Cancer (1988) 57:239-246.
Hornig, N., et al., "Evaluating combinations of costimulatory antibody-ligand fusion proteins for targeted cancer Immunotherapy" Cancer Immunol. Immunother. (2013) 62:1369-1380.
Ju, M.S., et al., "Aglycosylated full-length IgG antibodies: steps toward next-generation immunotherapeutics" Curr. Opin. Biotechnol. (2014) 30:128-39.
Kermer, V., et al., "Combining antibody-directed presentation of IL-15 and 4-1BBL in a trifunctional fusion protein for cancer immunotherapy" Mol. Cancer Ther. (2014) 13:112-121.
Kiefer, J.D., et al., "Immunocytokines and bispecific antibodies: two complementary strategies for the selective activation of immune cells at the tumor site" Immunol. Rev. (2016) 270:178-192.
Kim, J.A., et al., "Divergent effects of 4-1BB antibodies on antitumor immunity and on tumor-reactive T-cell generation" Cancer Res. (2001) 61:2031-2037.
Kohler, G., et al., "Continuous cultures of fused cells secreting antibody of predetermined specificity" Nature (1975) 256:495-497.
Kohrt, H.E., et al., "Targeting CD137 enhances the efficacy of cetuximab" J. Clin. Invest. (2014) 124(6):2668-2682.
Kohrt, H.E., et al., "Stimulation of natural killer cells with a CD137-specific antibody enhances trastuzumab efficacy in xenotransplant models of breast cancer" J. Clin. Invest. (2012) 122(3):1066-1075.
Kozbor, D., et al., "Specific immunoglobulin production and enhanced tumorigenicity following ascites growth of human hybridomas" J. Immunol. Methods (1985) 81:31-42.
Kwong, B., et al., "Localized immunotherapy via liposome-anchored Anti-CD137 + IL-2 prevents lethal toxicity and elicits local and systemic antitumor immunity" Cancer Res. (2013) 73:1547-1558.
Leabman, M.K., et al., "Effects of altered FcγR binding on antibody pharmacokinetics in cynomolgus monkeys" mAbs (2013) 5/6:896-903.
Lee, S.J., et al., "4-1 BB and OX40 dual costimulation synergistically stimulate primary specific CDS T cells for robust effector function" J. Immunol. (2004) 173:3002-3012.
Lee, H.W., et al., "4-1BB promotes the survival of CD8+ T lymphocytes by increasing expression of Bcl-xL and Bfl-1" J. Immunol. (2002) 169:4882-4888.
Li, S.Y., et al., "Immunotherapy of melanoma with the immune costimulatory monoclonal antibodies targeting CD137" Clin. Pharmacol. (2013) 5:47-53.
Li, F., et al., "Inhibitory Fcgamma receptor engagement drives adjuvant and anti-tumor activities of agonistic CD40 antibodies" Science (2011) 333:1030-1034.
Liu, R., et al., "Efficient inhibition of human B-cell lymphoma in SCID mice by synergistic antitumor effect of human 4-1 BB ligand/anti-CD20 fusion proteins and anti-CD3/anti-CD20 diabodies" J. Immunother. (2010) 33:500-509.
McMillin, D.W., et al., "Complete regression of large solid tumors using engineered drug-resistant hematopoietic cells and anti-CD137 immunotherapy" Hum. Gene Ther. (2006) 17:798-806.
Melero, I., et al., "Monoclonal antibodies against the 4-1BB T-cell activation molecule eradicate established tumors" Nat. Med. (1997) 3:682-685.
Miller, R.E., et al., "4-1BB-spacific monoclonal antibody promotes the generation of tumor-specific immune responses by direct activation of CDS T cells in a CD40-dependent manner" J. Immunol. (2002) 169:1792-1800.
Morales-Kastresana, A., et al., "Combined immunostimulatory monoclonal antibodies extend survival in an aggressive transgenic hepatocellular carcinoma mouse model" Clin. Cancer Res. (2013) 19:6151-6162.

(56) References Cited

OTHER PUBLICATIONS

Niu, L., et al., "Cytokine-mediated disruption of lymphocyte trafficking, hemopoiesis, and induction of lymphopenia, anemia, and thrombocytopenia in anti-CD137-treated mice" J. Immunol. (2007) 178:4194-4213.
Oganesyan, V., et al., "Structural characterization of a human Fc fragment engineered for lack of effector functions" Acta Crystallogr. D Biol. Crystallogr. (2008) 64(Pt 6): 700-704.
Palazon, A., et al., "Agonist anti-CD137 mAb act on tumor endothelial cells to enhance recruitment of activated T lymphocytes" Cancer Res. (2011) 71(3):801-11.
Pan, P.Y., et al., "OX40 ligation enhances primary and memory cytotoxic T lymphocyte responses in an immunotherapy for hepatic colon metastases" Mol. Ther. (2002) 6:528-536.
Pastor, F., et al., "Targeting 4-1BB costimulation to disseminated tumor lesions with bi-specific oligonucleotide aptamers" Mol. Ther. (2011) 19:1878-1886.
Pule, M., et al., "Artificial T-cell receptors" Cytotherapy (2003) 5(3):211-226.
Pulle, G., et al., "IL-15-dependent induction of 4-1BB promotes antigen-independent CDS memory T cell survival" J. Immunol. (2006) 176:2739-2748.
Rabu, C., et al., "Production of recombinant human trimeric CD137L (4-1BBL). Cross-linking is essential to its T cell co-stimulation activity" J. Biol. Chem. (2005) 280:41472-41481.
Sallin, M.A., et al., "The anti-lymphoma activities of anti-CD137 monoclonal antibodies are enhanced in FcgammaRIII(-/-) mice" Cancer Immunol. Immunother. (2014) 63:947-958.
Sanmamed, M.F., "Agonists of Co-stimulation in Cancer Immunotherapy Directed Against CD137, OX40, GITR, CD27, CD28, and ICOS" Semin. Oncol. (2015) 42:640-655.
Sazinsky, S.L., et al., "Aglycosylated immunoglobulin G1 variants productively engage activating Fc receptors" Proc. Natl. Acad. Sci. (2008) 105(51):20167-20172.
Schrand, B., et al., "Targeting 4-1 BB costimulation to the tumor stroma with bispecific aptamer conjugates enhances the therapeutic index of tumor immunotherapy" Cancer Immunol. Res. (2014) 2:867-877.
Shields, R.L., et al., "High Resolution Mapping of the Binding Site on Human IgG1 for FcgRI, FcgRII, FcgRIII, and FcRn and Design of IgG1 Variants with Improved Binding to the FcgR" J. Biol. Chem. (2001) 276(9):6591-604.
Shuford, W.W., et al., "4-1BB costimulatory signals preferentially induce CD8+ T cell proliferation and lead to the amplification in vivo of cytotoxic T cell responses" J. Exp. Med. (1997) 186:47-55.
Skrlec, K., et al., "Non-immunoglobulin scaffolds: a focus on their targets" Trends Biotech., (2015) 33(7):408-418.
So, T., et al., "Immune regulation and control of regulatory T cells by OX40 and 4-1 BB" Cytokine Growth Factor Rev. (2008) 19:253-262.
Southall, P.J., et al., "Immunohistological distribution of 5T4 antigen in normal and malignant tissues" Br. J Cancer (1990) 61:89-95.
Southgate, T.D., et al., "CXCR4 mediated chemotaxis is regulated by 5T4 oncofetal glycoprotein in mouse embryonic cells" PLoS ONE (2010) 5:e9982.
St. Rose, M.C., et al., "CD134/CD137 dual costimulation-elicited IFN-gamma maximizes effector T-cell function but limits Treg expansion" Immunol. Cell Biol. (2013) 91:173-183.
Stewart, R., et al., "The role of Fc gamma receptors in the activity of immunomodulatory antibodies for cancer" J. Immuno Therapy Cancer (2014) 2:29.
Strohl, W.R., "Optimization of Fc-mediated effector functions of monoclonal antibodies" Curr. Opin. Biotechnol. (2009) 20(6):685-91.
Sun, Y., et al., "Co-stimulation agonists as a new immunotherapy for autoimmune diseases" Trends in Molecular Medicine (2003) 9(11):P483-489.
Taraban, V.Y., et al., "Expression and costimulatory effects of the TNF receptor superfamily members CD134 (OX40) and CD137 (4-1 BB), and their role in the generation of anti-tumor immune responses" Eur. J. Immunol. (2002) 32:3617-3627.
Uno, T., et al., "Eradication of established tumors in mice by a combination antibody-based therapy" Nat. Med. (2006) 12:693-698.
Vaccaro, C., et al., "Engineering the Fc region of immunoglobulin G to modulate in vivo antibody levels" Nat. Biotechnol. (2005) 23(10):1283-8.
Vinay, D.S., et al., "Immunotherapy of cancer with 4-1 BB" Mol. Cancer Ther. (2012) 11:1062-1070.
Wang, W., et al., "NK cell-mediated antibody-dependent cellular cytotoxicity in cancer immunotherapy" Front. Immunol. (2015) 6:368.
Wei, H., et al., "Combinatorial PD-1 blockade and CD137 activation has therapeutic efficacy in murine cancer models and synergizes with cisplatin" PLoS ONE (2013) 8:e84927.
Westwood, J.A., et al., "Three agonist antibodies in combination with high-dose IL-2 eradicate orthotopic kidney cancer in mice" J. Transl. Med. (2010) 8:42.
Westwood, J.A., et al., "Combination anti-CD137 and anti-CD40 antibody therapy in murine myc-driven hematological cancers" Leuk. Res. (2014) 38:948-954.
Westwood, J.A., et al., "Routes of delivery for CpG and anti-CD137 for the treatment of orthotopic kidney tumors in mice" PLoS ONE (2014) 9:e95847.
White, A.L., et al., "Interaction with Fc{gamma}RIIB Is Critical for the Agonistic Activity of Anti-CD40 Monoclonal Antibody" J. Immunol. (2011) 187:1754-1763.
White, A.L., et al., "FcgammaRIIB controls the potency of agonistic anti-TNFR mAbs" Cancer Immunol. Immunother. (2013) 62:941-948.
Wilcox, R.A., et al., "Provision of antigen and CD137 signaling breaks immunological ignorance, promoting regression of poorly immunogenic tumors" J. Clin. Invest. (2012) 109:651-659.
Wilson, N.S., et al., "An Fcgamma receptor-dependent mechanism drives antibody-mediated target-receptor signaling in cancer cells" Cancer Cell (2011) 19:101-113.
Winter, G., et al., "Man-made antibodies" Nature (1991) 349:293-299.
Woods, A.M., et al., "Characterization of the murine 5T4 oncofoetal antigen: a target for immunotherapy in cancer" Biochem. J. (2002) 366(1):353-365.
Wyzgol, A., et al., "Trimer stabilization, oligomerization, and antibody-mediated cell surface immobilization improve the activity of soluble trimers of CD27L, CD40L, 41BBL, and glucocorticoid-induced INF receptor ligand" J. Immunol. (2009) 183:1851-1861.
Ye, Q., et al., "CD137 accurately identifies and enriches for naturally occurring tumor-reactive T cells in tumor" Clin. Cancer Res. (2014) 20:44-55.
Zhang, N., et al., "Targeted and untargeted CD137L fusion proteins for the immunotherapy of experimental solid tumors" Clin. Cancer Res. (2007) 13:2758-2767.
Orlandi, R., et al., "Cloning immunoglobulin variable domains for expression by the polymerase chain reaction" Proc. Natl. Acad. Sci. (1989) 86:3833-3837.
Gunde, T., et al., "A novel, monovalent tri-specific antibody-based molecule that simultaneously modulates PD-L1 and 4-1BB exhibits potent anti-tumoral activity in vivo", Poster #1532, Presented at American Association for Cancer Research (AACR) Annual Meeting, 2019, Atlanta, GA.
European Patent Application Application No. 17718928.9, "Annex A", submitted May 22, 2020.
Mayes, P., et al. "Bispecific Fc-silenced IgG1 antibody (MCLA-145) required PD-L1 binding to activate CD137" Poster #539, Presented at American Association for Cancer Research (AACR) Annual Meeting, 2019, Atlanta, GA.
Mariuzza, R.A., et al., "The Structural Basis of Antigen-Antibody Recognition" Ann. Rev. Biophys. Biophys. Chem. (1987) 16:139-59.
Colman, P.M., "Effects of amino acid sequence changes on antibody-antigen interactions" Research in Immunology (1994) 145(1):33-6.

(56) References Cited

OTHER PUBLICATIONS

Pan, Q., et al., "Blocking neuropilin-1 function has an additive effect with anti-VEGF to inhibit tumor growth" Cancer Cell (2007) 11(1):53-67.
Rudikoff, S., et al., "Single amino acid substitution altering antigen-binding specificity" Proc. Nat. Acad. Sci. USA (1982) 79:1979-1983.
Anonymous, "Polypeptide", Wikipedia, (Feb. 24, 2019), retrieved from https://simple.wikipedia.org/wiki/Polypeptide.
Anonymous, "Polypeptide", Biology Online Dictionary, (Oct. 12, 2020), retrieved from https://www.biologyonline.com/dictionary/polypeptide.
Anonymous, "Protein Structure", Nature, (Oct. 12, 2020), retrieved from https://www.nature.com/scitable/topicpage/proteinstructure-14122136/.
Anonymous, "Difference Between Polypeptide and Protein", Difference Between, (Oct. 12, 2020), retrieved from http://www.differencebetween.net/science/difference-between-polypeptide-and-protein/.
White, A.L., et al., "Conformation of the Human immunoglobulin G2 Hinge Imparts Superagonistic Properties to Immunostimulatory Anticancer Antibodies" Cancer cell (2015) 27(1):138-148.
Shi, S.Y., et al., "A biparatopic agonistic antibody that mimics fibroblast growth factor 21 ligand activity" Journal of Biological Chemistry (2018) 293(16):5909-5919.
Moraga, I., et al., "Tuning Cytokine Receptor Signaling by Re-orienting Dimer Geometry with Surrogate Ligands" Cell (2015) 160(6):1196-1208.
Dickopf, S., et al., "Format and geometries matter: Structure-based design defines the functionality of bispecific antibodies" Computational and Structural Biotechnology Journal (2020) 18:1221-1227.
Cheng, J.D., et al., "Individualized Patient Dosing in Phase I Clinical Trials: The Role of Escalation With Overdose Control in PNU-214936" Journal of Clinical Oncology (2004) 22(4):602-609.

* cited by examiner

BISPECIFIC POLYPEPTIDES AGAINST CD137

This application is a continuation application of U.S. patent application Ser. No. 16/094,127, filed Oct. 16, 2018, which is a § 371 application of PCT/EP2017/059656, filed Apr. 24, 2017, which in turn claims priority to GB Application 1607046.8, filed Apr. 22, 2016. The entire disclosure of each of the foregoing applications is incorporated by reference herein.

Incorporated herein by reference in its entirety is the Sequence Listing being concurrently submitted via EFS-Web as a text file named SeqList.txt, created Sep. 23, 2021, and having a size of 113,591 bytes.

BACKGROUND

Immunotherapy of Cancer

Cancer is a leading cause of premature deaths in the developed world. Immunotherapy of cancer aims to mount an effective immune response against tumour cells. This may be achieved by, for example, breaking tolerance against tumour antigen, augmenting anti-tumor immune responses, and stimulating local cytokine responses at the tumor site. The key effector cell of a long lasting anti-tumor immune response is the activated tumor specific effector T cell. Potent expansion of activated tumour-specific effector T cells can redirect the immune response towards the tumor. In this context, various immunosuppressive mechanisms induced by the tumor microenvironment suppress the activity of effector T cells. Several immunosuppressive mediators are expressed by the tumor cells. Such mediators inhibit T cell activation, either directly, or indirectly by inducing e.g. regulatory T cells (Treg) or myeloid-derived suppressor cells. Depleting, inhibiting, reverting or inactivating such regulatory cells may therefore provide anti-tumor effects and revert the immune suppression in the tumor microenvironment. Further, incomplete activation of effector T cells by, for example, dendritic cells can result in sub-optimally activated or anergic T cells, resulting in an inefficient anti-tumor response. In contrast, adequate induction by dendritic cells can generate a potent expansion of activated effector T cells, redirecting the immune response towards the tumor. In addition, Natural killer (NK) cells play an important role in tumor immunology by attacking tumor cells with down-regulated human leukocyte antigen (HLA) expression and by inducing antibody dependent cellular cytotoxicity (ADCC). Stimulation of NK cells may thus also reduce tumor growth.

Tumour-Associated Antigens Tumor-associated antigens (TAA) are cell surface proteins selectively expressed on tumor cells. The term tumor-associated indicates that TAA are not completely tumor-specific, but are rather over-expressed on the tumor. A vast number of TAA have been described and used in various therapeutic rationales, including monoclonal antibodies, T cell redirecting therapies with TAA-CD3 bispecific antibodies, immunocytokines and antibody drug conjugates. Some well-studied TAA include the EGFR family molecules (HER2, HER3 and EGFR/HER1), VEGFR, EpCAM, CEA, PSA, PSMA, EphA2, gp100, GD2, MUC1, CD20, CD19, CD22 and CD33, summarized in (Cheever et al., 2009).

5T4 (also designated trophoblast glycoprotein, TPBG, M6P1 and Waif1) is a well-defined TAA originally identified by Professor Peter Stern, University of Manchester (Hole and Stern, 1988). It is an oncofetal antigen expressed in a high proportion of patients in a variety of malignancies, including non-small cell lung, renal, pancreas, prostate, breast, colorectal, gastric, ovarian and cervix cancers as well as in acute lymphocytic leukemia, and has also been shown to be expressed in tumor-initiating cells (Castro et al., 2012; Damelin et al., 2011; Elkord et al., 2009; Southall et al., 1990).

5T4 expression is tumor-selective, with no or low expression in most normal tissues. In non-malignant tissue, 5T4 is mainly expressed in the placenta (trophoblast and amniotic epithelium) and at low levels in some specialised epithelia (Hole and Stern, 1988), as well as low at levels in other normal tissues (see US 2010/0021483). However, although low levels have been detected in some healthy tissue, the safety risk associated with this is considered low since expression levels in the tumor are considerably higher. This is supported by the fact that the phase III clinical programs, ANYARA and TroVax targeting 5T4 did not report severe 5T4-related toxicities.

Data from Stern et al. demonstrate that 5T4 regulates the functional activity of CXCR4 (Castro et al., 2012; Southgate et al., 2010). 5T4 binding antibodies or 5T4 knock-down resulted in inhibition of CXCR4-mediated cellular migration. The CXCR4 pathway is involved in tumor growth and metastasis. Therefore, targeting 5T4 in a CXCR4 inhibitory manner is likely to reduce tumor growth and/or spread.

CD137

CD137 (4-1BB, TNFRSF9) is a tumor necrosis factor (TNF) receptor (TNFR) superfamily member. Its role in cancer immunotherapy has been reviewed in e.g. (Bartkowiak and Curran, 2015). Activation of CD137 is dependent on receptor oligomerization (Rabu et al., 2005; Wyzgol et al., 2009) which is induced by binding to CD137L expressed as a trimer on the cell surface of antigen presenting cells (APCs) and other cell types. CD137 is expressed on various cell populations including activated $CD4^+$ and $CD8^+$ T cells, regulatory T cells (Treg), dendritic cells (DC), monocytes, mast cells, eosinophils and tumor endothelial cells. CD137 activation plays an important role in $CD8^+$ T cell activation and survival (Lee et al., 2002; Pulle et al., 2006). It sustains and augments effector functions and preferentially supports Th1 cytokine production (Shuford et al., 1997). In $CD4^+$ T cells, CD137 stimulation initially results in activation and later in activation-induced cell death, which is thought to explain why CD137 agonistic antibodies have shown therapeutic effect in tumor immunity as well as in autoimmunity (Zhang, J C I, 2007, Sun, Trends Mol Med, 2003). CD137 has also been reported to suppress Treg function or convert Tregs to cytotoxic $CD4^+$ T-cells (Akhmetzyanova et al., 2016; So et al., 2008).

CD137 is upregulated on NK cells activated by cytokines or CD16 (FcγRIII) stimulation (ref in Melero, CCR 19 (5)1044-53, 2013). Activation of CD137 has been shown to increase antibody-dependent cellular cytotoxicity (ADCC) activity of NK cells in both murine and human cells (Kohrt 2012 and 2014 J Clin Invest, reviewed by Hout 2012, Oncoimm). Further, CD137 is expressed on APCs, such as DCs and macrophages, and stimulation of CD137 on these cell types may induce immune activation that can result in tumor immunity.

Agonistic CD137 antibody has been shown to activate endothelial cells in the tumor environment, leading to upregulation of ICAM-1 and VCAM-1 and improved T cell recruitment (Palazon, Cancer Res, 2011).

Several studies have demonstrated induction of tumor immunity by treatment with agonistic CD137 mAb in preclinical models. The mode of action may include various cell types, with $CD8^+$ T cells being one of the main effector cells involved in CD137-induced tumor immunity (Dubrot et al., 2010; Gauttier et al., 2014; Kim et al., 2001; McMillin et al., 2006; Melero et al., 1997; Miller et al., 2002; Sallin et al., 2014; Taraban et al., 2002; Uno et al., 2006; Vinay and Kwon, 2012; Wilcox et al., 2002). In addition, it synergizes with several immunomodulators, including CpG, TRAIL, CD40, OX-40, DR5, PD-1/PD-L1, CTLA-4, Tim-3, IL-2 and IL-12 (Curran et al., 2011; Gray et al., 2008; Guo et al., 2013; Kwong et al., 2013; Lee et al., 2004; Morales-Kastresana et al., 2013; Pan et al., 2002; St Rose et al., 2013; Uno et al., 2006; Wei et al., 2013; Westwood et al., 2010; Westwood et al., 2014a; Westwood et al., 2014b). An important role of CD137 in the induction and maintenance of tumor immunity is further supported by the findings indicating that CD137+ tumor infiltrating T cells are tumor-specific and effectively protect from tumor growth (Ye et al., 2014).

Two CD137 antibodies are in clinical development. Urelumab (BMS-66513) is a fully human IgG4 antibody developed by Bristol-Myers Squibb. Several phase I and II studies in various indications are currently ongoing. A Phase II study with Urelumab as a second line therapy in metastatic melanoma was terminated in 2009 due to liver toxicity (Garber, 2011; Li and Liu, 2013). PF-05082566 is a fully human IgG2 antibody developed by Pfizer. It is currently in phase I development in lymphoma and various solid cancers and preliminary data suggest that it is well tolerated but with only modest anti-tumor effects.

Toxicity upon CD137 activation has been observed in patients as well as in mouse models (Ascierto et al., 2010; Dubrot et al., 2010; Niu et al., 2007). The toxicity includes skin toxicities and liver toxicities manifested as increased aspartate amino transferase/alanine amino transferase ratio (ASAT/ALAT) levels and cytokine release. This suggests that either the toxicity requires CD137 mediated pre-activation of immune cell populations (likely T cells) or it depends on secondary effects caused by antidrug-antibodies (ADA) response, potentially forming aggregates of CD137 antibodies that may lead to enhanced cross-linking. The toxicities seen in mice are reversible and seem to depend on TNFa/CD8+ cells (Ascierto et al., 2010). Toxicology studies in monkeys showed that both single and repeated dosing of up to 100 mg/kg once weekly for four weeks was tolerable with no skin or liver toxicity detected (Ascierto 2010 Semin Onc).

TNFR family members are dependent on receptor cross-linking for activation to be induced. Such crosslinking may either be induced by the natural ligand expressed on the cell surface of cells or by recombinant, multimerized ligand. Alternatively, it may be induced by an antibody binding to the receptor and cross-linked by its Fc region bound to an Fcγ receptor (FcγR). This cross-linking dependence has been shown for various TNFR members, including DR5, GITR, CD27 and CD40 (Li and Ravetch, 2011; White et al., 2011; Wilson et al., 2011a; Wilson et al., 2011b; Wyzgol et al., 2009). An important role for the inhibitory FcγRIIB (CD32B) in activation by agonistic TNFR family antibodies was shown in some studies (Li and Ravetch, 2011; White et al., 2011; White et al., 2013) whereas other data suggest that activation is induced by cross-linking of inhibitory as well as activating FcγRs (Li and Ravetch, 2011; Wilson et al., 2011a).

Similar to other TNFR members, activation of CD137 is dependent on receptor oligomerization. Hexamers of CD137L effectively induce CD137 activation, whereas monomeric or trimeric CD137L does not (Rabu et al., 2005; Wyzgol et al., 2009). Thus, it is likely that CD137 agonistic antibodies require cross-linking, e.g. via FcγR for effective activation to occur in vivo. However, in contrast to other TNFR members, FcγRII is not critical for induction of tumor immunity by CD137, whereas FcγRIII impairs tumor immunity (Sallin et al., 2014; Sanmamed et al., 2015) in mouse studies.

The translational relevance of the role of various FcγR in activation of CD137 and other TNFR superfamily members is uncertain, since the human FcγR distribution as well as the affinity of different IgG isotypes to different FcγR differ between mice and humans.

Despite progress in the development of immunotherapies for the treatment of various cancers over the last decade, there remains a need for new and efficacious agents.

Accordingly, the present invention seeks to provide improved polypeptide-based therapies for the treatment of cancer.

SUMMARY OF THE INVENTION

A first aspect of the invention provides a bispecific polypeptide comprising a first binding domain, designated B1, which is capable of binding specifically to CD137, and a second binding domain, designated B2, which is capable of specifically binding to a tumour cell-associated antigen.

Such bispecific compounds comprising one immune-activating moiety, e.g. a CD137 agonist, and one tumor-targeting moiety, e.g. a 5T4 binder, can be used to establish a highly effective and safe cancer immunotherapy.

Various types of tumor-localizing immunotherapeutic molecules, such as immunocytokines and bispecific antibodies have shown beneficial immune activation and inhibition of tumor growth in preclinical studies as well as in the clinic (reviewed in Kiefer and Neri, 2016).

To avoid systemic toxicity by CD137 activating agents, yet obtain high efficacy in the tumor area, the designs of the molecular format of a CD137 agonist may be optimised. For example, a good efficacy/safety profile can be obtained by a TAA-CD137 bispecific antibody that requires crosslinking by binding to the TAA for CD137 activation to occur. Then, pre-activated, CD137-expressing T cells residing in the tumor will preferentially be activated, whereas CD137 expressing cells in other tissues will not. This would allow focused activation of the relevant, tumor-specific T cells while limiting toxicity induced by generalised CD137 activation ('activation' in this context being a net immune activation that results in a tumor-directed T cell response, for example by down-regulation of Tregs suppressive function and/or upregulation of effector T cell function).

The clinical progress with immunocytokines has so far not been impressive and the side effects still remain since the tumor-binding entity only confers limited tumor localization, with the bulk of the immunocytokine ending up in other compartments. Bispecific antibodies that restrict the activity to the tumor as described in this invention would provide a clear advantage over immunocytokines since they are inactive in the absence of tumors.

Further, the bispecific polypeptides of the invention provide a distinct advantage over bispecific antibodies targeting CD3. CD3-targeting bispecific molecules use T cells as effector cells and are capable of activating T cells independent of TAA binding. Thus, they do not activate tumor specific T-cells in particular. The resulting anti-tumor effects are therefore not likely to generate a long lasting anti-tumor immunity. In addition, since CD3 is expressed on all T cells, systemic T cell activation is associated with toxicity issues. In contrast, the bispecific antibodies of the invention have the potential to selectively activate tumor specific T-cells and generate a long lasting tumour immunity.

Structure of Bispecific Polypeptide

A "polypeptide" is used herein in its broadest sense to refer to a compound of two or more subunit amino acids, amino acid analogs, or other peptidomimetics. The term "polypeptide" thus includes short peptide sequences as well as longer polypeptides and proteins. As used herein, the term "amino acid" refers to either natural and/or unnatural or synthetic amino acids, including both D or L optical isomers, and amino acid analogs and peptidomimetics.

The term "bispecific" as used herein means the polypeptide is capable of specifically binding at least two target entities.

In one preferred embodiment, the polypeptide is a bispecific antibody (numerous examples of which are described in detail below).

Thus, the first and/or second binding domains may be selected from the group consisting of antibodies and antigen-binding fragments thereof.

By "an antibody or an antigen-binding fragment thereof" we include substantially intact antibody molecules, as well as chimaeric antibodies, humanised antibodies, isolated human antibodies, single chain antibodies, bispecific antibodies, antibody heavy chains, antibody light chains, homodimers and heterodimers of antibody heavy and/or light chains, and antigen-binding fragments and derivatives of the same. Suitable antigen-binding fragments and derivatives include Fv fragments (e.g. single chain Fv and disulphide-bonded Fv), Fab-like fragments (e.g. Fab fragments, Fab' fragments and F(ab)2 fragments), single variable domains (e.g. VH and VL domains) and single domain antibodies (dAbs, including single and dual formats [i.e. dAb-linker-dAb], and nanobodies). The potential advantages of using antibody fragments, rather than whole antibodies, are several-fold. The smaller size of the fragments may lead to improved pharmacological properties, such as better penetration of solid tissue. Moreover, antigen-binding fragments such as Fab, Fv, ScFv and dAb antibody fragments can be expressed in and secreted from *E. coli*, thus allowing the facile production of large amounts of the said fragments.

In one embodiment, the antigen-binding fragment is selected from the group consisting of: Fv fragments (such as a single chain Fv fragment, or a disulphide-bonded Fv fragment), Fab-like fragments (such as a Fab fragment; a Fab' fragment or a $F(ab)_2$ fragment) and single domain antibodies.

For example, the first binding domain (1) and/or the second binding domain (B2) may comprise or consist of a Fab fragment.

Alternatively, or in addition, the first binding domain (1) and/or the second binding domain (B2) may comprise or consist of an Fv fragment (such as an scFv or di-sulphide bridged Fv). Where the binding domain is an scFv, the VH and VL regions therein may be joined by a linker sequence, for example:

[SEQ ID NO: 93]

GGGGSGGGGSGGGGS

It will be appreciated by persons skilled in the art that such scFv polypeptides may be glycosylated, for example N-glycosylated, on one or more amino acid residues.

The phrase "an antibody or an antigen-binding fragment thereof" is also intended to encompass antibody mimics (for example, non-antibody scaffold structures that have a high degree of stability yet allow variability to be introduced at certain positions). Those skilled in the art of biochemistry will be familiar with many such molecules, as discussed in Gebauer & Skerra, 2009, *Curr Opin Chem Biol* 13(3): 245-255 (the disclosures of which are incorporated herein by reference). Exemplary antibody mimics include: affibodies (also called Trinectins; Nygren, 2008, *FEBS J*, 275, 2668-2676); CTLDs (also called Tetranectins; Innovations Pharmac. Technol. (2006), 27-30); adnectins (also called monobodies; *Meth. Mol. Biol.*, 352 (2007), 95-109); anticalins (*Drug Discovery Today* (2005), 10, 23-33); DARPins (ankyrins; *Nat. Biotechnol.* (2004), 22, 575-582); avimers (*Nat. Biotechnol.* (2005), 23, 1556-1561); microbodies (*FEBS J*, (2007), 274, 86-95); peptide aptamers (*Expert. Opin. Biol. Ther.* (2005), 5, 783-797); Kunitz domains (*J. Pharmacol. Exp. Ther.* (2006) 318, 803-809); affilins (*Trends. Biotechnol.* (2005), 23, 514-522); affimers (Avacta Life Sciences, Wetherby, UK).

Also included within the scope of the invention are chimaeric T-cell receptors (also known as chimaeric T cell receptors, chimaeric immunoreceptors, and chimaeric antigen receptors or CARs) (see Pule et al., 2003, *Cytotherapy* 5(3):211-26, the disclosures of which are incorporated herein by reference). These are engineered receptors, which graft an arbitrary specificity onto an immune effector cell. Typically, CARs are used to graft the specificity of a monoclonal antibody onto a T cell; with transfer of their coding sequence facilitated by retroviral vectors. The most common form of such molecules is fusions comprising a single-chain variable fragment (scFv) derived from a monoclonal antibody fused to CD3-zeta transmembrane and endodomain. When T cells express this fusion molecule, they recognize and kill target cells that express the transferred monoclonal antibody specificity.

Persons skilled in the art will further appreciate that the invention also encompasses modified versions of antibodies and antigen-binding fragments thereof, whether existing now or in the future, e.g. modified by the covalent attachment of polyethylene glycol or another suitable polymer (see below).

Methods of generating antibodies and antibody fragments are well known in the art. For example, antibodies may be generated via any one of several methods which employ induction of in vivo production of antibody molecules, screening of immunoglobulin libraries (Orlandi et al, 1989. *Proc. Natl. Acad. Sci. U.S.A.* 86:3833-3837; Winter et al., 1991, *Nature* 349:293-299, the disclosures of which are incorporated herein by reference) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120, the disclosures of which are incorporated herein by reference).

Suitable methods for the production of monoclonal antibodies are also disclosed in "*Monoclonal Antibodies: A manual of techniques*", H Zola (CRC Press, 1988, the disclosures of which are incorporated herein by reference) and in "Monoclonal Hybridoma Antibodies: Techniques and Applications", J G R Hurrell (CRC Press, 1982, the disclosures of which are incorporated herein by reference).

Likewise, antibody fragments can be obtained using methods well known in the art (see, for example, Harlow &

Lane, 1988, "Antibodies: A Laboratory Manual", Cold Spring Harbor Laboratory, New York, the disclosures of which are incorporated herein by reference). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, human or humanised antibodies are preferably used. Humanised forms of non-human (e.g. murine) antibodies are genetically engineered chimaeric antibodies or antibody fragments having preferably minimal-portions derived from non-human antibodies. Humanised antibodies include antibodies in which complementary determining regions of a human antibody (recipient antibody) are replaced by residues from a complementary determining region of a non-human species (donor antibody) such as mouse, rat or rabbit having the desired functionality. In some instances, Fv framework residues of the human antibody are replaced by corresponding non-human residues. Humanised antibodies may also comprise residues which are found neither in the recipient antibody nor in the imported complementarity determining region or framework sequences. In general, the humanised antibody will comprise substantially all of at least one, and typically two, variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann et al., 1988, *Nature* 332:323-329; Presta, 1992, *Curr. Op. Struct. Biol.* 2:593-596, the disclosures of which are incorporated herein by reference).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Reichmann et al., 1988. *Nature* 332:323-327; Verhoeyen et al., 1988, *Science* 239: 1534-15361; U.S. Pat. No. 4,816,567, the disclosures of which are incorporated herein by reference) by substituting human complementarity determining regions with corresponding rodent complementarity determining regions. Accordingly, such humanised antibodies are chimaeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, *J. Mol. Biol.* 227:381; Marks et al., 1991, *J. Mol. Biol.* 222:581; Cole et al., 1985, In: Monoclonal antibodies and Cancer Therapy, Alan R. Liss, pp. 77; Boerner et al., 1991. *J. Immunol.* 147:86-95, the disclosures of which are incorporated herein by reference).

It will be appreciated by persons skilled in the art that the bispecific polypeptides, e.g. antibodies, of the present invention may be of any suitable structural format.

Thus, in exemplary embodiments of the bispecific antibodies of the invention:

(a) binding domain 1 and/or binding domain B2 is an intact IgG antibody (or, together, form an intact IgG antibody);

(b) binding domain 1 and/or binding domain B2 is an Fv fragment (e.g. an scFv);

(c) binding domain 1 and/or binding domain B2 is a Fab fragment; and/or (d) binding domain 1 and/or binding domain B2 is a single domain antibody (e.g. domain antibodies and nanobodies).

It will be appreciated by persons skilled in the art that the bispecific antibody may comprise a human Fc region, or a variant of a said region, where the region is an IgG1, IgG2, IgG3 or IgG4 region, preferably an IgG1 or IgG4 region.

Engineering the Fc region of a therapeutic monoclonal antibody or Fc fusion protein allows the generation of molecules that are better suited to the pharmacology activity required of them (Strohl, 2009, *Curr Opin Biotechnol* 20(6): 685-91, the disclosures of which are incorporated herein by reference).

(a) Engineered Fc Regions for Increased Half-Life

One approach to improve the efficacy of a therapeutic antibody is to increase its serum persistence, thereby allowing higher circulating levels, less frequent administration and reduced doses.

The half-life of an IgG depends on its pH-dependent binding to the neonatal receptor FcRn. FcRn, which is expressed on the surface of endothelial cells, binds the IgG in a pH-dependent manner and protects it from degradation.

Some antibodies that selectively bind the FcRn at pH 6.0, but not pH 7.4, exhibit a higher half-life in a variety of animal models.

Several mutations located at the interface between the CH2 and CH3 domains, such as T250Q/M428L (Hinton et al., 2004, *J Biol Chem.* 279(8):6213-6, the disclosures of which are incorporated herein by reference) and M252Y/S254T/T256E+H433K/N434F (Vaccaro et al., 2005, *Nat. Biotechnol.* 23(10):1283-8, the disclosures of which are incorporated herein by reference), have been shown to increase the binding affinity to FcRn and the half-life of IgG1 in vivo.

(b) Engineered Fc Regions for Altered Effector Function

To ensure lack of CD137 activation in the absence of the tumour antigen, the Fc portion of the bispecific antibody should bind with no or very low affinity to FcγR, since FcγR-mediated crosslinking of a CD137 antibody may induce activation. By "very low affinity" we include that the Fc portion exhibits at least 10 times reduced affinity to FcγRI, FcgRII and Ill compared to wild-type IgG1, as determined by the concentration where half maximal binding is achieved in flow cytometric analysis of FcγR expressing cells (Hezareh et al., 2001, *J Virol*, 75(24):12161-8) or by FcγR ELISA (Shields et al., 2001, *J Biol Chem.* 276(9): 6591-604).

Another factor to take into account is that engagement of FcγR's may also induce antibody-dependent cellular cytotoxicity (ADCC), antibody-dependent cellular phagocytosis (ADCP) and complement-dependent cytotoxicity (CDC) of cells coated with antibodies. Thus, to ensure tumor-dependent CD137 activation as well as to avoid depletion of CD137 expressing, tumor-reactive T effector cells, the isotype of a TAA-CD137 bispecific antibody should preferably be silent.

The four human IgG isotypes bind the activating Fcγ receptors (FcγRI, FcγRIIa, FcγRIIIa), the inhibitory FcγRIIb receptor, and the first component of complement (C1q) with different affinities, yielding very different effector functions (Bruhns et al., 2009, Blood. 113(16):3716-25, the disclosures of which are incorporated herein by reference). IgG1 molecules have the highest affinity and capacity to induce effector functions, whereas IgG2, IgG3 and IgG4 are less effective (Bruhns, 2012; Hogarth and Pietersz, 2012; Stewart et al., 2014) (Wang 2015 Front Im; Vidarson 2014 Fron Imm). In addition, certain mutations in the Fc region of IgG1 dramatically reduces FcγR affinity and effector function while retaining neonatal FcR (FcRn) interaction (Ju and Jung, 2014; Leabman et al., 2013; Oganesyan et al., 2008; Sazinsky et al., 2008).

The most widely used IgG1 mutants are N297A alone or in combination with D265A, as well as mutations at positions L234 and L235, including the so-called "LALA" double mutant L234A/L235A. Another position described to further silence IgG1 by mutation is P329 (see US 2012/0251531).

Thus, choosing a mutated IgG1 format with low effector function but retained binding to FcRn may result in a bispecific antibody with 5T4-dependent activation of CD137, and exhibiting a favorable efficacy/safety profile and good PK properties.

Advantageously, the polypeptide is incapable of inducing antibody dependent cell cytotoxicity (ADCC), antibody-dependent cellular phagocytosis (ADCP), and/or complement-dependent cytotoxicity (CDC). By "incapable" we include that the ability of the polypeptide to induce ADCC, etc., is at least 10-fold lower than compared to wild-type IgG1 as shown by e.g. monocyte-dependent ADCC or CDC assays described by Hezareh et al. 2001 (supra).

In one embodiment, the Fc region may be a variant of a human IgG1 Fc region comprising a mutation at one or more of the following positions:

L234, L235, P239, D265, N297 and/or P329.

Advantageously, alanine may be present at the mutated positions(s).

Optionally, the IgG1 variant may be a variant of a human IgG1 Fc region comprising mutations L234A and L235A (i.e. the LALA double mutant; see SEQ ID NO: 86).

It will be appreciated by persons skilled in the art that the bispecific polypeptides of the invention may be of several different structural formats (for example, see Chan & Carter, 2016, *Nature Reviews Immunology* 10, 301-316, the disclosures of which are incorporated herein by reference).

In exemplary embodiments, the bispecific antibody is selected from the groups consisting of:

(a) bivalent bispecific antibodies, such as IgG-scFv bispecific antibodies (for example, wherein 1 is an intact IgG and B2 is an scFv attached to 1 at the N-terminus of a light chain and/or at the C-terminus of a light chain and/or at the N-terminus of a heavy chain and/or at the C-terminus of a heavy chain of the IgG, or vice versa);

(b) monovalent bispecific antibodies, such as a DuoBody® (Genmab AS, Copenhagen, Denmark) or 'knob-in-hole' bispecific antibody (for example, an scFv-KIH, scFv-KIH$^r$, a BiTE-KIH or a BiTE-KIH$^r$ (see Xu et al., 2015, mAbs 7(1):231-242);

(c) $scFv_2$-Fc bispecific antibodies (such as ADAPTIR™ bispecific antibodies from Aptevo Therapeutics Inc, Seattle, US);

(d) BiTE/$scFv_2$ bispecific antibodies;

(e) DVD-Ig bispecific antibodies or other IgG-FAb, FAb-IgG bispecific antibodies regardless of bivalency or linkers/connectors employed;

(f) DART-based bispecific antibodies (for example, $DART_2$-Fc, $DART_2$-Fc or DART);

(g) DNL-$Fab_3$ bispecific antibodies; and (h) scFv-HSA-scFv bispecific antibodies.

For example, the bispecific antibody may be an IgG-scFv antibody (see FIG. 1). The IgG-scFv antibody (and, specifically, the scFv domain therein) may be in either VH-VL or VL-VH orientation. In one embodiment, the scFv may be stabilised by a S-S bridge between VH and VL.

In an alternative embodiment, the bispecific antibody may be an $scFv_2$-Fc antibody, for example a dimer wherein each polypeptide comprises, from the N-terminus to C-terminus, a first scFv, a hinge domain, an Fc domain and a second scFv (see FIG. 1).

In one embodiment, binding domain 1 and binding domain B2 are fused directly to each other.

In an alternative embodiment, binding domain 1 and binding domain B2 are joined via a polypeptide linker. For example, a polypeptide linker may be a short linker peptide between about 10 to about 25 amino acids. The linker is usually rich in glycine for flexibility, as well as serine or threonine for solubility, and can either connect the N-terminus of the VH with the C-terminus of the VL, or vice versa.

Thus, the linker may be selected from the group consisting of the amino acid sequence SGGGGSGGGGS (SEQ ID NO: 87), SGGGGSGGGGSAP (SEQ ID NO: 88), NFSQP (SEQ ID NO: 89), KRTVA (SEQ ID NO: 90), GGGSGGGG (SEQ ID NO: 91), GGGGSGGGGS, (SEQ ID NO: 92), GGGGSGGGGSGGGGS (SEQ ID NO: 93), THTCPPCPEPKSSDK (SEQ ID NO: 140), GGGS (SEQ ID NO: 141), EAAKEAAKGGGGS (SEQ ID NO: 142), EAAKEAAK (SEQ ID NO: 143), or (SG)m, where m=1 to 7.

In a further embodiment, binding domain 1 and binding domain B2 are separated by immunoglobulin constant regions (such as an Fc region) on a polypeptide.

The term "amino acid" as used herein includes the standard twenty genetically-encoded amino acids and their corresponding stereoisomers in the 'D' form (as compared to the natural 'L' form), omega-amino acids other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as "alanine" or "Ala" or "A", the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

In one embodiment, the antibody polypeptides as defined herein comprise or consist of L-amino acids.

It will be appreciated by persons skilled in the art that the antibody polypeptides of the invention may comprise or consist of one or more amino acids which have been modified or derivatised.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

Alternatively, or in addition, one or more amino acid may be glycosylated, such as N-linked glycosylation (in which glycan moieties are attached to a nitrogen of asparagine or arginine side chains) and/or O-linked glycosylation (in which glycan moieties are attached to the hydroxyl oxygen of serine, threonine, tyrosine, hydroxylysine or hydroxyproline). Methods for the production of glycosylated antibodies are well known in the art (for example, see Jefferis, 2009, *Nature Reviews Drug Discovery* 8:226-234, the disclosures of which are incorporated herein by reference).

It will be further appreciated by persons skilled in the art that peptidomimetic compounds may also be useful. The term 'peptidomimetic' refers to a compound that mimics the conformation and desirable features of a particular peptide as a therapeutic agent.

For example, the said polypeptide includes not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) *J. Immunol.* 159, 3230-3237, which is incorporated herein by reference. This approach involves making pseudopeptides containing changes involving the backbone, and not the orientation of side chains. Retro-inverse peptides, which contain NH—CO bonds instead of CO—NH peptide bonds, are much more resistant to proteolysis. Alternatively, the said polypeptide may be a peptidomimetic compound wherein one or more of the amino acid residues are linked by a -y($CH_2NH$)— bond in place of the conventional amide linkage.

In a further alternative, the peptide bond may be dispensed with altogether provided that an appropriate linker moiety which retains the spacing between the carbon atoms of the amino acid residues is used; it may be advantageous for the linker moiety to have substantially the same charge distribution and substantially the same planarity as a peptide bond.

It will also be appreciated that the said polypeptide may conveniently be blocked at its N- or C-terminus so as to help reduce susceptibility to exo-proteolytic digestion.

A variety of un-coded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, *Proc. Natl. Acad. Sci. USA* 75:2636 and Thursell et al., 1983, *Biochem. Biophys. Res. Comm.* 111:166, which are incorporated herein by reference.

In one embodiment, the bispecific polypeptide of the invention is capable of inducing tumour immunity. This can be tested in vitro in T cell activation assays, e.g. by measuring IL-2 and IFNγ production. Activation of effector T cells would indicate that a tumour specific T cell response can be achieved in vivo. Further, an anti-tumour response in an in vivo model, such as a mouse model would imply that a successful immune response towards the tumour has been achieved.

Thus, the bispecific polypeptide may modulate the activity of a target immune system cell, wherein said modulation is an increase or decrease in the activity of said cell. Such cells include T cells, dendritic cells and natural killer cells.

The immune system cell is typically a T cell. Thus, the antibody may increase the activity of a CD4+ or CD8+ effector T cell, or may decrease the activity of a regulatory T cell (Treg). In either case, the net effect of the antibody will be an increase in the activity of effector T cells, particularly CD8+ effector T cells. Methods for determining a change in the activity of effector T cells are well known and include, for example, measuring for an increase in the level of T cell cytokine production (e.g. IFN-γ or IL-2) or an increase in T cell proliferation in the presence of the antibody relative to the level of T cell cytokine production and/or T cell proliferation in the presence of a control. Assays for cell proliferation and/or cytokine production are well known.

For example, the polypeptide may be capable of inducing:

(a) activation of cytotoxic T cells, i.e. $CD8^+$ T cells;

(b) activation of helper T cells, i.e. $CD4^+$ T cells;

(c) activation of dendritic cells;

(d) activation of natural killer cells; and/or (e) reprograming of Tregs into effector T cells (see Akhmetzyanova et al., 2016, *J Immunol.* 196(1):484-92).

The polypeptide or binding domains of the invention can also be characterised and defined by their binding abilities. Standard assays to evaluate the binding ability of ligands towards targets are well known in the art, including for example, ELISAs, Western blots, RIAs, and flow cytometry analysis. The binding kinetics (e.g., binding affinity) of the polypeptide also can be assessed by standard assays known in the art, such as by Surface Plasmon Resonance analysis (SPR).

The terms "binding activity" and "binding affinity" are intended to refer to the tendency of a polypeptide molecule to bind or not to bind to a target. Binding affinity may be quantified by determining the dissociation constant (Kd) for a polypeptide and its target. A lower Kd is indicative of a higher affinity for a target. Similarly, the specificity of binding of a polypeptide to its target may be defined in terms of the comparative dissociation constants (Kd) of the polypeptide for its target as compared to the dissociation constant with respect to the polypeptide and another, non-target molecule.

The value of this dissociation constant can be determined directly by well-known methods, and can be computed even for complex mixtures by methods such as those, for example, set forth in Caceci et al. (Byte 9:340-362, 1984; the disclosures of which are incorporated herein by reference). For example, the Kd may be established using a double-filter nitrocellulose filter binding assay such as that disclosed by Wong & Lohman (Proc. Natl. Acad. Sci. USA 90, 5428-

5432, 1993). Other standard assays to evaluate the binding ability of ligands such as antibodies towards targets are known in the art, including for example, ELISAs, Western blots, RIAs, and flow cytometry analysis. The binding kinetics (e.g., binding affinity) of the antibody also can be assessed by standard assays known in the art, such as by Biacore™ system analysis.

A competitive binding assay can be conducted in which the binding of the antibody to the target is compared to the binding of the target by another, known ligand of that target, such as another antibody. The concentration at which 50% inhibition occurs is known as the Ki. Under ideal conditions, the Ki is equivalent to Kd. The Ki value will never be less than the Kd, so measurement of Ki can conveniently be substituted to provide an upper limit for Kd.

Alternative measures of binding affinity include EC50 or IC50. In this context EC50 indicates the concentration at which a polypeptide achieves 50% of its maximum binding to a fixed quantity of target. IC50 indicates the concentration at which a polypeptide inhibits 50% of the maximum binding of a fixed quantity of competitor to a fixed quantity of target. In both cases, a lower level of EC50 or IC50 indicates a higher affinity for a target. The EC50 and IC50 values of a ligand for its target can both be determined by well-known methods, for example ELISA. Suitable assays to assess the EC50 and IC50 of polypeptides are set out in the Examples.

A polypeptide of the invention is preferably capable of binding to its target with an affinity that is at least two-fold, 10-fold, 50-fold, 100-fold or greater than its affinity for binding to another non-target molecule.

CD137 Binding Domains

The bispecific polypeptides of the invention comprise a binding domain (1) which is capable of specifically binding to CD137.

Advantageously, binding domain 1 binds to human CD137 with a $K_D$ of less than $10\times10^{-9}$M, for example less than $4\times10^{-9}$M or less than $1.2\times10^{-9}$M.

In exemplary embodiments, binding domain 1 comprises:

(a) the three CDRs of the heavy chain and/or the three CDRs of the light chain of antibody 1200/1201 (SEQ ID NOs: 54, 55 and 79 and/or SEQ ID NOs: 46, 65 and 72);

(b) the three CDRs of the heavy chain and/or the three CDRs of the light chain of antibody 1202/1203 (SEQ ID NOs: 54, 55 and 80 and/or SEQ ID NOs: 60, 66 and 73);

(c) the three CDRs of the heavy chain and/or the three CDRs of the light chain of antibody 1204/1205 (SEQ ID NOs: 54, 55 and 81 and/or SEQ ID NOs: 61, 67, 74);

(d) the three CDRs of the heavy chain and/or the three CDRs of the light chain of antibody 1214/1215 (SEQ ID NOs: 54, 55 and 82 and/or SEQ ID NOs: 46, 68 and 75);

(e) the three CDRs of the heavy chain and/or the three CDRs of the light chain of antibody 1618/1619 (SEQ ID NOs: 54, 55 and 83 and/or SEQ ID NOs: 62, 69 and 76);

(f) the three CDRs of the heavy chain and/or the three CDRs of the light chain of antibody 1620/1621 (SEQ ID NOs: 54, 55 and 84 and/or SEQ ID NOs: 63, 70, and 77);

(g) the three CDRs of the heavy chain and/or the three CDRs of the light chain of antibody 1626/1627 (SEQ ID NOs: 54, 55 and 85 and/or SEQ ID NOs: 64, 71 and 78);

(h) the three CDRs of the heavy chain and/or the three CDRs of the light chain of antibody 3012/3013 (SEQ ID NOs: 156, 69 and 76 and/or SEQ ID NOs: 158, 155 and 83);

(i) the three CDRs of the heavy chain and/or the three CDRs of the light chain of antibody 3014/3015 (SEQ ID NOs: 62, 69 and 76 and/or SEQ ID NOs: 159, 160 and 83);

(j) the three CDRs of the heavy chain and/or the three CDRs of the light chain of antibody 3016/3017 (SEQ ID NOs: 62, 69 and 76 and/or SEQ ID NOs: 159, 155 and 83);

(k) the three CDRs of the heavy chain and/or the three CDRs of the light chain of antibody 3018/3019 (SEQ ID NOs: 156, 69 and 76 and/or SEQ ID NOs: 158, 161 and 83);

(L) the three CDRs of the heavy chain and/or the three CDRs of the light chain of antibody 3020/3021 (SEQ ID NOs: 156, 69 and 76 and/or SEQ ID NOs: 162, 163 and 83);

(m) the three CDRs of the heavy chain and/or the three CDRs of the light chain of antibody 3022/3023 (SEQ ID NOs: 156, 69 and 76 and/or SEQ ID NOs: 159, 155 and 83);

(n) the three CDRs of the heavy chain and/or the three CDRs of the light chain of antibody 3024/3025 (SEQ ID NOs: 156, 69 and 76 and/or SEQ ID NOs: 54, 55 and 83);

(o) the three CDRs of the heavy chain and/or the three CDRs of the light chain of antibody 3026/3027 (SEQ ID NOs: 156, 69 and 76 and/or SEQ ID NOs: 162, 165 and 83);

(p) the three CDRs of the heavy chain and/or the three CDRs of the light chain of antibody 3028/3029 (SEQ ID NOs: 157, 69 and 76 and/or SEQ ID NOs: 159, 166 and 83);

(q) the three CDRs of the heavy chain and/or the three CDRs of the light chain of antibody 3030/3031 (SEQ ID NOs: 156, 69 and 76 and/or SEQ ID NOs: 54, 166 and 83);

(r) the three CDRs of the heavy chain and/or the three CDRs of the light chain of antibody 3032/3033 (SEQ ID NOs: 156, 69 and 76 and/or SEQ ID NOs: 54, 55 and 83);

(s) the three CDRs of the heavy chain and/or the three CDRs of the light chain of antibody 3034/3035 (SEQ ID NOs: 62, 69 and 76 and/or SEQ ID NOs: 54, 155 and 83); or (t) the three CDRs of the heavy chain and/or the three CDRs of the light chain of antibody 3036/3037 (SEQ ID NOs: 156, 69 and 76 and/or SEQ ID NOs: 162, 155 and 83).

wherein the numbering of the antibody (e.g. Antibody X/Y) defines the heavy chain variable region (X) and the light chain variable region (Y), respectively (or, where a single number is indicated, the heavy chain variable region [X] only is defined).

Thus, binding domain 1 may comprise:

(a) the heavy chain variable region and/or the light chain variable region of antibody 1200/1201 (SEQ ID NO: 19 and/or SEQ ID NO: 17);

(b) the heavy chain variable region and/or the light chain variable region of antibody 1202/1203 (SEQ ID NO: 23 and/or SEQ ID NO: 21);

(c) the heavy chain variable region and/or the light chain variable region of antibody 1204/1205 (SEQ ID NO: 25 and/or SEQ ID NO: 27);

(d) the heavy chain variable region and/or the light chain variable region of antibody 1214/1215 (SEQ ID NO: 31 and/or SEQ ID NO: 29);
(e) the heavy chain variable region and/or the light chain variable region of antibody 1618/1619 (SEQ ID NO: 35 and/or SEQ ID NO: 33);
(f) the heavy chain variable region and/or the light chain variable region of antibody 1620/1621 (SEQ ID NO: 39 and/or SEQ ID NO: 37);
(g) the heavy chain variable region and/or the light chain variable region of antibody 1626/1627 (SEQ ID NO: 43 and/or SEQ ID NO: 41);
(h) the heavy chain variable region and/or the light chain variable region of antibody 3012/3013 (SEQ ID NO: 114 and/or SEQ ID NO: 115);
(i) the heavy chain variable region and/or the light chain variable region of antibody 3014/3015 (SEQ ID NO: 116 and/or SEQ ID NO: 117);
(j) the heavy chain variable region and/or the light chain variable region of antibody 3016/3017 (SEQ ID NO: 118 and/or SEQ ID NO: 119);
(k) the heavy chain variable region and/or the light chain variable region of antibody 3018/3019 (SEQ ID NO: 120 and/or SEQ ID NO: 121);
(l) the heavy chain variable region and/or the light chain variable region of antibody 3020/3021 (SEQ ID NO: 122 and/or SEQ ID NO: 123);
(m) the heavy chain variable region and/or the light chain variable region of antibody 3022/3023 (SEQ ID NO: 124 and/or SEQ ID NO: 125);
(n) the heavy chain variable region and/or the light chain variable region of antibody 3024/3025 (SEQ ID NO: 126 and/or SEQ ID NO: 127);
(o) the heavy chain variable region and/or the light chain variable region of antibody 3026/3027 (SEQ ID NO: 128 and/or SEQ ID NO: 129);
(p) the heavy chain variable region and/or the light chain variable region of antibody 3028/3029 (SEQ ID NO: 130 and/or SEQ ID NO: 131);
(q) the heavy chain variable region and/or the light chain variable region of antibody 3030/3031 (SEQ ID NO: 132 and/or SEQ ID NO: 133);
(r) the heavy chain variable region and/or the light chain variable region of antibody 3032/3033 (SEQ ID NO: 134 and/or SEQ ID NO: 135);
(s) the heavy chain variable region and/or the light chain variable region of antibody 3034/3035 (SEQ ID NO: 136 and/or SEQ ID NO: 137); or
(t) the heavy chain variable region and/or the light chain variable region of antibody 3036/3037 (SEQ ID NO: 138 and/or SEQ ID NO: 139).

It will be appreciated by persons skilled in the art that the bispecific polypeptides of the invention may alternatively comprise variants of the above-defined variable regions.

A variant of any one of the heavy or light chain amino acid sequences recited herein may be a substitution, deletion or addition variant of said sequence. A variant may comprise 1, 2, 3, 4, 5, up to 10, up to 20, up to 30 or more amino acid substitutions and/or deletions from the said sequence. "Deletion" variants may comprise the deletion of individual amino acids, deletion of small groups of amino acids such as 2, 3, 4 or 5 amino acids, or deletion of larger amino acid regions, such as the deletion of specific amino acid domains or other features. "Substitution" variants preferably involve the replacement of one or more amino acids with the same number of amino acids and making conservative amino acid substitutions. For example, an amino acid may be substituted with an alternative amino acid having similar properties, for example, another basic amino acid, another acidic amino acid, another neutral amino acid, another charged amino acid, another hydrophilic amino acid, another hydrophobic amino acid, another polar amino acid, another aromatic amino acid or another aliphatic amino acid. Some properties of the 20 main amino acids which can be used to select suitable substituents are as follows:

| | | | |
|---|---|---|---|
| Ala, A | aliphatic, hydrophobic, neutral | Met, M | hydrophobic, neutral |
| Cys, C | polar, hydrophobic, neutral | Asn, N | polar, hydrophilic, neutral |
| Asp, D | polar, hydrophilic, charged (−) | Pro, P | hydrophobic, neutral |
| Glu, E | polar, hydrophilic, charged (−) | Gln, Q | polar, hydrophilic, neutral |
| Phe, F | aromatic, hydrophobic, neutral | Arg, R | polar, hydrophilic, charged (+) |
| Gly, G | aliphatic, neutral | Ser, S | polar, hydrophilic, neutral |
| His, H | aromatic, polar, hydrophilic, charged (+) | Thr, T | polar, hydrophilic, neutral |
| Ile, I | aliphatic, hydrophobic, neutral | Val, V | aliphatic, hydrophobic, neutral |
| Lys, K | polar, hydrophilic, charged(+) | Trp, W | aromatic, hydrophobic, neutral |
| Leu, L | aliphatic, hydrophobic, neutral | Tyr, Y | aromatic, polar, hydrophobic |

Amino acids herein may be referred to by full name, three letter code or single letter code.

Preferred "derivatives" or "variants" include those in which instead of the naturally occurring amino acid the amino acid which appears in the sequence is a structural analog thereof. Amino acids used in the sequences may also be derivatised or modified, e.g. labelled, providing the function of the antibody is not significantly adversely affected.

Derivatives and variants as described above may be prepared during synthesis of the antibody or by post-production modification, or when the antibody is in recombinant form using the known techniques of site-directed mutagenesis, random mutagenesis, or enzymatic cleavage and/or ligation of nucleic acids.

Preferably variants have an amino acid sequence which has more than 60%, or more than 70%, e.g. 75 or 80%, preferably more than 85%, e.g. more than 90 or 95% amino acid identity to a sequence as shown in the sequences disclosed herein (e.g. the VH or VL region sequences, or CDR sequences therein). This level of amino acid identity may be seen across the full length of the relevant SEQ ID NO sequence or over a part of the sequence, such as across 20, 30, 50, 75, 100, 150, 200 or more amino acids, depending on the size of the full-length polypeptide.

For example, variants of the above CDR sequences may comprise one, two three, four, five, six, seven, eight or more amino acid mutations relative to the reference sequence (such as a deletion, substitution and/or insertion of an amino acid).

In connection with amino acid sequences, "sequence identity" refers to sequences which have the stated value when assessed using ClustalW (Thompson et al., 1994,

*Nucleic Acids Res.* 22(22):4673-80; the disclosures of which are incorporated herein by reference) with the following parameters:

Pairwise alignment parameters—Method: accurate, Matrix: PAM, Gap open penalty: 10.00, Gap extension penalty: 0.10;

Multiple alignment parameters—Matrix: PAM, Gap open penalty: 10.00, % identity for delay: 30, Penalize end gaps: on, Gap separation distance: 0, Negative matrix: no, Gap extension penalty: 0.20, Residue-specific gap penalties: on, Hydrophilic gap penalties: on, Hydrophilic residues: GPSNDQEKR. Sequence identity at a particular residue is intended to include identical residues which have simply been derivatised.

Thus, in one embodiment binding domain 1 may comprises one or more variants of the above-defined light chain variable regions and/or said heavy chain variable regions having at least 90% sequence identity thereto.

In preferred embodiments, binding domain 1 comprises:

(a) the heavy chain and/or the light chain of antibody 1200/1201;
(b) the heavy chain and/or the light chain of antibody 1202/1203;
(c) the heavy chain and/or the light chain of antibody 1204/1205;
(d) the heavy chain and/or the light chain of antibody 1214/1215;
(e) the heavy chain and/or the light chain of antibody 1618/1619;
(f) the heavy chain and/or the light chain of antibody 1620/1621;
(g) the heavy chain and/or the light chain of antibody 1626/1627;
(h) the heavy chain and/or the light chain of antibody 3012/3013;
(i) the heavy chain and/or the light chain of antibody 3014/3015;
(j) the heavy chain and/or the light chain of antibody 3016/3017;
(k) the heavy chain and/or the light chain of antibody 3018/3019;
(l) the heavy chain and/or the light chain of antibody 3020/3021;
(m) the heavy chain and/or the light chain of antibody 3022/3023;
(n) the heavy chain and/or the light chain of antibody 3024/3025;
(o) the heavy chain and/or the light chain of antibody 3026/3027;
(p) the heavy chain and/or the light chain of antibody 3028/3029;
(q) the heavy chain and/or the light chain of antibody 3030/3031;
(r) the heavy chain and/or the light chain of antibody 3032/3033;
(s) the heavy chain and/or the light chain of antibody 3034/3035; or
(t) the heavy chain and/or the light chain of antibody 3036/3037.

For example, binding domain 1 comprises the light chain variable region and the heavy chain variable region of antibody 1200/1201 (SEQ ID NO: 19 and/or SEQ ID NO: 17), or a variant which has more than 60%, or more than 70%, e.g. 75 or 80%, preferably more than 85%, e.g. more than 90 or 95% amino acid identity to SEQ ID NO: 19 and/or SEQ ID NO: 17).

Alternatively, binding domain 1 comprises the light chain variable region and the heavy chain variable region of antibody 1618/1619 (SEQ ID NO: 35 and/or SEQ ID NO: 33), or a variant which has more than 60%, or more than 70%, e.g. 75 or 80%, preferably more than 85%, e.g. more than 90 or 95% amino acid identity to SEQ ID NO: 35 and/or SEQ ID NO: 33).

Tumour Cell-Targeting Domains

The bispecific polypeptides of the invention further comprise a binding domain (B2) which is capable of specifically binding a tumour cell-associated antigen.

By "tumour cell-associated antigen" we include proteins accessible on the extracellular surface of tumour cells, such that they are accessible to the bispecific polypeptides of the invention following administration into the body. In one embodiment, the tumour cell-associated antigen is tumour specific, i.e. it is found exclusively on tumour cells and not on normal, healthy cells. However, it will be appreciated by persons skilled in the art that the tumour cell-associated antigen may be preferentially expressed on tumour cells, i.e. it is expressed on tumour cells at a higher level than on normal, healthy cells (thus, expression of the antigen on tumour cells may be at least five times more than on normal, healthy cells, for example expression levels on tumour cells of at least ten times more, twenty times more, fifty time more or greater).

In one embodiment, binding domain B2 binds to a tumour cell-associated antigen selected from the group consisting of:

(a) products of mutated oncogenes and tumour suppressor genes;
(b) overexpressed or aberrantly expressed cellular proteins;
(c) tumour antigens produced by oncogenic viruses;
(d) oncofetal antigens;
(e) altered cell surface glycolipids and glycoproteins;
(f) cell type-specific differentiation antigens;
(g) hypoxia-induced antigens;
(h) tumour peptides presented by MHC class I;
(i) epithelial tumour antigens;
(j) haematological tumour-associated antigens;
(k) cancer testis antigens; and
(l) melanoma antigens.

Thus, the tumour cell-associated antigen may be selected from the group consisting of 5T4, CD20, CD19, MUC-1, carcinoembryonic antigen (CEA), CA-125, C017-1A, EpCAM, HER2, EGFR, HER3, GD2, Podocalyxin, TROP-2, DLK-1, Ox1R, Nectin-4, FAP, EphA2, EphA3, mesothelin, E-cadherin, CD24 and VEGFR.

In one embodiment, the tumour cell-associated antigen is an oncofetal antigen. For example, the tumour cell-associated antigen may be 5T4 (for example, see UniProt Q13641).

In one embodiment, the tumour cell is a solid tumour cell.

For example, the solid tumour may be selected from the groups consisting of renal cell carcinoma, colorectal cancer, lung cancer, prostate cancer, breast cancer, melanomas, bladder cancer, brain/CNS cancer, cervical cancer, oesophageal cancer, gastric cancer, head/neck cancer, kidney cancer, liver cancer, lymphomas, ovarian cancer, pancreatic cancer and sarcomas.

Advantageously, binding domain B2 binds to the tumour cell-associated antigen with a $K_D$ of less than $10\times10^{-9}$M, for example less than $4\times10^{-9}$M or less than $1.2\times10^{-9}$M.

In exemplary embodiments, binding domain B2 comprises:

(a) the three CDRs of the heavy chain and/or the three CDRs of the light chain of antibody 1206/1207 (SEQ ID NOs: 54, 55 and 56 and/or SEQ ID NOs: 45, 47 and 50);

(b) the three CDRs of the heavy chain and/or the three CDRs of the light chain of antibody 1208/1135 (SEQ ID NOs: 54, 55 and 57 and/or SEQ ID NOs: 46, 48 and 51);

(c) the three CDRs of the heavy chain and/or the three CDRs of the light chain of antibody 1210/1211 (SEQ ID NOs: 54, 55 and 58 and/or SEQ ID NOs: 46, 48 and 52);

(d) the three CDRs of the heavy chain and/or the three CDRs of the light chain of antibody 1212/1213 (SEQ ID NOs: 54, 55 and 59 and/or SEQ ID NOs: 46, 49 and 53);

(e) the three CDRs of the heavy chain and/or the three CDRs of the light chain of antibody 2992/2993 (SEQ ID NOs: 144, 48 and 52 and/or SEQ ID NOs: 145, 55 and 58);

(f) the three CDRs of the heavy chain and/or the three CDRs of the light chain of antibody 2994/2995 (SEQ ID NOs: 146, 147 and 52 and/or SEQ ID NOs: 145, 55 and 58);

(g) the three CDRs of the heavy chain and/or the three CDRs of the light chain of antibody 2996/2997 (SEQ ID NOs: 146, 48 and 52 and/or SEQ ID NOs: 148, 55 and 58);

(h) the three CDRs of the heavy chain and/or the three CDRs of the light chain of antibody 2998/2999 (SEQ ID NOs: 146, 48 and 52 and/or SEQ ID NOs: 149, 55 and 58);

(i) the three CDRs of the heavy chain and/or the three CDRs of the light chain of antibody 3000/3001 (SEQ ID NOs: 150, 48 and 52 and/or SEQ ID NOs: 148, 151 and 58);

(j) the three CDRs of the heavy chain and/or the three CDRs of the light chain of antibody 3002/3003 (SEQ ID NOs: 152, 48 and 52 and/or SEQ ID NOs: 145, 55 and 58);

(k) the three CDRs of the heavy chain and/or the three CDRs of the light chain of antibody 3004/3005 (SEQ ID NOs: 146, 48 and 52 and/or SEQ ID NOs: 153, 55 and 58);

(l) the three CDRs of the heavy chain and/or the three CDRs of the light chain of antibody 3006/3007 (SEQ ID NOs: 144, 48 and 52 and/or SEQ ID NOs: 154, 155 and 58); or (m) the three CDRs of the heavy chain and/or the three CDRs of the light chain of antibody 3008/3009 (SEQ ID NOs: 146, 48 and 52 and/or SEQ ID NOs: 154, 55 and 58).

wherein the numbering of the antibody (e.g. Antibody X/Y) defines the heavy chain variable region (X) and the light chain variable region (Y), respectively (or, where a single number is indicated, the heavy chain variable region [X] only is defined).

Thus, binding domain B2 may comprise:

(a) the heavy chain variable region and/or the light chain variable region of antibody 1206/1207 (SEQ ID NO: 3 and/or SEQ ID NO: 1);

(b) the heavy chain variable region and/or the light chain variable region of antibody 1208/1135 (SEQ ID NO: 7 and/or SEQ ID NO: 5);

(c) the heavy chain variable region and/or the light chain variable region of antibody 1210/1211 (SEQ ID NO: 11 and/or SEQ ID NO: 9);

(d) the heavy chain variable region and/or the light chain variable region of antibody 1212/1213 (SEQ ID NO: 15 and/or SEQ ID NO: 13);

(e) the heavy chain variable region and/or the light chain variable region of antibody 2992/2993 (SEQ ID NO: 96 and/or SEQ ID NO: 97);

(f) the heavy chain variable region and/or the light chain variable region of antibody 2994/2995 (SEQ ID NO: 98 and/or SEQ ID NO: 99);

(g) the heavy chain variable region and/or the light chain variable region of antibody 2996/2997 (SEQ ID NO: 100 and/or SEQ ID NO: 101);

(h) the heavy chain variable region and/or the light chain variable region of antibody 2998/2999 (SEQ ID NO: 102 and/or SEQ ID NO: 103);

(i) the heavy chain variable region and/or the light chain variable region of antibody 3000/3001 (SEQ ID NO: 104 and/or SEQ ID NO: 105);

(j) the heavy chain variable region and/or the light chain variable region of antibody 3002/3003 (SEQ ID NO: 106 and/or SEQ ID NO: 107);

(k) the heavy chain variable region and/or the light chain variable region of antibody 3004/3005 (SEQ ID NO: 108 and/or SEQ ID NO: 109);

(l) the heavy chain variable region and/or the light chain variable region of antibody 3006/3007 (SEQ ID NO: 110 and/or SEQ ID NO: 111); or (m) the heavy chain variable region and/or the light chain variable region of antibody 3008/3009 (SEQ ID NO: 112 and/or SEQ ID NO: 113).

It will be appreciated by skilled persons that binding domain B2 may alternatively comprise variants of said light chain variable regions and/or said heavy chain variable regions, for example having at least 90% sequence identity thereto.

For example, variants of the above CDR sequences may comprise one, two three, four, five, six, seven, eight or more amino acid mutations relative to the reference sequence (such as a deletion, substitution and/or insertion of an amino acid).

In one embodiment, binding domain B2 comprises:

(a) the heavy chain and/or the light chain of antibody 1206/1207;

(b) the heavy chain and/or the light chain of antibody 1208/1135;

(c) the heavy chain and/or the light chain of antibody 1210/1211;

(d) the heavy chain and/or the light chain of antibody 1212/1213;

(e) the heavy chain and/or the light chain of antibody 2992/2993;

(f) the heavy chain and/or the light chain of antibody 2994/2995;

(g) the heavy chain and/or the light chain of antibody 2996/2993;

(h) the heavy chain and/or the light chain of antibody 2998/2999;

(i) the heavy chain and/or the light chain of antibody 3000/3001;

(j) the heavy chain and/or the light chain of antibody 3002/3003;

(k) the heavy chain and/or the light chain of antibody 3004/3005;

(l) the heavy chain and/or the light chain of antibody 3006/3007; or (m) the heavy chain and/or the light chain of antibody 3008/3009.

For example, binding domain B2 comprises the heavy chain variable region and the light chain variable region of antibody 1208/1135 (SEQ ID NO: 7 and SEQ ID NO: 5), or a variant which has more than 60%, or more than 70%, e.g. 75 or 80%, preferably more than 85%, e.g. more than 90 or 95% amino acid identity to SEQ ID NO: 7 and/or SEQ ID NO: 5).

Alternatively, binding domain B2 comprises the heavy chain variable region and the light chain variable region of antibody 1210/1211 (SEQ ID NO: 11 and SEQ ID NO: 9), or a variant which has more than 60%, or more than 70%, e.g. 75 or 80%, preferably more than 85%, e.g. more than 90 or 95% amino acid identity to SEQ ID NO: 11 and/or SEQ ID NO: 9).

Alternatively, binding domain B2 comprises the heavy chain variable region and the light chain variable region of antibody 2992/2993 (SEQ ID NO: 96 and SEQ ID NO: 97), or a variant which has more than 60%, or more than 70%, e.g. 75 or 80%, preferably more than 85%, e.g. more than 90 or 95% amino acid identity to SEQ ID NO: 96 and/or SEQ ID NO: 97.

Alternatively, binding domain B2 comprises the heavy chain variable region and the light chain variable region of antibody 2994/2995 (SEQ ID NO: 98 and SEQ ID NO: 99), or a variant which has more than 60%, or more than 70%, e.g. 75 or 80%, preferably more than 85%, e.g. more than 90 or 95% amino acid identity to SEQ ID NO: 98 and/or SEQ ID NO: 99.

Exemplary CD137—5T4 Bispecific Antibodies

In one preferred embodiment of the bispecific polypeptides of the invention, binding domain 1 is an IgG and binding domain B2 is an scFv. Conversely, binding domain 1 may be an scFv and binding domain B2 may be an IgG.

In an alternative embodiment of the bispecific polypeptides of the invention, binding domain 1 is an scFv and binding domain B2 is an scFv (e.g. in an $scFv_2$-Fc format).

In exemplary bispecific polypeptides of the invention:

(a) 1 comprises the three CDRs of the light chain and/or the three CDRs of the heavy chain of antibody 1200/1201 (SEQ ID NOs: 54, 55 and 79 and/or SEQ ID NOs: 46, 65 and 72) and B2 comprises the three CDRs of the light chain and/or the three CDRs of the heavy chain of antibody 1208/1135 (SEQ ID NOs: 54, 55 and 57 and/or SEQ ID NOs: 46, 48 and 51);

(b) 1 comprises the three CDRs of the light chain and/or the three CDRs of the heavy chain of antibody 1200/1201 (SEQ ID NOs: 54, 55 and 79 and/or SEQ ID NOs: 46, 65 and 72) and B2 comprises the three CDRs of the light chain and/or the three CDRs of the heavy chain of antibody 1210/1211 (SEQ ID NOs: 54, 55 and 58 and/or SEQ ID NOs: 46, 48 and 52);

(c) 1 comprises the three CDRs of the light chain and/or the three CDRs of the heavy chain of antibody 1618/1619 (SEQ ID NOs: 54, 55 and 83 and/or SEQ ID NOs: 62, 69 and 76) and B2 comprises the three CDRs of the light chain and/or the three CDRs of the heavy chain of antibody 1208/1135 (SEQ ID NOs: 54, 55 and 57 and/or SEQ ID NOs: 46, 48 and 51); or (d) 1 comprises the three CDRs of the light chain and/or the three CDRs of the heavy chain of antibody 1618/1619 (SEQ ID NOs: 54, 55 and 83 and/or SEQ ID NOs: 62, 69 and 76) and B2 comprises the three CDRs of the light chain and/or the three CDRs of the heavy chain of antibody 1210/1211 (SEQ ID NOs: 54, 55 and 58 and/or SEQ ID NOs: 46, 48 and 52).

Thus, in certain embodiments:

(a) 1 comprises the light chain variable region and/or the heavy chain variable region of antibody 1200/1201 (SEQ ID NO: 19 and/or SEQ ID NO: 17) and B2 comprises the light chain variable region and/or the heavy chain variable region of antibody 1208/1135 (SEQ ID NO: 7 and/or SEQ ID NO: 5);

(b) 1 comprises the light chain variable region and/or the heavy chain variable region of antibody 1200/1201 (SEQ ID NO: 19 and/or SEQ ID NO: 17) and B2 comprises the light chain variable region and/or the heavy chain variable region of antibody 1210/1211 (SEQ ID NO: 11 and/or SEQ ID NO: 9);

(c) 1 comprises the light chain variable region and/or the heavy chain variable region of antibody 1618/1619 (SEQ ID NO: 35 and/or SEQ ID NO: 33) and B2 comprises the light chain variable region and/or the heavy chain variable region of antibody 1208/1135 (SEQ ID NO: 7 and/or SEQ ID NO: 5);

(d) 1 comprises the light chain variable region and/or the heavy chain variable region of antibody 1618/1619 (SEQ ID NO: 35 and/or SEQ ID NO: 33) and B2 comprises the light chain variable region and/or the heavy chain variable region of antibody 1210/1211 (SEQ ID NO: 11 and/or SEQ ID NO: 9); or (e) variants of said light chain variable regions and/or said heavy chain variable regions, for example having at least 90% sequence identity thereto (as discussed above).

In a preferred embodiment, 1 comprises the light chain variable region and/or the heavy chain variable region of antibody 1200/1201 (SEQ ID NO: 19 and/or SEQ ID NO: 17) and B2 comprises the light chain variable region and/or the heavy chain variable region of antibody 1210/1211 (SEQ ID NO: 11 and/or SEQ ID NO: 9), or variants of said light chain variable regions and/or said heavy chain variable regions (for example, having at least 90% sequence identity thereto).

In an alternative preferred embodiment, 1 comprises the light chain variable region and/or the heavy chain variable region of antibody 1210/1211 (SEQ ID NO: 11 and/or SEQ ID NO: 9) and B2 comprises the light chain variable region and/or the heavy chain variable region of antibody 1618/1619 (SEQ ID NO: 35 and/or SEQ ID NO: 33), or variants of said light chain variable regions and/or said heavy chain variable regions (for example, having at least 90% sequence identity thereto).

Typically, the bispecific antibody polypeptides of the invention will comprise constant region sequences, in addition to the above-defined variable region sequences.

An exemplary heavy chain constant region amino acid sequence which may be combined with any VH region sequence disclosed herein (to form a complete heavy chain) is the following IgG1 heavy chain constant region sequence:

[SEQ ID NO: 94]

ASTKGPSVFPLAPSSKSTSGGTAALGCLVKDYFPEPVTVSWNSGALTSGVH

TFPAVLQSSGLYSLSSVVTVPSSSLGTQTYICNVNHKPSNTKVDKKVEPKS

CDKTHTCPPCPAPE LLGGPSVFLFPPKPKDTLMISRTPEVTCVVVDVSH

EDPEVKFNWYVDGVEVHNAKTKPREEQYNSTYRVVSVLTVLHQDWLNGKEY

-continued

```
KCKVSNKALPAPIEKTISKAKGQPREPQVYTLPPSRDELTKNQVSLTCLVK

GFYPSDIAVEWESNGQPENNYKTTPPVLDSDGSFFLYSKLTVDKSRWQQGN

VFSCSVMHEALHNHYTQKSLSLSPGK
```

or a variant thereof comprising the L234A and L235A ("LALA") mutations (see amino acid residues highlighted above).

Likewise, an exemplary light chain constant region amino acid sequence which may be combined with any VL region sequence disclosed herein (to form a complete light chain) is the kappa chain constant region sequence reproduced here:

```
                                        [SEQ ID NO: 95]
RTVAAPSVFIFPPSDEQLKSGTASVVCLLNNFYPREAKVQWKVDNALQSGN

SQESVTEQDSKDSTYSLSSTLTLSKADYEKHKVYACEVTHQGLSSPVTKSF

NRGEC.
```

Thus, the bispecific antibody of the invention may comprise:

(a) a binding domain (1) comprising a heavy chain variable region of any of SEQ ID NOs: 17, 21, 27, 29, 33, 37, 41, 114, 116, 118, 120, 122, 124, 126, 128, 130, 132, 134, 136 or 138 and a light chain variable region of any of SEQ ID NOs: 19, 23, 25, 31, 35, 39, 43, 115, 117, 119, 121, 123, 125, 127, 129, 131, 133, 135 or 139;

(b) a heavy chain constant region comprising an Fc region (for example, SEQ ID NO: 94 or 96);

(c) a binding domain (B2) comprising a heavy chain variable region of any of SEQ ID NOs: 1, 5, 9, 13, 96, 98, 100, 102, 104, 106, 108, 110 or 112 and a light chain variable region of any of SEQ ID NOs: 3, 7, 11, 15, 97, 99, 101, 103, 105, 107, 109, 111 or 113; and (d) optionally, a light chain constant region (for example SEQ ID NO:95).

In one preferred embodiment, the bispecific antibody of the invention is an IgG-scFv bispecific antibody (for example, wherein 1 is an intact IgG and B2 is an scFv attached to the C-terminus of a heavy chain of the IgG, or vice versa).

For example, the bispecific antibody may comprise the following components:

(a) two heavy chains each comprising, in order from the N-terminus to the C terminus:

[a VH sequence]-[an H chain constant region]-[a connector]-[an scFv]

wherein the scFv may comprise of consist of in order from the N-terminus to the C terminus:

[a VH sequence]-[a linker]-[a VL sequence], or vice versa (b) two light chains each comprising, in order from the N-terminus to the C terminus:

[a VL sequence]-[an L chain constant region]

In such "Morrison format" bispecific antibodies:

the VH sequences may be selected from any of those disclosed herein, for example from clone 1618 (SEQ ID NO: 33), clone 1210 (SEQ ID NO:9) or a variant thereof;

the H chain constant region may be selected from any of those disclosed herein, for example SEQ ID NO:86 or 94;

the connector may be selected from any of those disclosed herein, for example SEQ ID NOs:92 or 140 or 143;

the linker within the scFv may be selected from any of those disclosed herein, for example SEQ ID NO:93, and the VL sequence within the scFv may be selected from any of those disclosed herein, for example from clone 1619 (SEQ ID NO: 35), clone 1211 (11) or a variant thereof; and the L chain constant region may be selected from any of those disclosed herein, for example SEQ ID NO:95.

As discussed above, methods for the production of antibody polypeptides of the invention are well known in the art.

Conveniently, the antibody polypeptide is or comprises a recombinant polypeptide. Suitable methods for the production of such recombinant polypeptides are well known in the art, such as expression in prokaryotic or eukaryotic hosts cells (for example, see Green & Sambrook, 2012*, Molecular Cloning, A Laboratory Manual*, Fourth Edition, Cold Spring Harbor, New York, the relevant disclosures in which document are hereby incorporated by reference).

Antibody polypeptides of the invention can also be produced using a commercially available in vitro translation system, such as rabbit reticulocyte lysate or wheatgerm lysate (available from Promega). Preferably, the translation system is rabbit reticulocyte lysate. Conveniently, the translation system may be coupled to a transcription system, such as the TNT transcription-translation system (Promega). This system has the advantage of producing suitable mRNA transcript from an encoding DNA polynucleotide in the same reaction as the translation.

It will be appreciated by persons skilled in the art that antibody polypeptides of the invention may alternatively be synthesised artificially, for example using well known liquid-phase or solid phase synthesis techniques (such as t-Boc or Fmoc solid-phase peptide synthesis).

Polynucleotides, Vectors and Cells

A second aspect of the invention provides an isolated nucleic acid molecule encoding a bispecific polypeptide according to any one of the preceding claims, or a component polypeptide chain thereof. For example, the nucleic acid molecule may comprise any of the nucleotide sequences provided in Table A.

Thus, a polynucleotide of the invention may encode any polypeptide as described herein, or all or part of 1 or all or part of B2. The terms "nucleic acid molecule" and "polynucleotide" are used interchangeably herein and refer to a polymeric form of nucleotides of any length, either deoxyribonucleotides or ribonucleotides, or analogs thereof. Non-limiting examples of polynucleotides include a gene, a gene fragment, messenger RNA (mRNA), cDNA, recombinant polynucleotides, plasmids, vectors, isolated DNA of any sequence, isolated RNA of any sequence, nucleic acid probes, and primers. A polynucleotide of the invention may be provided in isolated or substantially isolated form. By substantially isolated, it is meant that there may be substantial, but not total, isolation of the polypeptide from any surrounding medium. The polynucleotides may be mixed with carriers or diluents which will not interfere with their intended use and still be regarded as substantially isolated.

A nucleic acid sequence which "encodes" a selected polypeptide is a nucleic acid molecule which is transcribed (in the case of DNA) and translated (in the case of mRNA) into a polypeptide in vivo when placed under the control of appropriate regulatory sequences. The boundaries of the coding sequence are determined by a start codon at the 5' (amino) terminus and a translation stop codon at the 3' (carboxy) terminus. For the purposes of the invention, such nucleic acid sequences can include, but are not limited to, cDNA from viral, prokaryotic or eukaryotic mRNA, genomic sequences from viral or prokaryotic DNA or RNA, and even synthetic DNA sequences. A transcription termination sequence may be located 3' to the coding sequence.

Representative polynucleotides which encode examples of a heavy chain or light chain amino acid sequence of an antibody may comprise or consist of any one of the nucleotide sequences disclosed herein, for example the sequences set out in Table A.

A suitable polynucleotide sequence may alternatively be a variant of one of these specific polynucleotide sequences. For example, a variant may be a substitution, deletion or addition variant of any of the above nucleic acid sequences. A variant polynucleotide may comprise 1, 2, 3, 4, 5, up to 10, up to 20, up to 30, up to 40, up to 50, up to 75 or more nucleic acid substitutions and/or deletions from the sequences given in the sequence listing.

Suitable variants may be at least 70% homologous to a polynucleotide of any one of nucleic acid sequences disclosed herein, preferably at least 80 or 90% and more preferably at least 95%, 97% or 99% homologous thereto. Preferably homology and identity at these levels is present at least with respect to the coding regions of the polynucleotides. Methods of measuring homology are well known in the art and it will be understood by those of skill in the art that in the present context, homology is calculated on the basis of nucleic acid identity. Such homology may exist over a region of at least 15, preferably at least 30, for instance at least 40, 60, 100, 200 or more contiguous nucleotides. Such homology may exist over the entire length of the unmodified polynucleotide sequence.

Methods of measuring polynucleotide homology or identity are known in the art. For example the UWGCG Package provides the BESTFIT program which can be used to calculate homology (e.g. used on its default settings) (Devereux et al, 1984, *Nucleic Acids Research* 12:387-395; the disclosures of which are incorporated herein by reference).

The PILEUP and BLAST algorithms can also be used to calculate homology or line up sequences (typically on their default settings), for example as described in Altschul, 1993, *J Mol Evol* 36:290-300; Altschul et al, 1990, *J Mol Biol* 215:403-10, the disclosures of which are incorporated herein by reference).

Software for performing BLAST analysis is publicly available through the National Centre for Biotechnology Information (http://www.ncbi.nlm.nih.gov/). This algorithm involves first identifying high scoring sequence pair (HSPs) by identifying short words of length W in the query sequence that either match or satisfy some positive-valued threshold score T when aligned with a word of the same length in a database sequence. T is referred to as the neighbourhood word score threshold (Altschul et al, supra). These initial neighbourhood word hits act as seeds for initiating searches to find HSPs containing them. The word hits are extended in both directions along each sequence for as far as the cumulative alignment score can be increased. Extensions for the word hits in each direction are halted when: the cumulative alignment score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff & Henikoff, 1992, *Proc. Natl. Acad. Sci. USA* 89:10915-10919; the disclosures of which are incorporated herein by reference) alignments (B) of 50, expectation (E) of 10, M=5, N=4, and a comparison of both strands.

The BLAST algorithm performs a statistical analysis of the similarity between two sequences; see e.g. Karlin & Altschul, 1993, *Proc. Natl. Acad. Sci. USA* 90:5873-5787; the disclosures of which are incorporated herein by reference. One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence to the second sequence is less than about 1, preferably less than about 0.1, more preferably less than about 0.01, and most preferably less than about 0.001.

The homologue may differ from a sequence in the relevant polynucleotide by less than 3, 5, 10, 15, 20 or more mutations (each of which may be a substitution, deletion or insertion). These mutations may be measured over a region of at least 30, for instance at least 40, 60 or 100 or more contiguous nucleotides of the homologue.

In one embodiment, a variant sequence may vary from the specific sequences given in the sequence listing by virtue of the redundancy in the genetic code. The DNA code has 4 primary nucleic acid residues (A, T, C and G) and uses these to "spell" three letter codons which represent the amino acids the proteins encoded in an organism's genes. The linear sequence of codons along the DNA molecule is translated into the linear sequence of amino acids in the protein(s) encoded by those genes. The code is highly degenerate, with 61 codons coding for the 20 natural amino acids and 3 codons representing "stop" signals. Thus, most amino acids are coded for by more than one codon—in fact several are coded for by four or more different codons. A variant polynucleotide of the invention may therefore encode the same polypeptide sequence as another polynucleotide of the invention, but may have a different nucleic acid sequence due to the use of different codons to encode the same amino acids.

A polypeptide of the invention may thus be produced from or delivered in the form of a polynucleotide which encodes, and is capable of expressing, it.

Polynucleotides of the invention can be synthesised according to methods well known in the art, as described by way of example in Green & Sambrook (2012, Molecular Cloning—a laboratory manual, 4th edition; Cold Spring Harbor Press; the disclosures of which are incorporated herein by reference).

The nucleic acid molecules of the present invention may be provided in the form of an expression cassette which includes control sequences operably linked to the inserted sequence, thus allowing for expression of the polypeptide of the invention in vivo. These expression cassettes, in turn, are typically provided within vectors (e.g., plasmids or recombinant viral vectors). Such an expression cassette may be administered directly to a host subject. Alternatively, a vector comprising a polynucleotide of the invention may be administered to a host subject. Preferably the polynucleotide is prepared and/or administered using a genetic vector. A suitable vector may be any vector which is capable of carrying a sufficient amount of genetic information, and allowing expression of a polypeptide of the invention.

The present invention thus includes expression vectors that comprise such polynucleotide sequences. Such expression vectors are routinely constructed in the art of molecular biology and may for example involve the use of plasmid DNA and appropriate initiators, promoters, enhancers and other elements, such as for example polyadenylation signals which may be necessary, and which are positioned in the correct orientation, in order to allow for expression of a peptide of the invention. Other suitable vectors would be apparent to persons skilled in the art (see Green & Sambrook, supra).

The invention also includes cells that have been modified to express a polypeptide of the invention. Such cells include transient, or preferably stable higher eukaryotic cell lines, such as mammalian cells or insect cells, lower eukaryotic cells, such as yeast or prokaryotic cells such as bacterial cells. Particular examples of cells which may be modified by insertion of vectors or expression cassettes encoding for a polypeptide of the invention include mammalian HEK293T, CHO, HeLa, NSO and COS cells. Preferably the cell line selected will be one which is not only stable, but also allows for mature glycosylation and cell surface expression of a polypeptide.

Such cell lines of the invention may be cultured using routine methods to produce a polypeptide of the invention, or may be used therapeutically or prophylactically to deliver antibodies of the invention to a subject. Alternatively, polynucleotides, expression cassettes or vectors of the invention may be administered to a cell from a subject ex vivo and the cell then returned to the body of the subject.

In one embodiment, the nucleic acid molecule encodes an antibody heavy chain or variable region thereof.

In one embodiment, the nucleic acid molecule encodes an antibody light chain or variable region thereof.

By "nucleic acid molecule" we include DNA (e.g. genomic DNA or complementary DNA) and mRNA molecules, which may be single- or double-stranded. By "isolated" we mean that the nucleic acid molecule is not located or otherwise provided within a cell.

In one embodiment, the nucleic acid molecule is a cDNA molecule.

It will be appreciated by persons skilled in the art that the nucleic acid molecule may be codon-optimised for expression of the antibody polypeptide in a particular host cell, e.g. for expression in human cells (for example, see Angov, 2011, *Biotechnol. J.* 6(6):650-659, the disclosures of which are incorporated herein by reference).

Also included within the scope of the invention are the following:

(a) a third aspect of the invention provides a vector (such as an expression vector) comprising a nucleic acid molecule according to the second aspect of the invention;
(b) a fourth aspect of the invention provides a host cell (such as a mammalian cell, e.g. human cell, or Chinese hamster ovary cell, e.g. CHOK1SV cells) comprising a nucleic acid molecule according to the second aspect of the invention or a vector according to the third aspect of the invention; and
(c) a fifth aspect of the invention provides a method of making an antibody polypeptide according to the first aspect of the invention comprising culturing a population of host cells according to the fourth aspect of the invention under conditions in which said polypeptide is expressed, and isolating the polypeptide therefrom.

In a sixth aspect, the present invention provides compositions comprising molecules of the invention, such as the antibodies, bispecific polypeptides, polynucleotides, vectors and cells described herein. For example, the invention provides a composition comprising one or more molecules of the invention, such as one or more antibodies and/or bispecific polypeptides of the invention, and at least one pharmaceutically acceptable carrier.

It will be appreciated by persons skilled in the art that additional compounds may also be included in the pharmaceutical compositions, including, chelating agents such as EDTA, citrate, EGTA or glutathione.

The pharmaceutical compositions may be prepared in a manner known in the art that is sufficiently storage stable and suitable for administration to humans and animals. For example, the pharmaceutical compositions may be lyophilised, e.g. through freeze drying, spray drying, spray cooling, or through use of particle formation from supercritical particle formation.

By "pharmaceutically acceptable" we mean a non-toxic material that does not decrease the effectiveness of the CD137 and 5T4-binding activity of the antibody polypeptide of the invention. Such pharmaceutically acceptable buffers, carriers or excipients are well-known in the art (see Remington's Pharmaceutical Sciences, 18th edition, A. R Gennaro, Ed., Mack Publishing Company (1990) and handbook of Pharmaceutical Excipients, 3rd edition, A. Kibbe, Ed., Pharmaceutical Press (2000), the disclosures of which are incorporated herein by reference).

The term "buffer" is intended to mean an aqueous solution containing an acid-base mixture with the purpose of stabilising pH. Examples of buffers are Trizma, Bicine, Tricine, MOPS, MOPSO, MOBS, Tris, Hepes, HEPBS, MES, phosphate, carbonate, acetate, citrate, glycolate, lactate, borate, ACES, ADA, tartrate, AMP, AMPD, AMPSO, BES, CABS, cacodylate, CHES, DIPSO, EPPS, ethanolamine, glycine, HEPPSO, imidazole, imidazolelactic acid, PIPES, SSC, SSPE, POPSO, TAPS, TABS, TAPSO and TES.

The term "diluent" is intended to mean an aqueous or non-aqueous solution with the purpose of diluting the antibody polypeptide in the pharmaceutical preparation. The diluent may be one or more of saline, water, polyethylene glycol, propylene glycol, ethanol or oils (such as safflower oil, corn oil, peanut oil, cottonseed oil or sesame oil).

The term "adjuvant" is intended to mean any compound added to the formulation to increase the biological effect of the antibody polypeptide of the invention. The adjuvant may be one or more of zinc, copper or silver salts with different anions, for example, but not limited to fluoride, chloride, bromide, iodide, tiocyanate, sulfite, hydroxide, phosphate, carbonate, lactate, glycolate, citrate, borate, tartrate, and acetates of different acyl composition. The adjuvant may also be cationic polymers such as cationic cellulose ethers, cationic cellulose esters, deacetylated hyaluronic acid, chitosan, cationic dendrimers, cationic synthetic polymers such as poly(vinyl imidazole), and cationic polypeptides such as polyhistidine, polylysine, polyarginine, and peptides containing these amino acids.

The excipient may be one or more of carbohydrates, polymers, lipids and minerals. Examples of carbohydrates include lactose, glucose, sucrose, mannitol, and cyclodextrines, which are added to the composition, e.g. for facilitating lyophilisation. Examples of polymers are starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone, all of different molecular weight, which are added to the composition, e.g., for viscosity control, for achieving bioadhesion, or for protecting the lipid from chemical and proteolytic degradation. Examples of lipids are fatty acids, phospholipids, mono-, di-, and triglycerides, ceramides, sphingolipids and glycolipids, all of different acyl chain length and saturation, egg lecithin, soy lecithin, hydrogenated egg and soy lecithin, which are added to the composition for reasons similar to those for polymers. Examples of minerals are talc, magnesium oxide, zinc oxide and titanium oxide, which are added to the composition to obtain benefits such as reduction of liquid accumulation or advantageous pigment properties.

The antibody polypeptides of the invention may be formulated into any type of pharmaceutical composition known in the art to be suitable for the delivery thereof.

In one embodiment, the pharmaceutical compositions of the invention may be in the form of a liposome, in which the antibody polypeptide is combined, in addition to other pharmaceutically acceptable carriers, with amphipathic agents such as lipids, which exist in aggregated forms as micelles, insoluble monolayers and liquid crystals. Suitable lipids for liposomal formulation include, without limitation, monoglycerides, diglycerides, sulfatides, lysolecithin, phospholipids, saponin, bile acids, and the like. Suitable lipids also include the lipids above modified by poly(ethylene glycol) in the polar headgroup for prolonging bloodstream circulation time. Preparation of such liposomal formulations is can be found in for example U.S. Pat. No. 4,235,871, the disclosures of which are incorporated herein by reference.

The pharmaceutical compositions of the invention may also be in the form of biodegradable microspheres. Aliphatic polyesters, such as poly(lactic acid) (PLA), poly(glycolic acid) (PGA), copolymers of PLA and PGA (PLGA) or poly(caprolactone) (PCL), and polyanhydrides have been widely used as biodegradable polymers in the production of microspheres. Preparations of such microspheres can be found in U.S. Pat. No. 5,851,451 and in EP 0 213 303, the disclosures of which are incorporated herein by reference.

In a further embodiment, the pharmaceutical compositions of the invention are provided in the form of polymer gels, where polymers such as starch, cellulose ethers, cellulose carboxymethylcellulose, hydroxypropylmethyl cellulose, hydroxyethyl cellulose, ethylhydroxyethyl cellulose, alginates, carageenans, hyaluronic acid and derivatives thereof, polyacrylic acid, polyvinyl imidazole, polysulphonate, polyethylenglycol/polyethylene oxide, polyethyleneoxide/polypropylene oxide copolymers, polyvinylalcohol/polyvinylacetate of different degree of hydrolysis, and polyvinylpyrrolidone are used for thickening of the solution containing the agent. The polymers may also comprise gelatin or collagen.

Alternatively, the antibody polypeptide may simply be dissolved in saline, water, polyethylene glycol, propylene glycol, ethanol or oils (such as safflower oil, corn oil, peanut oil, cottonseed oil or sesame oil), tragacanth gum, and/or various buffers.

It will be appreciated that the pharmaceutical compositions of the invention may include ions and a defined pH for potentiation of action of the active antibody polypeptide. Additionally, the compositions may be subjected to conventional pharmaceutical operations such as sterilisation and/or may contain conventional adjuvants such as preservatives, stabilisers, wetting agents, emulsifiers, buffers, fillers, etc.

The pharmaceutical compositions according to the invention may be administered via any suitable route known to those skilled in the art. Thus, possible routes of administration include parenteral (intravenous, subcutaneous, and intramuscular), topical, ocular, nasal, pulmonar, buccal, oral, parenteral, vaginal and rectal. Also administration from implants is possible.

In one preferred embodiment, the pharmaceutical compositions are administered parenterally, for example, intravenously, intracerebroventricularly, intraarticularly, intraarterially, intraperitoneally, intrathecally, intraventricularly, intrasternally, intracranially, intramuscularly or subcutaneously, or they may be administered by infusion techniques. They are conveniently used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Thus, the pharmaceutical compositions of the invention are particularly suitable for parenteral, e.g. intravenous, administration.

Alternatively, the pharmaceutical compositions may be administered intranasally or by inhalation (for example, in the form of an aerosol spray presentation from a pressurised container, pump, spray or nebuliser with the use of a suitable propellant, such as dichlorodifluoromethane, trichlorofluoro-methane, dichlorotetrafluoro-ethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas). In the case of a pressurised aerosol, the dosage unit may be determined by providing a valve to deliver a metered amount. The pressurised container, pump, spray or nebuliser may contain a solution or suspension of the active polypeptide, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

The pharmaceutical compositions will be administered to a patient in a pharmaceutically effective dose. A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art. The administration of the pharmaceutically effective dose can be carried out both by single administration in the form of an individual dose unit or else several smaller dose units and also by multiple administrations of subdivided doses at specific intervals. Alternatively, the does may be provided as a continuous infusion over a prolonged period.

Particularly preferred compositions are formulated for systemic administration.

The composition may preferably be formulated for sustained release over a period of time. Thus the composition may be provided in or as part of a matrix facilitating sustained release. Preferred sustained release matrices may comprise a montanide or γ-polyglutamic acid (PGA) nanoparticles.

The antibody polypeptides can be formulated at various concentrations, depending on the efficacy/toxicity of the polypeptide being used. For example, the formulation may comprise the active antibody polypeptide at a concentration of between 0.1 μM and 1 mM, more preferably between 1 μM and 500 μM, between 500 μM and 1 mM, between 300 μM and 700 μM, between 1 μM and 100 μM, between 100 μM and 200 μM, between 200 μM and 300 μM, between 300 μM and 400 μM, between 400 μM and 500 μM, between 500 μM and 600 μM, between 600 μM and 700 μM, between 800 μM and 900 μM or between 900 μM and 1 mM. Typically, the formulation comprises the active antibody polypeptide at a concentration of between 300 μM and 700 μM.

Typically, the therapeutic dose of the antibody polypeptide (with or without a therapeutic moiety) in a human patient will be in the range of 100 μg to 700 mg per administration (based on a body weight of 70 kg). For example, the maximum therapeutic dose may be in the range of 0.1 to 10 mg/kg per administration, e.g. between 0.1 and 5 mg/kg or between 1 and 5 mg/kg or between 0.1 and 2 mg/kg. It will be appreciated that such a dose may be administered at different intervals, as determined by the oncologist/physician; for example, a dose may be administered daily, twice-weekly, weekly, bi-weekly or monthly.

It will be appreciated by persons skilled in the art that the pharmaceutical compositions of the invention may be administered alone or in combination with other therapeutic agents used in the treatment of cancers, such as antimetabolites, alkylating agents, anthracyclines and other cytotoxic antibiotics, vinca alkyloids, etoposide, platinum compounds, taxanes, topoisomerase I inhibitors, other cytostatic drugs, antiproliferative immunosuppressants, corticosteroids, sex hormones and hormone antagonists, and other therapeutic antibodies (such as antibodies against a tumour-associated antigen or an immune checkpoint modulator).

For example, the pharmaceutical compositions of the invention may be administered in combination with an immunotherapeutic agent that binds a target selected from the group consisting of PD-1/PD-1L, CTLA-4, OX40, CD40, GITR, LAG3, TIM3, CD27 and KIR. Thus, the invention encompasses combination therapies comprising a bispecific polypeptide of the invention together with a further immunotherapeutic agent, effective in the treatment of cancer, which specifically binds to an immune checkpoint molecule. It will be appreciated that the therapeutic benefit of the further immunotherapeutic agent may be mediated by attenuating the function of an inhibitory immune checkpoint molecule and/or by activating the function of a stimulatory immune checkpoint or co-stimulatory molecule.

In one embodiment, the further immunotherapeutic agent is selected from the group consisting of:

(a) an immunotherapeutic agent that inhibits the function of PD-1 and/or PD-1L;

(b) an immunotherapeutic agent that inhibits the function of CTLA-4;

(c) an immunotherapeutic agent that activates the function of OX40; and (d) an immunotherapeutic agent that binds activates the function of CD40.

Thus, the further immunotherapeutic agent may be a PD1 inhibitor, such as an anti-PD1 antibody, or antigen-binding fragment thereof capable of inhibiting PD1 function (for example, Nivolumab, Pembrolizumab, Lambrolizumab, PDR-001, MEDI-0680 and AMP-224). Alternatively, the PD1 inhibitor may comprise or consist of an anti-PD-L1 antibody, or antigen-binding fragment thereof capable of inhibiting PD1 function (for example, Durvalumab, Atezolizumab, Avelumab and MDX-1105).

In another embodiment, the further immunotherapeutic agent is a CTLA-4 inhibitor, such as an anti-CTLA-4 antibody or antigen-binding portion thereof.

In a further embodiment, the further immunotherapeutic agent activates OX40, such as an agonistic anti-OX40 antibody or antigen-binding portion thereof.

In a further embodiment, the further immunotherapeutic agent activates CD40, such as an agonistic anti-CD40 antibody or antigen-binding portion thereof.

It will be appreciated by persons skilled in the art that the presence of the two active agents (as detailed above) may provide a synergistic benefit in the treatment of a tumour in a subject. By “synergistic” we include that the therapeutic effect of the two agents in combination (e.g. as determined by reference to the rate of growth or the size of the tumour) is greater than the additive therapeutic effect of the two agents administered on their own. Such synergism can be identified by testing the active agents, alone and in combination, in a relevant cell line model of the solid tumour.

Also within the scope of the present invention are kits comprising polypeptides or other compositions of the invention and instructions for use. The kit may further contain one or more additional reagents, such as an additional therapeutic or prophylactic agent as discussed above.

Medical Uses and Methods

The polypeptides in accordance with the present invention may be used in therapy or prophylaxis. In therapeutic applications, polypeptides or compositions are administered to a subject already suffering from a disorder or condition, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as “therapeutically effective amount”. In prophylactic applications, polypeptides or compositions are administered to a subject not yet exhibiting symptoms of a disorder or condition, in an amount sufficient to prevent or delay the development of symptoms. Such an amount is defined as a “prophylactically effective amount”. The subject may have been identified as being at risk of developing the disease or condition by any suitable means.

Thus, a seventh aspect of the invention provides a bispecific polypeptide according to the first aspect of the invention for use in medicine.

An eighth aspect of the invention provides a bispecific polypeptide according to the first aspect of the invention for use in treating a neoplastic disorder in a subject.

By 'treatment' we include both therapeutic and prophylactic treatment of the patient. The term 'prophylactic' is used to encompass the use of an agent, or formulation thereof, as described herein which either prevents or reduces the likelihood of a neoplastic disorder, or the spread, dissemination, or metastasis of cancer cells in a patient or subject. The term 'prophylactic' also encompasses the use of an agent, or formulation thereof, as described herein to prevent recurrence of a neoplastic disorder in a patient who has previously been treated for the neoplastic disorder.

In one embodiment, the neoplastic disorder is associated with the formation of solid tumours within the subject's body.

Thus, the solid tumour may be selected from the group consisting of prostate cancer, breast cancer, lung cancer, colorectal cancer, melanomas, bladder cancer, brain/CNS cancer, cervical cancer, oesophageal cancer, gastric cancer, head/neck cancer, kidney cancer, liver cancer, lymphomas, ovarian cancer, pancreatic cancer and sarcomas.

For example, the solid tumour may be selected from the groups consisting of renal cell carcinoma, colorectal cancer, lung cancer, prostate cancer and breast cancer.

A ninth aspect of the invention provides a use of a bispecific polypeptide according to the first aspect of the invention in the preparation of a medicament for treating or preventing a neoplastic disorder in a subject.

In one embodiment, the neoplastic disorder is associated with the formation of solid tumours within the subject's body (for example, as detailed above).

A tenth aspect of the invention provides a method for the treatment or diagnosis of a neoplastic disorder in a subject, comprising the step of administering to the subject an effective amount of a bispecific polypeptide according to the first aspect of the invention.

In one embodiment, the neoplastic disorder is associated with the formation of solid tumours within the subject's body (for example, as detailed above).

In one embodiment, the subject is human.

In one embodiment, the method comprises administering the bispecific antibody systemically.

In one embodiment, the methods further comprises administering to the subject one or more additional therapeutic agents.

The listing or discussion of an apparently prior-published document in this specification should not necessarily be taken as an acknowledgement that the document is part of the state of the art or is common general knowledge.

The use of the word "a" or "an" when used in conjunction with the term "comprising" in the claims and/or the specification may mean "one," but it is also consistent with the meaning of "one or more," "at least one," and "one or more than one."

These, and other, embodiments of the invention will be better appreciated and understood when considered in conjunction with the above description and the accompanying drawings. It should be understood, however, that the above description, while indicating various embodiments of the invention and numerous specific details thereof, is given by way of illustration and not of limitation. Many substitutions, modifications, additions and/or rearrangements may be made within the scope of the invention without departing from the spirit thereof, and the invention includes all such substitutions, modifications, additions and/or rearrangements.

The following drawings form part of the present specification and are included to further demonstrate certain aspects of the present invention. The invention may be better understood by reference to one or more of these drawings in combination with the detailed description of specific embodiments presented herein.

BRIEF DESCRIPTION OF THE FIGURES

FIG. 5A: Each of the indicated domains E1-E7 were replaced by mouse 5T4 sequence in human/mouse chimeras. FIG. 5B: aa 173-420 were replaced by mouse 5T4 sequence

Figure 13:
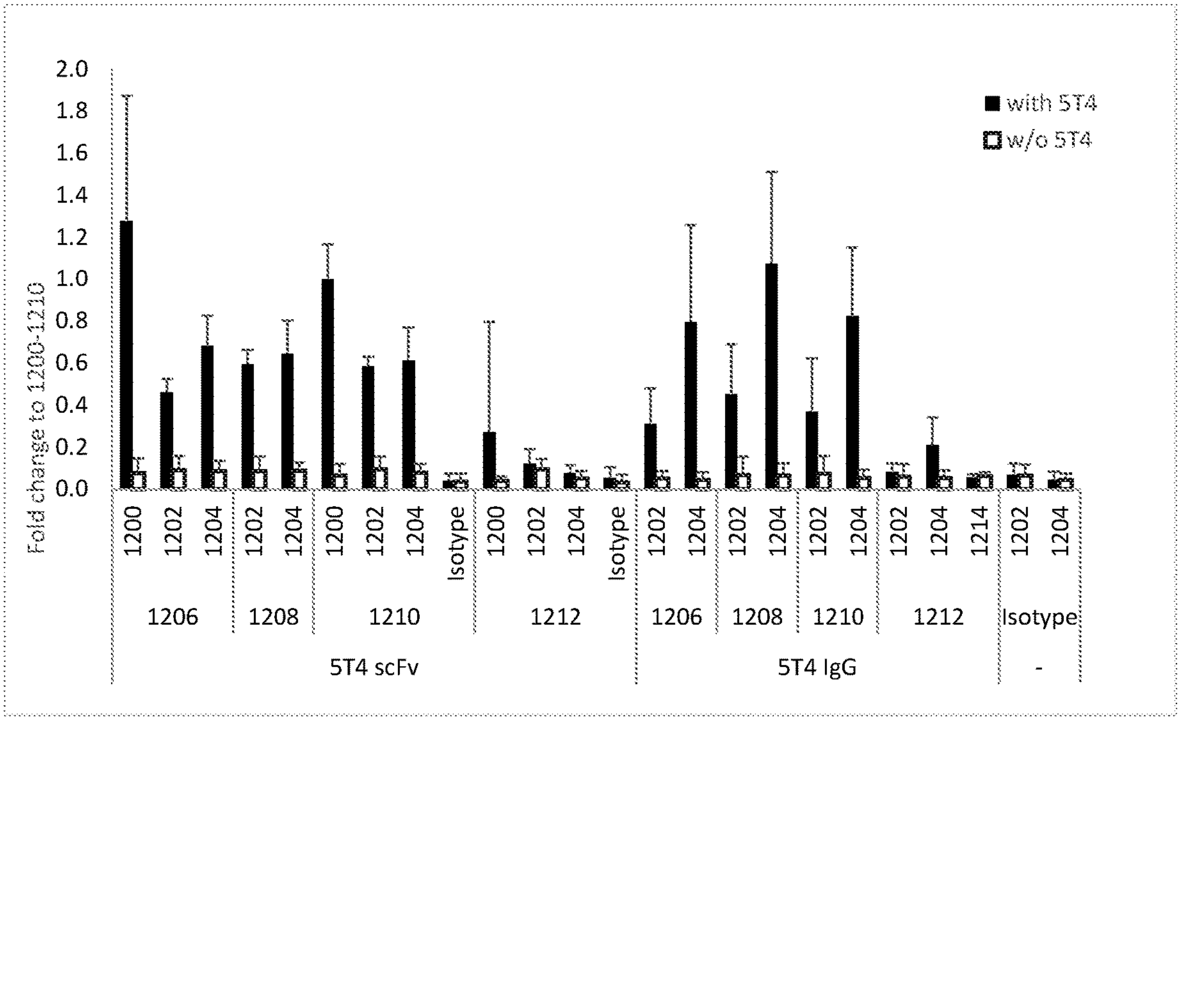

FIG. 13 shows 5T4-dependent T cell activation by exemplary bispecific antibodies (bsAb) of the invention. Each bsAb (1 μg/ml) was run in CD8 T cell assays based on 2-4 individual donors. The data is presented as mean fold change to reference (1200-1210) and error bars represent SD. The left part of the graph shows bispecific antibodies where the 5T4 scFv has been fused to CD137 IgG, i.e. 1200-1206 etc, whereas the right part of the graph shows bispecific antibodies where the CD137 scFv has been fused to 5T4 IgG, i.e. 1206-1200 etc.

Figure 14:
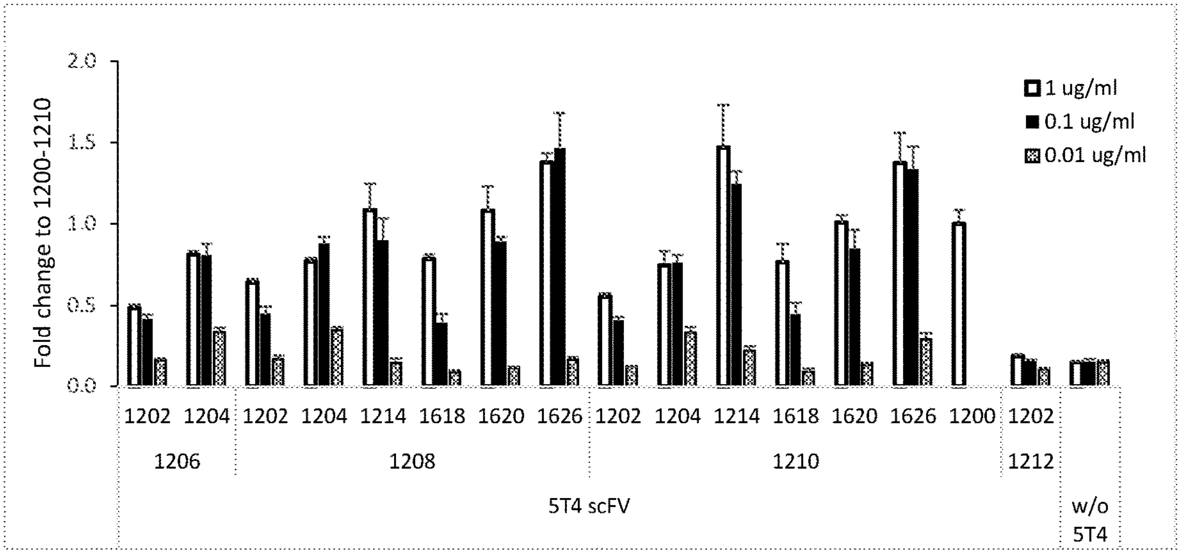
Figure 14:
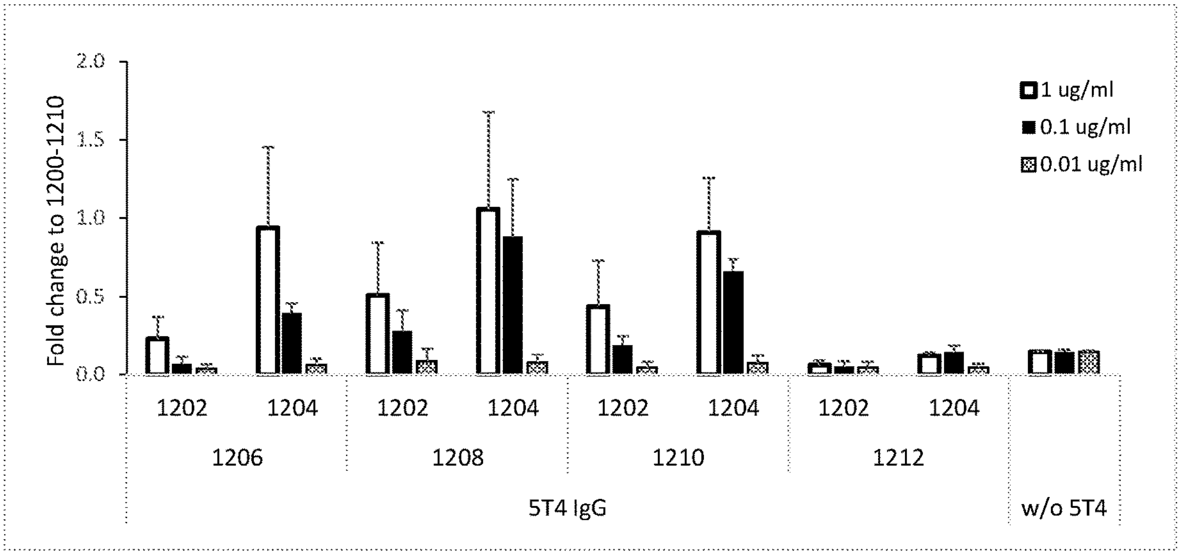

FIG. 14 shows the dose-response of 5T4-CD137 bsAbs showing 5T4 dependent T cell activation. Data is analysed as fold change to reference (1200-1210 at 1 μg/ml). Upper panel: CD137 agonist as IgG and 5T4 binder as scFv fused to C-terminus of IgG. Lower panel: 5T4 binder as IgG and CD137 agonist as scFv fused to C-terminus of IgG. Clone designation follows the same principle as described for FIG. 10.

Figure 15:
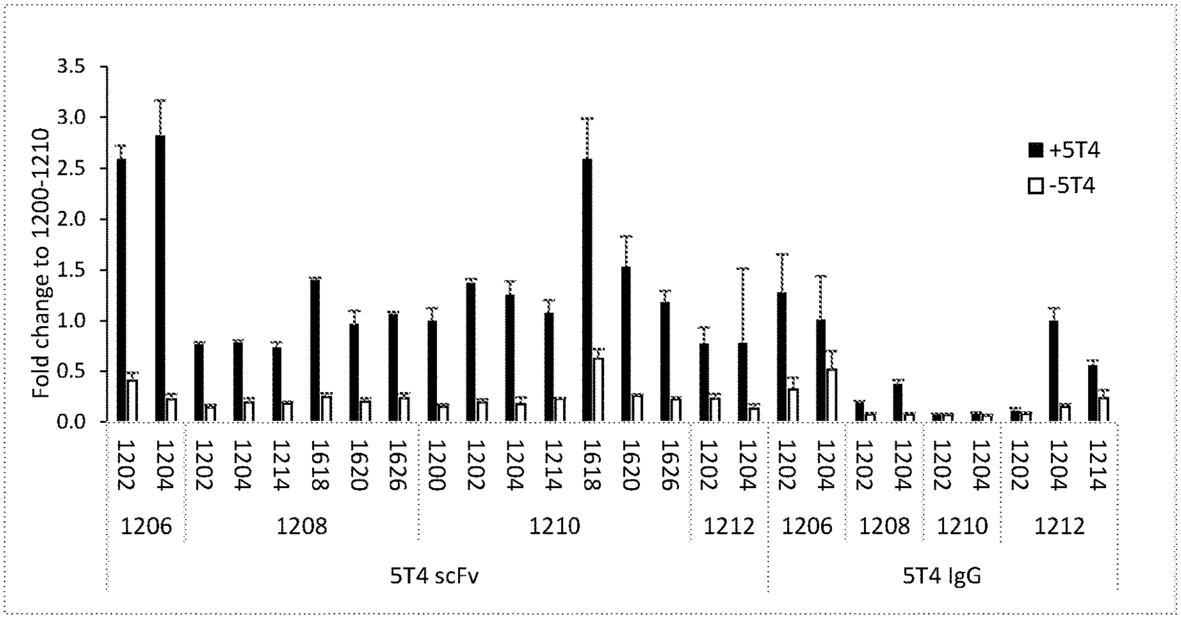

FIG. 15 shows the functional activity of exemplary 5T4-CD137 bispecific antibodies on human CD8+ T cells cultured with 5T4-expressing tumor cells. All generated bsAbs were evaluated at 1 μg/ml in the fully cell-based T cell assay to verify the results obtained in the assay performed with coated 5T4-Fc. Results are presented as fold change to reference (1200-1210) and the error bars are the SD. Clone designation follows the same principle as described for FIG. 10.

Figure 16A:
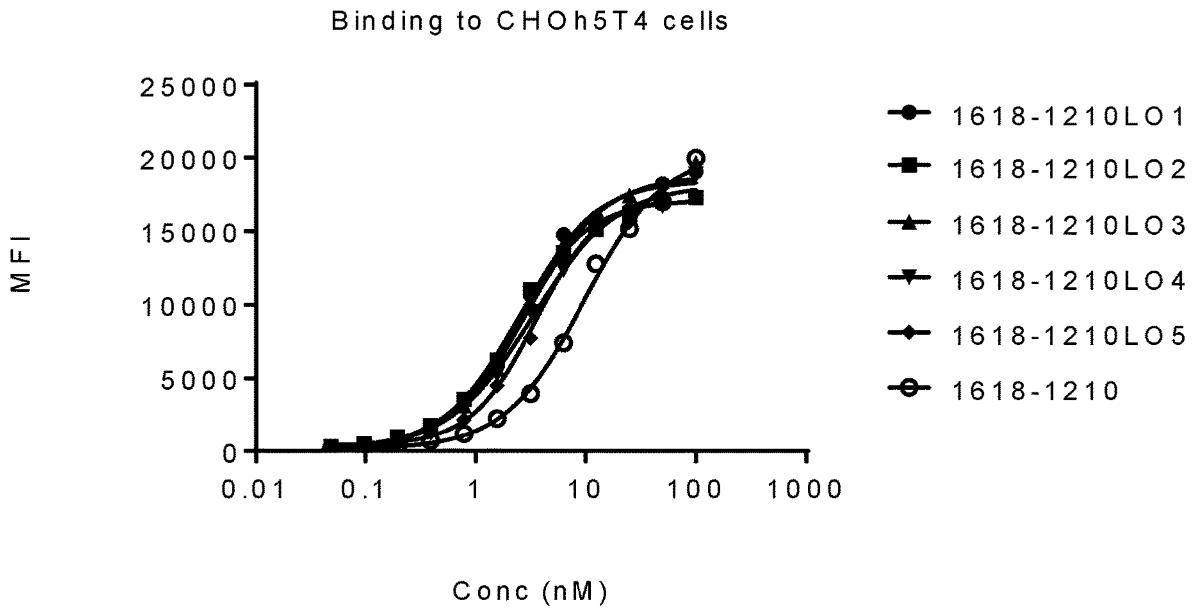
Figure 16B:
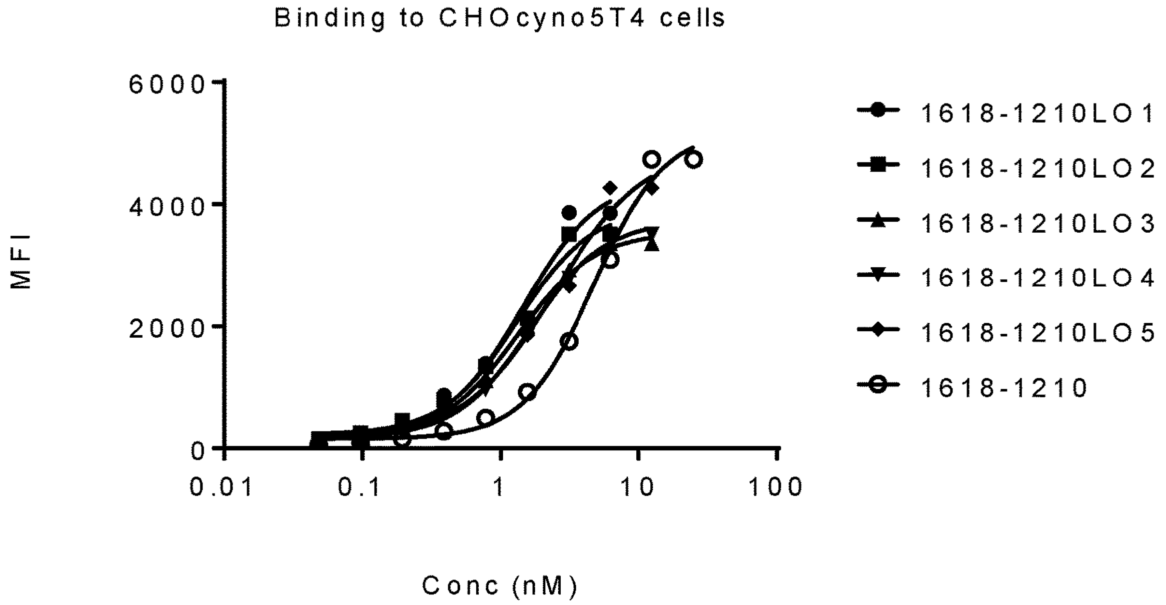

FIGS. 16A and 16B show binding curves for 5T4 lead optimised clones to (FIG. 16A) CHOh5T4 and (FIG. 16B) CHOcyno5T4 cells.

Figure 17A:
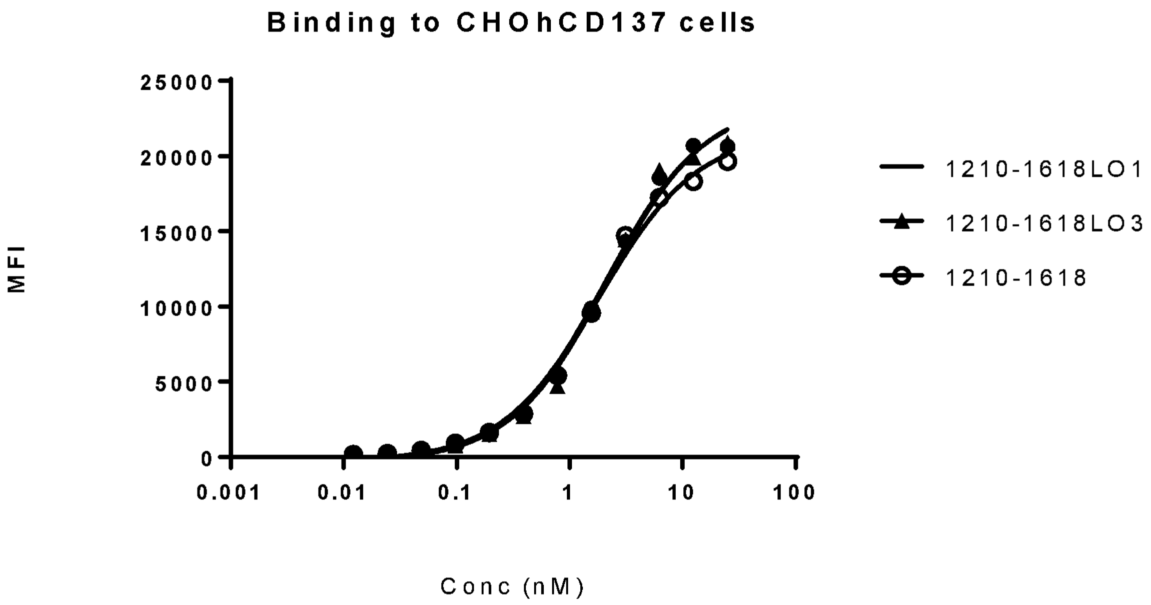
Figure 17B:
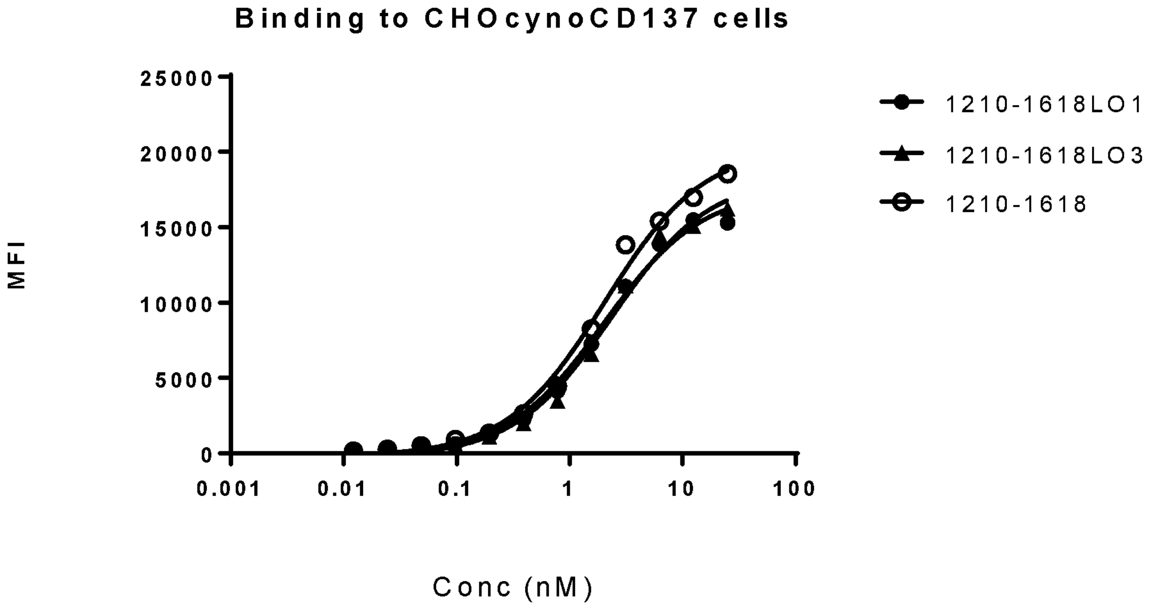

FIGS. 17A and 17B show binding curves for CD137 lead optimised clones to (FIG. 17A) CHOhCD137 and (FIG. 17B) CHOcynoCD137 cells.

Figure 18:
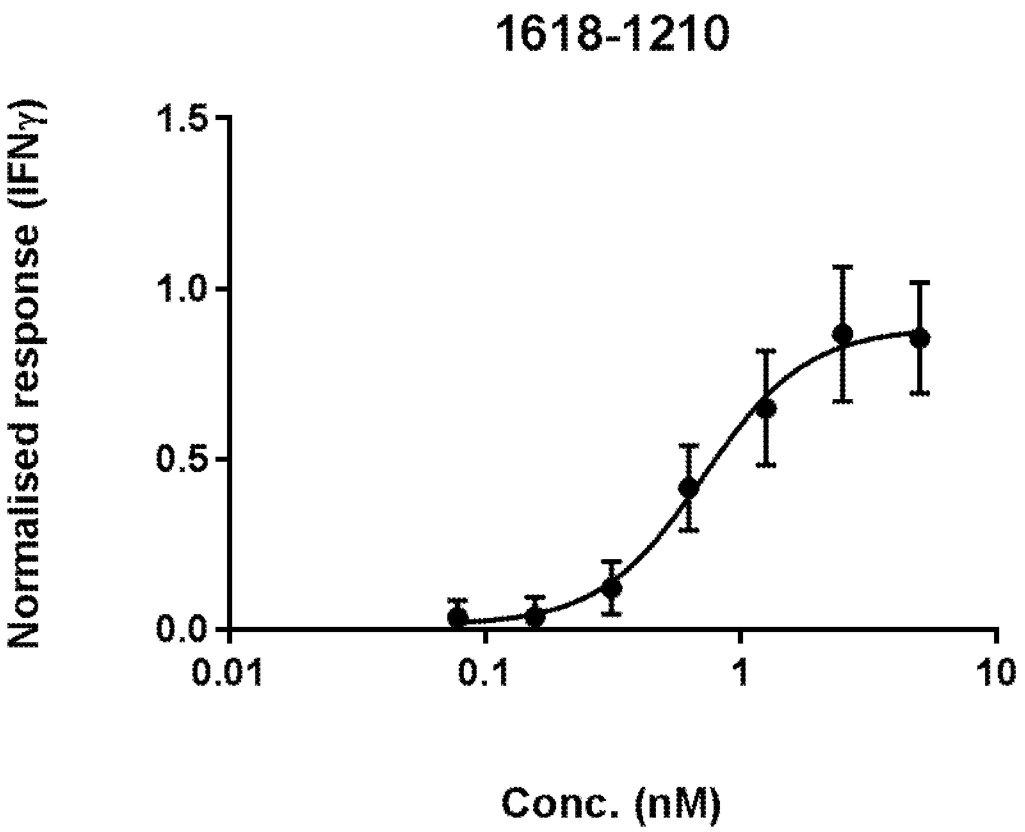

FIG. 18 shows the normalised interferon gamma (IFNγ) response in human CD8+ T cells cultured in 5T4-Fc coated plates, represented as a three-parameter sigmoidal dose-response model to enable determination of EC50.

Figure 19:
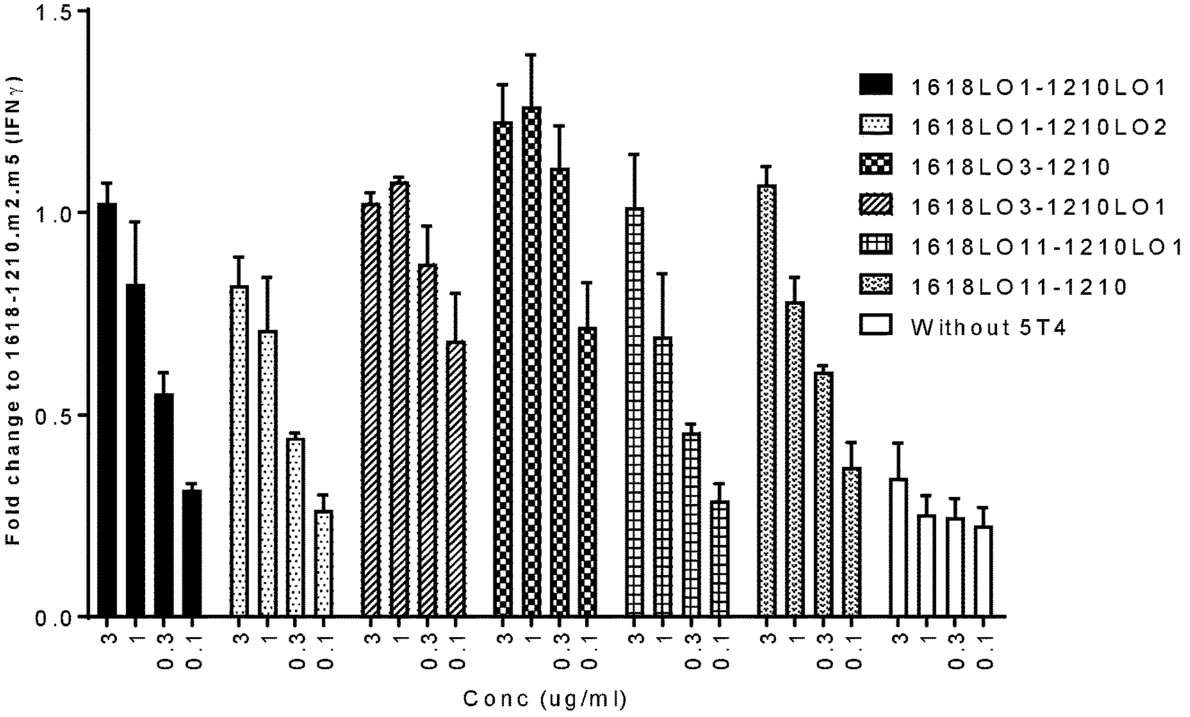

FIG. 19 shows results for lead optimised bsAb in a CD8+ T cell assay with crosslinked 5T4-Fc, with normalised IFNγ levels to enable correlation of results between assay plates.

Figure 20:
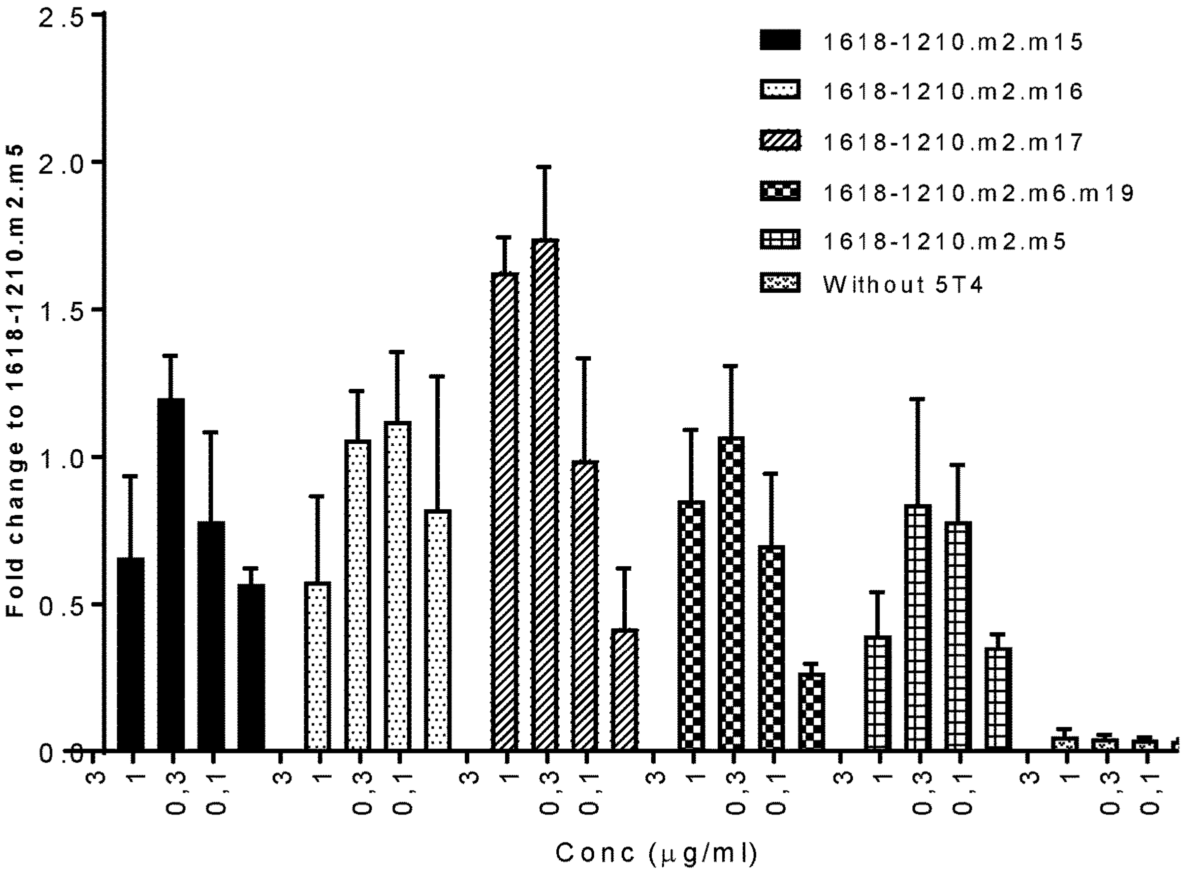

FIG. 20 shows results for bsAbs generated with different linkers in a CD8+ T cell assay with crosslinked 5T4-Fc, with normalised IFNγ levels to enable correlation of results between assay plates.

Figure 21:
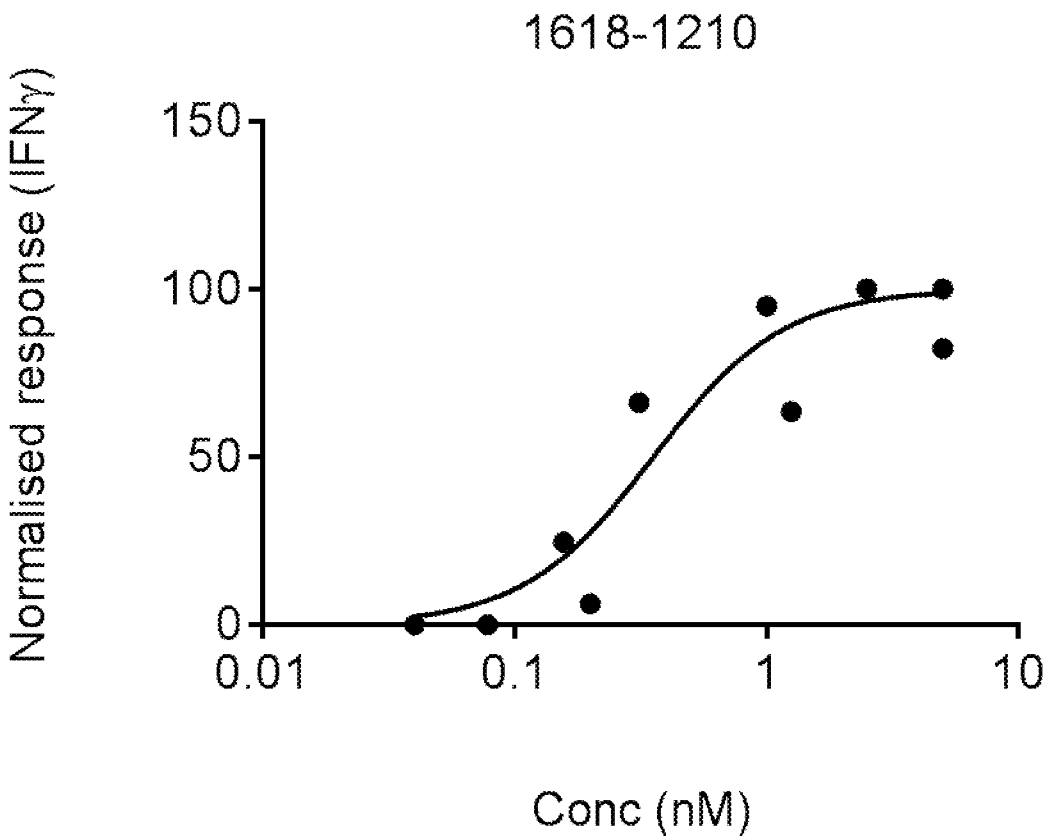

FIG. 21 shows the normalised interferon gamma (IFNγ) response using lead optimised bsAb in human $CD8^+$ T cells cultured with 5T4-expressing and 5T4-non-expressing tumour cells, represented as a three-parameter sigmoidal dose-response model to enable determination of EC50

Figure 22:
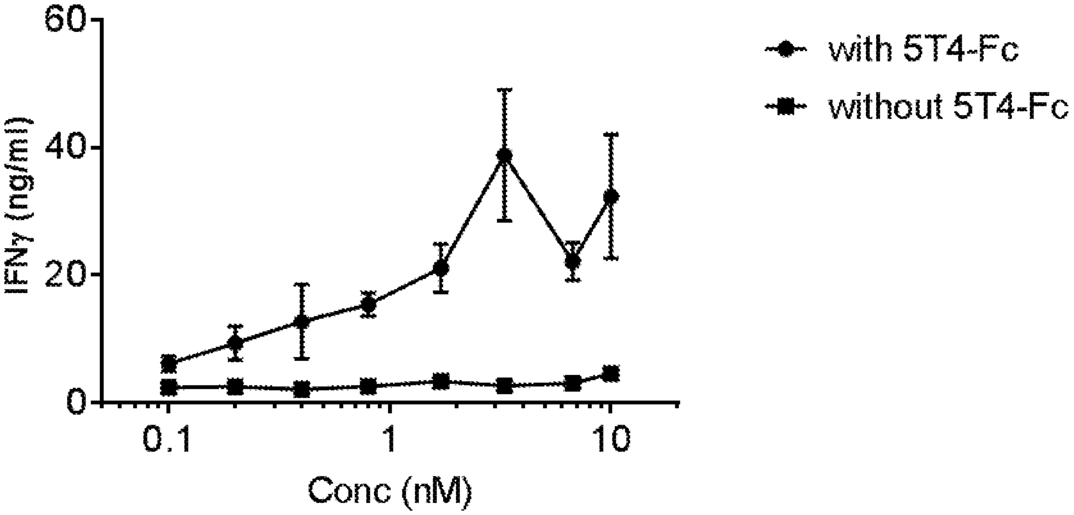

FIG. 22 shows the interferon gamma (IFNγ) response from CD137-mediated activation of PBMCs with and without the presence of 5T4-Fc.

Figure 23:
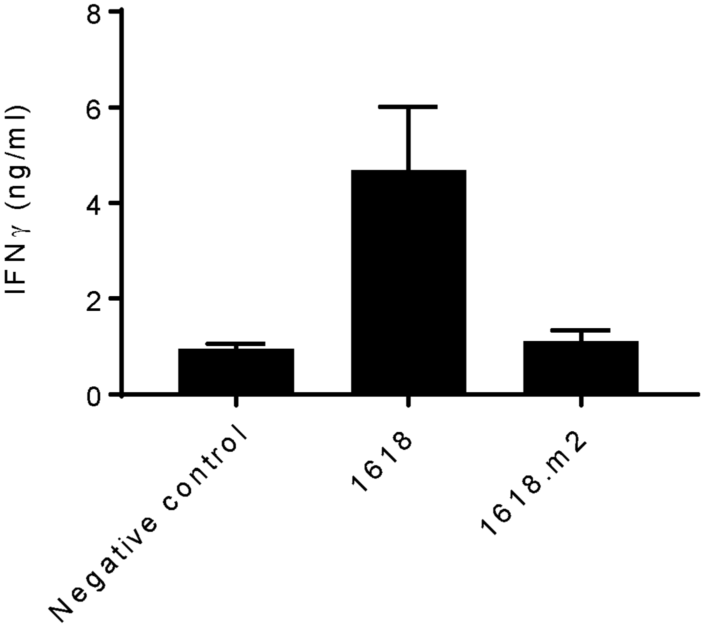

FIG. 23 shows the interferon gamma (IFNγ) response from co-culture of CD8+ T cells and CD32-expressing L cells.

Figure 24:
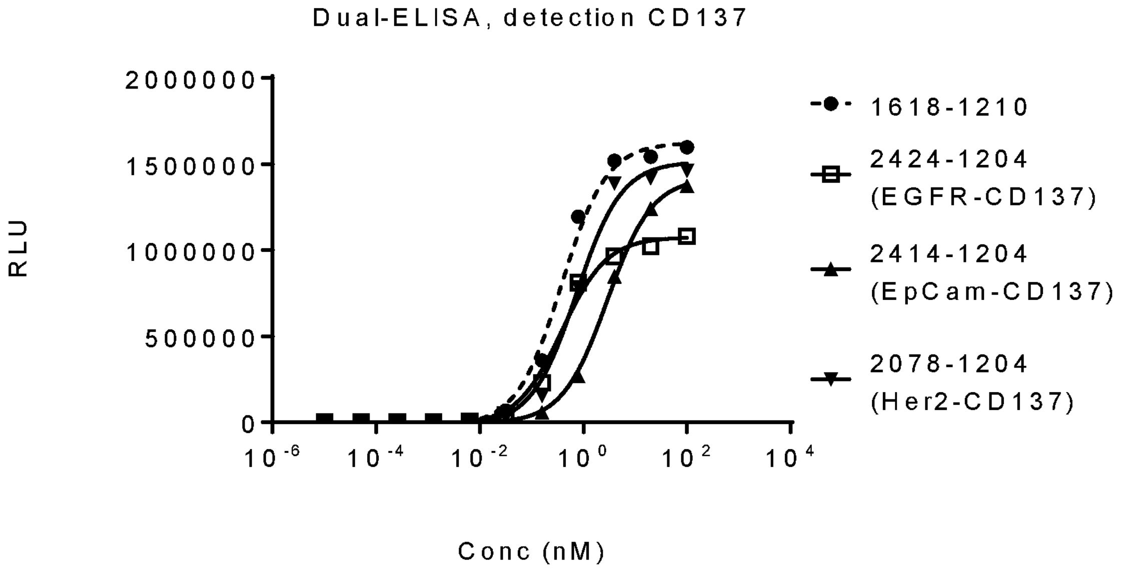

FIG. 24 shows results from a dual ELISA detecting CD137, for TAA-CD137 bispecific antibodies.

Figure 25A:
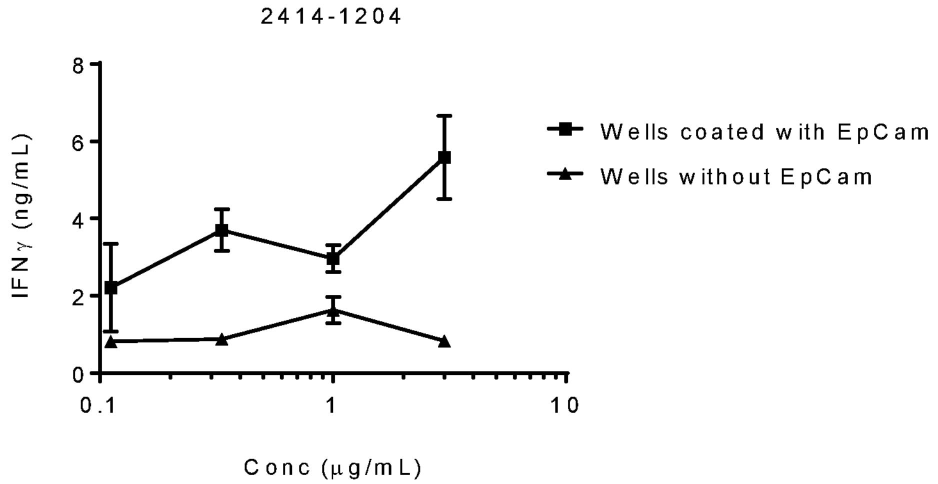
Figure 25B:
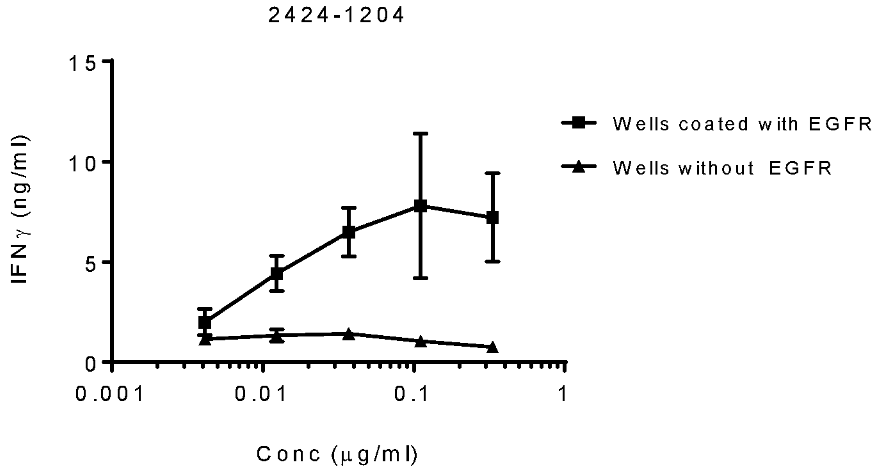
Figure 25C:
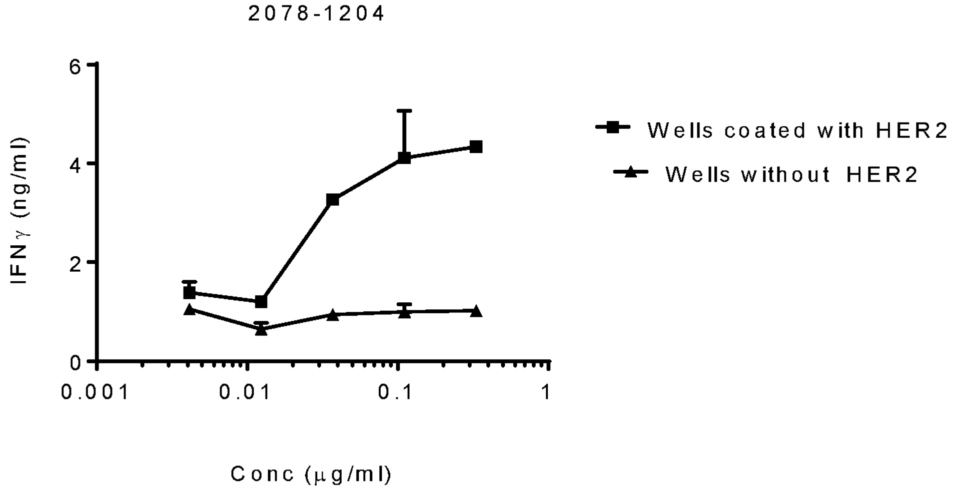

FIGS. 25A, 25B, and 25C show the interferon gamma (IFNγ) response using TAA-CD137 bispecific antibodies in CD8+ T cells cultured on CD3/TAA-coated plates where the TAA is (FIG. 25A) EpCAM, (FIG. 25B) EGFR and (FIG. 25C) Her2.

Figure 26:
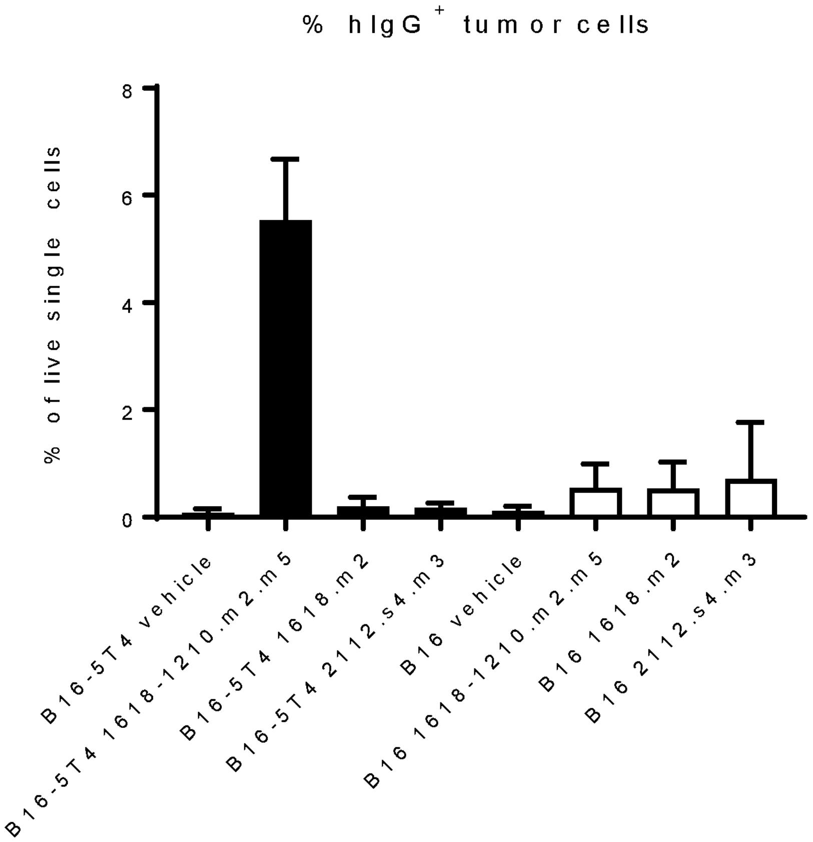

FIG. 26 shows 5T4-dependent localization of bispecific antibody to the antigen-expressing tumors. B16 and B16-5T4 tumors were collected from SCID-Beige mice treated with vehicle, 1618-1210 (bsAb), 1618 (anti-CD137 Mab) or 2112 (reference anti-CD137 Mab). Localization of antibody to the tumors was detected with anti-human IgG and analyzed by flow cytometry. The graph shows the frequency of human IgG+ cells among live cells (n=5).

Figure 27A:
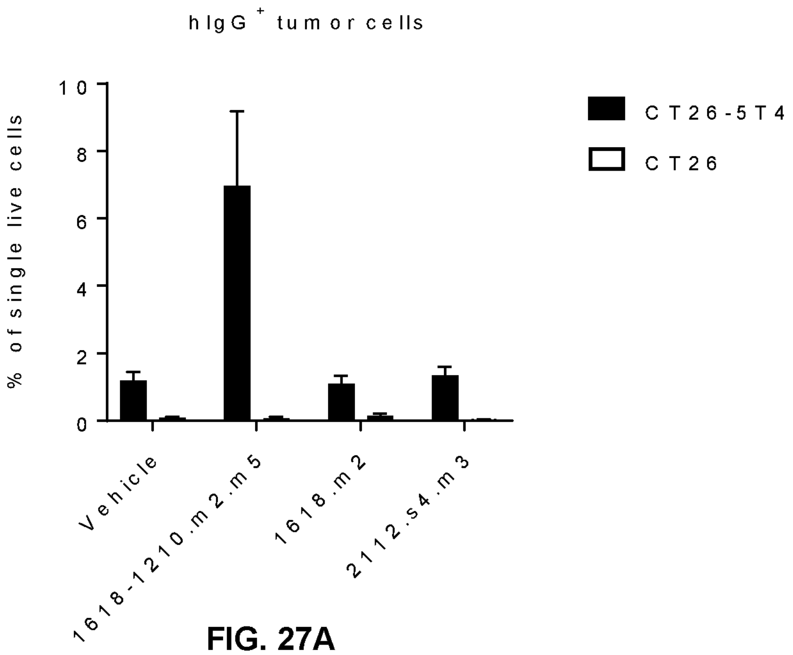
Figure 27B:
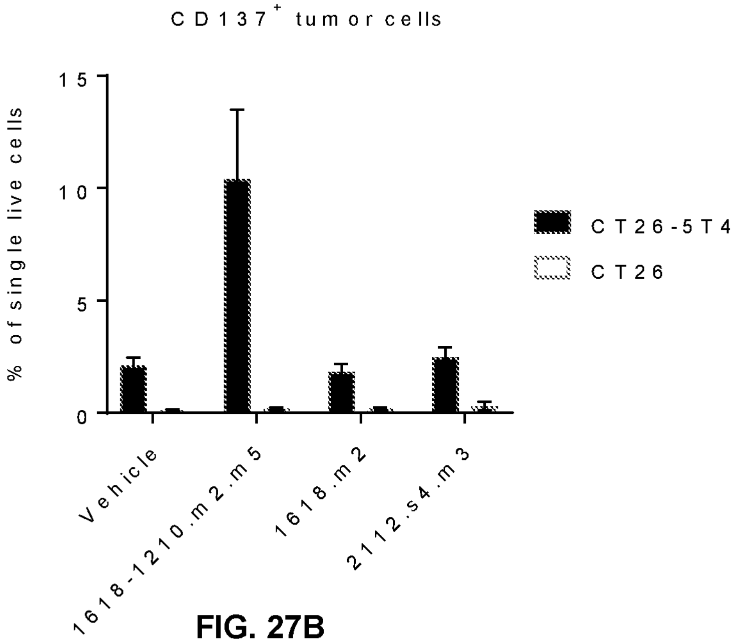

FIGS. 27A and 27B show 5T4-dependent localization of bispecific antibody to the antigen-expressing tumors. CT26 and CT26-5T4 tumors were collected from SCID-Beige mice treated with vehicle, 1618-1210, 1618 or 2112. Localization of antibody to the tumors was detected (FIG. 27A) with anti-human IgG or (FIG. 27B) by binding of biotinylated CD137, and analyzed by flow cytometry. The graphs show the frequency of positive cells among single, live tumor cells (n=5).

Figure 28:
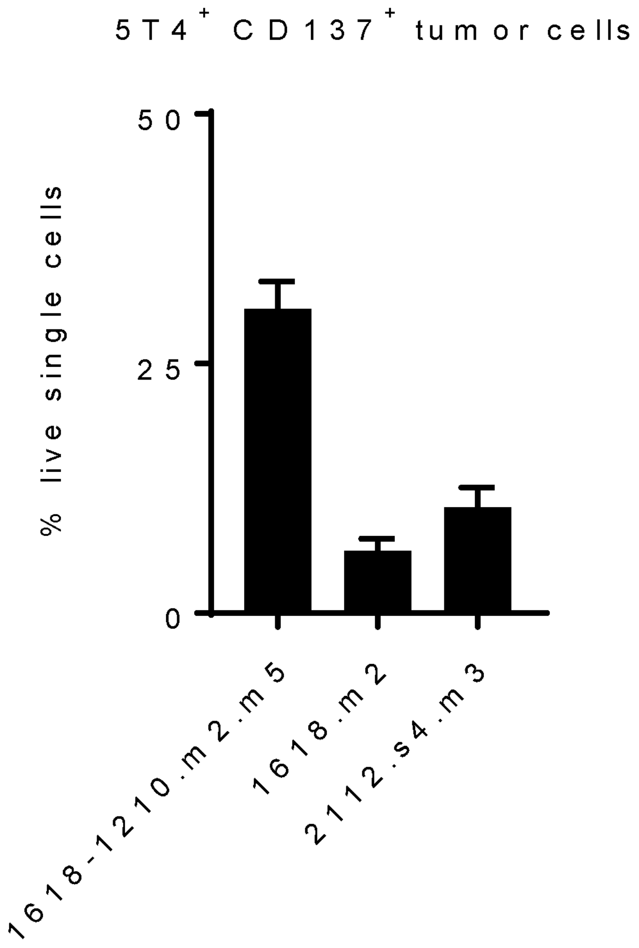

FIG. 28 shows the percentage of tumor cells that are positive for binding of biotinylated CD137 and the tumor antigen 5T4. SKOV-3 tumors were collected from SCID-Beige mice treated with vehicle, 1618-1210, 1618 or 2112. Localization of antibody to the 5T4 positive tumour cells was detected with anti-human IgG and anti-human 5T4-antibody. The graph show the frequency of double positive cells among single, live tumor cells (mCD45-CD45RA– (n=5/treatment).

TABLES (SEQUENCES)

TABLE A

VL and VH amino acid (aa) and nucleotide (nt) sequences

| SEQ ID NO. | CHAIN NO. | TYPE | SEQUENCE |
|---|---|---|---|
| 1 | 1206, heavy chain, VH | aa | EVQLLESGGGLVQPGGSLRL<br>SCAASGFTFSGSSMSWVRQA<br>PGKGLEWVSSIYYSGSGTYY<br>ADSVKGRFTISRDNSKNTLY<br>LQMNSLRAEDTAVYYCARYG<br>RNVHPYNLDYWGQGTLVTVS<br>S |
| 2 | 1206, heavy chain, VH | nt | GAGGTGCAGCTGTTGGAGAG<br>CGGGGGAGGCTTGGTACAGC<br>CTGGGGGGTCCCTGCGCCTC<br>TCCTGTGCAGCCAGCGGATT<br>CACCTTTTCTGGTTCTTCTA<br>TGTCTTGGGTCCGCCAGGCT<br>CCAGGGAAGGGGCTGGAGTG<br>GGTCTCATCTATTTACTACT<br>CTGGTTCTGGTACATACTAT<br>GCAGACTCCGTGAAGGGCCG<br>GTTCACCATCTCCCGTGACA<br>ATTCCAAGAACACGCTGTAT<br>CTGCAAATGAACAGCCTGCG<br>TGCCGAGGACACGGCTGTAT<br>ATTATTGTGCGCGCTACGGT<br>CGTAACGTTCATCCGTACAA<br>CTTGGACTATTGGGGCCAGG<br>GAACCCTGGTCACCGTCTCC<br>TCA |
| 3 | 1207, light chain VL | aa | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQGYYYLPTFGQ<br>GTKLEIK |
| 4 | 1207, light chain VL | nt | GACATCCAGATGACCCAGTC<br>TCCATCCTCCCTGAGCGCAT<br>CTGTAGGAGACCGCGTCACC |

TABLE A-continued

| VL and VH amino acid (aa) and nucleotide (nt) sequences | | | |
|---|---|---|---|
| SEQ ID NO. | CHAIN NO. | TYPE | SEQUENCE |
| | | | ATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCACGTTTCAGTGGCAGTGGAAGCGGGACAGATTTCACTCTCACCATCAGCAGTCTGCAACCTGAAGATTTTGCAACTTATTACTGTCAACAGGGTTACTACTACCTGCCCACTTTTGGCCAGGGGACCAAGCTGGAGATCAAA |
| 5 | 1208, heavy chain VH | aa | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARSPYYYGANWIDYWGQGTLVTVSS |
| 6 | 1208, heavy chain VH | nt | GAGGTGCAGCTGTTGGAGAGCGGGGGAGGCTTGGTACAGCCTGGGGGGTCCCTGCGCCTCTCCTGTGCAGCCAGCGGATTCACCTTTAGCAGCTATGCCATGAGCTGGGTCCGCCAGGCTCCAGGGAAGGGGCTGGAGTGGGTCTCAGCTATTAGTGGTAGTGGTGGTAGCACATACTATGCAGACTCCGTGAAGGGCCGGTTCACCATCTCCCGTGACAATTCCAAGAACACGCTGTATCTGCAAATGAACAGCCTGCGTGCCGAGGACACGGCTGTATATTATTGTGCGCGCTCTCCGTACTACTACGGTGCTAACTGGATTGACTATTGGGGCCAGGGAACCCTGGTCACCGTCTCCTCA |
| 7 | 1135, light chain VL | aa | DIQMTQSPSSLSASVGDRVTITCRASQSISSYLNWYQQKPGKAPKLLIYAASSLQSGVPSRFSGSGSGTDFTLTISSLQPEDFATYYCQQSYSTPYTFGQGTKLEIK |
| 8 | 1135, light chain VL | nt | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCACGTTTCAGTGGCAGTGGAAGCGGGACAGATTTCACTCTCACCATCAGCAGTCTGCAACCTGAAGATTTTGCAACTTATTACTGTCAACAGAGTTACAGTACCCCTTATACTTTTGGCCAGGGGACCAAGCTGGAGATCAAA |
| 9 | 1210, heavy chain VH | aa | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARYYGGYYSAWMDYWGQGTLVTVSS |
| 10 | 1210, heavy chain VH | nt | GAGGTGCAGCTGTTGGAGAGCGGGGGAGGCTTGGTACAGCCTGGGGGGTCCCTGCGCCTCTCCTGTGCAGCCAGCGGATTCACCTTTAGCAGCTATGCCATGAGCTGGGTCCGCCAGGCTCCAGGGAAGGGGCTGGAGTGGGTCTCAGCTATTAGTGGTAGTGGTGGTAGCACATACTATGCAGACTCCGTGAAGGGCCGGTTCACCATCTCCCGTGACAATTCCAAGAACACGCTGTATCTGCAAATGAACAGCCTGCGTGCCGAGGACACGGCTGTATATTATTGTGCGCGCTACTACGGTGGTTACTACTCTGCTTGGATGGACTATTGGGGCCAGGGAACCCTGGTCACCGTCTCCTCA |
| 11 | 1211, light chain VL | aa | DIQMTQSPSSLSASVGDRVTITCRASQSISSYLNWYQQKPGKAPKLLIYAASSLQSGVPSRFSGSGSGTDFTLTISSLQPEDFATYYCQQTYGYLHTFGQGTKLEIK |
| 12 | 1211, light chain VL | nt | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCACGTTTCAGTGGCAGTGGAAGCGGGACAGATTTCACTCTCACCATCAGCAGTCTGCAACCTGAAGATTTTGCAACTTATTACTGTCAACAGACTTACGGTTACCTGCACACTTTTGGCCAGGGGACCAAGCTGGAGATCAAA |
| 13 | 1212, heavy chain VH | aa | EVQLLESGGGLVQPGGSLRLSCAASGFTFSSYAMSWVRQAPGKGLEWVSYISSYGGYTSYADSVKGRFTISRDNSKNTLYLQMNSLRAEDTAVYYCARYHSGVLDYWGQGTLVTVSS |
| 14 | 1212, heavy chain VH | nt | GAGGTGCAGCTGTTGGAGAGCGGGGGAGGCTTGGTACAGCCTGGGGGGTCCCTGCGCCTCTCCTGTGCAGCCAGCGGATTCACCTTTAGCAGCTATGCCATGAGCTGGGTCCGCCAGGCTCCAGGGAAGGGGCTGGAGTGGGTCTCATACATTTCTTCTTACGGTGGTTACACATCTTATGCAGACTCCGTGAAGGGCCGGTTCACCATCTCCCGTGACAATTCCAAGAACACGCTGTATCTGCAAATGAACAGCCTGCGTGCCGAGGACACGGCTGTAT |

TABLE A-continued

VL and VH amino acid (aa) and nucleotide (nt) sequences

| SEQ ID NO. | CHAIN NO. | TYPE | SEQUENCE |
|---|---|---|---|
| | | | ATTATTGTGCGCGCTACCATTCTGGTGTTTTGGACTATTGGGGCCAGGGAACCCTGGTCACCGTCTCCTCA |
| 15 | 1213, light chain VL | aa | DIQMTQSPSSLSASVGDRVTITCRASQSISSYLNWYQQKPGKAPKLLIYAASSLQSGVPSRFSGSGSGTDFTLTISSLQPEDFATYYCQQYYYHYLLTFGQGTKLEIK |
| 16 | 1213, light chain VL | nt | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCACGTTTCAGTGGCAGTGGAAGCGGGACAGATTTCACTCTCACCATCAGCAGTCTGCAACCTGAAGATTTTGCAACTTATTACTGTCAACAGTACTACTACCATTACCTGCTCACTTTTGGCCAGGGGACCAAGCTGGAGATCAAA |
| 17 | 1200, heavy chain VH | aa | EVQLLESGGGLVQPGGSLRLSCAASGFTFSSYAMSWVRQAPGKGLEWVSGISGGGGGTYYADSVKGRFTISRDNSKNTLYLQMNSLRAEDTAVYYCARDVAYFDYWGQGTLVTVSS |
| 18 | 1200, heavy chain VH | nt | GAGGTGCAGCTGTTGGAGAGCGGGGGAGGCTTGGTACAGCCTGGGGGGTCCCTGCGCCTCTCCTGTGCAGCCAGCGGATTCACCTTTAGCAGCTATGCCATGAGCTGGGTCCGCCAGGCTCCAGGGAAGGGGCTGGAGTGGGTCTCAGGTATTTCTGGTGGTGGTGGTGGTACATACTATGCAGACTCCGTGAAGGGCCGGTTCACCATCTCCCGTGACAATTCCAAGAACACGCTGTATCTGCAAATGAACAGCCTGCGTGCCGAGGACACGGCTGTATATTATTGTGCGCGCGACGTTGCTTACTTTGACTATTGGGGCCAGGGAACCCTGGTCACCGTCTCCTCA |
| 19 | 1201, light chain VL | aa | DIQMTQSPSSLSASVGDRVTITCRASQSISSYLNWYQQKPGKAPKLLIYAASSLQSGVPSRFSGSGSGTDFTLTISSLQPEDFATYYCQQYYIPHTFGQGTKLEIK |
| 20 | 1201, light chain VL | nt | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCACGTTTCAGTGGCAGTGGAAG |

TABLE A-continued

VL and VH amino acid (aa) and nucleotide (nt) sequences

| SEQ ID NO. | CHAIN NO. | TYPE | SEQUENCE |
|---|---|---|---|
| | | | CGGGACAGATTTCACTCTCACCATCAgCAGTCTGCAACCTGAAGAtTTTGCAACTTATTACTGTCAACAGTACTACATTCCGCACACTTTTGGCCaGGGGACCaAGCTGGagaTCAAA |
| 21 | 1202, heavy chain VH | aa | EVQLLESGGGLVQPGGSLRLSCAASGFTFYGSSMSWVRQAPGKGLEWVSSIYYGSSGTYYADSVKGRFTISRDNSKNTLYLQMNSLRAEDTAVYYCARSYYGYFDYWGQGTLVTVSS |
| 22 | 1202, heavy chain VH | nt | GAGGTGCAGCTGTTGGAGAGCGGGGGAGGCTTGGTACAGCCTGGGGGGTCCCTGCGCCTCTCCTGTGCAGCCAGCGGATTCACCTTTTACGGTTCTTCTATGTCTTGGGTCCGCCAGGCTCCAGGGAAGGGGCTGGAGTGGGTCTCATCTATTTACTACGGTTCTTCTGGTACATACTATGCAGACTCCGTGAAGGGCCGGTTCACCATCTCCCGTGACAATTCCAAGAACACGCTGTATCTGCAAATGAACAGCCTGCGTGCCGAGGACACGGCTGTATATTATTGTGCGCGCTCTTACTACGGTTACTTTGACTATTGGGGCCAGGGAACCCTGGTCACCGTCTCCTCA |
| 23 | 1203, light chain VL | aa | DIQMTQSPSSLSASVGDRVTITCRASQSISSYLNWYQQKPGKAPKLLIYAASSLQSGVPSRFSGSGSGTDFTLTISSLQPEDFATYYCQQYYTVVPFTFGQGTKLEIK |
| 24 | 1203, light chain VL | nt | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTTTGCAAAGTGGGGTCCCATCACGTTTCAGTGGCAGTGGAAGCGGGACAGATTTCACTCTCACCATCAGCAGTCTGCAACCTGAAGATTTTGCAACTTATTACTGTCAACAGTACTACACTGTTGTTCCGTTCACTTTTGGCCAGGGGACCAAGCTGGAGATCAAA |
| 25 | 1205, light chain VL | aa | DIQMTQSPSSLSASVGDRVTITCRASQSISSYLNWYQQKPGKAPKLLIYAASSLQSGVPSRFSGSGSGTDFTLTISSLQPEDFATYYCQQSVPHYPFTFGQGTKLEIK |
| 26 | 1205, light chain VL | nt | GACATCCAGATGACCCAGTCTCCATCCTCCCTGAGCGCATCTGTAGGAGACCGCGTCACCATCACTTGCCGGGCAAGTCAGAGCATTAGCAGCTATTTAAATTGGTATCAGCAGAAACCAGGGAAAGCCCCTAAGCTCCTGATCTATGCTGCATCCAGTT |

TABLE A-continued

VL and VH amino acid (aa) and nucleotide (nt) sequences

| SEQ ID NO. | CHAIN NO. | TYPE | SEQUENCE |
|---|---|---|---|
| | | | TGCAAAGTGGGGTCCCATCA CGTTTCAGTGGCAGTGGAAG CGGGACAGATTTCACTCTCA CCATCAGCAGTCTGCAACCT GAAGATTTTGCAACTTATTA CTGTCAACAGTCTGTTCCGC ACTACCCGTTCACTTTTGGC CAGGGGACCAAGCTGGAGAT CAAA |
| 27 | 1204, heavy chain VH | aa | EVQLLESGGGLVQPGGSLRL SCAASGFTFSSYYMGWVRQA PGKGLEWVSGIGSYYGYTGY ADSVKGRFTISRDNSKNTLY LQMNSLRAEDTAVYYCARAY YDYNYYYAYFDYWGQGTLVT VSS |
| 28 | 1204, heavy chain VH | nt | GAGGTGCAGCTGTTGGAGAG CGGGGGAGGCTTGGTACAGC CTGGGGGGTCCCTGCGCCTC TCCTGTGCAGCCAGCGGATT CACCTTTTCTTCTTACTACA TGGGTTGGGTCCGCCAGGCT CCAGGGAAGGGGCTGGAGTG GGTCTCAGGTATTGGTTCTT ACTACGGTTACACAGGTTAT GCAGACTCCGTGAAGGGCCG GTTCACCATCTCCCGTGACA ATTCCAAGAACACGCTGTAT CTGCAAATGAACAGCCTGCG TGCCGAGGACACGGCTGTAT ATTATTGTGCGCGCGCTTAC TACGACTACAACTACTACTA CGCTTACTTTGACTATTGGG GCCAGGGAACCCTGGTCACC GTCTCCTCA |
| 29 | 1214 (VH) | aa | EVQLLESGGGLVQPGGSLRL SCAASGFTFSSYAMSWVRQA PGKGLEWVSSIGSGGGYTGY ADSVKGRFTISRDNSKNTLY LQMNSLRAEDTAVYYCARVG HPFDYWGQGTLVTVSS |
| 30 | 1214 (VH) | nt | GAGGTGCAGCTGTTGGAGAG CGGGGGAGGCTTGGTACAGC CTGGGGGGTCCCTGCGCCTC TCCTGTGCAGCCAGCGGATT CACCTTTAGCAGCTATGCCA TGAGCTGGGTCCGCCAGGCT CCAGGGAAGGGGCTGGAGTG GGTCTCATCTATTGGTTCTG GTGGTGGTTACACAGGTTAT GCAGACTCCGTGAAGGGCCG GTTCACCATCTCCCGTGACA ATTCCAAGAACACGCTGTAT CTGCAAATGAACAGCCTGCG TGCCGAGGACACGGCTGTAT ATTATTGTGCGCGCGTTGGT CATCCGTTTGACTATTGGGG CCAGGGAACCCTGGTCACCG TCTCCTCA |
| 31 | 1215 (VL) | aa | DIQMTQSPSSLSASVGDRVT ITCRASQSISSYLNWYQQKP GKAPKLLIYAASSLQSGVPS RFSGSGSGTDFTLTISSLQP EDFATYYCQQDAYPHTFGQG TKLEIK |
| 32 | 1215 (VL) | nt | GACATCCAGATGACCCAGTC TCCATCCTCCCTGAGCGCAT CTGTAGGAGACCGCGTCACC ATCACTTGCCGGGCAAGTCA GAGCATTAGCAGCTATTTAA ATTGGTATCAGCAGAAACCA GGGAAAGCCCCTAAGCTCCT GATCTATGCTGCATCCAGTT TGCAAAGTGGGGTCCCATCA CGTTTCAGTGGCAGTGGAAG CGGGACAGATTTCACTCTCA CCATCAGCAGTCTGCAACCT GAAGATTTTGCAACTTATTA CTGTCAACAGGACGCTTACC CGCACACTTTTGGCCAGGGG ACCAAGCTGGAGATCAAA |
| 33 | 1618 (VH) | aa | EVQLLESGGGLVQPGGSLRL SCAASGFTFSYGSMYWVRQA PGKGLEWVSSISSGSGSTYY ADSVKGRFTISRDNSKNTLY LQMNSLRAEDTAVYYCARSS YYGSYYSIDYWGQGTLVTVS S |
| 34 | 1618(VH) | nt | GAGGTGCAGCTGTTGGAGAG CGGGGGAGGCTTGGTACAGC CTGGGGGGTCCCTGCGCCTC TCCTGTGCAGCCAGCGGATT CACCTTTTCTTACGGTTCTA TGTACTGGGTCCGCCAGGCT CCAGGGAAGGGGCTGGAGTG GGTCTCATCTATTTCTTCTG GTTCTGGTTCTACATACTAT GCAGACTCCGTGAAGGGCCG GTTCACCATCTCCCGTGACA ATTCCAAGAACACGCTGTAT CTGCAAATGAACAGCCTGCG TGCCGAGGACACGGCTGTAT ATTATTGTGCGCGCTCTTCT TACTACGGTTCTTACTACTC TATTGACTATTGGGGCCAGG GAACCCTGGTCACCGTCTCC TCA |
| 35 | 1619 (VL) | aa | DIQMTQSPSSLSASVGDRVT ITCRASQSISSYLNWYQQKP GKAPKLLIYAASSLQSGVPS RFSGSGSGTDFTLTISSLQP EDFATYYCQQYYDNLPTFGQ GTKLEIK |
| 36 | 1619 (VL) | nt | GACATCCAGATGACCCAGTC TCCATCCTCCCTGAGCGCAT CTGTAGGAGACCGCGTCACC ATCACTTGCCGGGCAAGTCA GAGCATTAGCAGCTATTTAA ATTGGTATCAGCAGAAACCA GGGAAAGCCCCTAAGCTCCT GATCTATGCTGCATCCAGTT TGCAAAGTGGGGTCCCATCA CGTTTCAGTGGCAGTGGAAG CGGGACAGATTTCACTCTCA CCATCAGCAGTCTGCAACCT GAAGATTTTGCAACTTATTA CTGTCAACAGTACTACGACA ACCTGCCCACTTTTGGCCAG GGGACCAAGCTGGAGATCAA A |

TABLE A-continued

| VL and VH amino acid (aa) and nucleotide (nt) sequences | | | |
|---|---|---|---|
| SEQ ID NO. | CHAIN NO. | TYPE | SEQUENCE |
| 37 | 1620 (VH) | aa | EVQLLESGGGLVQPGGSLRL<br>SCAASGFTFSGYYMYWVRQA<br>PGKGLEWVSGISSSGSYTYY<br>ADSVKGRFTISRDNSKNTLY<br>LQMNSLRAEDTAVYYCARSV<br>GPYFDYWGQGTLVTVSS |
| 38 | 1620 (VH) | nt | GAGGTGCAGCTGTTGGAGAG<br>CGGGGGAGGCTTGGTACAGC<br>CTGGGGGGTCCCTGCGCCTC<br>TCCTGTGCAGCCAGCGGATT<br>CACCTTTTCTGGTTACTACA<br>TGTACTGGGTCCGCCAGGCT<br>CCAGGGAAGGGGCTGGAGTG<br>GGTCTCAGGTATTTCTTCTT<br>CTGGTTCTTACACATACTAT<br>GCAGACTCCGTGAAGGGCCG<br>GTTCACCATCTCCCGTGACA<br>ATTCCAAGAACACGCTGTAT<br>CTGCAAATGAACAGCCTGCG<br>TGCCGAGGACACGGCTGTAT<br>ATTATTGTGCGCGCTCTGTT<br>GGTCCGTACTTTGACTATTG<br>GGGCCAGGGAACCCTGGTCA<br>CCGTCTCCTCA |
| 39 | 1621 (VL) | aa | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQGVGPYTFGQG<br>TKLEIK |
| 40 | 1621 (VL) | nt | GACATCCAGATGACCCAGTC<br>TCCATCCTCCCTGAGCGCAT<br>CTGTAGGAGACCGCGTCACC<br>ATCACTTGCCGGGCAAGTCA<br>GAGCATTAGCAGCTATTTAA<br>ATTGGTATCAGCAGAAACCA<br>GGGAAAGCCCCTAAGCTCCT<br>GATCTATGCTGCATCCAGTT<br>TGCAAAGTGGGGTCCCATCA<br>CGTTTCAGTGGCAGTGGAAG<br>CGGGACAGATTTCACTCTCA<br>CCATCAGCAGTCTGCAACCT<br>GAAGATTTTGCAACTTATTA<br>CTGTCAACAGGGTGTTGGTC<br>CGTACACTTTTGGCCAGGGG<br>ACCAAGCTGGAGATCAAA |
| 41 | 1626 (VH) | aa | EVQLLESGGGLVQPGGSLRL<br>SCAASGFTFGGYSMYWVRQA<br>PGKGLEWVSSIGGYYYSTYY<br>ADSVKGRFTISRDNSKNTLY<br>LQMNSLRAEDTAVYYCARSY<br>YGSIDYWGQGTLVTVSS |
| 42 | 1626 (VH) | nt | GAGGTGCAGCTGTTGGAGAG<br>CGGGGGAGGCTTGGTACAGC<br>CTGGGGGGTCCCTGCGCCTC<br>TCCTGTGCAGCCAGCGGATT<br>CACCTTTGGTGGTTACTCTA<br>TGTACTGGGTCCGCCAGGCT<br>CCAGGGAAGGGGCTGGAGTG<br>GGTCTCATCTATTGGTGGTT<br>ACTACTACTCTACATACTAT<br>GCAGACTCCGTGAAGGGCCG<br>GTTCACCATCTCCCGTGACA<br>ATTCCAAGAACACGCTGTAT<br>CTGCAAATGAACAGCCTGCG<br>TGCCGAGGACACGGCTGTAT<br>ATTATTGTGCGCGCTCTTAC<br>TACGGTTCTATTGACTATTG<br>GGGCCAGGGAACCCTGGTCA<br>CCGTCTCCTCA |
| 43 | 1627 (VL) | aa | DIQMTQSPSSLSASVGDRVT<br>ITCRASQSISSYLNWYQQKP<br>GKAPKLLIYAASSLQSGVPS<br>RFSGSGSGTDFTLTISSLQP<br>EDFATYYCQQGTGYGPLTFG<br>QGTKLEIK |
| 44 | 1627 (VL) | nt | GACATCCAGATGACCCAGTC<br>TCCATCCTCCCTGAGCGCAT<br>CTGTAGGAGACCGCGTCACC<br>ATCACTTGCCGGGCAAGTCA<br>GAGCATTAGCAGCTATTTAA<br>ATTGGTATCAGCAGAAACCA<br>GGGAAAGCCCCTAAGCTCCT<br>GATCTATGCTGCATCCAGTT<br>TGCAAAGTGGGGTCCCATCA<br>CGTTTCAGTGGCAGTGGAAG<br>CGGGACAGATTTCACTCTCA<br>CCATCAGCAGTCTGCAACCT<br>GAAGATTTTGCAACTTATTA<br>CTGTCAACAGGGTACTGGTT<br>ACGGTCCGCTCACTTTTGGC<br>CAGGGGACCAAGCTGGAGAT<br>CAAA |

TABLE B

| 5T4 antibody sequences CDR sequences | | | | | | | | |
|---|---|---|---|---|---|---|---|---|
| Clone name (mAb) | VH | VL | H1 | H2 | H3 | L1 | L2 | L3 |
| 1206/1207 | 1206 | 1207 | GFTFSGSS (SEQ ID NO: 45) | IYYSGSGT (SEQ ID NO: 47) | ARYGRNVHPYNLDY (SEQ ID NO: 50) | QSISSY (SEQ ID NO: 54) | AAS (SEQ ID NO: 55) | QQGYYYLPT (SEQ ID NO: 56) |
| 1208/1135 | 1208 | 1135 | GFTFSSYA (SEQ ID NO: 46) | ISGSGGST (SEQ ID NO: 48) | ARSPYYYGANWIDY (SEQ ID NO: 51) | QSISSY (SEQ ID NO: 54) | AAS (SEQ ID NO: 55) | QQSYSTPYT (SEQ ID NO: 57) |

TABLE B-continued

| 5T4 antibody sequences CDR sequences | | | | | | | | |
|---|---|---|---|---|---|---|---|---|
| Clone name (mAb) | VH | VL | H1 | H2 | H3 | L1 | L2 | L3 |
| 1210/1211 | 1210 | 1211 | GFTFSSYA (SEQ ID NO: 46) | ISGSGGST (SEQ ID NO: 48) | ARYYGGYYSAWMDY (SEQ ID NO: 52) | QSISSY (SEQ ID NO: 54) | AAS (SEQ ID NO: 55) | QQTYGYLHT (SEQ ID NO: 58) |
| 1212/1213 | 1212 | 1213 | GFTFSSYA (SEQ ID NO: 46) | ISSYGGYT (SEQ ID NO: 49) | ARYHSGVLDY (SEQ ID NO: 53) | QSISSY (SEQ ID NO: 54) | AAS (SEQ ID NO: 55) | QQYYYHYLLT (SEQ ID NO: 59) |
| 2992/2993 | 2992 | 2993 | GFDFESYA (SEQ ID NO: 144) | ISGSGGST (SEQ ID NO: 48) | ARYYGGYYSAWMDY (SEQ ID NO: 52) | QSIRSA (SEQ ID NO: 145) | AAS (SEQ ID NO: 55) | QQTYGYLHT (SEQ ID NO: 58) |
| 2994/2995 | 2994 | 2995 | GFDFDSYA (SEQ ID NO: 146) | ISGRGGST (SEQ ID NO: 147) | ARYYGGYYSAWMDY (SEQ ID NO: 52) | QSIRSA (SEQ ID NO: 145) | AAS (SEQ ID NO: 55) | QQTYGYLHT (SEQ ID NO: 58) |
| 2996/2997 | 2996 | 2997 | GFDFDSYA (SEQ ID NO: 146) | ISGSGGST (SEQ ID NO: 48) | ARYYGGYYSAWMDY (SEQ ID NO: 52) | QSIRQA (SEQ ID NO: 148) | AAS (SEQ ID NO: 55) | QQTYGYLHT (SEQ ID NO: 58) |
| 2998/2999 | 2998 | 2999 | GFDFDSYA (SEQ ID NO: 146) | ISGSGGST (SEQ ID NO: 48) | ARYYGGYYSAWMDY (SEQ ID NO: 52) | QSISQA (SEQ ID NO: 149) | AAS (SEQ ID NO: 55) | QQTYGYLHT (SEQ ID NO: 58) |
| 3000/3001 | 3000 | 3001 | GFDFSSYA (SEQ ID NO: 150) | ISGSGGST (SEQ ID NO: 48 | ARYYGGYYSAWMDY (SEQ ID NO: 52) | QSIRQA (SEQ ID NO: 148) | AAD (SEQ ID NO: 151) | QQTYGYLHT (SEQ ID NO: 58) |
| 3002/3003 | 3002 | 3003 | GFTFDSYA (SEQ ID NO: 152) | ISGSGGST (SEQ ID NO: 48) | ARYYGGYYSAWMDY (SEQ ID NO: 52) | QSIRSA (SEQ ID NO: 145) | AAS (SEQ ID NO: 55) | QQTYGYLHT (SEQ ID NO: 58) |
| 3004/3005 | 3004 | 3005 | GFDFDSYA (SEQ ID NO: 146) | ISGSGGST (SEQ ID NO: 48 | ARYYGGYYSAWMDY (SEQ ID NO: 52) | QSISSA (SEQ ID NO: 153) | AAS (SEQ ID NO: 55) | QQTYGYLHT (SEQ ID NO: 58) |
| 3006/3007 | 3006 | 3007 | GFDFESYA (SEQ ID NO: 144) | ISGSGGST (SEQ ID NO: 48) | ARYYGGYYSAWMDY (SEQ ID NO: 52) | QSIHQA (SEQ ID NO: 154) | GAS (SEQ ID NO: 155) | QQTYGYLHT (SEQ ID NO: 58) |
| 3008/3009 | 3008 | 3009 | GFDFDSYA (SEQ ID NO: 146) | ISGSGGST (SEQ ID NO: 48) | ARYYGGYYSAWMDY (SEQ ID NO: 52) | QSIHQA (SEQ ID NO: 154) | AAS (SEQ ID NO:55) | QQTYGYLHT (SEQ ID NO: 58) |

TABLE C

CD137 antibodies CDR sequences

Table C(1) VH

| Antibody | CDRH1 | CDRH2 | CDRH3 |
|---|---|---|---|
| 1200/1201 | GFTFSSYA (SEQ ID NO: 46) | ISGGGGGT (SEQ ID NO: 65) | ARDVAYFDY (SEQ ID NO: 72) |
| 1202/1203 | GFTFYGSS (SEQ ID NO: 60) | IYYGSSGT (SEQ ID NO: 66) | ARSYYGYFDY (SEQ ID NO: 73) |
| 1204/1205 | GFTFSSYY (SEQ ID NO: 61) | IGSYYGYT (SEQ ID NO: 67) | ARAYYDYNYYYAYFDY (SEQ ID NO: 74) |
| 1214/1215 | GFTFSSYA (SEQ ID NO: 46) | IGSGGGYT (SEQ ID NO: 68) | ARVGHPFDY (SEQ ID NO: 75) |
| 1618/1619 | GFTFSYGS (SEQ ID NO: 62) | ISSGSGST (SEQ ID NO: 69) | ARSSYYGSYYSIDY (SEQ ID NO: 76) |
| 1620/1621 | GFTFSGYY (SEQ ID NO: 63) | ISSSGSYT (SEQ ID NO: 70) | ARSVGPYFDY (SEQ ID NO: 77) |
| 1626/1627 | GFTFGGYS (SEQ ID NO: 64) | IGGYYYST (SEQ ID NO: 71) | ARSYYGSIDY (SEQ ID NO: 78) |
| 3012/3013 | GFTFDYGS (SEQ ID NO: 156) | ISSGSGST (SEQ ID NO: 69) | ARSSYYGSYYSIDY (SEQ ID NO: 76) |
| 3014/3015 | GFTFSYGS (SEQ ID NO: 62) | ISSGSGST (SEQ ID NO: 69) | ARSSYYGSYYSIDY (SEQ ID NO: 76) |
| 3016/3017 | GFTFSYGS (SEQ ID NO: 62) | ISSGSGST (SEQ ID NO: 69) | ARSSYYGSYYSIDY (SEQ ID NO: 76) |
| 3018/3019 | GFTFDYGS (SEQ ID NO: 156) | ISSGSGST (SEQ ID NO: 69) | ARSSYYGSYYSIDY (SEQ ID NO: 76) |
| 3020/3021 | GFTFDYGS (SEQ ID NO: 156) | ISSGSGST (SEQ ID NO: 69) | ARSSYYGSYYSIDY (SEQ ID NO: 76) |
| 3022/3023 | GFTFDYGS (SEQ ID NO: 156) | ISSGSGST (SEQ ID NO: 69) | ARSSYYGSYYSIDY (SEQ ID NO: 76) |
| 3024/3025 | GFTFDYGS (SEQ ID NO: 156) | ISSGSGST (SEQ ID NO: 69) | ARSSYYGSYYSIDY (SEQ ID NO: 76) |
| 3026/3027 | GFTFDYGS (SEQ ID NO: 156) | ISSGSGST (SEQ ID NO: 69) | ARSSYYGSYYSIDY (SEQ ID NO: 76) |
| 3028/3029 | GFDFSYGS (SEQ ID NO: 157) | ISSGSGST (SEQ ID NO: 69) | ARSSYYGSYYSIDY (SEQ ID NO: 76) |
| 3030/3031 | GFTFDYGS (SEQ ID NO: 156) | ISSGSGST (SEQ ID NO: 69) | ARSSYYGSYYSIDY (SEQ ID NO: 76) |
| 3032/3033 | GFTFDYGS (SEQ ID NO: 156) | ISSGSGST (SEQ ID NO: 69) | ARSSYYGSYYSIDY (SEQ ID NO: 76) |
| 3034/3035 | GFTFSYGS (SEQ ID NO: 62) | ISSGSGST (SEQ ID NO: 69) | ARSSYYGSYYSIDY (SEQ ID NO: 76) |
| 3036/3037 | GFTFDYGS (SEQ ID NO: 156) | ISSGSGST (SEQ ID NO: 69) | ARSSYYGSYYSIDY (SEQ ID NO: 76) |

Table C(2) VL

| Antibody | CDRL1 | CDRL2 | CDRL3 |
|---|---|---|---|
| 1200/1201 | QSISSY (SEQ ID NO: 54) | AAS (SEQ ID NO: 55) | QQYYIPHT (SEQ ID NO: 79) |
| 1202/1203 | QSISSY (SEQ ID NO: 54) | AAS (SEQ ID NO: 55) | QQYYTVVPFT (SEQ ID NO: 80) |
| 1204/1205 | QSISSY (SEQ ID NO: 54) | AAS (SEQ ID NO: 55) | QQSVPHYPFT (SEQ ID NO: 81) |

TABLE C-continued

| CD137 antibodies CDR sequences | | | |
|---|---|---|---|
| 1214/1215 | QSISSY (SEQ ID NO: 54) | AAS (SEQ ID NO: 55) | QQDAYPHT (SEQ ID NO: 82) |
| 1618/1619 | QSISSY (SEQ ID NO: 54) | AAS (SEQ ID NO: 55) | QQYYDNLPT (SEQ ID NO: 83) |
| 1620/1621 | QSISSY (SEQ ID NO: 54) | AAS (SEQ ID NO: 55) | QQGVGPYT (SEQ ID NO: 84) |
| 1626/1627 | QSISSY (SEQ ID NO: 54) | AAS (SEQ ID NO: 55) | QQGTGYGPLT (SEQ ID NO: 85) |
| 3012/3013 | QSISQY (SEQ ID NO: 158) | GAS (SEQ ID NO: 155) | QQYYDNLPT (SEQ ID NO: 83) |
| 3014/3015 | QSIRQY (SEQ ID NO: 159) | SAD (SEQ ID NO: 160) | QQYYDNLPT (SEQ ID NO: 83) |
| 3016/3017 | QSIRQY (SEQ ID NO: 159) | GAS (SEQ ID NO: 155) | QQYYDNLPT (SEQ ID NO: 83) |
| 3018/3019 | QSISQY (SEQ ID NO: 158) | SAE (SEQ ID NO: 161) | QQYYDNLPT (SEQ ID NO: 83) |
| 3020/3021 | QSIRSY (SEQ ID NO: 162) | SAS (SEQ ID NO: 163) | QQYYDNLPT (SEQ ID NO: 83) |
| 3022/3023 | QSIRQY (SEQ ID NO: 159) | GAS (SEQ ID NO: 155) | QQYYDNLPT (SEQ ID NO: 83) |
| 3024/3025 | QSISSY (SEQ ID NO: 54) | AAS (SEQ ID NO: 55) | QQYYDNLPT (SEQ ID NO: 83) |
| 3026/3027 | QSIRSY (SEQ ID NO: 162) | GAD (SEQ ID NO: 165) | QQYYDNLPT (SEQ ID NO: 83) |
| 3028/3029 | QSIRQY (SEQ ID NO: 159) | GAE (SEQ ID NO: 166) | QQYYDNLPT (SEQ ID NO: 83) |
| 3030/3031 | QSISSY (SEQ ID NO: 54) | GAE (SEQ ID NO: 166) | QQYYDNLPT (SEQ ID NO: 83) |
| 3032/3033 | QSISSY (SEQ ID NO: 54) | AAS (SEQ ID NO: 55) | QQYYDNLPT (SEQ ID NO: 83) |
| 3034/3035 | QSISSY (SEQ ID NO: 54) | GAS (SEQ ID NO: 155) | QQYYDNLPT (SEQ ID NO: 83) |
| 3036/3037 | QSIRSY (SEQ ID NO: 162) | GAS (SEQ ID NO: 155) | QQYYDNLPT (SEQ ID NO: 83) |

Mutated IgG1 Antibody Sequence

IgG1 LALA-sequence (SEQ ID NO: 86)

ASTKGPSVFPLAPSSKSTSGGTAALGCLVKDYFPEPVTVSWN

SGALTSGVHTFPAVLQSSGLYSLSSVVTVPSSSLGTQTYICN

VNHKPSNTKVDKKVEPKSCDKTHTCPPCPAPEAAGGPSVFLF

PPKPKDTLMISRTPEVTCVVVDVSHEDPEVKFNWYVDGVEVH

NAKTKPREEQYNSTYRVVSVLTVLHQDWLNGKEYKCKVSNKA

LPAPIEKTISKAKGQPREPQVYTLPPSRDELTKNQVSLTCLV

KGFYPSDIAVEWESNGQPENNYKTTPPVLDSDGSFFLYSKLT

VDKSRWQQGNVFSCSVMHEALHNHYTQKSLSLSPGK

Linker Sequences (SEQ ID NO: 87)
SGGGGSGGGGS (SEQ ID NO: 88)
SGGGGSGGGGSAP (SEQ ID NO: 89)
NFSQP, (SEQ ID NO: 90)
KRTVA (SEQ ID NO: 91)
GGGSGGGG (SEQ ID NO: 92)
GGGGSGGGGS (SEQ ID NO: 93)
GGGGSGGGGSGGGGS (SG)m, where m=1 to 7.

IgG Constant Region Sequences

IgG1 heavy chain constant region sequence:

(SEQ ID NO: 94)

ASTKGPSVFPLAPSSKSTSGGTAALGCLVKDYFPEPVTVSWN

SGALTSGVHTFPAVLQSSGLYSLSSVVTVPSSSLGTQTYICN

VNHKPSNTKVDKKVEPKSCDKTHTCPPCPAPELLGGPSVFLF

PPKPKDTLMISRTPEVTCVVVDVSHEDPEVKFNWYVDGVEVH

NAKTKPREEQYNSTYRVVSVLTVLHQDWLNGKEYKCKVSNKA

LPAPIEKTISKAKGQPREPQVYTLPPSRDELTKNQVSLTCLV

KGFYPSDIAVEWESNGQPENNYKTTPPVLDSDGSFFLYSKLT

VDKSRWQQGNVFSCSVMHEALHNHYTQKSLSLSPGK

IgG1 Light Chain Constant Region Sequence:

(SEQ ID NO: 95)

RTVAAPSVFIFPPSDEQLKSGTASVVCLLNNFYPREAKVQWK

VDNALQSGNSQESVTEQDSKDSTYSLSSTLTLSKADYEKHKV

YACEVTHQGLSSPVTKSFNRGEC

Table D—Lead Optimised VH and VL Amino Acid Sequences for CD137 and 5T4

TABLE D(1)

| 5T4-specific VH sequences (optimised sequences from "1210"; SEQ ID NO: 9) | |
|---|---|
| 2992 | EVQLLESGGGLVQPGGSLRLSCAASGFDFESYAMSWVRQAPGKGLEWVSAISGSGGSTYYADSVKGRFTISRDNSKNTLYLQMNSLRAEDTAVYYCARYYGGYYSAVVMDYWGQGTLVTVSS (SEQ ID NO: 96) |
| 2994 | EVQLLESGGGLVQPGGSLRLSCAASGFDFDSYAMSWVRQAPGKGLEWVSAISGRGGSTYYADSVKGRFTISRDNSKNTLYLQMNSLRAEDTAVYYCARYYGGYYSAVVMDYWGQGTLVTVSS (SEQ ID NO: 98) |
| 2996 | EVQLLESGGGLVQPGGSLRLSCAASGFDFDSYAMSWVRQAPGKGLEWVSAISGSGGSTYYADSVKGRFTISRDNSKNTLYLQMNSLRAEDTAVYYCARYYGGYYSAVVMDYWGQGTLVTVSS (SEQ ID NO: 100) |
| 2998 | EVQLLESGGGLVQPGGSLRLSCAASGFDFDSYAMSWVRQAPGKGLEWVSAISGSGGSTYYADSVKGRFTISRDNSKNTLYLQMNSLRAEDTAVYYCARYYGGYYSAVVMDYWGQGTLVTVSS (SEQ ID NO: 102) |
| 3000 | EVQLLESGGGLVQPGGSLRLSCAASGFDFSSYAMSWVRQAPGKGLEWVSAISGSGGSTYYADSVKGRFTISRDNSKNTLYLQMNSLRAEDTAVYYCARYYGGYYSAVVMDYWGQGTLVTVSS (SEQ ID NO: 104) |
| 3002 | EVQLLESGGGLVQPGGSLRLSCAASGFTFDSYAMSWVRQAPGKGLEWVSAISGSGGSTYYADSVKGRFTISRDNSKNTLYLQMNSLRAEDTAVYYCARYYGGYYSAVVMDYWGQGTLVTVSS (SEQ ID NO: 106) |
| 3004 | EVQLLESGGGLVQPGGSLRLSCAASGFDFDSYAMSWVRQAPGKGLEWVSAISGSGGSTYYADSVKGRFTISRDNSKNTLYLQMNSLRAEDTAVYYCARYYGGYYSAVVMDYWGQGTLVTVSS (SEQ ID NO: 108) |
| 3006 | EVQLLESGGGLVQPGGSLRLSCAASGFDFESYAMSWVRQAPGKGLEWVSAISGSGGSTYYADSVKGRFTISRDNSKNTLYLQMNSLRAEDTAVYYCARYYGGYYSAVVMDYWGQGTLVTVSS (SEQ ID NO: 110) |
| 3008 | EVQLLESGGGLVQPGGSLRLSCAASGFDFDSYAMSWVRQAPGKGLEWVSAISGSGGSTYYADSVKGRFTISRDNSKNTLYLQMNSLRAEDTAVYYCARYYGGYYSAVVMDYWGQGTLVTVSS (SEQ ID NO: 112) |

TABLE D(2)

| CD137-specific VH sequences (optimised sequences from "1618"; SEQ ID NO: 33) | |
|---|---|
| 3012 | EVQLLESGGGLVQPGGSLRLSCAASGFTFDYGSMYWVRQAPGKGLEWVSSISSGSGSTYYADSVKGRFTISRDNSKNTLYLQMNSLRAEDTAVYYCARSSYYGSYYSIDYWGQGTLVTVSS (SEQ ID NO: 114) |
| 3014 | EVQLLESGGGLVQPGGSLRLSCAASGFTFSYGSMYWVRQAPGKGLEWVSSISSGSGSTHYADSVKGRFTISRDNSKNTLYLQMNSLRAEDTAVYYCARSSYYGSYYSIDYWGQGTLVTVSS (SEQ ID NO: 116) |
| 3016 | EVQLLESGGGLVQPGGSLRLSCAASGFTFSYGSMYWVRQAPGKGLEWVSSISSGSGSTHYADSVKGRFTISRDNSKNTLYLQMNSLRAEDTAVYYCARSSYYGSYYSIDYWGQGTLVTVSS (SEQ ID NO: 118) |

TABLE D(2)-continued

| CD137-specific VH sequences (optimised sequences from "1618"; SEQ ID NO: 33) | |
|---|---|
| 3018 | EVQLLESGGGLVQPGGSLRL<br>SCAASGFTFDYGSMYWVRQA<br>PGKGLEWVSSISSGSGSTYY<br>ADSVKGRFTISRDNSKNTLY<br>LQMNSLRAEDTAVYYCARSS<br>YYGSYYSIDYWGQGTLVTVS<br>S<br>(SEQ ID NO: 120) |
| 3020 | EVQLLESGGGLVQPGGSLRL<br>SCAASGFTFDYGSMYWVRQA<br>PGKGLEWVSSISSGSGSTYY<br>ADSVKGRFTISRDNSKNTLY<br>LQMNSLRAEDTAVYYCARSS<br>YYGSYYSIDYWGQGTLVTVS<br>S<br>(SEQ ID NO: 122) |
| 3022 | EVQLLESGGGLVQPGGSLRL<br>SCAASGFTFDYGSMYWVRQA<br>PGKGLEWVSSISSGSGSTYY<br>ADSVKGRFTISRDNSKNTLY<br>LQMNSLRAEDTAVYYCARSS<br>YYGSYYSIDYWGQGTLVTVS<br>S<br>(SEQ ID NO: 124) |
| 3024 | EVQLLESGGGLVQPGGSLRL<br>SCAASGFTFDYGSMYWVRQA<br>PGKGLEWVSSISSGSGSTYY<br>ADSVKGRFTISRDNSKNTLY<br>LQMNSLRAEDTAVYYCARSS<br>YYGSYYSIDYWGQGTLVTVS<br>S<br>(SEQ ID NO: 126) |
| 3026 | EVQLLESGGGLVQPGGSLRL<br>SCAASGFTFDYGSMYWVRQA<br>PGKGLEWVSSISSGSGSTHY<br>ADSVKGRFTISRDNSKNTLY<br>LQMNSLRAEDTAVYYCARSS<br>YYGSYYSIDYWGQGTLVTVS<br>S<br>(SEQ ID NO: 128) |
| 3028 | EVQLLESGGGLVQPGGSLRL<br>SCAASGFDFSYGSMYWVRQA<br>PGKGLEWVSSISSGSGSTYY<br>ADSVKGRFTISRDNSKNTLY<br>LQMNSLRAEDTAVYYCARSS<br>YYGSYYSIDYWGQGTLVTVS<br>S<br>(SEQ ID NO: 130) |
| 3030 | EVQLLESGGGLVQPGGSLRL<br>SCAASGFTFDYGSMYWVRQA<br>PGKGLEWVSSISSGSGSTHY<br>ADSVKGRFTISRDNSKNTLY<br>LQMNSLRAEDTAVYYCARSS<br>YYGSYYSIDYWGQGTLVTVS<br>S<br>(SEQ ID NO: 132) |
| 3032 | EVQLLESGGGLVQPGGSLRL<br>SCAASGFTFDYGSMYWVRQA<br>PGKGLEWVSSISSGSGSTYY<br>ADSVKGRFTISRDNSKNTLY<br>LQMNSLRAEDTAVYYCARSS<br>YYGSYYSIDYWGQGTLVTVS<br>S<br>(SEQ ID NO: 134) |
| 3034 | EVQLLESGGGLVQPGGSLRL<br>SCAASGFTFSYGSMYWVRQA<br>PGKGLEWVSSISSGSGSTHY<br>ADSVKGRFTISRDNSKNTLY<br>LQMNSLRAEDTAVYYCARSS<br>YYGSYYSIDYWGQGTLVTVS<br>S<br>(SEQ ID NO: 136) |
| 3036 | EVQLLESGGGLVQPGGSLRL<br>SCAASGFTFDYGSMYWVRQA<br>PGKGLEWVSSISSGSGSTYY<br>ADSVKGRFTISRDNSKNTLY<br>LQMNSLRAEDTAVYYCARSS<br>YYGSYYSIDYWGQGTLVTVS<br>S (SEQ ID NO: 138) |

TABLE D(3)

| 5T4-specific VL sequences (optimised sequences from "1211"; SEQ ID NO: 11) | |
|---|---|
| 2993 | DIQMTQSPSSLSASVGDRVT<br>ITCRASQSIRSALNWYQQK<br>PGKAPKLLIYAASSLQSGVP<br>SRFSGSGSGTDFTLTISSLQ<br>PEDFATYYCQQTYGYLHTFG<br>QGTKLEIK<br>(SEQ ID NO: 97) |
| 2995 | DIQMTQSPSSLSASVGDRVT<br>ITCRASQSIRSALNWYQQK<br>PGKAPKLLIYAASSLQSGVP<br>SRFSGSGSGTDFTLTISSLQ<br>PEDFATYYCQQTYGYLHTFG<br>QGTKLEIK<br>(SEQ ID NO: 99) |
| 2997 | DIQMTQSPSSLSASVGDRVT<br>ITCRASQSIRQALNWYQQK<br>PGKAPKLLIYAASSLHSGVP<br>SRFSGSGSGTDFTLTISSLQ<br>PEDFATYYCQQTYGYLHTFG<br>QGTKLEIK<br>(SEQ ID NO: 101) |
| 2999 | DIQMTQSPSSLSASVGDRVT<br>ITCRASQSISQALNWYQQK<br>PGKAPKLLIYAASSLHSGVP<br>SRFSGSGSGTDFTLTISSLQ<br>PEDFATYYCQQTYGYLHTFG<br>QGTKLEIK<br>(SEQ ID NO: 103) |
| 3001 | DIQMTQSPSSLSASVGDRVT<br>ITCRASQSIRQALNWYQQK<br>PGKAPKLLIYAADSLHSGVP<br>SRFSGSGSGTDFTLTISSLQ<br>PEDFATYYCQQTYGYLHTFG<br>QGTKLEIK<br>(SEQ ID NO: 105) |
| 3003 | DIQMTQSPSSLSASVGDRVT<br>ITCRASQSIRSALNWYQQK<br>PGKAPKLLIYAASSLHSGVP<br>SRFSGSGSGTDFTLTISSLQ<br>PEDFATYYCQQTYGYLHTFG<br>QGTKLEIK<br>(SEQ ID NO: 107) |
| 3005 | DIQMTQSPSSLSASVGDRVT<br>ITCRASQSISSALNWYQQK<br>PGKAPKLLIYAASSLHSGVP<br>SRFSGSGSGTDFTLTISSLQ<br>PEDFATYYCQQTYGYLHTFG<br>QGTKLEIK<br>(SEQ ID NO: 109) |

TABLE D(3)-continued

| 5T4-specific VL sequences (optimised sequences from "1211"; SEQ ID NO: 11) | |
|---|---|
| 3007 | DIQMTQSPSSLSASVGDRVT ITCRASQSIHQALNWYQQK PGKAPKLLIYGASSLQSGVP SRFSGSGSGTDFTLTISSLQ PEDFATYYCQQTYGYLHTFG QGTKLEIK (SEQ ID NO: 111) |
| 3009 | DIQMTQSPSSLSASVGDRVT ITCRASQSIHQALNWYQQK PGKAPKLLIYAASSLHSGVP SRFSGSGSGTDFTLTISSLQ PEDFATYYCQQTYGYLHTFG QGTKLEIK (SEQ ID NO: 113) |

TABLE D(4)

| CD137 specific VL sequences (optimised sequences from "1619"; SEQ ID NO: 35) | |
|---|---|
| 3013 | DIQMTQSPSSLSASVGDRVT ITCRASQSISQYLNWYQQK PGKAPKLLIYGASSLQSGVP SRFSGSGSGTDFTLTISSLQ PEDFATYYCQQYYDNLPTFG QGTKLEIK (SEQ ID NO: 115) |
| 3015 | DIQMTQSPSSLSASVGDRVT ITCRASQSIRQYLNWYQQK PGKAPKLLIYSADSLQSGVP SRFSGSGSGTDFTLTISSLQ PEDFATYYCQQYYDNLPTFG QGTKLEIK (SEQ ID NO: 117) |
| 3017 | DIQMTQSPSSLSASVGDRVT ITCRASQSIRQYLNWYQQK PGKAPKLLIYGASSLHSGVP SRFSGSGSGTDFTLTISSLQ PEDFATYYCQQYYDNLPTFG QGTKLEIK (SEQ ID NO: 119) |
| 3019 | DIQMTQSPSSLSASVGDRVT ITCRASQSISQYLNWYQQK PGKAPKLLIYSAESLQSGVP SRFSGSGSGTDFTLTISSLQ PEDFATYYCQQYYDNLPTFG QGTKLEIK (SEQ ID NO: 121) |
| 3021 | DIQMTQSPSSLSASVGDRVT ITCRASQSIRSYLNWYQQK PGKAPKLLIYSASSLQSGVP SRFSGSGSGTDFTLTISSLQ PEDFATYYCQQYYDNLPTFG QGTKLEIK (SEQ ID NO: 123) |
| 3023 | DIQMTQSPSSLSASVGDRVT ITCRASQSIRQYLNWYQQK PGKAPKLLIYGASSLQSGVP SRFSGSGSGTDFTLTISSLQ PEDFATYYCQQYYDNLPTFG QGTKLEIK (SEQ ID NO: 125) |
| 3025 | DIQMTQSPSSLSASVGDRVT ITCRASQSISSYLNWYQQK PGKAPKLLIYAASSLQSGVP |

TABLE D(4)-continued

| CD137 specific VL sequences (optimised sequences from "1619"; SEQ ID NO: 35) | |
|---|---|
| | SRFSGSGSGTDFTLTISSLQ PEDFATYYCQQYYDNLPTFG QGTKLEIK (SEQ ID NO: 127) |
| 3027 | DIQMTQSPSSLSASVGDRVT ITCRASQSIRSYLNWYQQK PGKAPKLLIYGADSLQSGVP SRFSGSGSGTDFTLTISSLQ PEDFATYYCQQYYDNLPTFG QGTKLEIK (SEQ ID NO: 129) |
| 3029 | DIQMTQSPSSLSASVGDRVT ITCRASQSIRQYLNWYQQK PGKAPKLLIYGAESLQSGVP SRFSGSGSGTDFTLTISSLQ PEDFATYYCQQYYDNLPTFG QGTKLEIK (SEQ ID NO: 131) |
| 3031 | DIQMTQSPSSLSASVGDRVT ITCRASQSISSYLNWYQQK PGKAPKLLIYGAESLQSGVP SRFSGSGSGTDFTLTISSLQ PEDFATYYCQQYYDNLPTFG QGTKLEIK (SEQ ID NO: 133) |
| 3033 | DIQMTQSPSSLSASVGDRVT ITCRASQSISSYLNWYQQK PGKAPKLLIYAASSLHSGVP SRFSGSGSGTDFTLTISSLQ PEDFATYYCQQYYDNLPTFG QGTKLEIK (SEQ ID NO: 135) |
| 3035 | DIQMTQSPSSLSASVGDRVT ITCRASQSISSYLNWYQQK PGKAPKLLIYGASSLHSGVP SRFSGSGSGTDFTLTISSLQ PEDFATYYCQQYYDNLPTFG QGTKLEIK (SEQ ID NO: 137) |
| 3037 | DIQMTQSPSSLSASVGDRVT ITCRASQSIRSYLNWYQQK PGKAPKLLIYGASSLHSGVP SRFSGSGSGTDFTLTISSLQ PEDFATYYCQQYYDNLPTFG QGTKLEIK (SEQ ID NO: 139) |

TABLE D(5)

| Connector sequences | | |
|---|---|---|
| Reference | Amino acid sequence | SEQ ID |
| m6 | GGGGSGGGGS | SEQ ID NO: 92 |
| m15 | THTCPPCPEPKSSDK | SEQ ID NO: 140 |
| m16 | GGGGS | SEQ ID NO: 141 |
| m17 | EAAKEAAKGGGGS | SEQ ID NO: 142 |
| m18 | EAAKEAAK | SEQ ID NO: 143 |

TABLE D(6)

Additional alterations (modifications)

| Reference | Alteration |
|---|---|
| m2 | L234A, L235A Fc mutations |
| m5 | G49C in heavy chain and Q120C in light chain of scFv |
| m19 | P15G, G16N, G17E, S18T in heavy chain of scFv |

TABLE E

Example describing how to translate the Antibody name into a full IgG sequence for bispecific antibodies in Morrison format

| Antibody name | Composition of construct | | | | Connector* | Additional alterations* |
|---|---|---|---|---|---|---|
| | A (VH of B1) | B (VL of B1) | C (VH of B2) | D (VL of B2) | | |
| 1618-1210LO1 | 1618 | 1619 | 2992 | 2993 | m6 | m2 |

*See Table D(5) and D(6) above for details

Heavy chain:
[A (underlined); Heavy chain Fc sequence with modification m2; connector m6 (italic); C (bold); linker; D (bold underlined)]
[SEQ ID NO: 167]
EVQLLESGGGLVQPGGSLRLSCAASGFTFSYGSMYW

VRQAPGKGLEWVSSISSGSGSTYYADSVKGRFTIS

RDNSKNTLYLQMNSLRAEDTAVYYCARSSYYGSYY

SIDYWGQGTLVTVSSASTKGPSVFPLAPSSKSTSG

GTAALGCLVKDYFPEPVTVSWNSGALTSGVHTFPA

VLQSSGLYSLSSVVTVPSSSLGTQTYICNVNHKPS

NTKVDKKVEPKSCDKTHTCPPCPAPEAAGGPSVFL

FPPKPKDTLMISRTPEVTCVVVDVSHEDPEVKFNV

VYVDGVEVHNAKTKPREEQYNSTYRVVSVLTVLHQ

DWLNGKEYKCKVSNKALPAPIEKTISKAKGQPREP

QVYTLPPSRDELTKNQVSLTCLVKGFYPSDIAVEW

ESNGQPENNYKTTPPVLDSDGSFFLYSKLTVDKSR

WQQGNVFSCSVMHEALHNHYTQKSLSLSPGK*GGGG*

*SGGGGS*EVQLLESGGGLVQPGGSLRLSCAASGFDF

ESYAMSWVRQAPGKGLEWVSAISGSGGSTYYADSV

KGRFTISRDNSKNTLYLQMNSLRAEDTAVYYCARY

YGGYYSAWMDYVVGQGTLVTVSSGGGGSGGGGSGG

GGS

DIQMTQSPSSLSASVGDRVTITCRASQSIRSALNWYQQKPGKAP

KLLIYAASSLQSGVPSRFSGSGSGTDFTLTISSL

QPEDFATYYCQQTYGYLHTFGQGTK

LEIK

Light chain:
[B (bold underlined); Light chain constant sequence]
[SEQ ID NO: 168]
DIQMTQSPSSLSASVGDRVTITCRASQSISSY

LNWYQQKPGKAPKLLIYAASSLQSGVP

SRFSGSGSGTDFTLTISSLQPEDFATYYCQQYYDNLPTFGQGTKLEIK

RTVAAPSVFIFPPSDEQLKSGTASVVCLLNNFYPRE

AKVQWKVDNALQSGNSQESVTEQDSKDSTYSLSSTL

TLSKADYEKHKVYACEVTHQGLSSPVTKSFNRGEC

EXAMPLES

Example 1—Selection of 5T4 Antibodies from Alligator-GOLD™ Library

Phage display selections against h5T4 were performed using the scFv library ALLIGATOR-GOLD™, a fully human scFv library containing more than $1\times10^{10}$ unique members (Alligator Bioscience AB, Lund, Sweden). Several different selection strategies were employed, including solid phase selection, selection in solution using biotinylated 5T4-Fc, selection with biotinylated 5T4-Fc coupled to streptavidin beads as well as one round of selection against 5T4 expressing B16 cells using a phage stock that previously had been selected against the recombinant h5T4-Fc. Prior to selection, phage stocks were pre-selected against streptavidin, Beriglobin or SLIT2 in order to remove potential binders to streptavidin, the Fc part of the target and binders cross reactive to other leucine rich repeat proteins.

To identify specific binders from the phage selection, approximately 1250 individual clones were screened in phage format using ELISA coated with 5T4-Fc or non-target protein (Biglycan or Orencia). This was followed by sequence analysis as well as screening as soluble scFv in full-curve ELISA, ELISA performed at 50° C. and FACS analysis of selected clones. Based on this, 14 unique candidate scFv were chosen which bound to recombinant 5T4 and to 5T4 expressing cells without showing positive response to non-target molecules or to 5T4 negative cells.

The selected 14 5T4 scFv clones were converted to full IgG1 for further characterization. A reference anti-5T4 antibody, designated 1628 (selected from a representative prior art disclosure), was used in this study as a positive control.

Among the 14 clones, four clones were selected for further evaluation in bispecific antibody format. These four clones are described further below, and compared to the reference clone 1628.

Example 2—Binding to Human 5T4 Measured by ELISA

Materials and Methods

ELISA was performed using a standard protocol. Plates (#655074, Greiner Bio-One GmbH, Germany) were pre-coated with 0.5 µg/ml 5T4-Fc (obtained from Peter L. Stern, University of Manchester) overnight. 5T4 antibodies were diluted from 6 to $1.5\times10^3$ µg/ml in 1:4 dilutions and added in duplicates of 50 µl to each well. Binding was detected with rabbit anti-h kappa L-chain-HRP (P0129, Dako Denmark) and the ELISA was developed with SuperSignal ELISA PICO Chemiluminescent substrate (Thermo Scientific Pierce, Rockford, IL USA) for 2-10 minutes and read in an automated microplate based multi-detection reader (FLUOstar OPTIMA, Netherlands).

Results and Conclusions

The results show that the majority of the 5T4 mAbs bind with similar potency to 5T4 as 1628 (Table 1) with EC50 values in the sub-nM range. However, clone 1208 exhibits a slightly higher EC50 value.

TABLE 1

Summary of the obtained EC50 in the ELISA of all 5T4 mAb with the confidence intervals and number of experiments

| Clone name | Mean EC50 (nM) | EC50 (nM) 95% Confidence Intervals | n |
|---|---|---|---|
| Reference 1628 | 0.56 | 0.3-1.0 | 8 |
| 1206 | 0.64 | 0.3-1.4 | 4 |
| 1208 | 2.24 | 2.0-2.4 | 1 |
| 1210 | 0.48 | 0.2-1.1 | 4 |
| 1212 | 0.56 | 0.2-1.2 | 4 |

Example 3—Binding to 5T4 Expressed on the Cell Surface Determined by Flow Cytometry Materials and Methods Analysis of 5T4 mAb binding with flow cytometry was performed using 5T4-transfected cell lines and as negative control, mock transfected cells. Three different transfected cell lines used were used for this study; B16, A9 and CHO, transfected either with a 5T4 construct or with an empty vector control construct. Cells were stained with 5T4 antibodies diluted in FACS buffer (PBS, 0.5% BSA and 0.02% $NaN_3$). Binding was detected with the secondary antibody anti-IgG (Fc)-PE (109-115-098, Jackson ImmunoResearch Europe, UK) diluted 1:100. Samples were analysed either on a FACSCalibur or a FACSverse (BD Biosciences, Heidelberg, Germany) and mean fluorescence intensity (MFI) determined.

Results and Conclusions

Figure 1:
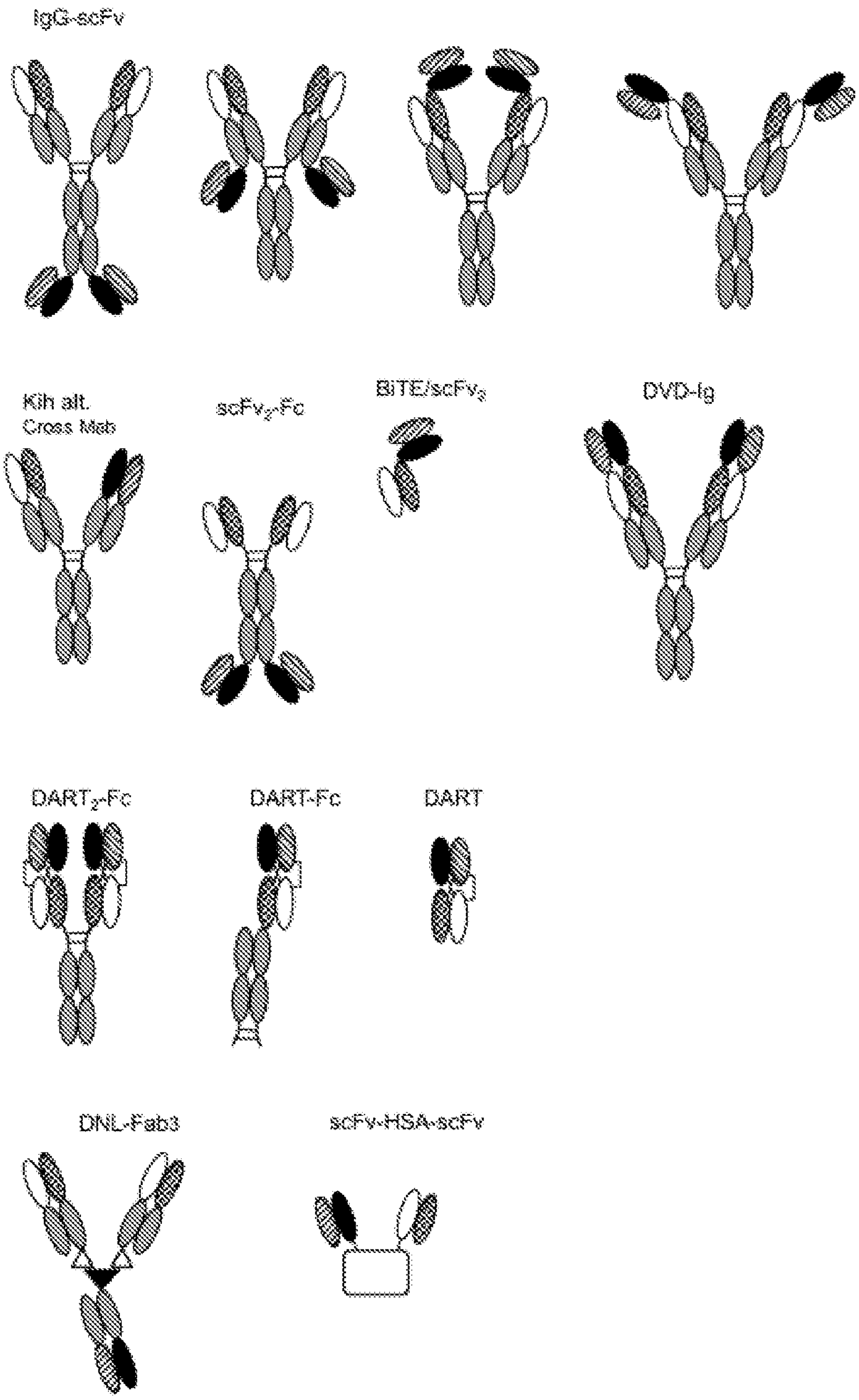
FIG. 1 shows a schematic representation of the structure of exemplary formats for a bispecific antibody of the invention. In each format, the constant regions are shown as filled light grey; variable heavy chain regions VH1 are shown as chequered black and white; variable light chain regions VL1 are shown as filled white; variable heavy chain regions VH2 are shown as filled black; and variable light chain regions VL2 are shown as white with diagonal lines. CD137 binding domains (binding domain 1) are typically represented as a pair of a chequered black and white domain with a filled white domain (VH1/VL1); tumour-associated antigen binding domains (binding domain 2) are typically represented as a pair of a filled black domain and a white domain with diagonal lines (VH2/VL2). However, in all of the formats shown, it will be appreciated that binding domains 1 and 2 may be switched. That is, a CD137 binding domain may occur in a position shown in this figure for a tumour-associated antigen domain, and vice versa.
Figure 2:
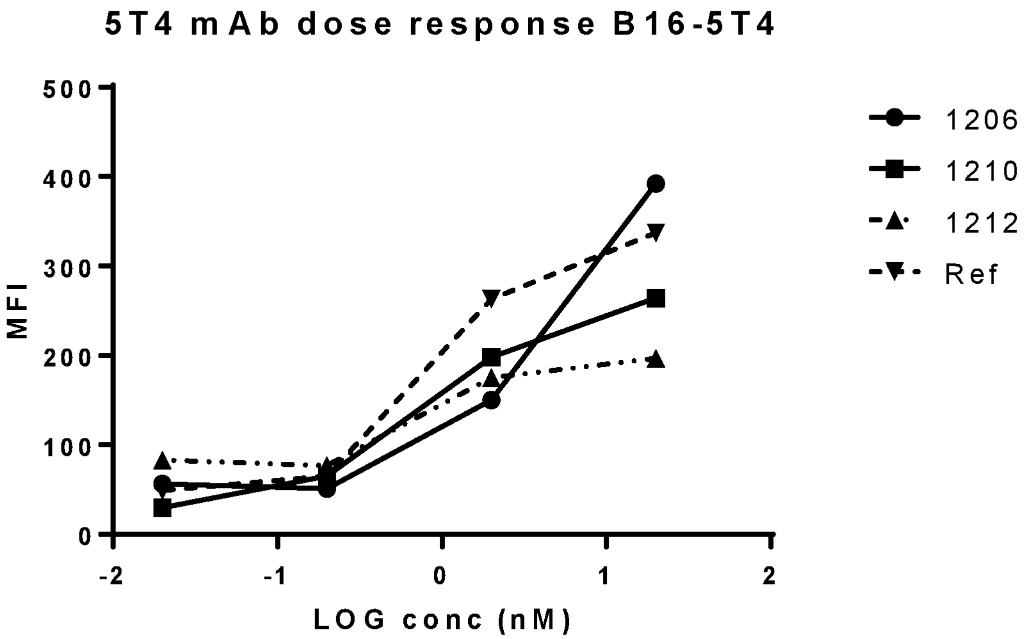
FIG. 2 shows an example of a dose-response experiment of 5T4 antibodies binding to 5T4-transfected B16 cells, analysed by flow cytometry.
Figure 3:
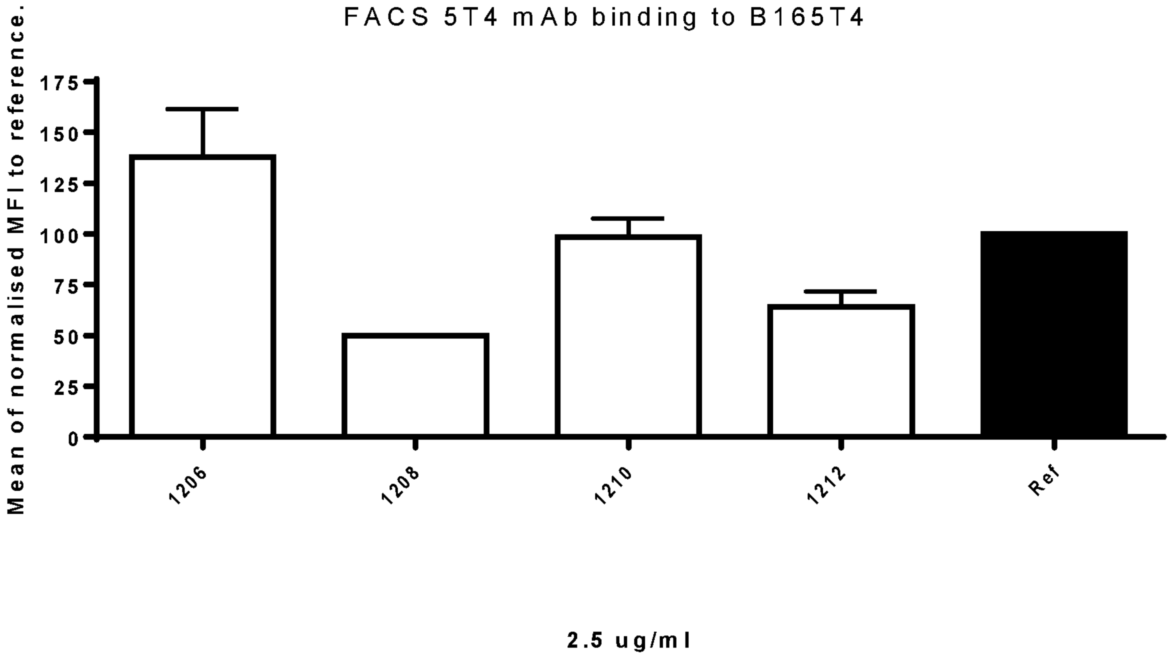
FIG. 3 shows flow cytometry data showing normalized mean fluorescence intensity (MFI) of 5T4 mAb binding at a concentration of 2.5 μg/ml to 5T4-transfected B16 cells. The figure shows the mean±SD of the pooled data from four experiments, with 1-4 data points for each antibody, as indicated in Table 2. MFI values were normalised to reference antibody 1628.

In flow cytometric analysis of 5T4 antibody binding to 5T4-transfected B16 cells, most antibodies show good binding. Large variations in EC50 values between individual experiments were observed. Therefore, results are summarized as mean EC50 in nM as well as mean EC50 normalized to the internal control 1628 (Table 2). An example of dose-response curves for binding of 5T4 mAb to 5T4-transfected B16 cells is shown in FIG. 2. In FIG. 3, normalized MFI values at a fixed concentration of 2.5 μg/ml antibody is shown. Taken together, the data indicate that most antibodies bind well to 5T4-transfected B 16 cells, with clone1208 exhibiting weaker binding.

TABLE 2

Potency of 5T4 antibodies as determined by flow cytometric analysis of 5T4-transfected B16 cells

| | EC50 (nM) | | Normalized EC50* | | |
|---|---|---|---|---|---|
| Clone | Mean | SD | Mean | SD | n |
| 1206 | 1.8 | 1.6 | 3.9 | 2.7 | 4 |
| 1208 | 0.7 | | 9.3 | | 1 |
| 1210 | 0.8 | 0.7 | 1.6 | 1.3 | 4 |
| 1212 | 1.4 | 2.2 | 1.1 | 0.3 | 4 |
| Reference 1628 | 1.1 | 1.4 | 1.0 | | 4 |

*EC50 value normalized to 1628

In a new attempt to calculate EC50 with flow cytometry a 5T4 mAb dose response experiment was performed using CHO cells stably transfected with human 5T4. A one to four titration series was performed starting from 2.5 nM. The data are summarized in Table 3.

TABLE 3

Summary of EC50 values, EC50 95% confidence intervals and EC50 normalised to 1628 in flow cytometric analysis of 5T4-transfected CHO cells. Data was normalised and the EC50 values were calculated by nonlinear regression.

| | 1206 | 1208 | 1210 | 1628 |
|---|---|---|---|---|
| EC50 nM | 0.51 | 2.07 | 0.81 | 0.51 |
| EC50 (95% confidence intervals) | 0.2 to 1.2 | 1.6. to 2.7 | 0.3 to 2.2 | 0.14 to 1.8 |
| Normalized to reference 1628 | 1.0 | 4.1 | 1.6 | 1.0 |

Finally, binding potency to 5T4-transfected A9 cells was evaluated in two individual experiments. As in the experiments performed with B16-5T4 cells, the absolute EC50 values determined in individual experiments vary, and data is therefore presented as normalized to the reference 1628 (Table 4). Results indicate that the 5T4 antibodies bind with comparable potency to the reference 1628.

TABLE 4

Potency of 5T4 antibodies as determined by flow cytometric analysis of 5T4-transfected A9 cells

| | Normalized EC50* | | |
|---|---|---|---|
| Clone | Mean | SD | n |
| 1206 | 2.9 | 1.9 | 2 |
| 1208 | 3.9 | 2.2 | 2 |
| 1210 | 1.8 | 0.2 | 2 |
| 1212 | 0.4 | — | 1 |
| 1628 | 1.0 | — | 2 |

*EC50 value normalized to reference 1628

To summarize, the binding potency of four 5T4 antibodies was evaluated by flow cytometry using three different 5T4-transfected cell lines (B16, CHO and A9). The conclusion from these studies is that all antibodies exhibit reasonable binding, with clone 1208 in general exhibiting lower potency than the other clones.

Example 4—Binding to Cynomolgus 5T4

Materials and Methods

The potency of 5T4 antibodies in binding to cynomolgus 5T4 was determined by flow cytometry. CHO cells were stably transfected with *Macaca mulatta* (cynomolgus) 5T4. Cells were stained with 5T4 antibodies diluted in FACS buffer (PBS, 0.5% BSA and 0.02% $NaN_3$) using a 1:4 titration starting at 2.5 nM. Binding was detected with the secondary antibody anti-IgG (Fc)-PE (109-115-098, Jackson ImmunoResearch Europe, UK) diluted 1:100. Samples were analysed either on a FACSCalibur or a FACSverse (BD Biosciences, Heidelberg, Germany) and mean fluorescence intensity (MFI) determined. Three experiments were performed with comparable results, although only one experiment included a full dose-response curve whereas the other two experiments included only three antibody concentrations. To compare the EC50 values between human and cynomolgus 5T4, the cy5T4/hu5T4 ratio was calculated from the experiment with the full dose-response.

Results and Conclusions

Figure 4:
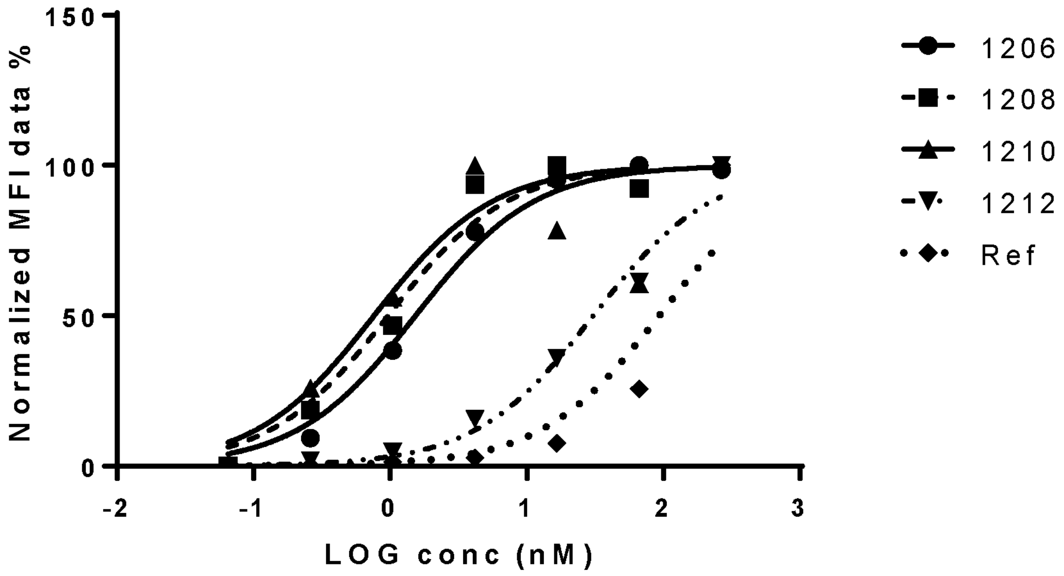
FIG. 4 shows dose-response analysis of 5T4 antibody binding to cynomolgus 5T4-transfected CHO cells.

The three experiments that were performed demonstrate good binding to cynomolgus 5T4 by clones 1206, 1208 and 1210 and weak binding by 1212 and the reference 1628 (FIG. 4, Table 5) Clone 1206 had a relatively good potency, but low efficacy. Comparison of the relative EC50 values between cynomolgus and human 5T4 for selected clones shows that clones 1206, 1208 and 1210 have a relatively high affinity for cynomolgus 5T4 whereas 1212 does not.

TABLE 5

EC50 values for cyno5T4 transfected cells and EC50 95% confidence intervals and the EC50cyno:EC50 human

| Antibody | 1206 | 1208 | 1210 | 1212 | 1628 |
|---|---|---|---|---|---|
| EC50 nM | 1.53 | 0.96 | 0.70 | 30.7 | 93.0 |
| EC50 (95% confidence intervals) | 1.1 to 2.1 | 0.5 to 1.8 | 0.3 to 1.7 | 21 to 45 | 37 to 235 |
| Ratio EC50cyno5T4/h5T4 | 3.0 | 0.5 | 0.9 | 140 | 182 |

Data were normalised and the EC50 values were calculated by nonlinear regression Example 5—Affinity Determined by Surface Plasmon Resonance Materials and Methods Binding kinetics of the 5T4-specific mAbs have been studied using two different SPR-based platforms, the Biacore 3000 (GE Healthcare) and the MASS-1 platform (Sierra Sensors). Briefly, 5T4 was captured at the sensor chip surface either via direct amine coupling (Biacore platform) or using a streptavidin coated chip and biotinylated 5T4 (MASS-1 platform). The different 5T4-specific mAbs were then injected over the chip in increasing concentrations and the association and dissociation rates studied in real time. A 1:1 Langmuir model was used for curve fitting.

Results and Conclusions

A summary of binding rate constants and affinities obtained using the two platforms is presented in Table 6. It should however be taken into consideration that the assay setup used allows for bivalent binding of the mAbs to the antigen. This will give rise to avidity effects that lead to a significant underestimation of the off-rates (kd) and thus also the affinity value (KD). The different 5T4 antibodies show different binding characteristics, with 1208 and the reference 1628 displaying very low off-rates while on-rates vary less between the binders. It is obvious that there are significant variations between the two assays, with an over 10-fold difference for 1206 and 1628. For 1628 this is likely due the difficulty in accurate curve fitting when the off-rate becomes very low (close to no dissociation).

TABLE 6

Summary of binding kinetics of 5T4-specific mAbs

| | Biacore | | | MASS-1 | | |
|---|---|---|---|---|---|---|
| Clone | ka (1/Ms) | kd (1/s) | KD (M) | ka (1/Ms) | kd (1/s) | KD (nM) |
| 1206 | 1.3E+05 | 2.8E−04 | 2.3E−09 | 1.4E+06 | 1.3E−04 | 9.7E−11 |
| 1208 | — | — | — | 2.1E+05 | 2.1E−06 | 9.8E−12 |
| 1210 | 5.0E+05 | 1.0E−04 | 2.0E−10 | 5.1E+05 | 1.9E−04 | 3.7E−10 |
| 1212 | 4.5E+05 | 8.1E−04 | 1.8E−10 | — | — | — |
| 1628 | 6.4E+05 | 2.6E−08 | 4.1E−14 | 1.5E+06 | 2.1E−06 | 1.5E−12 |

Example 6—Domain Mapping of 5T4 Antibodies

Materials and Methods

Figure 5A:
FIGS. 5A and 5B are an illustration of 5T4 chimeras used for epitope mapping of 5T4 antibodies.
Figure 5B:
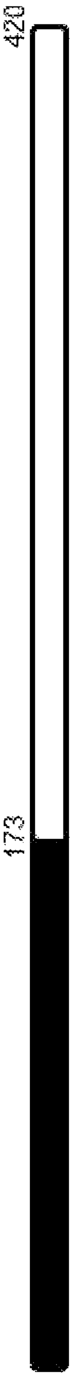

Epitope mapping was performed by investigation of loss of binding by the antibodies using a panel of human/mouse chimeric 5T4 constructs by flow cytometry. This strategy was possible since none of the 5T4 antibodies cross-react with murine 5T4. Two strategies were used for the epitope mapping as illustrated in FIG. 5. In one approach, seven human/mouse 5T4 chimeras were constructed based on dividing 5T4 into seven different domains (FIG. 5). By replacing each domain with the corresponding mouse sequence seven human/mouse 7 5T4 human/mouse chimeras were generated. The chimeras were generated using the human protein 5T4 sequence NP_006661.1 (reference mRNA sequence NM_006670.4) and the corresponding mouse sequence NP_035757.2 (reference mRNA sequence NM_011627.4). The human/mouse chimeric DNA constructs, as well as human and mouse wild-type 5T4, were cloned into pcDNA3.1 expression vectors. Stably transfected CHO cells were generated and 5T4 expressing cells enriched by MACS sorting, resulting in 60-80% positive cells. In the other approach, cells transfected with a human/mouse 5T4 chimera (Woods et al., 2002, *Biochem J* 366(1): 353-365) was used, in which mouse sequence in amino acid 173-420 replaced the human sequence (FIG. 5). As controls human 5T4 and mouse 5T4-transfected cells were used.

For flow cytometric analysis, cells were stained with different 5T4 antibodies diluted in FACS buffer (PBS, 0.5% BSA). Binding was detected with the secondary antibody anti-IgG (Fc)-PE (109-115-098, Jackson ImmunoResearch Europe, UK) diluted 1:100. Samples were analysed by FACSverse (BD Biosciences, Heidelberg, Germany) and % positive cells were determined. To compensate for variations in % 5T4 positive cells in the various transfected populations, binding levels were normalized within each chimera by dividing % positive cells for each clone with % positive cells for the clones resulting in the highest % positive cells (% pos $cells_{clonX}$/% positive $cell_{smax}$). A normalized value ≤0.75 was defined as mAb binding being dependent on the replaced region, whereas a normalized value ≤0.25 was defined as complete dependence.

Results and Conclusion

The four 5T4 antibodies were shown to be more or less dependent on at least one of domains E2, E3, E4, E6 or aa 173-420, whereas no clear dependence on E1, E5 or E7 was observed (Table 7).

All four antibodies had a distinct binding pattern:

1. Clone 1208; dependent on E2 and E4
2. Clone 1210; dependent on E2, E4 and aa173-420
3. Clone 1206; dependent on E2, E3, E4 and aa173-420
4. Clone 1212 dependent on E6 aa173-420

The reference antibody 1628 differed from all the exemplary antibodies of the invention, and was completely dependent on E4 and aa173-420.

TABLE 7

Summary of epitope mapping results summarized as normalized values for one representative experiment.

| Clone | Group | E1 | E2 | E3 | E4 | E5 | E6 | E7 | aa173-420 |
|---|---|---|---|---|---|---|---|---|---|
| 1628 | | 0.96 | 1.00 | 1.00 | **0.06** | 0.96 | 0.81 | 0.91 | **0.00** |
| 1208 | 1 | 0.95 | **0.68** | 0.96 | **0.65** | 1.00 | 0.94 | 0.99 | 1.00 |
| 1210 | 2 | 0.99 | **0.02** | 0.90 | **0.69** | 0.89 | 0.89 | 0.96 | **0.00** |

TABLE 7-continued

| Summary of epitope mapping results summarized as normalized values for one representative experiment. | | | | | | | | | |
|---|---|---|---|---|---|---|---|---|---|
| Clone | Group | E1 | E2 | E3 | E4 | E5 | E6 | E7 | aa173-420 |
| 1206 | 3 | 0.96 | **0.74** | **0.25** | **0.52** | 0.90 | 0.94 | 0.94 | **0.30** |
| 1212 | 4 | 0.89 | 0.90 | 0.93 | 1.00 | 0.84 | 0.03 | 0.88 | **−0.01** |

The experiment was repeated once for E2, E3 and E6 chimeras and three times for the E4 chimera with high reproducibility. mAbs with a normalized binding value ≤0.75 are indicated in bold.

Example 7—Selection of CD137 Antibodies from Alligator GOLD® Library

Phage display selections were performed using a human antibody (scFv) library, Alligator GOLD® (Alligator Bioscience, Lund, Sweden). Selections towards recombinant CD137 in soluble form, coated onto the surface of beads or tubes, or expressed on the surface of CD137-transfected cells were performed. CTLA4-Fc and an irrelevant His-tagged protein were used as non-targets included in excess in the selections. Prior to each selection round, the phage stocks were pre-selected towards biotinylated beriglobin, CTLA4-Fc, beads or CD137 negative cells to remove unspecific binders.

To identify specific binders from the phage selection, approximately 4500 individual clones were screened in phage format using ELISA coated with either recombinant target (CD137-Fc) or non-target (CTLA4-Fc) protein, followed by confirmation as soluble scFv for some clones. Clones exhibiting specific binding to CD137 were sequenced and unique clones were produced as IgG for further characterization.

Example 8—Binding to Human CD137 Measured by ELISA

Material and Methods

Binding of CD137 antibodies to recombinant human CD137 was determined by sandwich ELISA. Briefly, ELISA plates (Greiner #655074) coated with recombinant human CD137-Fc (R&D #838-4B) were incubated with serial dilutions of the various CD137 antibodies to be investigated. CD137 antibodies were detected using HRP-conjugated goat-anti-human kappa light chain (AbD Serotec #STAR127P) and developed with SuperSignal ELISA Pico Chemiluminescent substrate (Pierce #37069). EC50 values of the various antibodies were determined in 2-6 separate experiments.

Two different reference anti-CD137 antibodies have been used in this study, as positive controls (designated "1811/1812" and "1813/1814", both of which are available in the art).

Results and Conclusion

The majority of the antibodies exhibit EC50 values in a similar range as those of the reference antibodies, i.e. sub nM or low nM. Data are summarized in Table 8.

TABLE 8

| EC50 values (nM) of Alligator-GOLD-derived CD137 antibodies determined by ELISA for human CD137 | | | |
|---|---|---|---|
| Clone name | Mean | SD | n |
| 1811/1812 | 0.75 | 0.137 | 8 |
| 1813/1814 | 0.33 | 0.069 | 5 |
| 1200/1201 | 0.39 | 0.037 | 3 |
| 1202/1203 | 0.41 | 0.050 | 4 |
| 1204/1205 | 0.34 | 0.058 | 6 |
| 1214/1215 | 0.98 | 0.124 | 6 |
| 1618/1619 | 0.35 | 0.018 | 4 |
| 1620/1621 | 0.38 | 0.137 | 2 |
| 1626/1627 | 0.22 | 0.057 | 2 |

n = number of data points.

Example 9—Flow Cytometric Determination of Binding to Human and Cynomolgus CD137

Material and Methods

Binding and EC50 was determined using flow cytometric analysis of CHO cells transfected with human CD137, cynomolgus CD137 or empty vector. The extracellular part of human or cynomolgus CD137 was fused to the transmembrane and intracellular part of human CD40 and cloned into pcDNA3.1. The vector was subsequently stably transfected into CHO cells. Expression of CD137 was confirmed by flow cytometry using CD137 antibody (human CD137-PE, BD Biosciences #555956) for 30 min at 4° C. CD137-transfected and empty vector-transfected cells were incubated with CD137 antibodies for at least 1 h at 4° C. to saturate the binding. In order to minimize antibody internalization, 0.05% sodium azide was used in the incubation buffer and all work was performed on ice. The CD137 antibodies were detected using PE-conjugated anti-hIgG antibody (109-115-098, Jackson Immunoresearch laboratories), incubated for 30 min at 4° C. Directly after staining the cells were fixed with a paraformaldehyde solution (10× concentrate BD CellFIX, BD biosciences #340181). Cells were analyzed by flow cytometry using FACSVerse (BD Biosciences). The median fluorescence intensity (MFI) for each sample was determined and the dose response data was analysed using Graph Pad Prism.

MFI data was normalized for each antibody, where 0% is defined as the lowest value and 100% is the highest value in the dose titration for each antibody. EC50 and 95% confidence interval were calculated with Graph Pad Prism based on data from the two experiments (non-linear regression (curve fit), constraints set to 0 and 100).

Results and Conclusion

Figure 6:
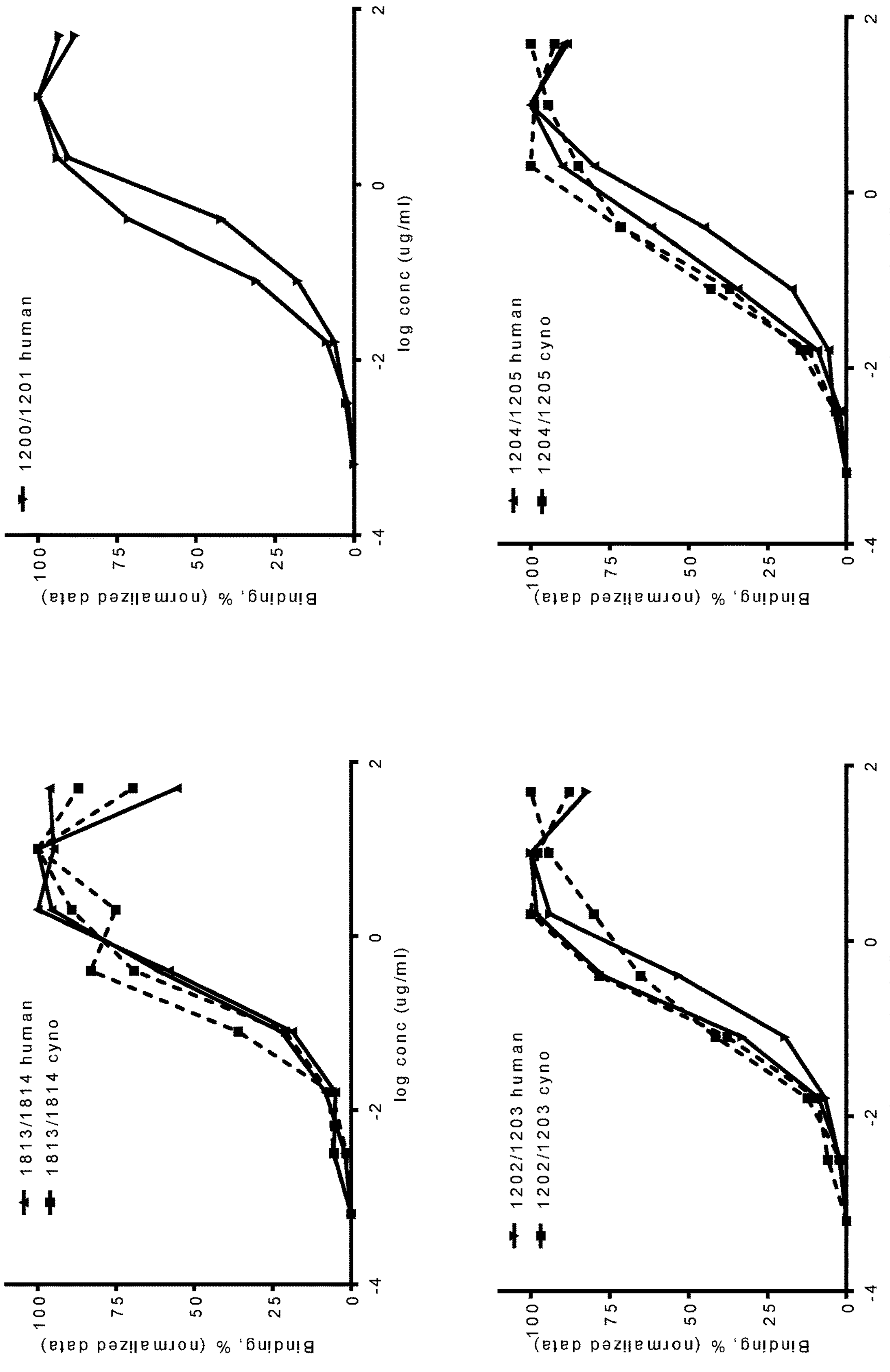
FIG. 6 shows binding of exemplary anti-CD137 antibodies to human and cynomolgus CD137. Data from two separate experiments are included.
Figure 6:
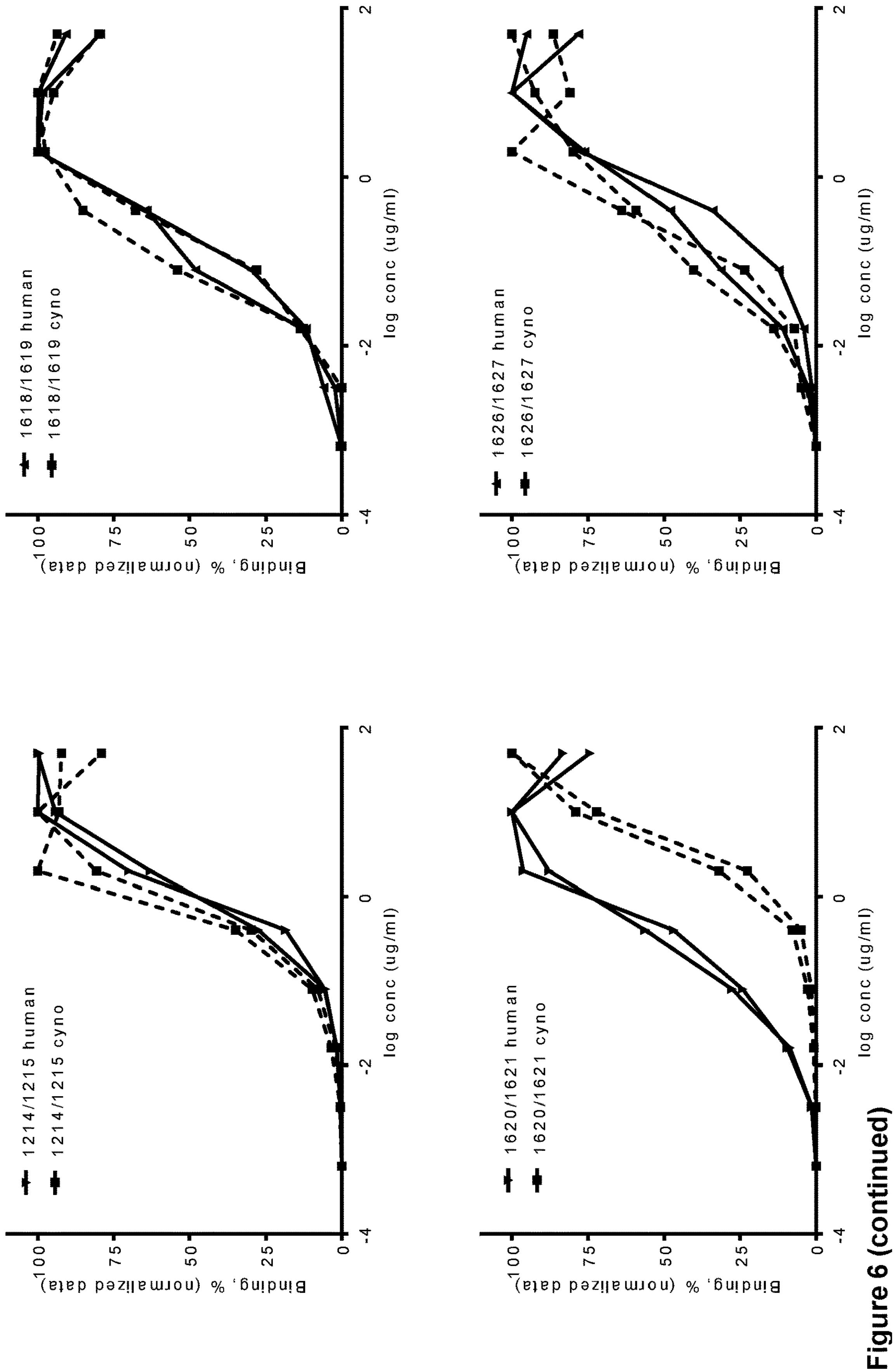

Binding to CHO-huCD137, CHO-cyCD137 and CHO-pcDNA was confirmed in two separate experiments (FIG. 6). All CD137 antibodies bind relatively well to human CD137 with EC50 comparable with the two reference antibodies 1811/1812 and 1813/1814. The majority of the CD137 antibodies tested bind well to cynomolgus CD137, except for reference antibody 1811/1812 and 1200/1201 (data not shown) which do not bind at all or very weakly, and clone 1620/1621 which binds weakly and does not reach a complete saturation. It should be noted that the maximum MFI obtained on the cynomolgus CD137 cells were 2-3 fold lower than on the human CD137 expressing cells, which indicate differences in receptor density on the cells.

The EC50 determination is presented as 95% confidence intervals for each CD137 antibody tested in order to include the inter and intra assay variations (Table 9).

TABLE 9

| 95% confidence intervals for the EC50 of each CD137 antibody determined as an average from two experiments of normalized data | | | |
|---|---|---|---|
| Clone name | Binding to human CD137, EC50 (μg/mL) | Binding to cyno CD137, EC50 (μg/mL) | Ratio, cyno:human |
| 1811/1812 | 1.00-1.99 | Nd | Nd |
| 1813/1814 | 0.21-0.31 | 0.13-0.24 | 0.69 |
| 1200/1201 | 0.20-0.36 | Nd | Nd |
| 1202/1203 | 0.16-0.27 | 0.11-0.17 | 0.67 |
| 1204/1205 | 0.23-0.39 | 0.11-0.16 | 0.43 |
| 1214/1215 | 0.89-1.28 | 0.41-0.80 | 0.54 |
| 1618/1619 | 0.11-0.19 | 0.086-0.15 | 0.77 |
| 1620/1621 | 0.20-0.42 | 3-5* | 14* |
| 1626/1627 | 0.38-0.67 | 0.16-0.27 | 0.41 |

*The estimated 95% confidence interval is likely underestimated

Nd: no data due to incomplete binding to target.

Example 10—Affinity of CD137 Antibodies Measured by Biacore

Material and Methods

Human CD137 (R&D systems) was immobilized to the Biacore™ sensor chip, CM5, using conventional amine coupling. The tested antibody and control (serially diluted ½ 10-0.63 nM) were analyzed for binding in HBS-P (GE, #BR-1003-68) at a flow rate of 30 μl/ml. The association was followed for 5 minutes and the dissociation for 15 minutes. Regeneration was performed twice using 10 mM Glycine pH 1.7 for 30 seconds. The kinetic parameters and the affinity constants were calculated using 1:1 Langmuir model.

Results and Conclusion

The affinities of the antibodies were in the nanomolar to sub-nanomolar range (Table 10) measured using bivalent antibodies flowed over CD137 coated on the chip surface.

TABLE 10

| Kinetic parameters measured by surface plasmon resonance | | | |
|---|---|---|---|
| Sample | ka (1/Ms) | kd (1/s) | KD (M) |
| 1200 | ND | ND | ND |
| 1202 | 6.76E+05 | 6.60E−04 | 9.76E−10 |
| 1204 | 2.54E+05 | 2.80E−04 | 1.10E−09 |
| 1214 | 4.54E+04 | 3.17E−05 | 6.99E−10 |
| 1618 | 1.02E+06 | 1.10E−04 | 1.07E−10 |
| 1620 | 3.92E+05 | 5.19E−04 | 1.32E−09 |
| 1626 | 2.32E+05 | 2.94E−04 | 1.27E−09 |
| 1814 | 1.05E+06 | 4.45E−04 | 4.24E−10 |

ND; not determined

Example 11—Target Specificity of the CD137 Antibodies Determined by ELISA

Material and Methods

Binding to TNFR superfamily members for which ELISA methods had already been established (CD40 and OX40) was evaluated to detect potential propensity to cross react to non-target proteins. In addition, a BLAST search was performed identifying TNFRSF21 as the most similar sequence (34% sequence identity). Since this sequence similarity is rather low, determination of non-target binding to OX40 and CD40 was considered sufficient.

ELISA plates (Greiner #655074) were coated with 50 μl/well of recombinant human OX40 (R&D #1493-CD), CD40-Fc (Ancell #504-820) or CD137 (R&D #838-4B) diluted to a final concentration of 0.5 μg/ml in PBS for 1 h at 37° C. or overnight at 4° C. Plates were washed with PBS+0.05% TWEEN20 (PBST), followed by block with PBST+1% bovine serum albumin (BSA). Antibody samples were prepared as serial 1/10 dilutions from 10-0.01 μg/ml in PBST+1% BSA and incubated for 1 h in room temperature, followed by detection using a horse radish peroxidase-conjugated anti-human kappa light chain antibody (AbD Serotec #STAR127P) and developed using SuperSignal ELISA Pico Chemiluminescent substrate (Pierce Thermo-Scientific #37069).

Results and Conclusion

The results from the two experiments were similar. One antibody (1202/1203) exhibited weak binding to OX40 and CD40, whereas none of the remaining antibody showed any detectable binding to either OX40 or CD40. An overview of antibodies analyzed, and results from the two experiments is shown in Table 11. The EC50 for 1202/1203 binding to CD137 in ELISA was determined as 0.41 nM, corresponding to approx. 0.06 μg/ml. The ELISA signal is very low even at 10 μg/ml, and the EC50 for binding to OX40 and CD40 is most likely higher than 10 μg/ml since the dilution curves have not reached a plateau.

Further, binding to primary PBL from multiple blood donors was tested. The binding to PBL was similar to Reference antibodies. No relevant unspecific binding to non-target proteins was detected.

TABLE 11

| Summary of CD137 antibody unspecific binding to OX40 and CD40 | | |
|---|---|---|
| pAb | Binding to OX40 and CD40 | EC50 CD137 |
| 1200/1201 | No | |
| 1202/1203 | Weak; EC50 > 40 nM | 0.4 nM |
| 1204/1205 | No | |
| 1214/1215 | No | |
| 1618/1619 | No | |
| 1620/1621 | No | |
| 1626/1627 | No | |

Example 12—Domain Mapping of Antibodies Binding to CD137

Material and Methods

The ability of each antibody to bind to a panel of human/mouse CD137 chimeras expressed on the surface of transfected cells was analyzed by flow cytometry.

Figure 7:
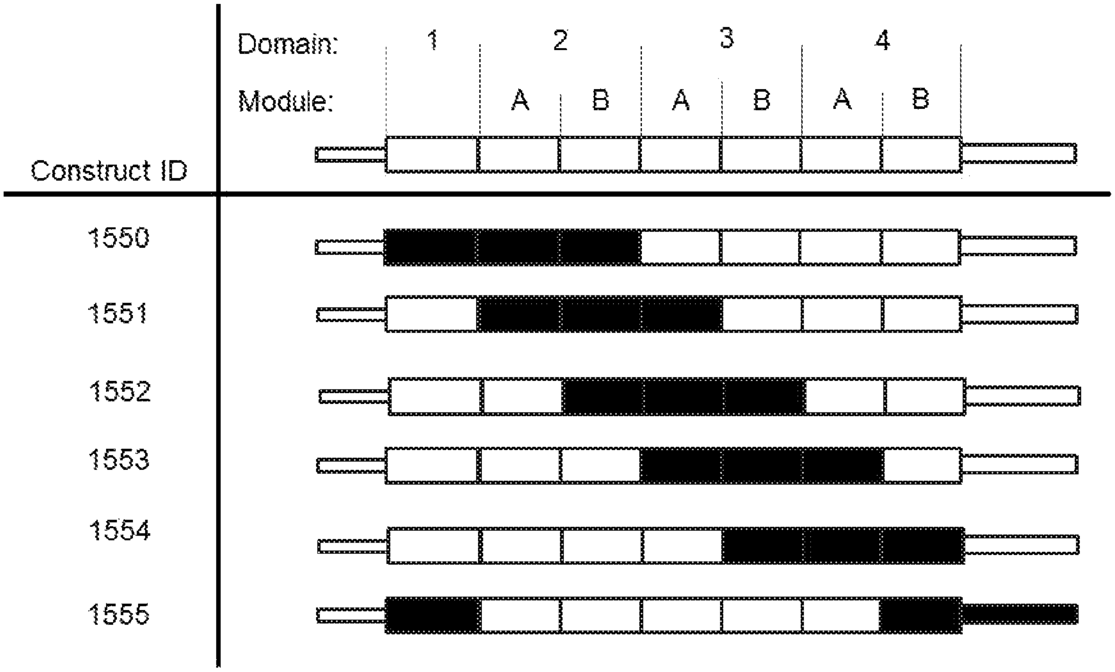
FIG. 7 shows an overview of human/mouse CD137 chimeras. Black: mouse sequence, white: human sequence.

The chimeras were designed by exchanging domains or modules of the human CD137 with the corresponding mouse domain (FIG. 7). Genes of CD137 human/mouse chimeras were synthesized (GenScript) and constructs cloned into pcDNA3.1 vector (Invitrogen) and transiently transfected into FreeStyle 293-F cells (Invitrogen). The transfected cells were incubated with CD137 antibodies and control antibodies, followed by incubation with anti-human IgG-PE (Jackson Immunoresearch) for detection and analyzed with FACS Verse (BD Biosciences). Binding to the different chimeric constructs was calculated as relative MFI compared to the binding of the isotype control, followed by normalization to the full-length human CD137 construct to minimize the effect of affinity differences between individual antibodies.

Results and Conclusion

Four binding patterns can be observed as described below. Data is summarized in Table 12.

Pattern A:

Antibodies 1811/1812 (Reference antibody) and 1618/1619 are dependent on domain 1.

Pattern B:

Antibodies 1200/1201, 1202/1203 and 1204/1205 are mainly dependent on domain 2. In addition, some loss of binding is also seen for construct 1555, indicating an impact of domain 1 as well.

Pattern C:

Antibodies 1813/1814 (Reference antibody) and 1620/1621 appear to be mainly dependent on domains 3B-4A. However, loss of binding is seen for all constructs, making this pattern quite similar to pattern D.

Pattern D:

For antibodies 1214/1215 and 1626/1627, no clear dependence on particular CD137 domains could be demonstrated. Instead, these antibodies exhibited extensive loss of binding for all chimeras. However, for 1214/1215, the results differed between the experiments (see Table 12).

TABLE 12

Median fluorescence intensity (MFI) for antibody sample/isotype control, normalized to full-length human CD137

| | Group | | | | | | | | | |
|---|---|---|---|---|---|---|---|---|---|---|
| | A | | B | | | C | | D | | |
| | Domain | | | | | | | | | |
| | 1 | | 2 | | | 3B-4A | | Unclear | | |
| | Clone | | | | | | | | | |
| | 1811 | 1618 | 1200 | 1202 | 1204 | 1813 | 1620 | 1626 | 1214 1215 | |
| | 1812 | 1619 | 1201 | 1203 | 1205 | 1814 | 1621 | 1627 | Exp 1 | Exp 2 |
| 1550 | 0.12 | 0.11 | 0.05 | 0.05 | 0.07 | 0.22 | 0.17 | 0.10 | 0.06 | 0.14 |
| 1551 | 0.41 | 0.67 | 0.04 | 0.05 | 0.11 | 0.37 | 0.33 | 0.11 | 0.07 | 0.15 |
| 1552 | 0.76 | 1.20 | 0.05 | 0.06 | 0.13 | 0.19 | 0.18 | 0.11 | 0.32 | 0.13 |
| 1553 | 1.07 | 1.24 | 0.65 | 0.65 | 0.85 | 0.17 | 0.17 | 0.14 | 0.41 | 0.15 |
| 1554 | 0.82 | 1.01 | 0.84 | 0.51 | 0.73 | 0.16 | 0.17 | 0.12 | 0.26 | 0.15 |
| 1555 | 0.11 | 0.12 | 0.24 | 0.26 | 0.28 | 0.26 | 0.32 | 0.29 | 0.30 | 0.45 |
| 1030* | 1 | 1 | 1 | 1 | 1 | 1 | 1 | 1 | 1 | 1 |

*Full-length CD137

Example 13—In Vitro Efficacy of CD137 Antibodies

Material and Methods

Agonistic activity of CD137 antibodies was evaluated in a T cell assay based on primary human CD8$^+$ T cells. Briefly, CD8$^+$ T cells were separated from human peripheral blood mononuclear cells by MACS separation (Miltenyi #130-096-495) according to the manufacturer's protocol. Cells were incubated in 96-well microtiter plates (NuncThermo Scientific #268200), pre-coated with anti-CD3 antibody (clone OKT3, Affymetrix eBioscience #16-0037) and titrated concentrations of the CD137 antibody to be tested. Following 72 or 96 hour incubation, culture medium was harvested and IFN-γ levels were determined by ELISA (BD #555142).

Each clone was analyzed in at least 6 donors and compared to the reference CD137 antibody 1811/1812 and the negative control antibody.

Due to large intra-donor variations the stimulation index (SI, fold induction by antibody compared to negative control) was determined for each sample and normalized to the stimulation index for the reference antibody 1811/1812.

Results and Conclusion

Several clones with efficacy comparable to the reference 1811/1812 were identified.

Figure 8:
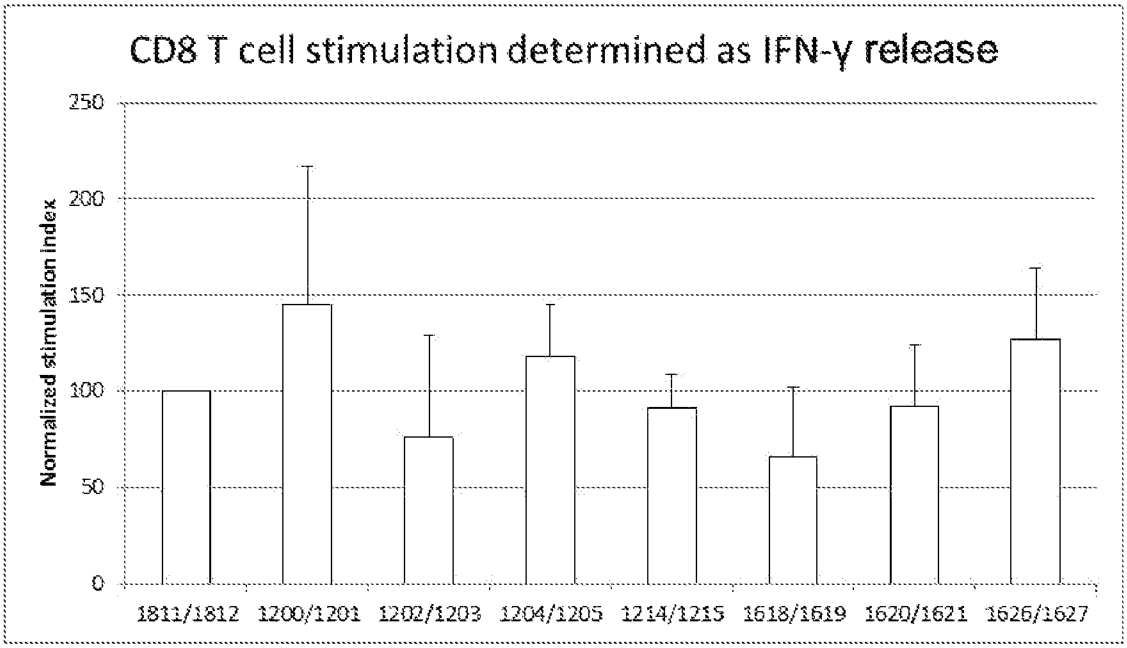
FIG. 8 shows stimulation index values normalized to reference 1811/1812.

Data are summarized in FIG. 8, which indicates the absolute IFN-γ levels induced by CD137 stimulation. However, all antibodies were not analyzed head-to-head in all donors, and the normalized SI is more relevant for comparison of the efficacy. The antibodies were evaluated in an IgG1 format, and the efficacy was measured using antibodies coated to the surface of the wells, which may influence the efficacy.

Example 14—Competitive Binding of CD137 Antibodies (Ligand Blocking)

Aim and Background

The aim was to determine if the exemplary CD137 antibodies block the CD137 ligand binding.

In the previous domain mapping experiment, the CD137 antibodies were divided in different groups based on their binding to similar subdomains of the CD137 antigen. If the CD137 antibodies bind to epitopes close to the ligand binding region, binding to the antigen can lead to partial or total blockade of ligand binding. Binding close to the CD137 ligand binding epitope may also affect the ligand binding due to steric hindrance or conformational changes of the CD137 ligand binding epitope. All CD137 antibodies were titrated against a fixed concentration of CD137L for evaluation of ligand blocking properties.

Material and Method

CHO-cells transfected with human CD137 were used for the ligand competition. The extracellular part of human CD137 was fused to the transmembrane and intracellular part of hCD40 and cloned into pcDNA3.1. The vector was subsequently stably transfected into CHO cells. The expression of CD137 was confirmed by staining with commercial antibody targeting CD137.

Figure 9:
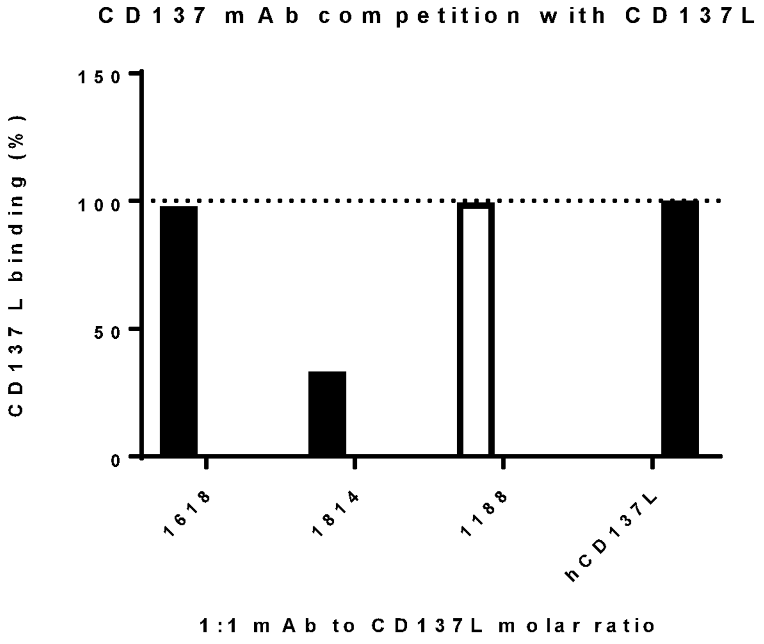
FIG. 9 shows the summary of two experiments of CD137 mAb competition with CD137L binding to CHO-huCD137 cells (25 μg/ml).

The CHO-huCD137 were pre-incubated with CD137 monoclonal antibodies, titrating down from 10:1 down to 0.01:1 molar ratio CD137 mAb (250 μg/ml) to CD137L (hCD137_CD8 Ligand) (Ancell #503-020), for 1 h at +4 C before the addition of CD137 ligand at a concentration at EC50. After co-incubation for another 30 min at +4 C, cells were washed and bound CD137 ligand was detected with αCD8a-PE (clone 53-6.7) (BD #553033) and fixed with paraformaldehyde (10× concentrate BD CellFIX, BD biosciences). Analysis was performed with FACSverse and the MFI (Median Fluorescence Intensity) was calculated with FlowJo software Results and Conclusion The CD137L blocking experiment was performed in duplicate. It can be concluded that not all CD137 mAbs tested were blocking the CD137 ligand binding (Table 13, FIG. 9). CD137 mAbs belonging to group B and C (1204 and 1620), binding to domain 2B-4A, were blocking the CD137L. Antibody 1814 also blocks the CD137L binding. 1618, belonging to group A which bound to domain 1, did not block CD137 ligand.

TABLE 13

Maximal CD137 ligand competition of the CD137 antibodies, mean out of two experiments

| Group (domain mapping) | CD137 mAb | CD137L, inhib. |
|---|---|---|
| A | 1618 | 2% |
| C | 1814 | 67% |

Example 15—Competitive Binding of CD137 Antibodies Measured by ELISA

Aim and Background

By competing the exemplary CD137 antibodies with each another, it is possible to determine antibodies binding to similar epitopes based on their blocking pattern. The competition ELISA is performed by co-incubating biotinylated CD137 antibodies with non-biotinylated CD137 antibodies when binding to coated CD137-Fc. Competition is defined as loss of signal from the biotinylated CD137 antibody. Low competition values could either be due to no competition between the antibodies or binding kinetics of the antibodies. Binding of one antibody could also lead to steric hindrance or conformational changes when binding the antigen which affects the binding of the other CD137 antibody.

Material and Methods

CD137 antibodies were biotinylated (EZ-link NHS-LC-Biotin, ThermoFisher) and intact binding properties to CD137-Fc were verified with ELISA by comparing EC50 between biotinylated and non-biotinylated anti-CD137 mAbs. Non-biotinylated anti-CD137 (anti-CD137-bio) was pre-incubated with CD137-Fc at concentrations 30 times higher than the determined EC50 for 0.5 h. Without washing, anti-CD137-bio was added and co-incubated for another 1 h. The binding of anti-CD137-bio was detected with Streptavidin-HRP (Pierce). Competition was calculated as the relative number by dividing the binding measured to other antibodies relative to its maximum competition (competing with itself). The relative values obtained were normalized against the maximum blocking capacity (Table 4).

TABLE 14

Summary of CD137 antibody competition ELISA from two experiments. Values are presented as % competition with CD137-bio.

| | Group comp ELISA | | | | | | | |
|---|---|---|---|---|---|---|---|---|
| | Pattern X | | Pattern Y | | | | | |
| | 1812 | 1618 | 1202 | 1204 | 1814 | 1620 | 1626 | 1214 |
| 1812-bio | 100 | 100 | 7 | 5 | 5 | 4 | 0 | 4 |
| 1814-bio | 15 | 21 | 41 | 74 | 94 | 61 | 57 | 99 |
| 1202-bio | 18 | 19 | 58 | 76 | 63 | 50 | 63 | 92 |
| 1214-bio | 12 | 6 | 81 | 92 | 78 | 80 | 77 | 99 |
| 1618-bio | 84 | 88 | 11 | 3 | 6 | 10 | 16 | 9 |
| 1620-bio | 4 | 7 | 49 | 93 | 100 | 82 | 79 | 100 |
| 1626-bio | 37 | 24 | 100 | 100 | 96 | 97 | 100 | 99 |
| 1204-bio | 23 | 28 | 71 | 88 | 72 | 66 | 66 | 97 |

Result and Conclusion

When normalizing the relative competition values for each antibody a competition pattern could be identified (Table 14). The antibodies 1812 and 1618 displayed a unique pattern in the competition ELISA (Pattern X). The other CD137 antibodies that were analyzed had a similar blocking pattern (Pattern Y). Differences in binding kinetics between those antibodies, may explain some of the minor variations in the binding patterns among these antibodies, although it cannot be excluded that the small variations within group Y reflects actual differences in the binding epitope.

Example 16—Crosslinking Dependency of CD137 mAbs

Material and Methods

The crosslinking dependency of CD137 antibodies was evaluated in a T cell assay based on primary human $CD8^+$ T cells. Briefly, cells were incubated in 96-well microtiter plates (NuncThermo Scientific #268200) pre-coated with anti-CD3 antibody (clone OKT3, Affymetrix eBioscience #16-0037). Titrated concentrations of CD137 antibodies in the presence and absence of crosslinking antibody, goat-anti human Fc F(ab')2 (Jackson Immuno #109-006-098) at 1:3 molar ratio were added to the plated. Following 72, culture medium was harvested and IFN-γ levels were determined by ELISA (BD #555142).

Results and Conclusion

Figure 10:
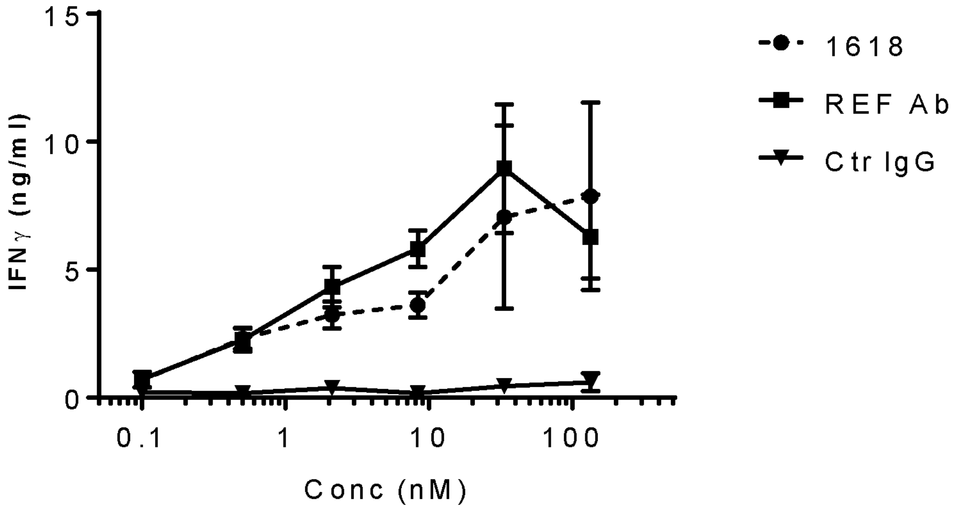
FIG. 10 shows CD137 activation in the presence of crosslinking antibody.
Figure 11:
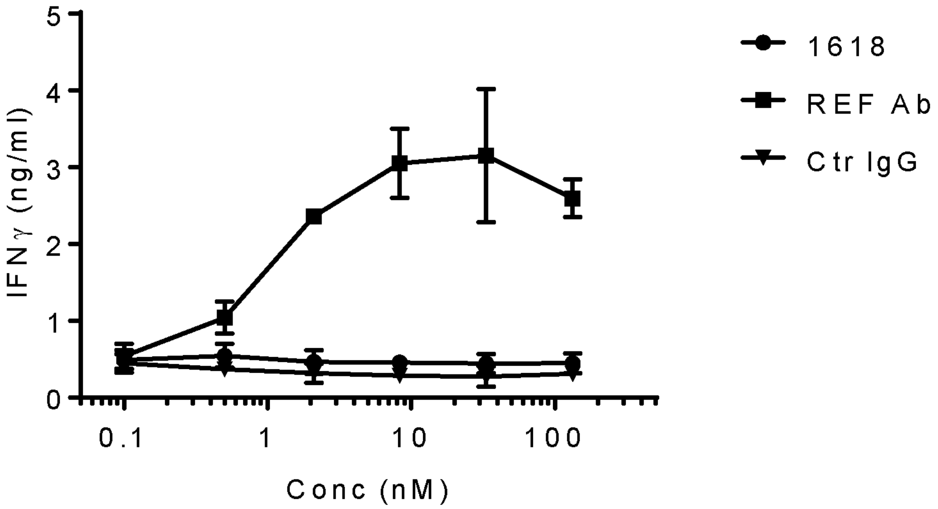
FIG. 11 shows CD137 activation in the absence of crosslinking antibody.

The results are summarised in FIG. 10 showing the CD137 activation in the presence of crosslinking antibody and FIG. 11 showing the activation in the absence of crosslinking antibody. From the results obtained it can be concluded that CD137 mAb clone 1618 is crosslinking dependent and the reference, a CD137 specific IgG4 antibody (REF Ab), is crosslinking independent, when it comes to CD137 mediated activation of CD137-expressing immune cells.

Example 17—Production of 5T4-CD137 Bispecific Antibodies

Materials and Methods

Thirty 5T4-CD137 bsAb, based on four 5T4 and eight CD137 antibodies were cloned as bsAb with one of the binding moieties cloned as a scFv and fused to the C-terminus of heavy chain of the IgG (i.e. in the Morrison format). The majority of the bsAb were clones with the 5T4 binder as scFv and the CD137 agonist as IgG, but in some constructs, a CD137 scFv was fused to the heavy chain of a 5T4 IgG (Table 15). In addition, four isotype control constructs, where either the 5T4 or the CD137 binder had been replaced with an isotype control antibody were included. bsAb were produced by transient transfection of Freestyle293 cells (Thermo Fischer) and purified by Protein A chromatography.

The bsAb designation was as follows:

First number indicates antibody clone name

Second number indicates scFv clone name

Thus, the designation "1200-1206" refers to the 5T4 binder 1206 (i.e. comprising the variable domain heavy and light chain sequences of antibody 1206/1207) in scFv format fused to the C-terminus of the Fc of the CD137 agonist antibody 1200 (i.e. comprising the variable domain heavy and light chain sequences of antibody 1200/1201).

TABLE 15

List of all 5T4-CD137 bsAb that were cloned and produced for further evaluation

| | Protein name | mAb target | mAb (clone name) | scFv target | scFv (clone name) |
|---|---|---|---|---|---|
| 1 | 1200-1206 | CD137 | 1200 | 5T4 | 1206 |
| 2 | 1200-1208 | CD137 | 1200 | 5T4 | 1208 |
| 3 | 1200-1210 | CD137 | 1200 | 5T4 | 1210 |
| 4 | 1200-1212 | CD137 | 1200 | 5T4 | 1212 |
| 5 | 1202-1206 | CD137 | 1202 | 5T4 | 1206 |
| 6 | 1202-1208 | CD137 | 1202 | 5T4 | 1208 |
| 7 | 1202-1210 | CD137 | 1202 | 5T4 | 1210 |
| 8 | 1202-1212 | CD137 | 1202 | 5T4 | 1212 |
| 9 | 1204-1206 | CD137 | 1204 | 5T4 | 1206 |
| 10 | 1204-1208 | CD137 | 1204 | 5T4 | 1208 |
| 11 | 1204-1210 | CD137 | 1204 | 5T4 | 1210 |
| 12 | 1204-1212 | CD137 | 1204 | 5T4 | 1212 |
| 13 | 1210-1202 | 5T4 | 1210 | CD137 | 1202 |
| 14 | 1210-1204 | 5T4 | 1210 | CD137 | 1204 |
| 15 | 1210-1214* | 5T4 | 1210 | CD137 | 1214 |
| 16 | 1212-1202 | 5T4 | 1212 | CD137 | 1202 |
| 17 | 1212-1204 | 5T4 | 1212 | CD137 | 1204 |
| 18 | 1212-1214 | 5T4 | 1212 | CD137 | 1214 |
| 19 | 1206-1202 | 5T4 | 1206 | CD137 | 1202 |
| 20 | 1206-1204 | 5T4 | 1206 | CD137 | 1204 |
| 21 | 1208-1202 | 5T4 | 1208 | CD137 | 1202 |
| 22 | 1208-1204 | 5T4 | 1208 | CD137 | 1204 |
| 23 | 1214-1208 | CD137 | 1214 | 5T4 | 1208 |
| 24 | 1618-1208 | CD137 | 1618 | 5T4 | 1208 |
| 25 | 1620-1208 | CD137 | 1620 | 5T4 | 1208 |
| 26 | 1626-1208 | CD137 | 1626 | 5T4 | 1208 |
| 27 | 1214-1210 | CD137 | 1214 | 5T4 | 1210 |
| 28 | 1618-1210 | CD137 | 1618 | 5T4 | 1210 |
| 29 | 1620-1210 | CD137 | 1620 | 5T4 | 1210 |
| 30 | 1626-1210 | CD137 | 1626 | 5T4 | 1210 |
| | 1862-1210 | Isotype control | 1862 | 5T4 | 1210 |
| | 1862-1212 | Isotype control | 1862 | 5T4 | 1212 |
| | 1202-1862 | CD137 | 1202 | Isotype control | 1862 |
| | 1204-1862 | CD137 | 1204 | Isotype control | 1862 |

*No expression

Example 18—Binding to Human CD137 and 5T4 by 5T4-CD137 Bispecific Antibodies Measured by ELISA

Materials and Methods

Bispecific binding to both targets, 00137 and 5T4, was evaluated using a standard ELISA protocol. Plates (#655074, Greiner Bio-One GmbH, Germany) were precoated with 0.5 μg/ml 5T4-Fc (obtained from Professor Peter Stern, University of Manchester) overnight. CD137-5T4 bsAb were diluted from 8 to $2\times10^{-3}$ μg/ml in 1:4 dilutions and added in duplicates of 50 μl to each well. CD137-bio (Ancell #502-030) was used as detection antibody at 0.5 μg/ml and the binding was detected with Streptavidin-HRP (Pierce #21126). The ELISA was developed with SuperSignal ELISA PICO Chemiluminescent substrate (Thermo Scientific Pierce, Rockford, IL USA) during 2-10 minutes and read in an automated microplate based multi-detection reader (FLUOstar OPTIMA, Netherlands).

Results and Conclusions

Figure 12:
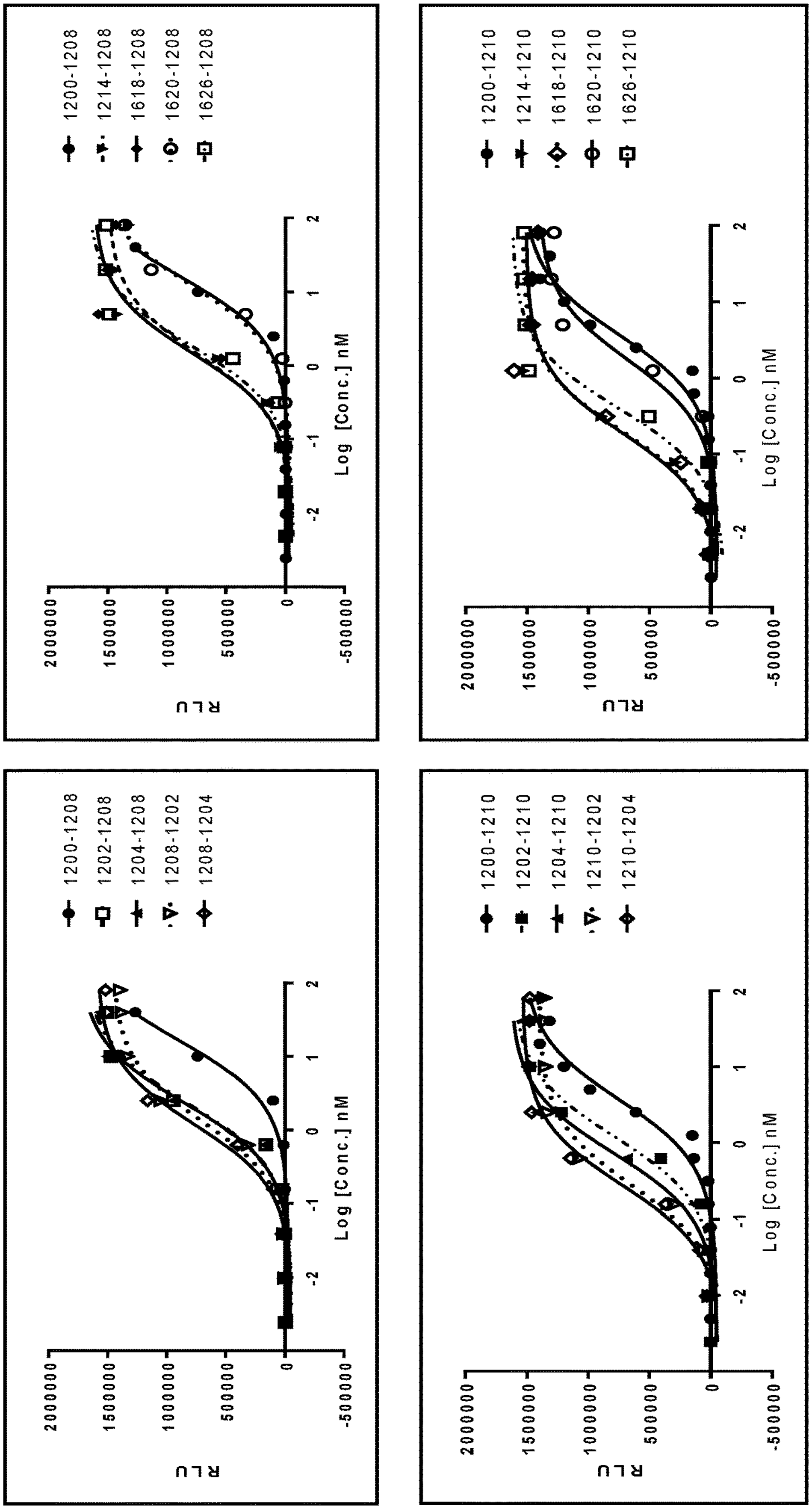
FIG. 12 shows dose-response curves in dual ELISA of 5T4-CD137 bispecific antibodies. Each graph includes data based on one 5T4 binder (1206 [i.e. 1206/1207], 1208, 1210 or 1212) combined with various CD137 agonistic antibodies (1200 [i.e. 1200/1201], 1202, 1204, 1214, 1618, 1620 or 1626).
Figure 12:
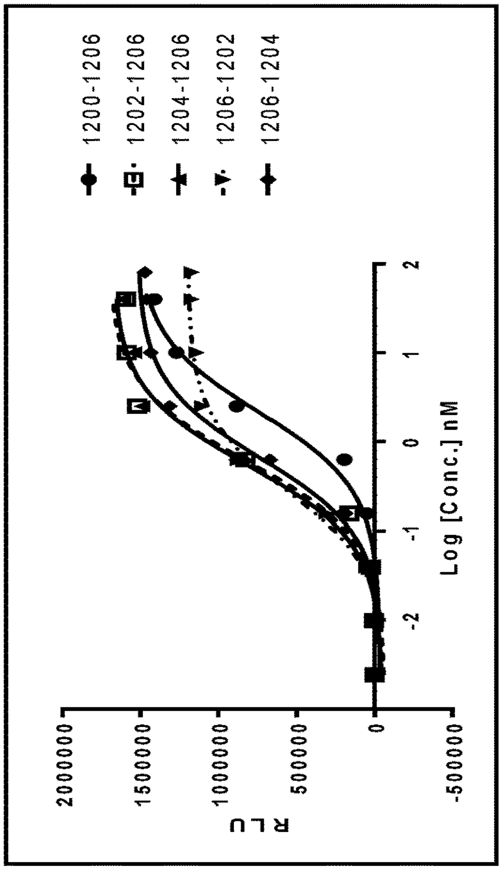
Figure 12:
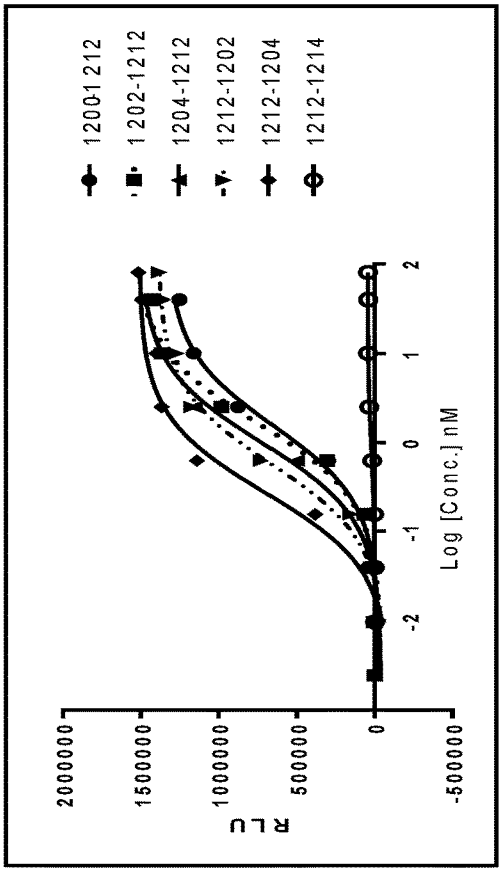

The majority of the bsAb bound to both targets in dual ELISA with EC50 values at sub- or low nM range. However, some bsAb exhibited considerably higher EC50 values, indicating poor affinity to either or both targets in this antibody—scFv combination. Dose response curves are shown in FIG. 12 and EC50 values are summarized in Table 16.

TABLE 16

EC50 values of dual binding of 5T4-CD137 bispecific antibodies

| Clone | EC50 (nM) | 95% Confidence Intervals (nM) |
|---|---|---|
| 1200-1206 | 2.17 | 1.3-3.7 |
| 1202-1206 | 0.61 | 0.3-1.2 |
| 1204-1206 | 0.54 | 0.3-0.9 |
| 1206-1202 | 0.28 | 0.2-0.4 |
| 1206-1204 | 0.66 | 0.4-1.1 |
| 1200-1208 | 16.82 | 7.9-35.8 |
| 1202-1208 | 2.25 | 1.1-4.7 |
| 1204-1208 | 2.34 | 1.2-4.6 |
| 1214-1208 | 1.40 | 0.5-4.1 |
| 1618-1208 | 1.47 | 0.4-5.2 |
| 1620-1208 | 12.70 | 5.7-28.4 |
| 1626-1208 | 1.91 | 0.6-5.9 |
| 1208-1202 | 1.32 | 0.7-2.5 |
| 1208-1204 | 1.21 | 0.7-2.1 |
| 1200-1210 | 3.73 | 2.6-5.3 |
| 1202-1210 | 1.20 | 0.6-2.4 |
| 1204-1210 | 0.73 | 0.4-1.4 |
| 1214-1210 | 0.19 | 0.1-0.5 |
| 1618-1210 | 0.20 | 0.1-0.6 |
| 1620-1210 | 1.74 | 0.7-4.1 |
| 1626-1210 | 0.40 | 0.1-1.2 |
| 1210-1202 | 0.28 | 0.1-0.6 |
| 1210-1204 | 0.28 | 0.1-0.5 |
| 1200-1212 | 1.55 | 1.0-2.3 |
| 1202-1212 | 1.67 | 1.0-2.7 |
| 1204-1212 | 1.01 | 0.6-1.6 |
| 1212-1202 | 0.57 | 0.4-0.9 |
| 1212-1204 | 0.27 | 0.2-0.5 |
| 1212-1214 | 0.79 | 0.5-1.3 |

Example 19—Affinity of CD137-5T4 Bispecific Antibodies Measured by Surface Plasmon Resonance

Materials and Methods

Binding kinetics of a selection of the CD137-5T4 bsAbs was evaluated using the SPR-based MASS-1 platform (Sierra Sensors). Briefly, CD137 or 5T4 was captured at the sensor chip surface using a streptavidin coated chip and biotinylated antigen. The different CD137-5T4 bsAbs were then injected over the chip in increasing concentrations and the association and dissociation rates studied in real time.

Results and Conclusions

A summary of the obtained binding rate constants and affinities obtained is presented in Table 17. It should be taken into consideration that the assay setup used allows for bivalent binding of the bsAbs to the antigen. This will give rise to avidity effects that lead to a significant underestimation of the off-rates (kd) and thus also the affinity value (KD). This makes comparisons to other compounds troublesome, but the obtained values are valid for comparisons within the dataset.

The results from the kinetics analysis confirm retained affinity of the CD137-specific mAb part of the bispecific molecule, while the scFv part displays reduced 5T4 affinity as compared to the parental mAb. As expected, the conformational changes induced by a flexibility reducing linker in the scFv format has a negative effect on the antigen binding affinity. In the case of 1210 this effect is only minor, while the affinity of 1208 is reduced about 6 times.

TABLE 17

Summary of binding kinetics of CD137/5T4-specific bsAbs

| bsAb | Antigen | Fit model | ka (1/Ms) | kd (1/s) | KD (M) | parental mAb KD (M) |
|---|---|---|---|---|---|---|
| 1618-1208 | CD137 | 1:1 Langmuir | 9.40E+05 | 1.09E−04 | 1.16E−10 | 1.56E−10 |
| 1618-1208 | 5T4 | 1:1 Langmuir | 7.65E+04 | 4.62E−05 | 6.01E−10 | 9.63E−11 |
| 1618-1210 | CD137 | 1:1 Langmuir | 1.26E+06 | 1.62E−04 | 1.29E−10 | 1.56E−10 |
| 1618-1210 | 5T4 | 1:1 Langmuir | 4.86E+05 | 4.55E−04 | 9.37E−10 | 4.37E−10 |

Example 20—Functional Activity of 5T4-CD137 Bispecific Antibodies on Human CD8+ T Cells Cultured in 5T4-Fc Coated Plates Materials and Methods The functional activity of 5T4-CD137 bsAb was evaluated in a CD8 T cell assay, where cells were cultured in microtiter plates coated with 5T4-Fc and CD3 antibody. Peripheral blood mononuclear cells (MNC) were isolated by density gradient centrifugation using Ficoll-Paque (p 1.077 g/ml) (GE Healthcare #17-1440-02) from leucocyte concentrates obtained from healthy donors (Clinical Immunology and Transfusion Medicine, Labmedicin Region Skane, Lund Sweden). $CD8^{+}$T cells were enriched by negative selection using the $CD8^{+}$ T cell isolation kit (Miltenyi 130-096-495). Plates were coated overnight at 4° C. with 3 μg/ml αCD3, clone OKT3 (Affymetrix eBioscience #16-0037-85), washed and coated with 5 μg/ml 5T4-Fc for 2 h at 37° C. After the 5T4-Fc coating, plates were washed and blocked for a minimum of 30 minutes with RPMI (Gibco #61870010) containing 10% FCS (Heat inactivated, Gibco #10270-106 lot 41Q9248K) and 10 mM Hepes (Gibco #15630056).

CD137-5T4 bsAbs were diluted in RPMI containing 10% FCS and 10 mM Hepes and added to the plates 30 minutes before addition of $CD8^{+}$ T cells ($0.07\times10^{6}$ cells/well). Assay plates were incubated for either 68 or 92 h at 37° C., and culture supernatant harvested. IFN-γ levels in the supernatants were measured by ELISA (BD OptiEIA #555142). Results are shown as fold change compared to CE_1200-1210, which was used as an internal control in all experiments.

Results and Conclusions

Results from the first set of bsAbs used at a fixed concentration of 1 μg/ml (FIG. 13) show that the majority of the bsAbs based on either of the 5T4 binders 1206, 1208 or 1210 were functional in the T cell assay, whereas those that were based on the 5T4 antibody 1212 were not. Data also suggest that bsAb based on CD137 clone 1202 may have lower efficacy and/or potency compared to bsAb based on CD137 clones 1204 and 1200. The agonistic effect of the 5T4-CD137 bsAb was dependent on cross-linking by 5T4, since no activation was obtained in the absence of 5T4 or using bsAb comprising one isotype control moiety.

Based on these results, a second set of bsAbs based on five new CD137 clones as IgG and the 5T4 clones 1208 and 1210 as scFv were investigated. 5T4 binders 1212 and 1206 were excluded due to poor functional activity as bsAb, and low Tm value and thus poor stability as scFv, respectively. Functional activity of all bsAb is summarized in FIG. 14.

Example 21—Functional Activity of 5T4-CD137 Bispecific Antibodies on Human CD8+ T Cells Cultured with 5T4-Expressing Tumor Cells Materials and Methods CD8 T cells were isolated as described above, and cultured in the presence of 5T4-expressing cells B16 cells. B16 cells transfected with empty vector were used as negative control. CD3 stimulation was performed with αCD3 (OKT-3) coated beads (Dynal M-450 Tosylactivated #14013) according to the manufactures protocol.

Irradiated B16 tumor cells (6000 cells/well) were added to the 96 well plates and let to attached for 2 h. CD137-5T4 bsAbs were added and incubated for 30 minutes prior to addition of $CD8^{+}$ T cells ($0.1\times10^{6}$ cells/well) and αCD3 coated beads ($0.5\times10^{5}$ beads/well). Plates were cultured for 68 or 92 h and IFN-γ levels in the media measured by ELISA (BD OptiEIA #555142).

Results and Conclusions

Results from the fully cell-based assay show that the majority of the bsAb are functional and that the effect is 5T4-specific, with no activation induced by 5T4 negative B 16 cells or isotype-CD137 bsAb (FIG. 15).

Example 22—Optimization of Affinity and Biophysical Properties of Bispecific Antibodies: Optimization of 5T4-Specific Variable Domains Material and Methods The aim of the optimization was to generate versions of the 5T4-specific 1210/1211 antibody in regards to affinity and biophysical properties. Selections were performed towards 5T4 with lead optimized library 1210LOlib1. In total, 170 unique clones were identified in the initial primary screening with good target signal as well as target/non-target ratio. These clones were further investigated in an extended primary screening with regards to temperature stability. The temperature stability evaluation showed that the majority of the identified unique clones displayed a better stability compared to the wild type 1210/1211 scFv clone. The top 96 clones were further evaluated in a dose-response ELISA and they all showed a similar and acceptable binding behaviour. Sequence analysis from the test-screening and primary screening showed similar trends.

The top 96 identified clones from the primary and the extended primary screening were further re-cloned as the scFv-part in the Morrison-format, with 1618/1619 as the monoclonal antibody (mAb) part, and were evaluated based on binding, affinity and stability.

Kinetic measurements were performed using the Octet RED96 platform equipped with Anti-human Fab-CH1 $2^{nd}$ generation sensor tips (ForteBio). Bispecific antibodies were diluted to 1.5 μg/ml in 1× kinetic buffer (ForteBio) and coupled to the biosensors. Human 5T4 (produced in-house) was diluted in 1× Kinetics Buffer to 50 nM, 10 nM and 2 nM. Binding kinetics were studied in 1× Kinetics buffer where association was allowed for 300 sec followed by dissociation for 600 sec. Sensor tips were regenerated using 10 mM glycine, pH 2.2. Data generated were referenced by subtracting a parallel buffer blank, the baseline was aligned with the y-axis, inter-step correlation by alignment against dissociation was performed and the data were smoothed by a Savitzky-Golay filter in the data analysis software (v.9.0.0.14). The processed data were fitted using a 1:1 *Langmuir* binding model with $X^2$ as a measurement of fitting accuracy.

Results and Conclusions

The data are summarised in Table 18. Overall, the lead optimized variants behaved very similarly in the EC50 evaluation in ELISA. The affinity evaluation showed that the affinity (KD) had been improved between 3 to more than 10 times compared to the wild type 1618-1210 clone. The EC50 evaluation on cells also showed similar behaviour of the different optimized variants and all showed an improved performance compared to the wild type 1618-1210 clone. In regards to stability, the top performing clones show less than 10% aggregation after protein A purification and have a Tm higher than the Tm of the Fc (>70° C.) as measured by HPLC and DSF respectively.

ratio. These clones were further investigated in an extended primary screening with regards to temperature stability. The temperature stability evaluation allowed for identification of the best performing unique clones in regards to temperature stability compared to the wild type 1618/1619 scFv clone. The top 50 clones were further evaluated in a dose-response ELISA and they all showed a similar and acceptable binding behaviour. Sequence analysis from the test-screening and primary screening showed similar trends.

The top 50 identified clones from the primary and the extended primary screening were further re-cloned as the scFv-part in the Morrison-format, with 1210/1211 as the monoclonal antibody (mAb) part, and were evaluated based on binding, affinity and stability.

Kinetic measurements were performed using the Octet RED96 platform equipped with Anti-human Fab-CH1 $2^{nd}$ generation sensor tips (ForteBio). Bispecific antibodies were diluted to 1.5 μg/ml in 1× kinetic buffer (ForteBio) and coupled to the biosensors. Human CD137-Fc (R&D Systems, #838-4B) was diluted in 1× Kinetics Buffer to 50 nM, 10 nM and 2 nM. Binding kinetics were studied in 1× Kinetics buffer where association was allowed for 300 sec followed by dissociation for 600 sec. Sensor tips were regenerated using 10 mM glycine, pH 2.2. Data generated were referenced by subtracting a parallel buffer blank, the baseline was aligned with the y-axis, inter-step correlation by alignment against dissociation was performed and the data were smoothed by a Savitzky-Golay filter in the data analysis software (v.9.0.0.14). The processed data were fitted using a 1:1 Langmuir binding model with $X^2$ as a measurement of fitting accuracy.

TABLE 18

Summary of affinity measurements of optimized 5T4-specific variable domains

| Antibody name | Composition of construct (amino acid sequences) A (VH of B1) | B (VL of B1) | C (VH of B2) | D (VL of B2) | Connector* | Additional alteration* | Affinity measurements Octet (5T4) KD (M) | kon(1/Ms) | kdis(1/s) |
|---|---|---|---|---|---|---|---|---|---|
| 1618-1210LO1 | 1618 | 1619 | 2992 | 2993 | m6 | m2 | 1.47E−10 | 2.23E+05 | 3.29E−05 |
| 1618-1210LO2 | 1618 | 1619 | 2994 | 2995 | m6 | m2 | 2.70E−10 | 1.67E+05 | 4.50E−05 |
| 1618-1210LO3 | 1618 | 1619 | 2996 | 2997 | m6 | m2 | 3.49E−10 | 2.12E+05 | 7.40E−05 |
| 1618-1210LO4 | 1618 | 1619 | 2998 | 2999 | m6 | m2 | 3.82E−10 | 2.02E+05 | 7.73E−05 |
| 1618-1210LO5 | 1618 | 1619 | 3000 | 3001 | m6 | m2 | 4.67E−10 | 1.64E+05 | 7.65E−05 |
| 1618-1210LO6 | 1618 | 1619 | 3002 | 3003 | m6 | m2 | 4.69E−10 | 2.27E+05 | 1.06E−04 |
| 1618-1210LO7 | 1618 | 1619 | 3004 | 3005 | m6 | m2 | 4.95E−10 | 1.68E+05 | 8.29E−05 |
| 1618-1210LO8 | 1618 | 1619 | 3006 | 3007 | m6 | m2 | 4.98E−10 | 1.77E+05 | 8.83E−05 |
| 1618-1210LO9 | 1618 | 1619 | 3008 | 3009 | m6 | m2 | 5.34E−10 | 2.35E+05 | 1.25E−04 |

*see Table D(5) and D(6) for details

Example 23—Optimization of Affinity and Biophysical Properties of Bispecific Antibodies: Optimization of CD137-Specific Variable Domains Material and Methods The aim of the optimization was to generate versions of the CD137-specific 1618/1619 antibody in regards to affinity and biophysical properties. Selections were performed towards CD137 with lead optimized library 1618LOlib1. In total, 153 unique clones were identified in the initial primary screening with good target signal as well as target/non-target Results and Conclusions The data are summarised in Table 19. Overall, the lead optimized variants behaved very similarly in the EC50 evaluation in ELISA. The affinity evaluation showed that the affinity (KD) were comparable to the wild type 1210-1618 clone. The EC50 evaluation on cells also showed similar behaviour of the different optimized variants. In regards to stability, the top performing clones show less than 6% aggregation after protein A purification and have a Tm between 54° C.-59° C. as measured by HPLC and DSF respectively.

TABLE 19

Summary of affinity measurements of optimized CD137-specific variable domains

| Antibody name | Composition of construct (amino acid sequences) A (VH of B1) | B (VL of B1) | C (VH of B2) | D (VL of B2) | Connector* | Additional alteration* | Affinity measurements Octet (CD137) KD (M) | kon(1/Ms) | kdis(1/s) |
|---|---|---|---|---|---|---|---|---|---|
| 1210-1618LO1 | 1210 | 1211 | 3012 | 3013 | m6 | m2 | 1.58E−09 | 2.18E+05 | 3.44E−04 |
| 1210-1618LO2 | 1210 | 1211 | 3014 | 3015 | m6 | m2 | 1.64E−09 | 2.81E+05 | 4.61E−04 |
| 1210-1618LO3 | 1210 | 1211 | 3016 | 3017 | m6 | m2 | 1.90E−09 | 3.45E+05 | 6.54E−04 |
| 1210-1618LO4 | 1210 | 1211 | 3018 | 3019 | m6 | m2 | 2.38E−09 | 2.89E+05 | 6.87E−04 |
| 1210-1618LO5 | 1210 | 1211 | 3020 | 3021 | m6 | m2 | 2.56E−09 | 2.62E+05 | 6.72E−04 |
| 1210-1618LO6 | 1210 | 1211 | 3022 | 3023 | m6 | m2 | 2.57E−09 | 2.99E+05 | 7.68E−04 |
| 1210-1618LO7 | 1210 | 1211 | 3024 | 3025 | m6 | m2 | 2.86E−09 | 2.85E+05 | 8.14E−04 |
| 1210-1618LO8 | 1210 | 1211 | 3026 | 3027 | m6 | m2 | 2.98E−09 | 2.19E+05 | 6.53E−04 |
| 1210-1618LO9 | 1210 | 1211 | 3028 | 3029 | m6 | m2 | 3.24E−09 | 3.32E+05 | 1.08E−03 |
| 1210-1618LO10 | 1210 | 1211 | 3030 | 3031 | m6 | m2 | 3.38E−09 | 2.80E+05 | 9.48E−04 |
| 1210-1618LO11 | 1210 | 1211 | 3032 | 3033 | m6 | m2 | 3.66E−09 | 2.89E+05 | 1.06E−03 |
| 1210-1618LO12 | 1210 | 1211 | 3034 | 3035 | m6 | m2 | 2.38E−09 | 3.83E+05 | 9.11E−04 |
| 1210-1618LO13 | 1210 | 1211 | 3036 | 3037 | m6 | m2 | 2.82E−09 | 3.52E+05 | 9.95E−04 |

*see Table D(5) and D(6) for details

Example 24—Optimization of Affinity and Biophysical Properties of Bispecific Antibodies: Dual ELISA Analysis of Optimized Bispecific Antibodies Material and Methods Optimized bispecific antibodies with improved biophysical properties were obtained using different strategies including combining lead optimized binding domains and the use of additional mutations and connectors.

The bispecific antibody in this example is an IgG-scFv bispecific antibody. The CD137 binding domain is an intact IgG and the 5T4 binding domain is an scFv attached to the C-terminus of a heavy chain of the IgG. The bispecific antibodies comprise for example the following components: (1) Two heavy chains each comprising, in order from the N-terminus to the C terminus: [a VH sequence; A in Table 20]-[an H chain constant region of IgG1 subtype with no mutations unless stated by an mX suffix in Table 20]-[an m6, m15, m16 or m17 connector]-[a scFv, wherein the variable chains (heavy or light) are ordered from the N-terminus to the C terminus so that chain C in Table 20 is followed by a linker and then followed by Chain D in Table 20]; and (2) Two light chains each comprising, in order from the N-terminus to the C terminus: [a VL sequence; B in Table 20]-[an L chain constant region].

The scFv for some of the bispecific antibodies in this example carry recombinant N-glycosylation sites placed either in the Optimized bispecific antibody encoding genes were designed in house and synthesized at GeneArt (Thermo Fisher, Life Technologies) or generated by standard cloning methods into expression vectors. Bispecific antibodies were produced by transient transfection of Expi293™ (Thermo Fischer Scientific) and purified by Protein A chromatography. Bispecific binding to both targets, CD137 and 5T4, was evaluated using a standard ELISA protocol. Plates (#655074, Greiner Bio-One GmbH, Germany) were pre-coated with 0.5 μg/ml 5T4-Fc (obtained from Professor Peter Stern, University of Manchester) overnight. CD137-5T4 bsAb were diluted from 8 to $2\times10^3$ μg/ml in 1:4 dilutions and added in duplicates of 50 μl to each well. CD137-bio (Ancell #502-030) was used as detection antibody at 0.5 μg/ml and the binding was detected with Streptavidin-HRP (Pierce #21126). The ELISA was developed with SuperSignal ELISA PICO Chemiluminescent substrate (Thermo Scientific Pierce, Rockford, IL USA) during 2-10 minutes and read in an automated microplate based multi-detection reader (FLUOstar OPTIMA, Netherlands).

Results and Conclusions

The data are summarised in Table 20. The optimized bispecific antibodies, consisting of lead optimized CD137 binding domains and/or lead optimized 5T4 binding domains and/or stabilised bispecific antibodies using novel connectors and/or additional stabilising strategies including reversed heavy and light chain order or N-glycosylation sites, display dual binding for both targets, CD137 and 5T4. Binding domains with improved binding such as for example 1210LO1 and 1210LO2 provide improved dual binding as observed as lower EC50 values compared to bispecific antibodies comprising non-optimized 1210 binding domains.

TABLE 20

Summary of Dual ELISA measurements of optimized CD137/5T4-specific bsAbs

| Antibody name | Composition of construct (amino acid sequence) A (VH of B1) | B (VL of B1) | C (VH of B2) | D (VL of B2) | Connector* | Additional alteration* | EC50 Dual ELISA |
|---|---|---|---|---|---|---|---|
| 1618LO1-1210LO1 | 3012 | 3013 | 2992 | 2993 | m6 | m2 | 0.5 |
| 1618LO1-1210LO2 | 3012 | 3013 | 2994 | 2995 | m6 | m2 | 0.5 |

TABLE 20-continued

Summary of Dual ELISA measurements of optimized CD137/5T4-specific bsAbs

| Antibody name | Composition of construct (amino acid sequence) A (VH of B1) | B (VL of B1) | C (VH of B2) | D (VL of B2) | Connector* | Additional alteration* | EC50 Dual ELISA |
|---|---|---|---|---|---|---|---|
| 1618LO3-1210LO1 | 3016 | 3017 | 2992 | 2993 | m6 | m2 | 0.5 |
| 1618LO3-1210LO2 | 3016 | 3017 | 2994 | 2995 | m6 | m2 | 0.4 |
| 1618LO3-1210 | 3016 | 3017 | 1210 | 1211 | m6 | m2 | 0.9 |
| 1618LO11-1210LO1 | 3032 | 3033 | 2992 | 2993 | m6 | m2 | 0.5 |
| 1618LO11-1210LO2 | 3032 | 3033 | 2994 | 2995 | m6 | m2 | 0.6 |
| 1618LO11-1210 | 3032 | 3033 | 1210 | 1211 | m6 | m2 | 1.1 |
| 1210-1618.m2.m15 | 1210 | 1211 | 1618 | 1619 | m15 | m2 | 0.4 |
| 1210-1618.m2.m16 | 1210 | 1211 | 1618 | 1619 | m16 | m2 | 0.4 |
| 1210-1618.m2.m7.m15 | 1210 | 1211 | 1619 | 1618 | m15 | m2 | 0.7 |
| 1210-1618.m2.m7.m17 | 1210 | 1211 | 1619 | 1618 | m17 | m2 | 0.6 |
| 1210-1618.m2.m7.m18 | 1210 | 1211 | 1619 | 1618 | m18 | m2 | 0.4 |
| 1618-1210.m2.m15 | 1618 | 1619 | 1210 | 1211 | m15 | m2 | 0.5 |
| 1618-1210.m2.m16 | 1618 | 1619 | 1210 | 1211 | m16 | m2 | 0.5 |
| 1618-1210.m2.m17 | 1618 | 1619 | 1210 | 1211 | m17 | m2 | 0.5 |
| 1618-1210.m2.m7.m15 | 1618 | 1619 | 1211 | 1210 | m15 | m2 | 5.3 |
| 1618-1210.m2.m7.m16 | 1618 | 1619 | 1211 | 1210 | m16 | m2 | 3.7 |
| 1618-1210.m2.m7.m17 | 1618 | 1619 | 1211 | 1210 | m17 | m2 | 1.2 |
| 1618-1210.m2.m7.m18 | 1618 | 1619 | 1211 | 1210 | m18 | m2 | 2.6 |
| 1618-1210.m2.m6.m19 | 1618 | 1619 | 1210 | 1211 | m6 | m2, m19 | 0.4 |
| 1618-1210.m2.m6.m20 | 1618 | 1619 | 1210 | 1211 | m6 | m2, m20 | 0.4 |

*see Table D(5) and D(6) for details

Example 25—Binding of Lead Optimised 5T4 Clones to Cells Expressing 5T4, Measured by Flow Cytometry Materials and Methods Analysis of 5T4 mAb binding with flow cytometry was performed using human and *Macaca* mulatta (cynomolgus) 5T4-transfected CHO-K cell lines and as negative control, mock transfected cells. Cells were stained with 5T4 lead optimised clones (scFv in bsAb format) diluted in FACS buffer (PBS, 0.5% BSA and 0.02% $NaN_3$). Binding was detected with the secondary antibody anti-IgG (Fc)-PE (109-115-098, Jackson ImmunoResearch Europe, UK) diluted 1:100. Samples were run on a FACSverse (BD Biosciences, Heidelberg, Germany) and mean fluorescence intensity (MFI) was determined using the FlowJo software.

ELISA was performed using a standard protocol. Plates (#655074, Greiner Bio-One GmbH, Germany) were pre-coated with 0.5 μg/ml 5T4-Fc (produced in-house) overnight. 5T4 antibodies were diluted in PBST+1% BSA and 50 μl was added to each well. Binding was detected with anti-human kappa light chain antibody (AbD Serotec #STAR127P) and the ELISA was developed with SuperSignal ELISA PICO Chemiluminescent substrate (Thermo Scientific Pierce, Rockford, IL USA) for 2-10 minutes and read in an automated microplate based multi-detection reader (FLUOstar OPTIMA, Netherlands).

Results and Conclusions

Binding curves for CHOh5T4 and CHOcyno5T4 cells can be seen in FIG. 16 (A and B). All the lead optimized variants have similar binding potency towards both human and cyno 5T4 expressing cells as well as towards human 5T4 measured with ELISA compared to the original antibody. The lead optimized variants have an improved affinity for both human and cyno 5T4 as measured with both ELISA and FACS.

Example 26—Binding of Lead Optimised CD137 Clones to Cells Expressing CD137, Measured by Flow Cytometry Material and Methods Analysis of CD137 mAb binding with flow cytometry was performed using human and cyno CD137-transfected CHO-K cell lines and as negative control, mock transfected cells. Cells were stained with CD137 lead optimised clones (as scFv in bsAb format) diluted in FACS buffer (PBS, 0.5% BSA and 0.02% $NaN_3$). Binding was detected with the secondary antibody anti-IgG (Fc)-PE (109-115-098, Jackson ImmunoResearch Europe, UK) diluted 1:100. Samples were run on a FACSverse (BD Biosciences, Heidelberg, Germany) and mean fluorescence intensity (MFI) was determined using the FlowJo software.

ELISA plates (Greiner #655074) were coated with 50 μl/well of recombinant CD137 (R&D #838-4B) diluted to a final concentration of 0.5 μg/ml in PBS for 1 h at 37° C. or overnight at 4° C. Plates were washed with PBS+0.05% TWEEN20 (PBST), followed by block with PBST+1% bovine serum albumin (BSA). Antibody samples were diluted in PBST+1% BSA and incubated for 1 h in room temperature, followed by detection using a horse radish peroxidase-conjugated anti-human kappa light chain antibody (AbD Serotec #STAR127P) and developed using SuperSignal ELISA Pico Chemiluminescent substrate (Pierce ThermoScientific #37069).

Results and Conclusions

Binding curves of the bispecific antibodies to CHOhCD137 and CHOcynoCD137 cells can be seen in FIG. 17 (A and B).

The EC50 values are comparable to the wild type 1210-1618 (1618 as scFv) clone for both human and cyno CD137.

Example 27—In Vitro Activity of Lead Optimised 5T4-CD137 (1618-1210) Bispecific Antibodies in an IFNγ Release Assay Using Human CD8+ T Cells on 5T4 Coated Plates Material and Methods The functional activity of the 5T4-CD137 bsAb was evaluated in a CD8+ T cell assay, where cells were cultured in microtiter plates coated with 5T4-Fc and CD3 antibody. Peripheral blood mononuclear cells (MNC) were isolated by density gradient centrifugation using Ficoll-Paque (ρ 1.077 g/ml) (GE Healthcare #17-1440-02) from leucocyte concentrates obtained from healthy donors (Clinical Immunology and Transfusion Medicine, Labmedicin Region Skane, Lund Sweden). CD8+ T cells were enriched by negative selection using the CD8+ T cell isolation kit (Miltenyi 130-096-495). Plates were coated overnight at 4° C. with 3 μg/ml αCD3, clone OKT3 (Affymetrix eBioscience #16-0037-85), washed and coated with 5 μg/ml 5T4-Fc for 2 h at 37° C. After the 5T4-Fc coating, plates were washed and blocked for a minimum of 30 minutes with RPMI (Gibco #61870010) containing 10% FCS (Heat inactivated, Gibco #10270-106 lot 41Q9248K) and 10 mM Hepes (Gibco #15630056). 1618-1210 bsAb was diluted in RPMI containing 10% FCS and 10 mM Hepes and added to the plates 30 minutes before addition of CD8+ T cells ($0.07\times10^6$ cells/well). Assay plates were incubated for 68 h at 37° C., and culture supernatant harvested. IFN-γ levels in the supernatants were measured by ELISA (BD OptiEIA #555142).

Results and Conclusions

The potency of the 1618-1210 bsAb was determined to EC50 0.6-0.9 nM using human CD8+ T cells cultured in 5T4-Fc coated plates and was based on two experiments and a total of six donors. The data were normalised and the EC50 was determined using a three-parameter sigmoidal dose-response model (FIG. 18).

Bispecific antibodies variants with optimized variable domains of 1618-1619 and 1210-1211 were generated as outlined in Table D, Table E, Table 18, Table 19 and Table 20. The generated bsAbs variants with optimized variable sequences were functional in the CD8+ T cell assay with crosslinked 5T4-Fc as seen in FIG. 19. To correlate the results from the different assay plates the calculated IFNγ levels were normalised to a plate reference.

Bispecific antibodies were also generated with different linkers as outlined in the Table D, Table E and Table 20, and were evaluated in the CD8 T cell assay. As shown in FIG. 20 the generated bsAbs could induce a CD137 activation only in the presence of the tumour antigen. As in previous FIG. 19, the obtained IFNγ values were normalised to a positive control in the plate.

Example 28—In Vitro Activity of Lead Optimised 5T4-CD137 (1618-1210) Bispecific Antibodies in an IFNγ Release Assay Using Human CD8+ T Cells Cultured with 5T4-Expressing Tumor Cells (B16-5T4)

Material and Methods

CD8+ T cells were isolated as described above, and cultured in the presence of tumour associated antigen (TAA) 5T4-expressing cells B16 cells. B16 cells transfected with empty vector were used as negative control. CD3 stimulation was performed with αCD3 (OKT3) coated beads (Dynal M-450 Tosylactivated #14013) according to the manufacturer's protocol.

Irradiated B16 tumour cells (6000 cells/well) were added to the 96 well plates and left to attach for 2 hours. CD137-5T4 bsAbs were added and incubated for 30 minutes prior to addition of CD8+ T cells ($0.1\times10^6$ cells/well) and αCD3 coated beads ($0.5\times10^5$ beads/well). Plates were cultured for 68 hours and IFN-γ levels in the media were measured by ELISA (BD OptiEIA #555142).

Results and Conclusions

The bispecific antibody 1618-1210 induced IFNγ production in CD8+ T cells in a dose dependent manner when cultured on cells expressing 5T4 (TAA), but not when cultured on cells that do not express 5T4. The results further confirm that CD137-TAA antibodies stimulate T cells only in the presence of tumour antigens. The potency of 1618-1210 bsAb was determined to EC50 0.2-0.7 nM in the CD8+ T cell assay performed with B16-5T4 expressing tumour cells. The EC50 was based on the normalised data from two donors and determined by using a three-parameter sigmoidal dose-response model (FIG. 21).

Example 29—In Vitro Activity of Lead Optimised 5T4-CD137 (1618-1210) Bispecific Antibodies in an IFNγ Release Assay Using Human PBMCs Cultured in 5T4-Fc Coated Plates Material and Methods The functional activity of 5T4-CD137 bsAb was evaluated in a PBMC assay, where cells were cultured in microtiter plates coated with 5T4-Fc antibody. Peripheral blood mononuclear cells (PBMC) were isolated by density gradient centrifugation using Ficoll-Paque (p 1.077 g/ml) (GE Healthcare #17-1440-02) from leucocyte concentrates obtained from healthy donors (Clinical Immunology and Transfusion Medicine, Labmedicin Region Skane, Lund Sweden). CD8+ T cells were enriched by negative selection using the CD8+ T cell isolation kit (Miltenyi 130-096-495). Plates were coated with 5 μg/ml 5T4-Fc for 2 h at 37° C. After the 5T4-Fc coating, plates were washed and blocked for a minimum of 30 minutes with RPMI (Gibco #61870010) containing 10% FCS (Heat inactivated, Gibco #10270-106 lot 41Q9248K) and 10 mM Hepes (Gibco #15630056).

1618-1210 bsAb were diluted in RPMI containing 10% FCS and 10 mM Hepes and added to the plates 30 minutes before addition of CD8+ T cells ($0.1\times10^6$ cells/well). CD3 stimulation was performed with 1 μg/ml soluble αCD3. Assay plates were incubated for 68 hours at 37° C., and culture supernatant harvested. IFN-γ levels in the supernatants were measured by ELISA (BD OptiEIA #555142).

Results and Conclusions

The results shown in FIG. 22 demonstrate that the bispecific antibody 1618-1210.m2 induced a TAA (5T4)-dependent CD137 mediated activation of PBMCs. No activation of PBMCs was detected without 5T4 present in the assay.

Example 30—In Vitro Activity of Lead Optimised 5T4-CD137 Bispecific Antibodies in an IFNγ Release Assay Using Human CD8+ T Cells Cultured with CD32 (FcγRII)-Expressing L Cells Material and Methods CD8 T cells were isolated as described above, and cultured in the presence of CD32-expressing L cells. CD3 stimulation was performed with αCD3 (OKT3) coated beads (Dynal M-450 Tosylactivated #14013) according to the manufacturer's protocol.

Irradiated CD32 L cells (10000 cells/well) were added to the 96 well plates and left to attach for 2 hours. CD137 (1618) mAb with and without the LALA mutation was added and incubated for 30 minutes prior to addition of CD8+ T cells ($0.1\times10^6$ cells/well) and αCD3 coated beads ($0.5\times10^5$ beads/well). Plates were cultured for 68 hours and IFN-γ levels in the media were measured by ELISA (BD OptiEIA #555142).

Results and Conclusions

Results from the co-culture assay of CD32-expressing cells with CD8+ T cells, shown in FIG. 23, demonstrate that CD137 activation is only induced by 1618 containing the wt IgG1 and not by the Fc silenced 1618 IgG1 containing the LALA mutation, further supporting the conclusion that activation of T cells via CD137 with antibodies such as 1618/1619 requires cross linking.

Example 31—Binding of TAA-CD137 Bispecific Antibodies Measured by Dual-Binding ELISA Material and Methods Bispecific antibodies against three tumor associated antigens (TAA), EpCAM, HER2 and EGFR were generated. A scFv (1204/1205) binding to CD137 was fused to the C-terminal end of three different IgG antibodies with the sequences corresponding to the binding domains of Edrecolomab, Cetuximab and Herceptin. bsAbs were produced by transient transfection of Expi293™ (Thermo Fischer Scientific) and purified by Protein A chromatography.

Bispecific binding to both targets, CD137 and TAA, was evaluated using a standard ELISA protocol. Plates (#655074, Greiner Bio-One GmbH, Germany) were precoated with 0.5 μg/ml TAA (hEGFR-His, SinoBiological #10001-H08H, hEpCAM-Fc, SinoBiological #10694-H02H, HER2-His, SinoBiological #10004-H08H and 5T4-Fc) overnight. TAA-bsAb were diluted from 20 μg/ml in 1:4 dilutions and added in duplicates of 50 μl to each well. CD137-bio (Ancell #502-030) was used as detection antibody at 0.5 μg/ml and the binding was detected with Streptavidin-HRP (Pierce #21126). The ELISA was developed with SuperSignal ELISA PICO Chemiluminescent substrate (Thermo Scientific Pierce, Rockford, IL USA) during 2-10 minutes and read in an automated microplate based multi-detection reader (FLUOstar OPTIMA, Netherlands).

Results and Conclusions

The generated TAA-CD137 bsAbs bound to both targets in the dual ELISA with EC50 values in the low nM range (Table 21, FIG. 24).

TABLE 21

Summary of the generated TAA-CD137 bsAbs

| mAb | scFv | bsAb name |
|---|---|---|
| EpCam (2414) | CD137 (1204) | 2414-1204 |
| EGFR (2424) | CD137 (1204) | 2424-1204 |
| Her2 (2078) | CD137 (1204) | 2078-1204 |

Example 32—In Vitro Activity of TAA-CD137 Bispecific Antibodies in an IFNγ Release Assay Using Human CD8+ T Cells Cultured in TAA Coated Plates Material and Methods The functional activity of the three TAA-CD137 bsAbs binding to EpCAM, EGFR and Her2 was evaluated in a CD8+ T cell assay, where cells were cultured in microtiter plates coated with CD3 antibody and either EGFR, EpCam or Her2. As negative controls, parallel wells were coated with only CD3 antibody. Peripheral blood mononuclear cells (PBMCs) were isolated by density gradient centrifugation using Ficoll-Paque (ρ 1.077 g/ml) (GE Healthcare #17-1440-02) from leucocyte concentrates obtained from healthy donors (Clinical Immunology and Transfusion Medicine, Labmedicin Region Skane, Lund Sweden). CD8+ T cells were enriched by negative selection using the CD8+ T cell isolation kit (Miltenyi 130-096-495). Plates were coated overnight at 4° C. with 3 μg/ml αCD3, clone OKT3 (Affymetrix eBioscience #16-0037-85), washed and coated with 5 μg/ml TAA for 2 h at 37° C. After the TAA coating, plates were washed and blocked for a minimum of 30 minutes with RPMI (Gibco #61870010) containing 10% FCS (Heat inactivated, Gibco #10270-106 lot 41Q9248K) and 10 mM Hepes (Gibco #15630056).

TAA-CD137 bsAbs were diluted in RPMI containing 10% FCS and 10 mM Hepes and added to the plates 30 minutes before addition of $CD8^+$ T cells ($0.07\times10^6$ cells/well). Assay plates were incubated for 68 hours at 37° C., and culture supernatant harvested. IFN-γ levels in the supernatants were measured by ELISA (BD OptiEIA #555142).

Results and Conclusions

The functionality of the EpCAM-1204 (FIG. 25(A)), EGFR-1204 (FIG. 25(B)) and Her2-CD137 (FIG. 25(C)) bsAbs was analysed and it was concluded that all of the generated bsAbs induced TAA mediated CD137 activation in the presence of TAA and not in the absence of TAA (wells coated with only CD3 antibody). This strongly indicates that the TAA-dependent CD137-mediated immune cell activation generated by CD137-TAA antibodies is a general phenomenon applicable to all types of cell surface expressed TAA.

Example 33—In Vivo Anti-Tumor Effect of Bispecific Antibody 1618-1210 in a CT26-5T4 Colon Cancer Model Summary The anti-tumor effect of 1618-1210 (an exemplary antibody targeting CD137 and 5T4) was investigated using transgenic mice for human CD137 and subcutaneous syngeneic tumor model of CT26 colon carcinoma expressing human 5T4.

The bispecific antibody 1618-1210 demonstrated tumor volume inhibition compared to monoclonal antibody 1618 targeting CD137.

Material and Methods

Human 4-1EE knock-in mouse model was developed by Prof. Lieping Chen and heterozygote F1 females were used in the experiments. The heterozygotes were generated by breeding male homozygotes for human CD137 in C57 background together with BalbC females. All experiments were done by approval of Malmö/Lund ethical committee. CT26 colon cancer cells were obtained from ATCC and transfected with human 5T4. The CT26-5T4 cell line growing in log phase was injected subcutaneously ($0.5\times10^6$ cells in 100 μL on day 0 (DO)) into the right hind/flank. Intraperitoneal treatments (1.33 nM) were done on days 7, 10, and 13.

The tumor was measured in width, length and height with a calliper, of which the tumor volume was calculated (w/2× l/2×h/2×pi×(4/3)). The animals were terminated before the tumor volume reached 2 $cm^3$, at wounding, or affected health of the mice.

The data were analysed for tumor volume inhibition by the bispecific antibody compared to the monoclonal antibody using GraphPad Prism and Excel.

Results and Conclusions

Anti-tumor efficacy was demonstrated using treatment with bispecific antibody 1618-1210 compared to treatment with monoclonal antibody 1618 at days 8-22 in the form of tumor growth inhibition. The percentage of tumor volume inhibition ranged from 0-68% when treated with 1618-1210 (see Table 22).

In conclusion, the anti-tumor effect of 1618-1210 was investigated using transgenic mice for human CD137 and a subcutaneous tumor model of CT26 colon carcinoma transfected with human 5T4. The bispecific antibody 1618-1210 demonstrated tumor volume inhibition compared to monoclonal CD137 mAb 1618.

TABLE 22

| Tumor inhibition | |
|---|---|
| Day after tumor inoculation | Tumor growth inhibition (tumor volume) by bispecific Ab compared to monospecific Ab |
| D 0 | 0% |
| D 6 | 5% |
| D 8 | 17% |
| D 10 | 43% |
| D 13 | 68% |
| D 15 | 65% |
| D 17 | 50% |
| D 20 | 45% |
| D 22 | 45% |

Example 34—Bispecific 5T4-CD137 Antibodies Localize to the Tumor Area

Material and Methods

Female SCID-Beige mice (7-8 w) from Taconic (Denmark) were used in the experiments. All experiments were done by approval of the Malmö/Lund ethical committee.

Twin Tumor Studies (B16 and CT26 Tumors)

B16.F10 wt (B16) melanoma was obtained from ATCC and cultivated according to recommendations by ATCC. B16-5T4 was obtained from Professor Peter Stern and cultivated in the same medium, supplemented with 1.2 mg/mL G418. CT26 and CT26-5T4 cells were cultivated in RPMI, 10% FCS, NaPy and HEPES. CT-5T4 medium was supplemented with 1.2 mg/mL G418.

For B16 and CT26 tumors, twin tumor studies were performed and each mouse received one 5T4 negative and one positive tumor at each side of the flank. The cell lines, growing in log phase, were injected subcutaneously ($1\times10^5$ cells in 100 μL at day 0). Human PBMCs ($10\times10^6$ in 100 μL), isolated from leukocyte concentrates, were injected intraperitoneally on the same day. Leukocyte concentrates were obtained from Lund University Hospital.

Intraperitoneal antibody treatments (100 μg) were done on days 6 and 13 for B16 tumors and days 6, 13 and 20 for CT26 tumors.

Single Tumor Studies (SKOV-3 Tumors)

For SKOV-3 tumors, each mouse received a single tumor in the right flank. The cell line, growing in log phase, was injected subcutaneously ($10\times10^6$ cells in 100 μL on day 0).

Human PBMCs ($10\times10^6$ in 100 μL), isolated from leukocyte concentrates, were injected intraperitoneally once the average tumor volume reached above 100 $mm^3$. Intraperitoneal antibody treatments (100 μg) were done starting at 6 days after the PBMC transfer, on days 55, 62 and 67.

FACS Analysis

Mice were sacrificed 24 h after the final treatment and tumors were collected. Tumors were enzymatically digested using Liberase TL (Roche #05401020001) and DNase I (Roche #10104159001). Digested tumor material was passed through a 70 m cell strainer (Fisher Scientific #22363548) and the resulting single cell suspension was stained for FACS analysis.

Unspecific antibody binding was blocked using mouse IgG (Jackson ImmunoResearch #015-000-003) and Fc block (BD #553141). Dead cells were detected using Fixable Viability Stain 450 (BD #562247) according to manufacturer's instructions. Binding of antibody (human IgG) to the tumor cells was detected using goat-anti-human IgG-PE (Jackson ImmunoResearch #109-115-098). Samples were run on a FACSVerse (BD) and data were analysed using FlowJo software.

Results

Localization of 1618-1210.m2.m5 to 5T4-Positive B16 and CT26 Tumors in SCID-Beige Mice Binding of human IgG was clearly detectable on approximately 6% of the cells in B16-5T4 tumors from mice treated with 1618-1210.m2.m5, but not in B16.F10 wt tumors from the same mice. Mice treated with 1618.m2 or 2112.s4.m3 had human IgG bound to <1% of cells irrespective of tumor type (FIG. 26).

A similar observation was made in CT26 tumor-bearing mice. Antibody localization was again observed specifically in 5T4-expressing tumors. Similar to B16 tumors, human IgG was detectable in approximately 8% of the viable tumor cells in mice treated with 1618-1210.m2.m5, but not with 1618.m2 or 2112.s4.m3. Additionally, biotinylated CD137 was also bound specifically by cells from 5T4-expressing tumors, from mice treated with 1618-1210.m2.m5 (FIG. 27).

Localization of 1618-1210.m2.m5 to SKOV-3 Tumors

Similar to what was observed for CT26 tumors, binding of biotinylated CD137 was observed in SKOV-3 tumors from mice treated with 1618-1210.m2.m5, but not 1618.m2 or 2112.s4.m3. Additionally, cells that had bound CD137 also expressed 5T4, suggesting that the bispecific antibody targets specifically 5T4-expressing cells and remains intact within the tumor (FIG. 28).

Conclusion

These data show that the bispecific antibody 1618-1210.m2.m5 binds selectively to 5T4-expressing tumors in vivo. In contrast, the CD137 monospecific antibodies 1618.m2 and 2112.s4.m3 do not localize to the tumors.

Example 35—Enhanced Tm of Optimized 5T4 and CD137 Binders

Tm measurements were performed on soluble scFv or bispecific antibodies using protein fluorescence with the UNcle platform (Unchained Labs). Onset of aggregation was measured with static light scattering (SLS) with the UNcle platform. Measurements were performed in the temperature range 20° C.-95° C. with ramping speed of 0.4° C. per min. in PBS and at a protein concentration range of 0.12-1.32 mg/ml. The data analysis was performed with the UNcle Analysis software version 2.0 using default settings.

As can be seen in Table 23, the optimized sequences exhibit improved Tm1 and Tagg compared to the wildtype sequences (1618 and 1210, respectively).

In Table 24, the Tm1 and Tagg for exemplary bispecific antibodies (in Morrison format) is displayed. The data shows that the thermostability is increased when the optimized sequences are employed in the bispecific format.

TABLE 23

| scFv antibody name | Sequence ID | | Tm1 (° C.) | Tagg (° C.) |
|---|---|---|---|---|
| 1618 | 1618 | 1619 | 56.9 | 51.8 |
| 1210 | 1210 | 1211 | 72.7 | 70.5 |
| 1210LO1 | 2992 | 2993 | 78.8 | 75.0 |
| 1618LO1 | 3012 | 3013 | 59.5 | 58.0 |
| 1618LO3 | 3016 | 3017 | 58.3 | 56.3 |
| 1618LO11 | 3032 | 3033 | 60.3 | 58.8 |
| 1618LO12 | 3034 | 3035 | 58.8 | 56.9 |
| 1618LO13 | 3036 | 3037 | 60.5 | 58.1 |

TABLE 24

| | Composition of construct (amino acid sequences) | | | | | | | |
|---|---|---|---|---|---|---|---|---|
| Antibody name | A (VH of B1) | B (VL of B1) | C (VH of B2) | D (VL of B2 | Connector* | Additional alterations* | Tm1 (° C.) | Tagg (° C.) |
| 1618LO1-1210LO1 | 3012 | 3013 | 2992 | 2993 | m6 | m2 | 74.7 | 74.5 |
| 1618LO1-1210LO2 | 3012 | 3013 | 2994 | 2995 | m6 | m2 | 73.2 | 72.6 |
| 1618LO1-1210 | 3012 | 3013 | 1210 | 1211 | m6 | m2 | 71.1 | 71.1 |
| 1618LO3-1210LO1 | 3016 | 3017 | 2992 | 2993 | m6 | m2 | 73.5 | 73.5 |
| 1618LO3-1210LO2 | 3016 | 3017 | 2994 | 2995 | m6 | m2 | 73.0 | 72.8 |
| 1618LO3-1210 | 3016 | 3017 | 1210 | 1211 | m6 | m2 | 71.7 | 70.8 |
| 1618LO11-1210LO1 | 3032 | 3033 | 2992 | 2993 | m6 | m2 | 74.1 | 74.4 |
| 1618LO11-1210LO2 | 3032 | 3033 | 2994 | 2995 | m6 | m2 | 73.5 | 73.7 |
| 1618LO11-1210 | 3032 | 3033 | 1210 | 1211 | m6 | m2 | 71.3 | 71.9 |

*See Tables D(5) and D(6) for details

REFERENCES

Akhmetzyanova, I., Zelinskyy, G., Littwitz-Salomon, E., Malyshkina, A., Dietze, K. K., Streeck, H., Brandau, S., and Dittmer, U. (2016) CD137 Agonist Therapy Can Reprogram Regulatory T Cells into Cytotoxic CD4+ T Cells with Antitumor Activity. *J. Immunol.* 196, 484-492.

Ascierto, P. A., Simeone, E., Sznol, M., Fu, Y. X., and Melero, I. (2010) Clinical experiences with anti-CD137 and anti-PD1 therapeutic antibodies. *Semin. Oncol.* 37, 508-516.

Bartkowiak, T. and Curran, M. A. (2015) 4-1 BB Agonists: Multi-Potent Potentiators of Tumor Immunity. Front Oncol. 5, 117.

Boghaert, E. R., Sridharan, L., Khandke, K. M., Armellino, D., Ryan, M. G., Myers, K., Harrop, R., Kunz, A., Hamann, P. R., Marquette, K., Dougher, M., DiJoseph, J. F., and Damle, N. K. (2008) The oncofetal protein, 5T4, is a suitable target for antibody-guided anti-cancer chemotherapy with calicheamicin. *Int J Oncol.* 32, 221-234.

Castro, F. V., McGinn, O. J., Krishnan, S., Marinov, G., Li, J., Rutkowski, A. J., Elkord, E., Burt, D. J., Holland, M., Vaghjiani, R., Gallego, A., Saha, V., and Stern, P. L. (2012) 5T4 oncofetal antigen is expressed in high risk of relapse childhood pre-B acute lymphoblastic leukemia and is associated with a more invasive and chemotactic phenotype. *Leukemia.*

Cheever, M. A., Allison, J. P., Ferris, A. S., Finn, O. J., Hastings, B. M., Hecht, T. T., Mellman, I., Prindiville, S. A., Viner, J. L., Weiner, L. M., and Matrisian, L. M. (2009) The prioritization of cancer antigens: a national cancer institute pilot project for the acceleration of translational research. *Clin. Cancer Res.* 15, 5323-5337.

Curran, M. A., Kim, M., Montalvo, W., Al-Shamkhani, A., and Allison, J. P. (2011) Combination CTLA-4 blockade and 4-1BB activation enhances tumor rejection by increasing T-cell infiltration, proliferation, and cytokine production. *PLoS. ONE.* 6, e19499.

Damelin, M., Geles, K. G., Follettie, M. T., Yuan, P., Baxter, M., Golas, J., DiJoseph, J. F., Karnoub, M., Huang, S., Diesl, V., Behrens, C., Choe, S. E., Rios, C., Gruzas, J., Sridharan, L., Dougher, M., Kunz, A., Hamann, P. R., Evans, D., Armellino, D., Khandke, K., Marquette, K., Tchistiakova, L., Boghaert, E. R., Abraham, R. T., Wistuba, I. I., and Zhou, B. B. (2011) Delineation of a cellular hierarchy in lung cancer reveals an oncofetal antigen expressed on tumor-initiating cells. *Cancer Res* 71, 4236-4246.

Dubrot, J., Milheiro, F., Alfaro, C., Palazon, A., Martinez-Forero, I., Perez-Gracia, J. L., Morales-Kastresana, A., Romero-Trevejo, J. L., Ochoa, M. C., Hervas-Stubbs, S., Prieto, J., Jure-Kunkel, M., Chen, L., and Melero, I. (2010) Treatment with anti-CD137 mAbs causes intense accumulations of liver T cells without selective antitumor immunotherapeutic effects in this organ. *Cancer Immunol. Immunother.* 59, 1223-1233.

Elkord, E., Shablak, A., Stern, P. L., and Hawkins, R. E. (2009) 5T4 as a target for immunotherapy in renal cell carcinoma. *Expert Rev Anticancer Ther* 9, 1705-1709.

Forsberg, G., Ohlsson, L., Brodin, T., Bjork, P., Lando, P. A., Shaw, D., Stern, P. L., and Dohlsten, M. (2001) Therapy of human non-small-cell lung carcinoma using antibody targeting of a modified superantigen. *Br. J Cancer* 85, 129-136.

Garber, K. (2011) Beyond ipilimumab: new approaches target the immunological synapse. *J Natl Cancer Inst.* 103, 1079-1082.

Gauttier, V., Judor, J. P., Le, G., V, Cany, J., Ferry, N., and Conchon, S. (2014) Agonistic anti-CD137 antibody treatment leads to antitumor response in mice with liver cancer. *Int. J. Cancer* 135, 2857-2867.

Gray, J. C., French, R. R., James, S., Al-Shamkhani, A., Johnson, P. W., and Glennie, M. J. (2008) Optimising anti-tumour CD8 T-cell responses using combinations of immunomodulatory antibodies. *Eur. J. Immunol.* 38, 2499-2511.

Guo, Z., Cheng, D., Xia, Z., Luan, M., Wu, L., Wang, G., and Zhang, S. (2013) Combined TIM-3 blockade and CD137 activation affords the long-term protection in a murine model of ovarian cancer. *J. Transl. Med.* 11, 215.

Hole, N. and Stern, P. L. (1988) A 72 kD trophoblast glycoprotein defined by a monoclonal antibody. *Br. J Cancer* 57, 239-246.

Hornig, N., Reinhardt, K., Kermer, V., Kontermann, R. E., and Muller, D. (2013) Evaluating combinations of costimulatory antibody-ligand fusion proteins for targeted cancer immunotherapy. Cancer *Immunol Immunother.*

Kermer, V., Hornig, N., Harder, M., Bondarieva, A., Kontermann, R. E., and Muller, D. (2014) Combining antibody-directed presentation of IL-15 and 4-1BBL in a trifunctional fusion protein for cancer immunotherapy. *Mol. Cancer Ther.* 13, 112-121.

Kiefer, J. D. and Neri, D. (2016) Immunocytokines and bispecific antibodies: two complementary strategies for the selective activation of immune cells at the tumor site. *Immunol. Rev.* 270, 178-192.

Kim, J. A., Averbook, B. J., Chambers, K., Rothchild, K., Kjaergaard, J., Papay, R., and Shu, S. (2001) *Divergent effects of* 4-1BB antibodies on antitumor immunity and on tumor-reactive T-cell generation. *Cancer Res* 61, 2031-2037.

Kwong, B., Gai, S. A., Elkhader, J., Wittrup, K. D., and Irvine, D. J. (2013) Localized immunotherapy via liposome-anchored Anti-CD137+IL-2 prevents lethal toxicity and elicits local and systemic antitumor immunity. *Cancer Res.* 73, 1547-1558.

Lee, H. W., Park, S. J., Choi, B. K., Kim, H. H., Nam, K. O., and Kwon, B. S. (2002) 4-1BB promotes the survival of CD8+ T lymphocytes by increasing expression of Bcl-xL and Bfl-1. *J Immunol* 169, 4882-4888.

Lee, S. J., Myers, L., Muralimohan, G., Dai, J., Qiao, Y., Li, Z., Mittler, R. S., and Vella, A. T. (2004) 4-1BB and OX40 dual costimulation synergistically stimulate primary specific CD8 T cells for robust effector function. *J. Immunol.* 173, 3002-3012.

Li, F. and Ravetch, J. V. (2011) Inhibitory Fcgamma receptor engagement drives adjuvant and anti-tumor activities of agonistic CD40 antibodies. *Science* 333, 1030-1034.

Li, S. Y. and Liu, Y. (2013) Immunotherapy of melanoma with the immune costimulatory monoclonal antibodies targeting CD137. *Clin. Pharmacol.* 5, 47-53.

Liu, R., Jiang, W., Yang, M., Guo, H., Zhang, Y., Wang, J., Zhu, H., Shi, R., Fan, D., Yang, C., Zhu, Z., Xie, Y., and Xiong, D. (2010) Efficient inhibition of human B-cell lymphoma in SCID mice by synergistic antitumor effect of human 4-1 BB ligand/anti-CD20 fusion proteins and anti-CD3/anti-CD20 diabodies. *J. Immunother.* 33, 500-509.

McMillin, D. W., Hewes, B., Gangadharan, B., Archer, D. R., Mittler, R. S., and Spencer, H. T. (2006) Complete regression of large solid tumors using engineered drug-resistant hematopoietic cells and anti-CD137 immunotherapy. *Hum. Gene Ther* 17, 798-806.

Melero, I., Shuford, W. W., Newby, S. A., Aruffo, A., Ledbetter, J. A., Hellstrom, K. E., Mittler, R. S., and Chen, L. (1997) Monoclonal antibodies against the 4-1BB T-cell activation molecule eradicate established tumors. *Nat Med* 3, 682-685.

Miller, R. E., Jones, J., Le, T., Whitmore, J., Boiani, N., Gliniak, B., and Lynch, D. H. (2002) 4-1BB-specific monoclonal antibody promotes the generation of tumor-specific immune responses by direct activation of CD8 T cells in a CD40-dependent manner. *J Immunol* 169, 1792-1800.

Morales-Kastresana, A., Sanmamed, M. F., Rodriguez, I., Palazon, A., Martinez-Forero, I., Labiano, S., Hervas-Stubbs, S., Sangro, B., Ochoa, C., Rouzaut, A., Azpilikueta, A., Bolanos, E., Jure-Kunkel, M., Gutgemann, I., and Melero, I. (2013) Combined immunostimulatory monoclonal antibodies extend survival in an aggressive transgenic hepatocellular carcinoma mouse model. *Clin. Cancer Res.* 19, 6151-6162.

Niu, L., Strahotin, S., Hewes, B., Zhang, B., Zhang, Y., Archer, D., Spencer, T., Dillehay, D., Kwon, B., Chen, L., Vella, A. T., and Mittler, R. S. (2007) Cytokine-mediated disruption of lymphocyte trafficking, hemopoiesis, and induction of lymphopenia, anemia, and thrombocytopenia in anti-CD137-treated mice. *J. Immunol.* 178, 4194-4213.

Pan, P. Y., Zang, Y., Weber, K., Meseck, M. L., and Chen, S. H. (2002) OX40 ligation enhances primary and memory cytotoxic T lymphocyte responses in an immunotherapy for hepatic colon metastases. *Mol Ther* 6, 528-536.

Pastor, F., Kolonias, D., McNamara, J. O., and Gilboa, E. (2011) Targeting 4-1BB costimulation to disseminated tumor lesions with bi-specific oligonucleotide aptamers. *Mol Ther* 19, 1878-1886.

Pulle, G., Vidric, M., and Watts, T. H. (2006) IL-15-dependent induction of 4-1BB promotes antigen-independent CD8 memory T cell survival. *J Immunol* 176, 2739-2748.

Rabu, C., Quemener, A., Jacques, Y., Echasserieau, K., Vusio, P., and Lang, F. (2005) Production of recombinant human trimeric CD137L (4-1BBL). Cross-linking is essential to its T cell co-stimulation activity. *J Biol Chem* 280, 41472-41481.

Sallin, M. A., Zhang, X., So, E. C., Burch, E., Cai, L., Lin, W., Chapoval, A. I., and Strome, S. E. (2014) The anti-lymphoma activities of anti-CD137 monoclonal antibodies are enhanced in FcgammaRIII(−/−) mice. *Cancer Immunol. Immunother.* 63, 947-958.

Sanmamed, M. F., Pastor, F., Rodriguez, A., Perez-Gracia, J. L., Rodriguez-Ruiz, M. E., Jure-Kunkel, M., and Melero, I. (2015) Agonists of Co-stimulation in Cancer Immunotherapy Directed Against CD137, OX40, GITR, CD27, CD28, and ICOS. *Semin. Oncol.* 42, 640-655.

Schrand, B., Berezhnoy, A., Brenneman, R., Williams, A., Levay, A., Kong, L. Y., Rao, G., Zhou, S., Heimberger, A. B., and Gilboa, E. (2014) Targeting 4-1BB costimulation to the tumor stroma with bispecific aptamer conjugates enhances the therapeutic index of tumor immunotherapy. *Cancer Immunol. Res.* 2, 867-877.

Shuford, W. W., Klussman, K., Tritchler, D. D., Loo, D. T., Chalupny, J., Siadak, A. W., Brown, T. J., Emswiler, J., Raecho, H., Larsen, C. P., Pearson, T. C., Ledbetter, J. A., Aruffo, A., and Mittler, R. S. (1997) 4-1BB costimulatory signals preferentially induce CD8+ T cell proliferation and lead to the amplification in vivo of cytotoxic T cell responses. *J Exp. Med* 186, 47-55.

So, T., Lee, S. W., and Croft, M. (2008) Immune regulation and control of regulatory T cells by OX40 and 4-1BB. *Cytokine Growth Factor Rev.* 19, 253-262.

Southall, P. J., Boxer, G. M., Bagshawe, K. D., Hole, N., Bromley, M., and Stern, P. L. (1990) Immunohistological distribution of 5T4 antigen in normal and malignant tissues. *Br. J Cancer* 61, 89-95.

Southgate, T. D., McGinn, O. J., Castro, F. V., Rutkowski, A. J., Al-Muftah, M., Marinov, G., Smethurst, G. J., Shaw, D., Ward, C. M., Miller, C. J., and Stern, P. L. (2010) CXCR4 mediated chemotaxis is regulated by 5T4 oncofetal glycoprotein in mouse embryonic cells. *PLoS. ONE.* 5, e9982.

St Rose, M. C., Taylor, R. A., Bandyopadhyay, S., Qui, H. Z., Hagymasi, A. T., Vella, A. T., and Adler, A. J. (2013) CD134/CD137 dual costimulation-elicited IFN-gamma maximizes effector T-cell function but limits Treg expansion. *Immunol. Cell Biol.* 91, 173-183.

Taraban, V. Y., Rowley, T. F., O'Brien, L., Chan, H. T., Haswell, L. E., Green, M. H., Tutt, A. L., Glennie, M. J., and AI-Shamkhani, A. (2002) Expression and costimulatory effects of the TNF receptor superfamily members CD134 (OX40) and CD137 (4-1BB), and their role in the generation of anti-tumor immune responses. *Eur J Immunol* 32, 3617-3627.

Uno, T., Takeda, K., Kojima, Y., Yoshizawa, H., Akiba, H., Mittler, R. S., Gejyo, F., Okumura, K., Yagita, H., and Smyth, M. J. (2006) Eradication of established tumors in mice by a combination antibody-based therapy. *Nat. Med.* 12, 693-698.

Vinay, D. S. and Kwon, B. S. (2012) Immunotherapy of cancer with 4-1BB. *Mol. Cancer Ther.* 11, 1062-1070.

Wei, H., Zhao, L., Li, W., Fan, K., Qian, W., Hou, S., Wang, H., Dai, M., Hellstrom, I., Hellstrom, K. E., and Guo, Y. (2013) Combinatorial PD-1 blockade and CD137 activation has therapeutic efficacy in murine cancer models and synergizes with cisplatin. *PLoS. ONE.* 8, e84927.

Westwood, J. A., Darcy, P. K., Guru, P. M., Sharkey, J., Pegram, H. J., Amos, S. M., Smyth, M. J., and Kershaw, M. H. (2010) Three agonist antibodies in combination with high-dose IL-2 eradicate orthotopic kidney cancer in mice. *J. Transl. Med.* 8, 42.

Westwood, J. A., Matthews, G. M., Shortt, J., Faulkner, D., Pegram, H. J., Duong, C. P., Chesi, M., Bergsagel, P. L., Sharp, L. L., Huhn, R. D., Darcy, P. K., Johnstone, R. W., and Kershaw, M. H. (2014a) Combination anti-CD137 and anti-CD40 antibody therapy in murine myc-driven hematological cancers. *Leuk. Res.* 38, 948-954.

Westwood, J. A., Potdevin Hunnam, T. C., Pegram, H. J., Hicks, R. J., Darcy, P. K., and Kershaw, M. H. (2014b) Routes of delivery for CpG and anti-CD137 for the treatment of orthotopic kidney tumors in mice. *PLoS. ONE.* 9, e95847.

White, A. L., Chan, H. T., French, R. R., Beers, S. A., Cragg, M. S., Johnson, P. W., and Glennie, M. J. (2013) FcgammaRlotalotaB controls the potency of agonistic anti-TNFR mAbs. *Cancer Immunol Immunother* 62, 941-948.

White, A. L., Chan, H. T., Roghanian, A., French, R. R., Mockridge, C. I., Tutt, A. L., Dixon, S. V., Ajona, D., Verbeek, J. S., AI-Shamkhani, A., Cragg, M. S., Beers, S. A., and Glennie, M. J. (2011) Interaction with Fc{gamma}RIIB Is Critical for the Agonistic Activity of Anti-CD40 Monoclonal Antibody. *J Immunol* 187, 1754-1763.

Wilcox, R. A., Flies, D. B., Zhu, G., Johnson, A. J., Tamada, K., Chapoval, A. I., Strome, S. E., Pease, L. R., and Chen, L. (2002) Provision of antigen and CD137 signaling breaks immunological ignorance, promoting regression of poorly immunogenic tumors. *J Clin Invest* 109, 651-659.

Wilson, N. S., Yang, B., Yang, A., Loeser, S., Marsters, S., Lawrence, D., Li, Y., Pitti, R., Totpal, K., Yee, S., Ross, S., Vernes, J. M., Lu, Y., Adams, C., Offringa, R., Kelley, B., Hymowitz, S., Daniel, D., Meng, G., and Ashkenazi, A. (2011b) An Fcgamma receptor-dependent mechanism drives antibody-mediated target-receptor signaling in cancer cells. *Cancer Cell* 19, 101-113.

Wilson, N. S., Yang, B., Yang, A., Loeser, S., Marsters, S., Lawrence, D., Li, Y., Pitti, R., Totpal, K., Yee, S., Ross, S., Vernes, J. M., Lu, Y., Adams, C., Offringa, R., Kelley, B., Hymowitz, S., Daniel, D., Meng, G., and Ashkenazi, A. (2011a) An Fcgamma receptor-dependent mechanism drives antibody-mediated target-receptor signaling in cancer cells. *Cancer Cell* 19, 101-113.

Wyzgol, A., Muller, N., Fick, A., Munkel, S., Grigoleit, G. U., Pfizenmaier, K., and Wajant, H. (2009) Trimer stabilization, oligomerization, and antibody-mediated cell surface immobilization improve the activity of soluble trimers of CD27L, CD40L, 41BBL, and glucocorticoid-induced TNF receptor ligand. *J Immunol* 183, 1851-1861.

Ye, Q., Song, D. G., Poussin, M., Yamamoto, T., Best, A., Li, C., Coukos, G., and Powell, D. J., Jr. (2014) CD137 accurately identifies and enriches for naturally occurring tumor-reactive T cells in tumor. *Clin Cancer Res* 20, 44-55.

Zhang, N., Sadun, R. E., Arias, R. S., Flanagan, M. L., Sachsman, S. M., Nien, Y. C., Khawli, L. A., Hu, P., and Epstein, A. L. (2007) Targeted and untargeted CD137L fusion proteins for the immunotherapy of experimental solid tumors. *Clin. Cancer Res.* 13, 2758-2767.

The invention claimed is:

1. An antibody or antigen-binding fragment thereof that specifically binds to 5T4, wherein the antibody or antigen-binding fragment thereof comprises one of the following combinations of Complementarity Determining Regions (CDRs):

(a) the three CDRs of the heavy chain and the three CDRs of the light chain of antibody 1210/1211 (SEQ ID NOs: 54, 55 and 58 and SEQ ID NOs: 46, 48 and 52);

(b) the three CDRs of the heavy chain and the three CDRs of the light chain of antibody 2992/2993 (SEQ ID NOs: 144, 48 and 52 and SEQ ID NOs: 145, 55 and 58); or (c) the three CDRs of the heavy chain and the three CDRs of the light chain of antibody 2994/2995 (SEQ ID NOS: 146, 147 and 52 and SEQ ID NOs: 145, 55 and 58).

2. The antibody or antigen-binding fragment thereof according to claim 1, wherein the antigen-binding fragment is selected from the group consisting of: Fv fragments, single chain Fv fragments, disulphide-bonded Fv fragments, Fab fragments, Fab' fragments, and $F(ab)_2$ fragments.

3. The antibody or antigen-binding fragment thereof according to claim 1, wherein:

(a) the antibody or antigen-binding fragment thereof is an intact IgG antibody;

(b) the antibody or antigen-binding fragment thereof is an Fv fragment; and/or (c) the antibody or antigen-binding fragment thereof is a Fab fragment.

4. The antibody or antigen-binding fragment thereof according to claim 1, wherein the antibody or antigen-binding fragment thereof is incapable of inducing antibody dependent cell cytotoxicity (ADCC), antibody-dependent cellular phagocytosis (ADCP) and/or complement-dependent cytotoxicity (CDC).

5. The antibody or antigen-binding fragment thereof according to claim 1, wherein the antibody or antigen-binding fragment thereof comprises:

(a) the heavy chain variable region and/or the light chain variable region of antibody 1210/1211 (SEQ ID NO: 11 and/or SEQ ID NO: 9);

(b) the heavy chain variable region and/or the light chain variable region of antibody 2992/2993 (SEQ ID NO: 96 and/or SEQ ID NO: 97); or (c) the heavy chain variable region and/or the light chain variable region of antibody 2994/2995 (SEQ ID NO: 98 and/or SEQ ID NO: 99).

6. The antibody or antigen-binding fragment thereof according to claim 1, comprising a heavy chain constant region having an amino acid sequence of SEQ ID NO: 94 and/or a light chain constant region having an amino acid sequence of SEQ ID NO: 95.

7. The antibody or antigen-binding fragment thereof according to claim 1, wherein the antibody or antigen-binding fragment thereof comprises at least one of the following:

(a) an Fc region comprising 'LALA' mutations;

(b) an scFv comprising mutations in the heavy and light chain variable regions to cysteine residues capable of forming a disulphide bridge; and/or (c) an scFv comprising mutation in the heavy chain variable region to create one or more N-glycosylation sites.

8. A pharmaceutical composition comprising an effective amount of an antibody or antigen-binding fragment thereof according to claim 1 and a pharmaceutically-acceptable diluent, carrier or excipient, optionally adapted for parenteral delivery or adapted for intravenous delivery.

9. The antibody or antigen-binding fragment thereof according to claim 1, wherein the antibody or antigen-binding fragment thereof comprises:

(a) the heavy chain and/or the light chain of antibody 1210/1211;

(b) the heavy chain and/or the light chain of antibody 2992/2993; or (c) the heavy chain and/or the light chain of antibody 2994/2995.

10. The antibody or antigen-binding fragment thereof according to claim 1, wherein the antibody or antigen-binding fragment thereof comprises:

the light chain variable region and the heavy chain variable region of antibody 1210/1211 (SEQ ID NO: 11 and SEQ ID NO: 9), or a variant which has more than 90% amino acid identity to SEQ ID NO: 11 and/or SEQ ID NO: 9; or the light chain variable region and the heavy chain variable region of antibody 2992/2993 (SEQ ID NO: 96 and SEQ ID NO: 97), or a variant which has more than 90% amino acid identity to SEQ ID NO: 96 and/or SEQ ID NO: 97; or the light chain variable region and the heavy chain variable region of antibody 2994/2995 (SEQ ID NO: 98 and SEQ ID NO: 99), or a variant which has more than 90% amino acid identity to SEQ ID NO: 98 and/or SEQ ID NO: 99.

11. The antibody or antigen-binding fragment thereof according to claim 1, wherein the antibody or antigen-binding fragment thereof comprises a human Fc region or a variant of human Fc region, where the region is an IgG1, IgG2, IgG3 or IgG4 region.

12. The antibody or antigen-binding fragment thereof according to claim 1, wherein the Fc exhibits no or very low affinity for FcgR.

13. The antibody or antigen-binding fragment thereof according to claim 1, wherein the Fc region is a variant of a human IgG1 Fc region comprising a mutation at one or more of the following positions: L234, L235, P239, D265, N297 and/or P329.

14. The antibody or antigen-binding fragment thereof according to claim 13, wherein alanine is present at the mutated positions(s).

15. The antibody or antigen-binding fragment thereof according to claim 13, wherein the Fc region is a variant of a human IgG1 Fc region comprising the double mutations L234A and L235A.

16. The antibody or antigen-binding fragment thereof according to claim 1, wherein the antibody or antigen-binding fragment thereof is capable of inducing tumour immunity.

17. The antibody or antigen-binding fragment thereof according to claim 1, wherein the antibody or antigen-binding fragment thereof is capable of inducing:

(a) activation of cytotoxic T cells;

(b) activation of helper T cells;

(c) activation of dendritic cells;

(d) activation of natural killer cells; and/or (e) reprograming of Tregs into effector T cells.

* * * * *

SEQUENCE LISTING

```
<160> NUMBER OF SEQ ID NOS: 168

<210> SEQ ID NO 1
<211> LENGTH: 121
<212> TYPE: PRT
<213> ORGANISM: Artificial Sequence
<220> FEATURE:
<223> OTHER INFORMATION: 1206, heavy chain, VH

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Gly Ser
            20                  25                  30

Ser Met Ser Trp Val Arg Gln Ala Pro Gly Lys Gly Leu Glu Trp Val
        35                  40                  45

Ser Ser Ile Tyr Tyr Ser Gly Ser Gly Thr Tyr Tyr Ala Asp Ser Val
    50                  55                  60
```

```
Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Arg Asn Val His Pro Tyr Asn Leu Asp Tyr Trp Gly
            100                 105                 110

Gln Gly Thr Leu Val Thr Val Ser Ser
        115                 120


<210> SEQ ID NO 2
<211> LENGTH: 363
<212> TYPE: DNA
<213> ORGANISM: Artificial Sequence
<220> FEATURE:
<223> OTHER INFORMATION: 1206, heavy chain, VH

<400> SEQUENCE: 2

gaggtgcagc tgttggagag cgggggaggc ttggtacagc ctggggggtc cctgcgcctc      60

tcctgtgcag ccagcggatt caccttttct ggttcttcta tgtcttgggt ccgccaggct     120

ccagggaagg ggctggagtg ggtctcatct atttactact ctggttctgg tacatactat     180

gcagactccg tgaagggccg gttcaccatc tcccgtgaca attccaagaa cacgctgtat     240

ctgcaaatga acagcctgcg tgccgaggac acggctgtat attattgtgc gcgctacggt     300

cgtaacgttc atccgtacaa cttggactat tggggccagg gaaccctggt caccgtctcc     360

tca                                                                   363


<210> SEQ ID NO 3
<211> LENGTH: 107
<212> TYPE: PRT
<213> ORGANISM: Artificial Sequence
<220> FEATURE:
<223> OTHER INFORMATION: 1207, light chain VL

<400> SEQUENCE: 3

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Tyr Tyr Leu Pro
                85                  90                  95

Thr Phe Gly Gln Gly Thr Lys Leu Glu Ile Lys
            100                 105


<210> SEQ ID NO 4
<211> LENGTH: 321
<212> TYPE: DNA
<213> ORGANISM: Artificial Sequence
<220> FEATURE:
<223> OTHER INFORMATION: 1207, light chain VL

<400> SEQUENCE: 4

gacatccaga tgacccagtc tccatcctcc ctgagcgcat ctgtaggaga ccgcgtcacc      60
```

-continued

```
atcacttgcc gggcaagtca gagcattagc agctatttaa attggtatca gcagaaacca    120

gggaaagccc ctaagctcct gatctatgct gcatccagtt tgcaaagtgg ggtcccatca    180

cgtttcagtg gcagtggaag cgggacagat ttcactctca ccatcagcag tctgcaacct    240

gaagattttg caacttatta ctgtcaacag ggttactact acctgcccac ttttggccag    300

gggaccaagc tggagatcaa a                                              321
```

<210> SEQ ID NO 5
<211> LENGTH: 121
<212> TYPE: PRT
<213> ORGANISM: Artificial Sequence
<220> FEATURE:
<223> OTHER INFORMATION: 1208, heavy chain VH

<400> SEQUENCE: 5

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Pro Tyr Tyr Tyr Gly Ala Asn Trp Ile Asp Tyr Trp Gly
            100                 105                 110

Gln Gly Thr Leu Val Thr Val Ser Ser
        115                 120
```

<210> SEQ ID NO 6
<211> LENGTH: 363
<212> TYPE: DNA
<213> ORGANISM: Artificial Sequence
<220> FEATURE:
<223> OTHER INFORMATION: 1208, heavy chain VH

<400> SEQUENCE: 6

```
gaggtgcagc tgttggagag cgggggaggc ttggtacagc ctggggggtc cctgcgcctc     60

tcctgtgcag ccagcggatt cacctttagc agctatgcca tgagctgggt ccgccaggct    120

ccagggaagg ggctggagtg ggtctcagct attagtggta gtggtggtag cacatactat    180

gcagactccg tgaagggccg gttcaccatc tcccgtgaca attccaagaa cacgctgtat    240

ctgcaaatga acagcctgcg tgccgaggac acggctgtat attattgtgc gcgctctccg    300

tactactacg gtgctaactg gattgactat tggggccagg gaaccctggt caccgtctcc    360

tca                                                                  363
```

<210> SEQ ID NO 7
<211> LENGTH: 107
<212> TYPE: PRT
<213> ORGANISM: Artificial Sequence
<220> FEATURE:
<223> OTHER INFORMATION: 1135, light chain VL

<400> SEQUENCE: 7

```
Asp Ile Gln Met Thr Gln Ser Pro Ser Ser Leu Ser Ala Ser Val Gly
```

-continued

```
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Tyr
                85                  90                  95

Thr Phe Gly Gln Gly Thr Lys Leu Glu Ile Lys
            100                 105
```

<210> SEQ ID NO 8
<211> LENGTH: 321
<212> TYPE: DNA
<213> ORGANISM: Artificial Sequence
<220> FEATURE:
<223> OTHER INFORMATION: 1135, light chain VL

<400> SEQUENCE: 8

```
gacatccaga tgacccagtc tccatcctcc ctgagcgcat ctgtaggaga ccgcgtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

cgtttcagtg gcagtggaag cgggacagat ttcactctca ccatcagcag tctgcaacct    240

gaagattttg caacttatta ctgtcaacag agttacagta ccccttatac ttttggccag    300

gggaccaagc tggagatcaa a                                              321
```

<210> SEQ ID NO 9
<211> LENGTH: 121
<212> TYPE: PRT
<213> ORGANISM: Artificial Sequence
<220> FEATURE:
<223> OTHER INFORMATION: 1210, heavy chain VH

<400> SEQUENCE: 9

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120
```

<210> SEQ ID NO 10
<211> LENGTH: 363

-continued

<212> TYPE: DNA
<213> ORGANISM: Artificial Sequence
<220> FEATURE:
<223> OTHER INFORMATION: 1210, heavy chain VH

<400> SEQUENCE: 10
gaggtgcagc tgttggagag cgggggaggc ttggtacagc ctgggggtc cctgcgcctc 60 tcctgtgcag ccagcggatt cacctttagc agctatgcca tgagctgggt ccgccaggct 120
ccagggaagg ggctggagtg ggtctcagct attagtggta gtggtggtag cacatactat 180
gcagactccg tgaagggccg gttcaccatc tcccgtgaca attccaagaa cacgctgtat 240
ctgcaaatga acagcctgcg tgccgaggac acggctgtat attattgtgc gcgctactac 300
ggtggttact actctgcttg gatggactat tggggccagg gaaccctggt caccgtctcc 360
tca 363

<210> SEQ ID NO 11
<211> LENGTH: 107
<212> TYPE: PRT
<213> ORGANISM: Artificial Sequence
<220> FEATURE:
<223> OTHER INFORMATION: 1211, light chain VL

<400> SEQUENCE: 11

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Tyr Gly Tyr Leu His
85 90 95

Thr Phe Gly Gln Gly Thr Lys Leu Glu Ile Lys
100 105

<210> SEQ ID NO 12
<211> LENGTH: 321
<212> TYPE: DNA
<213> ORGANISM: Artificial Sequence
<220> FEATURE:
<223> OTHER INFORMATION: 1211, light chain VL

<400> SEQUENCE: 12
gacatccaga tgacccagtc tccatcctcc ctgagcgcat ctgtaggaga ccgcgtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
cgtttcagtg gcagtggaag cgggacagat ttcactctca ccatcagcag tctgcaacct 240
gaagattttg caacttatta ctgtcaacag acttacggtt acctgcacac ttttggccag 300
gggaccaagc tggagatcaa a 321

<210> SEQ ID NO 13
<211> LENGTH: 117
<212> TYPE: PRT
<213> ORGANISM: Artificial Sequence
<220> FEATURE:
<223> OTHER INFORMATION: 1212, heavy chain VH

<400> SEQUENCE: 13

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Tyr Ile Ser Ser Tyr Gly Gly Tyr Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr His Ser Gly Val Leu Asp Tyr Trp Gly Gln Gly Thr Leu
            100                 105                 110

Val Thr Val Ser Ser
        115

<210> SEQ ID NO 14
<211> LENGTH: 351
<212> TYPE: DNA
<213> ORGANISM: Artificial Sequence
<220> FEATURE:
<223> OTHER INFORMATION: 1212, heavy chain VH

<400> SEQUENCE: 14
gaggtgcagc tgttggagag cgggggaggc ttggtacagc ctggggggtc cctgcgcctc     60
tcctgtgcag ccagcggatt cacctttagc agctatgcca tgagctgggt ccgccaggct    120
ccagggaagg ggctggagtg ggtctcatac atttcttctt acggtggtta cacatcttat    180
gcagactccg tgaagggccg gttcaccatc tcccgtgaca attccaagaa cacgctgtat    240
ctgcaaatga acagcctgcg tgccgaggac acggctgtat attattgtgc gcgctaccat    300
tctggtgttt tggactattg gggccaggga accctggtca ccgtctcctc a             351

<210> SEQ ID NO 15
<211> LENGTH: 108
<212> TYPE: PRT
<213> ORGANISM: Artificial Sequence
<220> FEATURE:
<223> OTHER INFORMATION: 1213, light chain VL

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Tyr His Tyr Leu
                85                  90                  95

Leu Thr Phe Gly Gln Gly Thr Lys Leu Glu Ile Lys
100 105

<210> SEQ ID NO 16
<211> LENGTH: 324
<212> TYPE: DNA
<213> ORGANISM: Artificial Sequence
<220> FEATURE:
<223> OTHER INFORMATION: 1213, light chain VL

<400> SEQUENCE: 16
gacatccaga tgacccagtc tccatcctcc ctgagcgcat ctgtaggaga ccgcgtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
cgtttcagtg gcagtggaag cgggacagat ttcactctca ccatcagcag tctgcaacct 240
gaagattttg caacttatta ctgtcaacag tactactacc attacctgct cacttttggc 300
caggggacca agctggagat caaa 324

<210> SEQ ID NO 17
<211> LENGTH: 116
<212> TYPE: PRT
<213> ORGANISM: Artificial Sequence
<220> FEATURE:
<223> OTHER INFORMATION: 1200, heavy chain VH

<400> SEQUENCE: 17

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ser Gly Ile Ser Gly Gly Gly Gly Gly Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asp Val Ala Tyr Phe Asp Tyr Trp Gly Gln Gly Thr Leu Val
100 105 110

Thr Val Ser Ser
115

<210> SEQ ID NO 18
<211> LENGTH: 348
<212> TYPE: DNA
<213> ORGANISM: Artificial Sequence
<220> FEATURE:
<223> OTHER INFORMATION: 1200, heavy chain VH

<400> SEQUENCE: 18
gaggtgcagc tgttggagag cgggggaggc ttggtacagc ctggggggtc cctgcgcctc 60
tcctgtgcag ccagcggatt cacctttagc agctatgcca tgagctgggt ccgccaggct 120
ccagggaagg ggctggagtg ggtctcaggt atttctggtg gtggtggtgg tacatactat 180
gcagactccg tgaagggccg gttcaccatc tcccgtgaca attccaagaa cacgctgtat 240
ctgcaaatga acagcctgcg tgccgaggac acggctgtat attattgtgc gcgcgacgtt 300
gcttactttg actattgggg ccagggaacc ctggtcaccg tctcctca 348

<210> SEQ ID NO 19
<211> LENGTH: 106
<212> TYPE: PRT
<213> ORGANISM: Artificial Sequence
<220> FEATURE:
<223> OTHER INFORMATION: 1201, light chain VL

<400> SEQUENCE: 19

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Pro His Thr
85 90 95

Phe Gly Gln Gly Thr Lys Leu Glu Ile Lys
100 105

<210> SEQ ID NO 20
<211> LENGTH: 318
<212> TYPE: DNA
<213> ORGANISM: Artificial Sequence
<220> FEATURE:
<223> OTHER INFORMATION: 1201, light chain VL

<400> SEQUENCE: 20
gacatccaga tgacccagtc tccatcctcc ctgagcgcat ctgtaggaga ccgcgtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
cgtttcagtg gcagtggaag cgggacagat ttcactctca ccatcagcag tctgcaacct 240
gaagattttg caacttatta ctgtcaacag tactacattc cgcacacttt tggccagggg 300
accaagctgg agatcaaa 318

<210> SEQ ID NO 21
<211> LENGTH: 117
<212> TYPE: PRT
<213> ORGANISM: Artificial Sequence
<220> FEATURE:
<223> OTHER INFORMATION: 1202, heavy chain VH

<400> SEQUENCE: 21

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Tyr Gly Ser
20 25 30

Ser Met Ser Trp Val Arg Gln Ala Pro Gly Lys Gly Leu Glu Trp Val
35 40 45

Ser Ser Ile Tyr Tyr Gly Ser Ser Gly Thr Tyr Tyr Ala Asp Ser Val
50 55 60

Lys Gly Arg Phe Thr Ile Ser Arg Asp Asn Ser Lys Asn Thr Leu Tyr
65 70 75 80

```
Leu Gln Met Asn Ser Leu Arg Ala Glu Asp Thr Ala Val Tyr Tyr Cys
                85                  90                  95

Ala Arg Ser Tyr Tyr Gly Tyr Phe Asp Tyr Trp Gly Gln Gly Thr Leu
            100                 105                 110

Val Thr Val Ser Ser
        115


<210> SEQ ID NO 22
<211> LENGTH: 351
<212> TYPE: DNA
<213> ORGANISM: Artificial Sequence
<220> FEATURE:
<223> OTHER INFORMATION: 1202, heavy chain VH

<400> SEQUENCE: 22

gaggtgcagc tgttggagag cgggggaggc ttggtacagc ctggggggtc cctgcgcctc      60

tcctgtgcag ccagcggatt caccttttac ggttcttcta tgtcttgggt ccgccaggct     120

ccagggaagg ggctggagtg ggtctcatct atttactacg gttcttctgg tacatactat     180

gcagactccg tgaagggccg gttcaccatc tcccgtgaca attccaagaa cacgctgtat     240

ctgcaaatga acagcctgcg tgccgaggac acggctgtat attattgtgc gcgctcttac     300

tacggttact ttgactattg gggccaggga accctggtca ccgtctcctc a              351


<210> SEQ ID NO 23
<211> LENGTH: 108
<212> TYPE: PRT
<213> ORGANISM: Artificial Sequence
<220> FEATURE:
<223> OTHER INFORMATION: 1203, light chain VL

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Val Val Pro
                85                  90                  95

Phe Thr Phe Gly Gln Gly Thr Lys Leu Glu Ile Lys
            100                 105


<210> SEQ ID NO 24
<211> LENGTH: 324
<212> TYPE: DNA
<213> ORGANISM: Artificial Sequence
<220> FEATURE:
<223> OTHER INFORMATION: 1203, light chain VL

<400> SEQUENCE: 24

gacatccaga tgacccagtc tccatcctcc ctgagcgcat ctgtaggaga ccgcgtcacc      60

atcacttgcc gggcaagtca gagcattagc agctatttaa attggtatca gcagaaacca     120

gggaaagccc ctaagctcct gatctatgct gcatccagtt tgcaaagtgg ggtcccatca     180
```

```
cgtttcagtg gcagtggaag cgggacagat ttcactctca ccatcagcag tctgcaacct    240

gaagattttg caacttatta ctgtcaacag tactacactg ttgttccgtt cacttttggc    300

caggggacca agctggagat caaa                                           324
```

```
<210> SEQ ID NO 25
<211> LENGTH: 108
<212> TYPE: PRT
<213> ORGANISM: Artificial Sequence
<220> FEATURE:
<223> OTHER INFORMATION: 1205, light chain VL

<400> SEQUENCE: 25

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Val Pro His Tyr Pro
                85                  90                  95

Phe Thr Phe Gly Gln Gly Thr Lys Leu Glu Ile Lys
            100                 105
```

```
<210> SEQ ID NO 26
<211> LENGTH: 324
<212> TYPE: DNA
<213> ORGANISM: Artificial Sequence
<220> FEATURE:
<223> OTHER INFORMATION: 1205, light chain VL

<400> SEQUENCE: 26

gacatccaga tgacccagtc tccatcctcc ctgagcgcat ctgtaggaga ccgcgtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

cgtttcagtg gcagtggaag cgggacagat ttcactctca ccatcagcag tctgcaacct    240

gaagattttg caacttatta ctgtcaacag tctgttccgc actacccgtt cacttttggc    300

caggggacca agctggagat caaa                                           324
```

```
<210> SEQ ID NO 27
<211> LENGTH: 123
<212> TYPE: PRT
<213> ORGANISM: Artificial Sequence
<220> FEATURE:
<223> OTHER INFORMATION: 1204, heavy chain VH

<400> SEQUENCE: 27

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Gly Trp Val Arg Gln Ala Pro Gly Lys Gly Leu Glu Trp Val
        35                  40                  45

Ser Gly Ile Gly Ser Tyr Tyr Gly Tyr Thr Gly Tyr Ala Asp Ser Val
```

```
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Tyr Tyr Asp Tyr Asn Tyr Tyr Tyr Ala Tyr Phe Asp Tyr
            100                 105                 110

Trp Gly Gln Gly Thr Leu Val Thr Val Ser Ser
        115                 120


<210> SEQ ID NO 28
<211> LENGTH: 369
<212> TYPE: DNA
<213> ORGANISM: Artificial Sequence
<220> FEATURE:
<223> OTHER INFORMATION: 1204, heavy chain VH

<400> SEQUENCE: 28

gaggtgcagc tgttggagag cgggggaggc ttggtacagc ctggggggtc cctgcgcctc     60

tcctgtgcag ccagcggatt caccttttct tcttactaca tgggttgggt ccgccaggct    120

ccagggaagg ggctggagtg ggtctcaggt attggttctt actacggtta cacaggttat    180

gcagactccg tgaagggccg gttcaccatc tcccgtgaca attccaagaa cacgctgtat    240

ctgcaaatga acagcctgcg tgccgaggac acggctgtat attattgtgc gcgcgcttac    300

tacgactaca actactacta cgcttacttt gactattggg gccagggaac cctggtcacc    360

gtctcctca                                                           369


<210> SEQ ID NO 29
<211> LENGTH: 116
<212> TYPE: PRT
<213> ORGANISM: Artificial Sequence
<220> FEATURE:
<223> OTHER INFORMATION: 1214 (VH)

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Gly Ser Gly Gly Gly Tyr Thr Gly Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Gly His Pro Phe Asp Tyr Trp Gly Gln Gly Thr Leu Val
            100                 105                 110

Thr Val Ser Ser
        115


<210> SEQ ID NO 30
<211> LENGTH: 348
<212> TYPE: DNA
<213> ORGANISM: Artificial Sequence
<220> FEATURE:
<223> OTHER INFORMATION: 1214 (VH)
```

<400> SEQUENCE: 30
gaggtgcagc tgttggagag cgggggaggc ttggtacagc ctgggggtc cctgcgcctc 60 tcctgtgcag ccagcggatt cacctttagc agctatgcca tgagctgggt ccgccaggct 120
ccagggaagg ggctggagtg ggtctcatct attggttctg gtggtggtta cacaggttat 180
gcagactccg tgaagggccg gttcaccatc tcccgtgaca attccaagaa cacgctgtat 240
ctgcaaatga acagcctgcg tgccgaggac acggctgtat attattgtgc gcgcgttggt 300
catccgtttg actattgggg ccagggaacc ctggtcaccg tctcctca 348

<210> SEQ ID NO 31
<211> LENGTH: 106
<212> TYPE: PRT
<213> ORGANISM: Artificial Sequence
<220> FEATURE:
<223> OTHER INFORMATION: 1215 (VL)

<400> SEQUENCE: 31

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Asp Ala Tyr Pro His Thr
85 90 95

Phe Gly Gln Gly Thr Lys Leu Glu Ile Lys
100 105

<210> SEQ ID NO 32
<211> LENGTH: 318
<212> TYPE: DNA
<213> ORGANISM: Artificial Sequence
<220> FEATURE:
<223> OTHER INFORMATION: 1215 (VL)

<400> SEQUENCE: 32
gacatccaga tgacccagtc tccatcctcc ctgagcgcat ctgtaggaga ccgcgtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
cgtttcagtg gcagtggaag cgggacagat ttcactctca ccatcagcag tctgcaacct 240
gaagattttg caacttatta ctgtcaacag gacgcttacc cgcacacttt tggccagggg 300
accaagctgg agatcaaa 318

<210> SEQ ID NO 33
<211> LENGTH: 121
<212> TYPE: PRT
<213> ORGANISM: Artificial Sequence
<220> FEATURE:
<223> OTHER INFORMATION: 1618 (VH)

<400> SEQUENCE: 33

Glu Val Gln Leu Leu Glu Ser Gly Gly Gly Leu Val Gln Pro Gly Gly

-continued

```
1               5                   10                  15

Ser Leu Arg Leu Ser Cys Ala Ala Ser Gly Phe Thr Phe Ser Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120


<210> SEQ ID NO 34
<211> LENGTH: 363
<212> TYPE: DNA
<213> ORGANISM: Artificial Sequence
<220> FEATURE:
<223> OTHER INFORMATION: 1618 (VH)

<400> SEQUENCE: 34

gaggtgcagc tgttggagag cgggggaggc ttggtacagc ctgggggtc cctgcgcctc      60

tcctgtgcag ccagcggatt caccttttct tacggttcta tgtactgggt ccgccaggct    120

ccagggaagg ggctggagtg ggtctcatct atttcttctg gttctggttc tacatactat    180

gcagactccg tgaagggccg gttcaccatc tcccgtgaca attccaagaa cacgctgtat    240

ctgcaaatga acagcctgcg tgccgaggac acggctgtat attattgtgc gcgctcttct    300

tactacggtt cttactactc tattgactat tggggccagg gaaccctggt caccgtctcc    360

tca                                                                  363


<210> SEQ ID NO 35
<211> LENGTH: 107
<212> TYPE: PRT
<213> ORGANISM: Artificial Sequence
<220> FEATURE:
<223> OTHER INFORMATION: 1619 (VL)

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105
```

<210> SEQ ID NO 36
<211> LENGTH: 321
<212> TYPE: DNA
<213> ORGANISM: Artificial Sequence
<220> FEATURE:
<223> OTHER INFORMATION: 1619 (VL)

<400> SEQUENCE: 36
gacatccaga tgacccagtc tccatcctcc ctgagcgcat ctgtaggaga ccgcgtcacc 60
atcacttgcc gggcaagtca gagcattagc agctatttaa attggtatca gcagaaacca 120
gggaaagccc ctaagctcct gatctatgct gcatccagtt tgcaaagtgg ggtcccatca 180
cgtttcagtg gcagtggaag cgggacagat ttcactctca ccatcagcag tctgcaacct 240
gaagattttg caacttatta ctgtcaacag tactacgaca acctgcccac ttttggccag 300
gggaccaagc tggagatcaa a 321

<210> SEQ ID NO 37
<211> LENGTH: 117
<212> TYPE: PRT
<213> ORGANISM: Artificial Sequence
<220> FEATURE:
<223> OTHER INFORMATION: 1620 (VH)

<400> SEQUENCE: 37

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Gly Tyr
20 25 30

Tyr Met Tyr Trp Val Arg Gln Ala Pro Gly Lys Gly Leu Glu Trp Val
35 40 45

Ser Gly Ile Ser Ser Ser Gly Ser Tyr Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Val Gly Pro Tyr Phe Asp Tyr Trp Gly Gln Gly Thr Leu
100 105 110

Val Thr Val Ser Ser
115

<210> SEQ ID NO 38
<211> LENGTH: 351
<212> TYPE: DNA
<213> ORGANISM: Artificial Sequence
<220> FEATURE:
<223> OTHER INFORMATION: 1620 (VH)

<400> SEQUENCE: 38
gaggtgcagc tgttggagag cgggggaggc ttggtacagc ctggggggtc cctgcgcctc 60
tcctgtgcag ccagcggatt caccttttct ggttactaca tgtactgggt ccgccaggct 120
ccagggaagg ggctggagtg ggtctcaggt atttcttctt ctggttctta cacatactat 180
gcagactccg tgaagggccg gttcaccatc tcccgtgaca attccaagaa cacgctgtat 240
ctgcaaatga acagcctgcg tgccgaggac acggctgtat attattgtgc gcgctctgtt 300
ggtccgtact ttgactattg gggccaggga accctggtca ccgtctcctc a 351

<210> SEQ ID NO 39

<211> LENGTH: 106
<212> TYPE: PRT
<213> ORGANISM: Artificial Sequence
<220> FEATURE:
<223> OTHER INFORMATION: 1621 (VL)

<400> SEQUENCE: 39

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Val Gly Pro Tyr Thr
                85                  90                  95

Phe Gly Gln Gly Thr Lys Leu Glu Ile Lys
            100                 105
```

<210> SEQ ID NO 40
<211> LENGTH: 318
<212> TYPE: DNA
<213> ORGANISM: Artificial Sequence
<220> FEATURE:
<223> OTHER INFORMATION: 1621 (VL)

<400> SEQUENCE: 40

```
gacatccaga tgacccagtc tccatcctcc ctgagcgcat ctgtaggaga ccgcgtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

cgtttcagtg gcagtggaag cgggacagat ttcactctca ccatcagcag tctgcaacct    240

gaagattttg caacttatta ctgtcaacag ggtgttggtc cgtacacttt tggccagggg    300

accaagctgg agatcaaa                                                  318
```

<210> SEQ ID NO 41
<211> LENGTH: 117
<212> TYPE: PRT
<213> ORGANISM: Artificial Sequence
<220> FEATURE:
<223> OTHER INFORMATION: 1626 (VH)

<400> SEQUENCE: 41

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Gly Gly Tyr
            20                  25                  30

Ser Met Tyr Trp Val Arg Gln Ala Pro Gly Lys Gly Leu Glu Trp Val
        35                  40                  45

Ser Ser Ile Gly Gly Tyr Tyr Tyr Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95
```

```
Ala Arg Ser Tyr Tyr Gly Ser Ile Asp Tyr Trp Gly Gln Gly Thr Leu
            100                 105                 110

Val Thr Val Ser Ser
        115


<210> SEQ ID NO 42
<211> LENGTH: 351
<212> TYPE: DNA
<213> ORGANISM: Artificial Sequence
<220> FEATURE:
<223> OTHER INFORMATION: 1626 (VH)

<400> SEQUENCE: 42

gaggtgcagc tgttggagag cgggggaggc ttggtacagc ctggggggtc cctgcgcctc     60

tcctgtgcag ccagcggatt cacctttggt ggttactcta tgtactgggt ccgccaggct    120

ccagggaagg ggctggagtg ggtctcatct attggtggtt actactactc tacatactat    180

gcagactccg tgaagggccg gttcaccatc tcccgtgaca attccaagaa cacgctgtat    240

ctgcaaatga acagcctgcg tgccgaggac acggctgtat attattgtgc gcgctcttac    300

tacggttcta ttgactattg gggccaggga accctggtca ccgtctcctc a             351


<210> SEQ ID NO 43
<211> LENGTH: 108
<212> TYPE: PRT
<213> ORGANISM: Artificial Sequence
<220> FEATURE:
<223> OTHER INFORMATION: 1627 (VL)

<400> SEQUENCE: 43

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Thr Gly Tyr Gly Pro
                85                  90                  95

Leu Thr Phe Gly Gln Gly Thr Lys Leu Glu Ile Lys
            100                 105


<210> SEQ ID NO 44
<211> LENGTH: 324
<212> TYPE: DNA
<213> ORGANISM: Artificial Sequence
<220> FEATURE:
<223> OTHER INFORMATION: 1627 (VL)

<400> SEQUENCE: 44

gacatccaga tgacccagtc tccatcctcc ctgagcgcat ctgtaggaga ccgcgtcacc     60

atcacttgcc gggcaagtca gagcattagc agctatttaa attggtatca gcagaaacca    120

gggaaagccc ctaagctcct gatctatgct gcatccagtt tgcaaagtgg ggtcccatca    180

cgtttcagtg gcagtggaag cgggacagat ttcactctca ccatcagcag tctgcaacct    240

gaagattttg caacttatta ctgtcaacag ggtactggtt acggtccgct cacttttggc    300
```

-continued

```
caggggacca agctggagat caaa                                          324


<210> SEQ ID NO 45
<211> LENGTH: 8
<212> TYPE: PRT
<213> ORGANISM: Artificial Sequence
<220> FEATURE:
<223> OTHER INFORMATION: CDR H1 from 1206 (VH)

<400> SEQUENCE: 45

Gly Phe Thr Phe Ser Gly Ser Ser
1               5


<210> SEQ ID NO 46
<211> LENGTH: 8
<212> TYPE: PRT
<213> ORGANISM: Artificial Sequence
<220> FEATURE:
<223> OTHER INFORMATION: CDR H1 from 1200 (VH) or 1208 (VH) or 1210 (VH)
      or 1212 (VH) or 1214 (VH)

<400> SEQUENCE: 46

Gly Phe Thr Phe Ser Ser Tyr Ala
1               5


<210> SEQ ID NO 47
<211> LENGTH: 8
<212> TYPE: PRT
<213> ORGANISM: Artificial Sequence
<220> FEATURE:
<223> OTHER INFORMATION: CDR H2 from 1206 (VH)

<400> SEQUENCE: 47

Ile Tyr Tyr Ser Gly Ser Gly Thr
1               5


<210> SEQ ID NO 48
<211> LENGTH: 8
<212> TYPE: PRT
<213> ORGANISM: Artificial Sequence
<220> FEATURE:
<223> OTHER INFORMATION: CDR H2 from 1208 (VH) or 1210 (VH) or 2992 (VH)
      or 2996 (VH) or 2998 (VH) or 3000 (VH) or 3002 (VH) or 3004 (VH)
      or 3006 (VH) or 3008 (VH)

<400> SEQUENCE: 48

Ile Ser Gly Ser Gly Gly Ser Thr
1               5


<210> SEQ ID NO 49
<211> LENGTH: 8
<212> TYPE: PRT
<213> ORGANISM: Artificial Sequence
<220> FEATURE:
<223> OTHER INFORMATION: CDR H2 from 1212 (VH)

<400> SEQUENCE: 49

Ile Ser Ser Tyr Gly Gly Tyr Thr
1               5


<210> SEQ ID NO 50
<211> LENGTH: 14
<212> TYPE: PRT
<213> ORGANISM: Artificial Sequence
<220> FEATURE:
<223> OTHER INFORMATION: CDR H3 from 1206 (VH)

<400> SEQUENCE: 50
```

Ala Arg Tyr Gly Arg Asn Val His Pro Tyr Asn Leu Asp Tyr
1 5 10

<210> SEQ ID NO 51
<211> LENGTH: 14
<212> TYPE: PRT
<213> ORGANISM: Artificial Sequence
<220> FEATURE:
<223> OTHER INFORMATION: CDR H3 from 1208 (VH)

<400> SEQUENCE: 51

Ala Arg Ser Pro Tyr Tyr Tyr Gly Ala Asn Trp Ile Asp Tyr
1 5 10

<210> SEQ ID NO 52
<211> LENGTH: 14
<212> TYPE: PRT
<213> ORGANISM: Artificial Sequence
<220> FEATURE:
<223> OTHER INFORMATION: CDR H3 from 1210 (VH) or 2992 (VH) or 2994 (VH) or 2996 (VH) or 2998 (VH) or 3000 (VH) or 3002 (VH) or 3004 (VH) or 3006 (VH) or 3008 (VH)

<400> SEQUENCE: 52

Ala Arg Tyr Tyr Gly Gly Tyr Tyr Ser Ala Trp Met Asp Tyr
1 5 10

<210> SEQ ID NO 53
<211> LENGTH: 10
<212> TYPE: PRT
<213> ORGANISM: Artificial Sequence
<220> FEATURE:
<223> OTHER INFORMATION: CDR H3 1212 (VH)

<400> SEQUENCE: 53

Ala Arg Tyr His Ser Gly Val Leu Asp Tyr
1 5 10

<210> SEQ ID NO 54
<211> LENGTH: 6
<212> TYPE: PRT
<213> ORGANISM: Artificial Sequence
<220> FEATURE:
<223> OTHER INFORMATION: CDR L1 from 1207 (VL) or 1135 (VL) or 1211 (VL) or 1213 (VL) or 1201 (VL) or 1203 (VL) or 1205 (VL) or 1215 (VL) or 1619 (VL) or 1621 (VL) or 1627 (VL) or 3025 (VL) or 3031 (VL) or 3033 (VL) or 3035 (VL)

<400> SEQUENCE: 54

Gln Ser Ile Ser Ser Tyr
1 5

<210> SEQ ID NO 55
<211> LENGTH: 3
<212> TYPE: PRT
<213> ORGANISM: Artificial Sequence
<220> FEATURE:
<223> OTHER INFORMATION: L2

<400> SEQUENCE: 55

Ala Ala Ser
1

<210> SEQ ID NO 56
<211> LENGTH: 9
<212> TYPE: PRT
<213> ORGANISM: Artificial Sequence
<220> FEATURE:
<223> OTHER INFORMATION: CDR L3 from 1207 (VL)

<400> SEQUENCE: 56

Gln Gln Gly Tyr Tyr Tyr Leu Pro Thr
1 5

<210> SEQ ID NO 57
<211> LENGTH: 9
<212> TYPE: PRT
<213> ORGANISM: Artificial Sequence
<220> FEATURE:
<223> OTHER INFORMATION: CDR L3 from 1135 (VL)

<400> SEQUENCE: 57

Gln Gln Ser Tyr Ser Thr Pro Tyr Thr
1 5

<210> SEQ ID NO 58
<211> LENGTH: 9
<212> TYPE: PRT
<213> ORGANISM: Artificial Sequence
<220> FEATURE:
<223> OTHER INFORMATION: CDR L3 from 1211 (VL) or 2993 (VL) or 2995 (VL)
or 2997 (VL) or 2999 (VL) or 3001 (VL) or 3003 (VL) or 3005 (VL)
or 3007 (VL) or 3009 (VL)

<400> SEQUENCE: 58

Gln Gln Thr Tyr Gly Tyr Leu His Thr
1 5

<210> SEQ ID NO 59
<211> LENGTH: 10
<212> TYPE: PRT
<213> ORGANISM: Artificial Sequence
<220> FEATURE:
<223> OTHER INFORMATION: CDR L3 from 1213 (VL)

<400> SEQUENCE: 59

Gln Gln Tyr Tyr Tyr His Tyr Leu Leu Thr
1 5 10

<210> SEQ ID NO 60
<211> LENGTH: 8
<212> TYPE: PRT
<213> ORGANISM: Artificial Sequence
<220> FEATURE:
<223> OTHER INFORMATION: CDR H1 from 1202 (VH)

<400> SEQUENCE: 60

Gly Phe Thr Phe Tyr Gly Ser Ser
1 5

<210> SEQ ID NO 61
<211> LENGTH: 8
<212> TYPE: PRT
<213> ORGANISM: Artificial Sequence
<220> FEATURE:
<223> OTHER INFORMATION: CDR H1 from 1204 (VH)

<400> SEQUENCE: 61

Gly Phe Thr Phe Ser Ser Tyr Tyr
1 5

<210> SEQ ID NO 62
<211> LENGTH: 8
<212> TYPE: PRT

<213> ORGANISM: Artificial Sequence
<220> FEATURE:
<223> OTHER INFORMATION: CDR H1 from 1618 (VH) or 3014 (VH) or 3016 (VH) or 3034 (VH)

<400> SEQUENCE: 62

Gly Phe Thr Phe Ser Tyr Gly Ser
1 5

<210> SEQ ID NO 63
<211> LENGTH: 8
<212> TYPE: PRT
<213> ORGANISM: Artificial Sequence
<220> FEATURE:
<223> OTHER INFORMATION: CDR H1 from 1620 (VH)

<400> SEQUENCE: 63

Gly Phe Thr Phe Ser Gly Tyr Tyr
1 5

<210> SEQ ID NO 64
<211> LENGTH: 8
<212> TYPE: PRT
<213> ORGANISM: Artificial Sequence
<220> FEATURE:
<223> OTHER INFORMATION: CDR H1 from 1626 (VH)

<400> SEQUENCE: 64

Gly Phe Thr Phe Gly Gly Tyr Ser
1 5

<210> SEQ ID NO 65
<211> LENGTH: 8
<212> TYPE: PRT
<213> ORGANISM: Artificial Sequence
<220> FEATURE:
<223> OTHER INFORMATION: CDR H2 from 1200 (VH)

<400> SEQUENCE: 65

Ile Ser Gly Gly Gly Gly Gly Thr
1 5

<210> SEQ ID NO 66
<211> LENGTH: 8
<212> TYPE: PRT
<213> ORGANISM: Artificial Sequence
<220> FEATURE:
<223> OTHER INFORMATION: CDR H2 from 1202 (VH)

<400> SEQUENCE: 66

Ile Tyr Tyr Gly Ser Ser Gly Thr
1 5

<210> SEQ ID NO 67
<211> LENGTH: 8
<212> TYPE: PRT
<213> ORGANISM: Artificial Sequence
<220> FEATURE:
<223> OTHER INFORMATION: CDR H2 from 1204 (VH)

<400> SEQUENCE: 67

Ile Gly Ser Tyr Tyr Gly Tyr Thr
1 5

<210> SEQ ID NO 68
<211> LENGTH: 8
<212> TYPE: PRT

<213> ORGANISM: Artificial Sequence
<220> FEATURE:
<223> OTHER INFORMATION: CDR H2 from 1214 (VH)

<400> SEQUENCE: 68

Ile Gly Ser Gly Gly Gly Tyr Thr
1 5

<210> SEQ ID NO 69
<211> LENGTH: 8
<212> TYPE: PRT
<213> ORGANISM: Artificial Sequence
<220> FEATURE:
<223> OTHER INFORMATION: CDR H2 from 1618 (VH) or 3012 (VH) or 3014 (VH)
or 3016 (VH) or 3018 (VH) or 3020 (VH) or 3022 (VH) or 3024 (VH)
or 3026 (VH) or 3028 (VH) or 3030 (VH) or 3032 (VH) or 3034 (VH)
or 3036 (VH

<400> SEQUENCE: 69

Ile Ser Ser Gly Ser Gly Ser Thr
1 5

<210> SEQ ID NO 70
<211> LENGTH: 8
<212> TYPE: PRT
<213> ORGANISM: Artificial Sequence
<220> FEATURE:
<223> OTHER INFORMATION: CDR H2 from 1620 (VH)

<400> SEQUENCE: 70

Ile Ser Ser Ser Gly Ser Tyr Thr
1 5

<210> SEQ ID NO 71
<211> LENGTH: 8
<212> TYPE: PRT
<213> ORGANISM: Artificial Sequence
<220> FEATURE:
<223> OTHER INFORMATION: CDR H2 from 1626 (VH)

<400> SEQUENCE: 71

Ile Gly Gly Tyr Tyr Tyr Ser Thr
1 5

<210> SEQ ID NO 72
<211> LENGTH: 9
<212> TYPE: PRT
<213> ORGANISM: Artificial Sequence
<220> FEATURE:
<223> OTHER INFORMATION: CDR H3 from 1200 (VH)

<400> SEQUENCE: 72

Ala Arg Asp Val Ala Tyr Phe Asp Tyr
1 5

<210> SEQ ID NO 73
<211> LENGTH: 10
<212> TYPE: PRT
<213> ORGANISM: Artificial Sequence
<220> FEATURE:
<223> OTHER INFORMATION: CDR H3 from 1202 (VH)

<400> SEQUENCE: 73

Ala Arg Ser Tyr Tyr Gly Tyr Phe Asp Tyr
1 5 10

<210> SEQ ID NO 74

<211> LENGTH: 16
<212> TYPE: PRT
<213> ORGANISM: Artificial Sequence
<220> FEATURE:
<223> OTHER INFORMATION: CDR H3 from 1204 (VH)

<400> SEQUENCE: 74

Ala Arg Ala Tyr Tyr Asp Tyr Asn Tyr Tyr Tyr Ala Tyr Phe Asp Tyr
1 5 10 15

<210> SEQ ID NO 75
<211> LENGTH: 9
<212> TYPE: PRT
<213> ORGANISM: Artificial Sequence
<220> FEATURE:
<223> OTHER INFORMATION: CDR H3 from 1214 (VH)

<400> SEQUENCE: 75

Ala Arg Val Gly His Pro Phe Asp Tyr
1 5

<210> SEQ ID NO 76
<211> LENGTH: 14
<212> TYPE: PRT
<213> ORGANISM: Artificial Sequence
<220> FEATURE:
<223> OTHER INFORMATION: CDR H3 from 1618 (VH) or 3012 (VH) or 3014 (VH) or 3016 (VH) or 3018 (VH) or 3020 (VH) or 3022 (VH) or 3024 (VH) or 3026 (VH) or 3028 (VH) or 3030 (VH) or 3032 (VH) or 3034 (VH) or 3036 (VH)

<400> SEQUENCE: 76

Ala Arg Ser Ser Tyr Tyr Gly Ser Tyr Tyr Ser Ile Asp Tyr
1 5 10

<210> SEQ ID NO 77
<211> LENGTH: 10
<212> TYPE: PRT
<213> ORGANISM: Artificial Sequence
<220> FEATURE:
<223> OTHER INFORMATION: CDR H3 from 1620 (VH)

<400> SEQUENCE: 77

Ala Arg Ser Val Gly Pro Tyr Phe Asp Tyr
1 5 10

<210> SEQ ID NO 78
<211> LENGTH: 10
<212> TYPE: PRT
<213> ORGANISM: Artificial Sequence
<220> FEATURE:
<223> OTHER INFORMATION: CDR H3 from 1626 (VH)

<400> SEQUENCE: 78

Ala Arg Ser Tyr Tyr Gly Ser Ile Asp Tyr
1 5 10

<210> SEQ ID NO 79
<211> LENGTH: 8
<212> TYPE: PRT
<213> ORGANISM: Artificial Sequence
<220> FEATURE:
<223> OTHER INFORMATION: CDR L3 from 1201 (VL)

<400> SEQUENCE: 79

Gln Gln Tyr Tyr Ile Pro His Thr
1 5

<210> SEQ ID NO 80
<211> LENGTH: 10
<212> TYPE: PRT
<213> ORGANISM: Artificial Sequence
<220> FEATURE:
<223> OTHER INFORMATION: CDR L3 from 1203 (VL)

<400> SEQUENCE: 80

Gln Gln Tyr Tyr Thr Val Val Pro Phe Thr
1               5                   10

<210> SEQ ID NO 81
<211> LENGTH: 10
<212> TYPE: PRT
<213> ORGANISM: Artificial Sequence
<220> FEATURE:
<223> OTHER INFORMATION: CDR L3 from 1205 (VL)

<400> SEQUENCE: 81

Gln Gln Ser Val Pro His Tyr Pro Phe Thr
1               5                   10

<210> SEQ ID NO 82
<211> LENGTH: 8
<212> TYPE: PRT
<213> ORGANISM: Artificial Sequence
<220> FEATURE:
<223> OTHER INFORMATION: CDR L3 from 1215 (VL)

<400> SEQUENCE: 82

Gln Gln Asp Ala Tyr Pro His Thr
1               5

<210> SEQ ID NO 83
<211> LENGTH: 9
<212> TYPE: PRT
<213> ORGANISM: Artificial Sequence
<220> FEATURE:
<223> OTHER INFORMATION: CDR L3 from 1619 (VL) or 3013 (VL) or 3015 (VL)
      or 3017 (VL) or 3019 (VL) or 3021 (VL) or 3023 (VL) or 3025 (VL)
      or 3027 (VL) or 3029 (VL) or 3031 (VL) or 3033 (VL) or 3035 (VL)
      or 3037 (VL)

<400> SEQUENCE: 83

Gln Gln Tyr Tyr Asp Asn Leu Pro Thr
1               5

<210> SEQ ID NO 84
<211> LENGTH: 8
<212> TYPE: PRT
<213> ORGANISM: Artificial Sequence
<220> FEATURE:
<223> OTHER INFORMATION: CDR L3 from 1621 (VL)

<400> SEQUENCE: 84

Gln Gln Gly Val Gly Pro Tyr Thr
1               5

<210> SEQ ID NO 85
<211> LENGTH: 10
<212> TYPE: PRT
<213> ORGANISM: Artificial Sequence
<220> FEATURE:
<223> OTHER INFORMATION: CDR L3 from 1627 (VL)

<400> SEQUENCE: 85

Gln Gln Gly Thr Gly Tyr Gly Pro Leu Thr 1 5 10

<210> SEQ ID NO 86
<211> LENGTH: 330
<212> TYPE: PRT
<213> ORGANISM: Artificial Sequence
<220> FEATURE:
<223> OTHER INFORMATION: IgG1 LALA-sequence

<400> SEQUENCE: 86

Ala Ser Thr Lys Gly Pro Ser Val Phe Pro Leu Ala Pro Ser Ser Lys
1 5 10 15

Ser Thr Ser Gly Gly Thr Ala Ala Leu Gly Cys Leu Val Lys Asp Tyr
20 25 30

Phe Pro Glu Pro Val Thr Val Ser Trp Asn Ser Gly Ala Leu Thr Ser
35 40 45

Gly Val His Thr Phe Pro Ala Val Leu Gln Ser Ser Gly Leu Tyr Ser
50 55 60

Leu Ser Ser Val Val Thr Val Pro Ser Ser Ser Leu Gly Thr Gln Thr
65 70 75 80

Tyr Ile Cys Asn Val Asn His Lys Pro Ser Asn Thr Lys Val Asp Lys
85 90 95

Lys Val Glu Pro Lys Ser Cys Asp Lys Thr His Thr Cys Pro Pro Cys
100 105 110

Pro Ala Pro Glu Ala Ala Gly Gly Pro Ser Val Phe Leu Phe Pro Pro
115 120 125

Lys Pro Lys Asp Thr Leu Met Ile Ser Arg Thr Pro Glu Val Thr Cys
130 135 140

Val Val Val Asp Val Ser His Glu Asp Pro Glu Val Lys Phe Asn Trp
145 150 155 160

Tyr Val Asp Gly Val Glu Val His Asn Ala Lys Thr Lys Pro Arg Glu
165 170 175

Glu Gln Tyr Asn Ser Thr Tyr Arg Val Val Ser Val Leu Thr Val Leu
180 185 190

His Gln Asp Trp Leu Asn Gly Lys Glu Tyr Lys Cys Lys Val Ser Asn
195 200 205

Lys Ala Leu Pro Ala Pro Ile Glu Lys Thr Ile Ser Lys Ala Lys Gly
210 215 220

Gln Pro Arg Glu Pro Gln Val Tyr Thr Leu Pro Pro Ser Arg Asp Glu
225 230 235 240

Leu Thr Lys Asn Gln Val Ser Leu Thr Cys Leu Val Lys Gly Phe Tyr
245 250 255

Pro Ser Asp Ile Ala Val Glu Trp Glu Ser Asn Gly Gln Pro Glu Asn
260 265 270

Asn Tyr Lys Thr Thr Pro Pro Val Leu Asp Ser Asp Gly Ser Phe Phe
275 280 285

Leu Tyr Ser Lys Leu Thr Val Asp Lys Ser Arg Trp Gln Gln Gly Asn
290 295 300

Val Phe Ser Cys Ser Val Met His Glu Ala Leu His Asn His Tyr Thr
305 310 315 320

Gln Lys Ser Leu Ser Leu Ser Pro Gly Lys
325 330

<210> SEQ ID NO 87
<211> LENGTH: 11
<212> TYPE: PRT

-continued

<213> ORGANISM: Artificial Sequence
<220> FEATURE:
<223> OTHER INFORMATION: Linker

<400> SEQUENCE: 87

Ser Gly Gly Gly Gly Ser Gly Gly Gly Gly Ser
1 5 10

<210> SEQ ID NO 88
<211> LENGTH: 13
<212> TYPE: PRT
<213> ORGANISM: Artificial Sequence
<220> FEATURE:
<223> OTHER INFORMATION: Linker

<400> SEQUENCE: 88

Ser Gly Gly Gly Gly Ser Gly Gly Gly Gly Ser Ala Pro
1 5 10

<210> SEQ ID NO 89
<211> LENGTH: 5
<212> TYPE: PRT
<213> ORGANISM: Artificial Sequence
<220> FEATURE:
<223> OTHER INFORMATION: Linker

<400> SEQUENCE: 89

Asn Phe Ser Gln Pro
1 5

<210> SEQ ID NO 90
<211> LENGTH: 5
<212> TYPE: PRT
<213> ORGANISM: Artificial Sequence
<220> FEATURE:
<223> OTHER INFORMATION: Linker

<400> SEQUENCE: 90

Lys Arg Thr Val Ala
1 5

<210> SEQ ID NO 91
<211> LENGTH: 8
<212> TYPE: PRT
<213> ORGANISM: Artificial Sequence
<220> FEATURE:
<223> OTHER INFORMATION: Linker

<400> SEQUENCE: 91

Gly Gly Gly Ser Gly Gly Gly Gly
1 5

<210> SEQ ID NO 92
<211> LENGTH: 10
<212> TYPE: PRT
<213> ORGANISM: Artificial Sequence
<220> FEATURE:
<223> OTHER INFORMATION: Linker (also connector sequence m6)

<400> SEQUENCE: 92

Gly Gly Gly Gly Ser Gly Gly Gly Gly Ser
1 5 10

<210> SEQ ID NO 93
<211> LENGTH: 15
<212> TYPE: PRT
<213> ORGANISM: Artificial Sequence

```
<220> FEATURE:
<223> OTHER INFORMATION: Linker

<400> SEQUENCE: 93

Gly Gly Gly Gly Ser Gly Gly Gly Gly Ser Gly Gly Gly Gly Ser
1               5                   10                  15


<210> SEQ ID NO 94
<211> LENGTH: 330
<212> TYPE: PRT
<213> ORGANISM: Artificial Sequence
<220> FEATURE:
<223> OTHER INFORMATION: IgG1 heavy chain constant region sequence

<400> SEQUENCE: 94

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
```

325 330

<210> SEQ ID NO 95
<211> LENGTH: 107
<212> TYPE: PRT
<213> ORGANISM: Artificial Sequence
<220> FEATURE:
<223> OTHER INFORMATION: IgG1 light chain constant region sequence

<400> SEQUENCE: 95

Arg Thr Val Ala Ala Pro Ser Val Phe Ile Phe Pro Pro Ser Asp Glu
1 5 10 15

Gln Leu Lys Ser Gly Thr Ala Ser Val Val Cys Leu Leu Asn Asn Phe
20 25 30

Tyr Pro Arg Glu Ala Lys Val Gln Trp Lys Val Asp Asn Ala Leu Gln
35 40 45

Ser Gly Asn Ser Gln Glu Ser Val Thr Glu Gln Asp Ser Lys Asp Ser
50 55 60

Thr Tyr Ser Leu Ser Ser Thr Leu Thr Leu Ser Lys Ala Asp Tyr Glu
65 70 75 80

Lys His Lys Val Tyr Ala Cys Glu Val Thr His Gln Gly Leu Ser Ser
85 90 95

Pro Val Thr Lys Ser Phe Asn Arg Gly Glu Cys
100 105

<210> SEQ ID NO 96
<211> LENGTH: 121
<212> TYPE: PRT
<213> ORGANISM: Artificial Sequence
<220> FEATURE:
<223> OTHER INFORMATION: 5T4-specific VH sequence 2992 optimized from
1210 (VH)

<400> SEQUENCE: 96

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Asp Phe Glu Ser Tyr
20 25 30

Ala Met Ser Trp Val Arg Gln Ala Pro Gly Lys Gly Leu Glu Trp Val
35 40 45

Ser Ala Ile Ser Gly Ser Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Tyr Tyr Gly Gly Tyr Tyr Ser Ala Trp Met Asp Tyr Trp Gly
100 105 110

Gln Gly Thr Leu Val Thr Val Ser Ser
115 120

<210> SEQ ID NO 97
<211> LENGTH: 107
<212> TYPE: PRT
<213> ORGANISM: Artificial Sequence
<220> FEATURE:
<223> OTHER INFORMATION: 5T4-specific VL sequence 2993 optimized from
1211 (VL)

<400> SEQUENCE: 97

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Ala
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Gln Gly Thr Lys Leu Glu Ile Lys
            100                 105


<210> SEQ ID NO 98
<211> LENGTH: 121
<212> TYPE: PRT
<213> ORGANISM: Artificial Sequence
<220> FEATURE:
<223> OTHER INFORMATION: 5T4-specific VH sequence 2994 optimized from
      1210 (VH)

<400> SEQUENCE: 98

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asp Ser Tyr
            20                  25                  30

Ala Met Ser Trp Val Arg Gln Ala Pro Gly Lys Gly Leu Glu Trp Val
        35                  40                  45

Ser Ala Ile Ser Gly Arg Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120


<210> SEQ ID NO 99
<211> LENGTH: 107
<212> TYPE: PRT
<213> ORGANISM: Artificial Sequence
<220> FEATURE:
<223> OTHER INFORMATION: 5T4-specific VL sequence 2995 optimized from
      1211 (VL)

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Ala
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60
```

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Gln Gly Thr Lys Leu Glu Ile Lys
            100                 105


<210> SEQ ID NO 100
<211> LENGTH: 121
<212> TYPE: PRT
<213> ORGANISM: Artificial Sequence
<220> FEATURE:
<223> OTHER INFORMATION: 5T4-specific VH sequence 2996 optimized from
      1210 (VH)

<400> SEQUENCE: 100

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asp Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120


<210> SEQ ID NO 101
<211> LENGTH: 107
<212> TYPE: PRT
<213> ORGANISM: Artificial Sequence
<220> FEATURE:
<223> OTHER INFORMATION: 5T4-specific VL sequence 2997 optimized from
      1211 (VL)

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Gln Ala
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Gln Gly Thr Lys Leu Glu Ile Lys
            100                 105


<210> SEQ ID NO 102
<211> LENGTH: 121
```

<212> TYPE: PRT
<213> ORGANISM: Artificial Sequence
<220> FEATURE:
<223> OTHER INFORMATION: 5T4-specific VH sequence 2998 optimized from 1210 (VH)

<400> SEQUENCE: 102

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asp Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120
```

<210> SEQ ID NO 103
<211> LENGTH: 107
<212> TYPE: PRT
<213> ORGANISM: Artificial Sequence
<220> FEATURE:
<223> OTHER INFORMATION: 5T4-specific VL sequence 2999 optimized from 1211 (VL)

<400> SEQUENCE: 103

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gln Ala
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Gln Gly Thr Lys Leu Glu Ile Lys
            100                 105
```

<210> SEQ ID NO 104
<211> LENGTH: 121
<212> TYPE: PRT
<213> ORGANISM: Artificial Sequence
<220> FEATURE:
<223> OTHER INFORMATION: 5T4-specific VH sequence 3000 optimized from 1210 (VH)

<400> SEQUENCE: 104

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Ser Ser Tyr
```

```
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120


<210> SEQ ID NO 105
<211> LENGTH: 107
<212> TYPE: PRT
<213> ORGANISM: Artificial Sequence
<220> FEATURE:
<223> OTHER INFORMATION: 5T4-specific VL sequence 3001 optimized from
      1211 (VL)

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Gln Ala
            20                  25                  30

Leu Asn Trp Tyr Gln Gln Lys Pro Gly Lys Ala Pro Lys Leu Leu Ile
        35                  40                  45

Tyr Ala Ala Asp Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Gln Gly Thr Lys Leu Glu Ile Lys
            100                 105


<210> SEQ ID NO 106
<211> LENGTH: 121
<212> TYPE: PRT
<213> ORGANISM: Artificial Sequence
<220> FEATURE:
<223> OTHER INFORMATION: 5T4-specific VH sequence 3002 optimized from
      1210 (VH)

<400> SEQUENCE: 106

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120


<210> SEQ ID NO 107
<211> LENGTH: 107
<212> TYPE: PRT
<213> ORGANISM: Artificial Sequence
<220> FEATURE:
<223> OTHER INFORMATION: 5T4-specific VL sequence 3003 optimized from
      1211 (VL)

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Ala
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Gln Gly Thr Lys Leu Glu Ile Lys
            100                 105


<210> SEQ ID NO 108
<211> LENGTH: 121
<212> TYPE: PRT
<213> ORGANISM: Artificial Sequence
<220> FEATURE:
<223> OTHER INFORMATION: 5T4-specific VH sequence 3004 optimized from
      1210 (VH)

<400> SEQUENCE: 108

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asp Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120


<210> SEQ ID NO 109
<211> LENGTH: 107
<212> TYPE: PRT
```

<213> ORGANISM: Artificial Sequence
<220> FEATURE:
<223> OTHER INFORMATION: 5T4-specific VL sequence 3005 optimized from 1211 (VL)

<400> SEQUENCE: 109

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Ala
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Gln Gly Thr Lys Leu Glu Ile Lys
            100                 105
```

<210> SEQ ID NO 110
<211> LENGTH: 121
<212> TYPE: PRT
<213> ORGANISM: Artificial Sequence
<220> FEATURE:
<223> OTHER INFORMATION: 5T4-specific VH sequence 3006 optimized from 1210 (VH)

<400> SEQUENCE: 110

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Glu Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120
```

<210> SEQ ID NO 111
<211> LENGTH: 107
<212> TYPE: PRT
<213> ORGANISM: Artificial Sequence
<220> FEATURE:
<223> OTHER INFORMATION: 5T4-specific VL sequence 3007 optimized from 1211 (VL)

<400> SEQUENCE: 111

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile His Gln Ala
            20                  25                  30
```

```
Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95

Thr Phe Gly Gln Gly Thr Lys Leu Glu Ile Lys
            100                 105


<210> SEQ ID NO 112
<211> LENGTH: 121
<212> TYPE: PRT
<213> ORGANISM: Artificial Sequence
<220> FEATURE:
<223> OTHER INFORMATION: 5T4-specific VH sequence 3008 optimized from
      1210 (VH)

<400> SEQUENCE: 112

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Asp Phe Asp Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Tyr Gly Gly Tyr Tyr Ser Ala Trp Met Asp Tyr Trp Gly
            100                 105                 110

Gln Gly Thr Leu Val Thr Val Ser Ser
        115                 120


<210> SEQ ID NO 113
<211> LENGTH: 107
<212> TYPE: PRT
<213> ORGANISM: Artificial Sequence
<220> FEATURE:
<223> OTHER INFORMATION: 5T4-specific VL sequence 3009 optimized from
      1211 (VL)

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile His Gln Ala
            20                  25                  30

Leu Asn Trp Tyr Gln Gln Lys Pro Gly Lys Ala Pro Lys Leu Leu Ile
        35                  40                  45

Tyr Ala Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Tyr Gly Tyr Leu His
                85                  90                  95
```

```
Thr Phe Gly Gln Gly Thr Lys Leu Glu Ile Lys
            100                 105


<210> SEQ ID NO 114
<211> LENGTH: 121
<212> TYPE: PRT
<213> ORGANISM: Artificial Sequence
<220> FEATURE:
<223> OTHER INFORMATION: CD137-specific VH sequence 3012 optimized from
      1618 (VH)

<400> SEQUENCE: 114

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120


<210> SEQ ID NO 115
<211> LENGTH: 107
<212> TYPE: PRT
<213> ORGANISM: Artificial Sequence
<220> FEATURE:
<223> OTHER INFORMATION: CD137-specific VL sequence 3013 optimized from
      1619 (VL)

<400> SEQUENCE: 115

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gln Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105


<210> SEQ ID NO 116
<211> LENGTH: 121
<212> TYPE: PRT
<213> ORGANISM: Artificial Sequence
<220> FEATURE:
<223> OTHER INFORMATION: CD137-specific VH sequence 3014 optimized from
      1618 (VH)
```

<400> SEQUENCE: 116

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Tyr Gly
20 25 30

Ser Met Tyr Trp Val Arg Gln Ala Pro Gly Lys Gly Leu Glu Trp Val
35 40 45

Ser Ser Ile Ser Ser Gly Ser Gly Ser Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Ser Tyr Tyr Gly Ser Tyr Tyr Ser Ile Asp Tyr Trp Gly
100 105 110

Gln Gly Thr Leu Val Thr Val Ser Ser
115 120

<210> SEQ ID NO 117
<211> LENGTH: 107
<212> TYPE: PRT
<213> ORGANISM: Artificial Sequence
<220> FEATURE:
<223> OTHER INFORMATION: CD137-specific VL sequence 3015 optimized from 1619 (VL)

<400> SEQUENCE: 117

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Arg Gln Tyr
20 25 30

Leu Asn Trp Tyr Gln Gln Lys Pro Gly Lys Ala Pro Lys Leu Leu Ile
35 40 45

Tyr Ser Ala Asp Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Asp Asn Leu Pro
85 90 95

Thr Phe Gly Gln Gly Thr Lys Leu Glu Ile Lys
100 105

<210> SEQ ID NO 118
<211> LENGTH: 121
<212> TYPE: PRT
<213> ORGANISM: Artificial Sequence
<220> FEATURE:
<223> OTHER INFORMATION: CD137-specific VH sequence 3016 optimized from 1618 (VH)

<400> SEQUENCE: 118

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Tyr Gly
20 25 30

Ser Met Tyr Trp Val Arg Gln Ala Pro Gly Lys Gly Leu Glu Trp Val
35 40 45

```
Ser Ser Ile Ser Ser Gly Ser Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120


<210> SEQ ID NO 119
<211> LENGTH: 107
<212> TYPE: PRT
<213> ORGANISM: Artificial Sequence
<220> FEATURE:
<223> OTHER INFORMATION: CD137-specific VL sequence 3017 optimized from
      1619 (VL)

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Gln Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105


<210> SEQ ID NO 120
<211> LENGTH: 121
<212> TYPE: PRT
<213> ORGANISM: Artificial Sequence
<220> FEATURE:
<223> OTHER INFORMATION: CD137-specific VH sequence 3018 optimized from
      1618 (VH)

<400> SEQUENCE: 120

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110
```

```
Gln Gly Thr Leu Val Thr Val Ser Ser
        115                 120


<210> SEQ ID NO 121
<211> LENGTH: 107
<212> TYPE: PRT
<213> ORGANISM: Artificial Sequence
<220> FEATURE:
<223> OTHER INFORMATION: CD137-specific VL sequence 3019 optimized from
      1619 (VL)

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Gln Tyr
            20                  25                  30

Leu Asn Trp Tyr Gln Gln Lys Pro Gly Lys Ala Pro Lys Leu Leu Ile
        35                  40                  45

Tyr Ser Ala Glu Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105


<210> SEQ ID NO 122
<211> LENGTH: 121
<212> TYPE: PRT
<213> ORGANISM: Artificial Sequence
<220> FEATURE:
<223> OTHER INFORMATION: CD137-specific VH sequence 3020 optimized from
      1618 (VH)

<400> SEQUENCE: 122

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120


<210> SEQ ID NO 123
<211> LENGTH: 107
<212> TYPE: PRT
<213> ORGANISM: Artificial Sequence
<220> FEATURE:
<223> OTHER INFORMATION: CD137-specific VL sequence 3021 optimized from
      1619 (VL)
```

<400> SEQUENCE: 123

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Arg Ser Tyr
20 25 30

Leu Asn Trp Tyr Gln Gln Lys Pro Gly Lys Ala Pro Lys Leu Leu Ile
35 40 45

Tyr Ser Ala Ser Ser Leu Gln Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Asp Asn Leu Pro
85 90 95

Thr Phe Gly Gln Gly Thr Lys Leu Glu Ile Lys
100 105

<210> SEQ ID NO 124
<211> LENGTH: 121
<212> TYPE: PRT
<213> ORGANISM: Artificial Sequence
<220> FEATURE:
<223> OTHER INFORMATION: CD137-specific VH sequence 3022 optimized from 1618 (VH)

<400> SEQUENCE: 124

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Asp Tyr Gly
20 25 30

Ser Met Tyr Trp Val Arg Gln Ala Pro Gly Lys Gly Leu Glu Trp Val
35 40 45

Ser Ser Ile Ser Ser Gly Ser Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Ser Tyr Tyr Gly Ser Tyr Tyr Ser Ile Asp Tyr Trp Gly
100 105 110

Gln Gly Thr Leu Val Thr Val Ser Ser
115 120

<210> SEQ ID NO 125
<211> LENGTH: 107
<212> TYPE: PRT
<213> ORGANISM: Artificial Sequence
<220> FEATURE:
<223> OTHER INFORMATION: CD137-specific VL sequence 3023 optimized from 1619 (VL)

<400> SEQUENCE: 125

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Arg Gln Tyr
20 25 30

Leu Asn Trp Tyr Gln Gln Lys Pro Gly Lys Ala Pro Lys Leu Leu Ile
35 40 45

Tyr Gly Ala Ser Ser Leu Gln Ser Gly Val Pro Ser Arg Phe Ser Gly

```
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105


<210> SEQ ID NO 126
<211> LENGTH: 121
<212> TYPE: PRT
<213> ORGANISM: Artificial Sequence
<220> FEATURE:
<223> OTHER INFORMATION: CD137-specific VH sequence 3024 optimized from
      1618 (VH)

<400> SEQUENCE: 126

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120


<210> SEQ ID NO 127
<211> LENGTH: 107
<212> TYPE: PRT
<213> ORGANISM: Artificial Sequence
<220> FEATURE:
<223> OTHER INFORMATION: CD137-specific VL sequence 3025 optimized from
      1619 (VL)

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105
```

```
<210> SEQ ID NO 128
<211> LENGTH: 121
<212> TYPE: PRT
<213> ORGANISM: Artificial Sequence
<220> FEATURE:
<223> OTHER INFORMATION: CD137-specific VH sequence 3026 optimized from
      1618 (VH)

<400> SEQUENCE: 128

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120


<210> SEQ ID NO 129
<211> LENGTH: 107
<212> TYPE: PRT
<213> ORGANISM: Artificial Sequence
<220> FEATURE:
<223> OTHER INFORMATION: CD137-specific VL sequence 3027 optimized from
      1619 (VL)

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Asn Trp Tyr Gln Gln Lys Pro Gly Lys Ala Pro Lys Leu Leu Ile
        35                  40                  45

Tyr Gly Ala Asp Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105


<210> SEQ ID NO 130
<211> LENGTH: 121
<212> TYPE: PRT
<213> ORGANISM: Artificial Sequence
<220> FEATURE:
<223> OTHER INFORMATION: CD137-specific VH sequence 3028 optimized from
      1618 (VH)

<400> SEQUENCE: 130

Glu Val Gln Leu Leu Glu Ser Gly Gly Gly Leu Val Gln Pro Gly Gly
1               5                   10                  15
```

```
Ser Leu Arg Leu Ser Cys Ala Ala Ser Gly Phe Asp Phe Ser Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120


<210> SEQ ID NO 131
<211> LENGTH: 107
<212> TYPE: PRT
<213> ORGANISM: Artificial Sequence
<220> FEATURE:
<223> OTHER INFORMATION: CD137-specific VL sequence 3029 optimized from
      1619 (VL)

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Gln Tyr
            20                  25                  30

Leu Asn Trp Tyr Gln Gln Lys Pro Gly Lys Ala Pro Lys Leu Leu Ile
        35                  40                  45

Tyr Gly Ala Glu Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105


<210> SEQ ID NO 132
<211> LENGTH: 121
<212> TYPE: PRT
<213> ORGANISM: Artificial Sequence
<220> FEATURE:
<223> OTHER INFORMATION: CD137-specific VH sequence 3030 optimized from
      1618 (VH)

<400> SEQUENCE: 132

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr His Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120


<210> SEQ ID NO 133
<211> LENGTH: 107
<212> TYPE: PRT
<213> ORGANISM: Artificial Sequence
<220> FEATURE:
<223> OTHER INFORMATION: CD137-specific VL sequence 3031 optimized from
      1619 (VL)

<400> SEQUENCE: 133

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Glu Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105


<210> SEQ ID NO 134
<211> LENGTH: 121
<212> TYPE: PRT
<213> ORGANISM: Artificial Sequence
<220> FEATURE:
<223> OTHER INFORMATION: CD137-specific VH sequence 3032 optimized from
      1618 (VH)

<400> SEQUENCE: 134

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120


<210> SEQ ID NO 135
```

<211> LENGTH: 107
<212> TYPE: PRT
<213> ORGANISM: Artificial Sequence
<220> FEATURE:
<223> OTHER INFORMATION: CD137-specific VL sequence 3033 optimized from
1619 (VL)

<400> SEQUENCE: 135

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Ser Tyr
20 25 30

Leu Asn Trp Tyr Gln Gln Lys Pro Gly Lys Ala Pro Lys Leu Leu Ile
35 40 45

Tyr Ala Ala Ser Ser Leu His Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Asp Asn Leu Pro
85 90 95

Thr Phe Gly Gln Gly Thr Lys Leu Glu Ile Lys
100 105

<210> SEQ ID NO 136
<211> LENGTH: 121
<212> TYPE: PRT
<213> ORGANISM: Artificial Sequence
<220> FEATURE:
<223> OTHER INFORMATION: CD137-specific VH sequence 3034 optimized from
1618 (VH)

<400> SEQUENCE: 136

Glu Val Gln Leu Leu Glu Ser Gly Gly Gly Leu Val Gln Pro Gly Gly
1 5 10 15

Ser Leu Arg Leu Ser Cys Ala Ala Ser Gly Phe Thr Phe Ser Tyr Gly
20 25 30

Ser Met Tyr Trp Val Arg Gln Ala Pro Gly Lys Gly Leu Glu Trp Val
35 40 45

Ser Ser Ile Ser Ser Gly Ser Gly Ser Thr His Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Ser Ser Tyr Tyr Gly Ser Tyr Tyr Ser Ile Asp Tyr Trp Gly
100 105 110

Gln Gly Thr Leu Val Thr Val Ser Ser
115 120

<210> SEQ ID NO 137
<211> LENGTH: 107
<212> TYPE: PRT
<213> ORGANISM: Artificial Sequence
<220> FEATURE:
<223> OTHER INFORMATION: CD137-specific VL sequence 3035 optimized from
1619 (VL)

<400> SEQUENCE: 137

Asp Ile Gln Met Thr Gln Ser Pro Ser Ser Leu Ser Ala Ser Val Gly
1 5 10 15

```
Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys
            100                 105


<210> SEQ ID NO 138
<211> LENGTH: 121
<212> TYPE: PRT
<213> ORGANISM: Artificial Sequence
<220> FEATURE:
<223> OTHER INFORMATION: CD137-specific VH sequence 3036 optimized from
      1618 (VH)

<400> SEQUENCE: 138

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser
        115                 120


<210> SEQ ID NO 139
<211> LENGTH: 107
<212> TYPE: PRT
<213> ORGANISM: Artificial Sequence
<220> FEATURE:
<223> OTHER INFORMATION: CD137-specific VL sequence 3037 optimized from
      1619 (VL)

<400> SEQUENCE: 139

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Arg Ser Tyr
            20                  25                  30

Leu Asn Trp Tyr Gln Gln Lys Pro Gly Lys Ala Pro Lys Leu Leu Ile
        35                  40                  45

Tyr Gly Ala Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

Glu Asp Phe Ala Thr Tyr Tyr Cys Gln Gln Tyr Tyr Asp Asn Leu Pro
85 90 95

Thr Phe Gly Gln Gly Thr Lys Leu Glu Ile Lys
100 105

<210> SEQ ID NO 140
<211> LENGTH: 15
<212> TYPE: PRT
<213> ORGANISM: Artificial Sequence
<220> FEATURE:
<223> OTHER INFORMATION: connector sequence m15

<400> SEQUENCE: 140

Thr His Thr Cys Pro Pro Cys Pro Glu Pro Lys Ser Ser Asp Lys
1 5 10 15

<210> SEQ ID NO 141
<211> LENGTH: 5
<212> TYPE: PRT
<213> ORGANISM: Artificial Sequence
<220> FEATURE:
<223> OTHER INFORMATION: connector sequence m16

<400> SEQUENCE: 141

Gly Gly Gly Gly Ser
1 5

<210> SEQ ID NO 142
<211> LENGTH: 13
<212> TYPE: PRT
<213> ORGANISM: Artificial Sequence
<220> FEATURE:
<223> OTHER INFORMATION: connector sequence m17

<400> SEQUENCE: 142

Glu Ala Ala Lys Glu Ala Ala Lys Gly Gly Gly Gly Ser
1 5 10

<210> SEQ ID NO 143
<211> LENGTH: 8
<212> TYPE: PRT
<213> ORGANISM: Artificial Sequence
<220> FEATURE:
<223> OTHER INFORMATION: connector sequence m18

<400> SEQUENCE: 143

Glu Ala Ala Lys Glu Ala Ala Lys
1 5

<210> SEQ ID NO 144
<211> LENGTH: 8
<212> TYPE: PRT
<213> ORGANISM: Artificial Sequence
<220> FEATURE:
<223> OTHER INFORMATION: CDR H1 from 2992 (VH) or 3006 (VH)

<400> SEQUENCE: 144

Gly Phe Asp Phe Glu Ser Tyr Ala
1 5

<210> SEQ ID NO 145
<211> LENGTH: 6
<212> TYPE: PRT
<213> ORGANISM: Artificial Sequence
<220> FEATURE:
<223> OTHER INFORMATION: CDR L1 from 2993 (VL) or 2995 (VL) or 3003 (VL)

<400> SEQUENCE: 145

Gln Ser Ile Arg Ser Ala
1 5

<210> SEQ ID NO 146
<211> LENGTH: 8
<212> TYPE: PRT
<213> ORGANISM: Artificial Sequence
<220> FEATURE:
<223> OTHER INFORMATION: CDR H1 from 2994 (VH) or 2996 (VH) or 2998 (VH) or 3004 (VH) or 3008 (VH)

<400> SEQUENCE: 146

Gly Phe Asp Phe Asp Ser Tyr Ala
1 5

<210> SEQ ID NO 147
<211> LENGTH: 8
<212> TYPE: PRT
<213> ORGANISM: Artificial Sequence
<220> FEATURE:
<223> OTHER INFORMATION: CDR H2 from 2994 (VH)

<400> SEQUENCE: 147

Ile Ser Gly Arg Gly Gly Ser Thr
1 5

<210> SEQ ID NO 148
<211> LENGTH: 6
<212> TYPE: PRT
<213> ORGANISM: Artificial Sequence
<220> FEATURE:
<223> OTHER INFORMATION: CDR L1 from 2997 (VL) or 3001 (VL)

<400> SEQUENCE: 148

Gln Ser Ile Arg Gln Ala
1 5

<210> SEQ ID NO 149
<211> LENGTH: 6
<212> TYPE: PRT
<213> ORGANISM: Artificial Sequence
<220> FEATURE:
<223> OTHER INFORMATION: CDR L1 from 2999 (VL)

<400> SEQUENCE: 149

Gln Ser Ile Ser Gln Ala
1 5

<210> SEQ ID NO 150
<211> LENGTH: 8
<212> TYPE: PRT
<213> ORGANISM: Artificial Sequence
<220> FEATURE:
<223> OTHER INFORMATION: CDR H1 from 3000 (VH)

<400> SEQUENCE: 150

Gly Phe Asp Phe Ser Ser Tyr Ala
1 5

<210> SEQ ID NO 151
<211> LENGTH: 3
<212> TYPE: PRT
<213> ORGANISM: Artificial Sequence
<220> FEATURE:
<223> OTHER INFORMATION: L2

<400> SEQUENCE: 151

Ala Ala Asp
1

<210> SEQ ID NO 152
<211> LENGTH: 8
<212> TYPE: PRT
<213> ORGANISM: Artificial Sequence
<220> FEATURE:
<223> OTHER INFORMATION: CDR H1 from 3002 (VH)

<400> SEQUENCE: 152

Gly Phe Thr Phe Asp Ser Tyr Ala
1 5

<210> SEQ ID NO 153
<211> LENGTH: 6
<212> TYPE: PRT
<213> ORGANISM: Artificial Sequence
<220> FEATURE:
<223> OTHER INFORMATION: CDR L1 from 3005 (VL)

<400> SEQUENCE: 153

Gln Ser Ile Ser Ser Ala
1 5

<210> SEQ ID NO 154
<211> LENGTH: 6
<212> TYPE: PRT
<213> ORGANISM: Artificial Sequence
<220> FEATURE:
<223> OTHER INFORMATION: CDR L1 from 3007 (VL) or 3009 (VL)

<400> SEQUENCE: 154

Gln Ser Ile His Gln Ala
1 5

<210> SEQ ID NO 155
<211> LENGTH: 3
<212> TYPE: PRT
<213> ORGANISM: Artificial Sequence
<220> FEATURE:
<223> OTHER INFORMATION: L2

<400> SEQUENCE: 155

Gly Ala Ser
1

<210> SEQ ID NO 156
<211> LENGTH: 8
<212> TYPE: PRT
<213> ORGANISM: Artificial Sequence
<220> FEATURE:
<223> OTHER INFORMATION: CDR H1 from 3012 (VH) or 3018 (VH) or 3020 (VH) or 3022 (VH) or 3024 (VH) or 3026 (VH) or 3030 (VH) or 3032 (VH) or 3036 (VH)

<400> SEQUENCE: 156

Gly Phe Thr Phe Asp Tyr Gly Ser
1 5

<210> SEQ ID NO 157
<211> LENGTH: 8
<212> TYPE: PRT
<213> ORGANISM: Artificial Sequence
<220> FEATURE:
<223> OTHER INFORMATION: CDR H1 from 3028 (VH)

<400> SEQUENCE: 157

Gly Phe Asp Phe Ser Tyr Gly Ser
1 5

<210> SEQ ID NO 158
<211> LENGTH: 6
<212> TYPE: PRT
<213> ORGANISM: Artificial Sequence
<220> FEATURE:
<223> OTHER INFORMATION: CDR L1 from 3013 (VL) or 3019 (VL)

<400> SEQUENCE: 158

Gln Ser Ile Ser Gln Tyr
1 5

<210> SEQ ID NO 159
<211> LENGTH: 6
<212> TYPE: PRT
<213> ORGANISM: Artificial Sequence
<220> FEATURE:
<223> OTHER INFORMATION: CDR L1 from 3015 (VL) or 3017 (VL) or 3023 (VL) or 3029 (VL)

<400> SEQUENCE: 159

Gln Ser Ile Arg Gln Tyr
1 5

<210> SEQ ID NO 160
<211> LENGTH: 3
<212> TYPE: PRT
<213> ORGANISM: Artificial Sequence
<220> FEATURE:
<223> OTHER INFORMATION: L2

<400> SEQUENCE: 160

Ser Ala Asp
1

<210> SEQ ID NO 161
<211> LENGTH: 3
<212> TYPE: PRT
<213> ORGANISM: Artificial Sequence
<220> FEATURE:
<223> OTHER INFORMATION: L2

<400> SEQUENCE: 161

Ser Ala Glu
1

<210> SEQ ID NO 162
<211> LENGTH: 6
<212> TYPE: PRT
<213> ORGANISM: Artificial Sequence
<220> FEATURE:
<223> OTHER INFORMATION: CDR L1 from 3021 (VL) or 3027 (VL) or 3037 (VL)

<400> SEQUENCE: 162

Gln Ser Ile Arg Ser Tyr
1 5

<210> SEQ ID NO 163
<211> LENGTH: 3
<212> TYPE: PRT
<213> ORGANISM: Artificial Sequence
<220> FEATURE:
<223> OTHER INFORMATION: L2

<400> SEQUENCE: 163

Ser Ala Ser
1

<210> SEQ ID NO 164

<400> SEQUENCE: 164

000

<210> SEQ ID NO 165
<211> LENGTH: 3
<212> TYPE: PRT
<213> ORGANISM: Artificial Sequence
<220> FEATURE:
<223> OTHER INFORMATION: L2

<400> SEQUENCE: 165

Gly Ala Asp
1

<210> SEQ ID NO 166
<211> LENGTH: 3
<212> TYPE: PRT
<213> ORGANISM: Artificial Sequence
<220> FEATURE:
<223> OTHER INFORMATION: L2

<400> SEQUENCE: 166

Gly Ala Glu
1

<210> SEQ ID NO 167
<211> LENGTH: 704
<212> TYPE: PRT
<213> ORGANISM: Artificial Sequence
<220> FEATURE:
<223> OTHER INFORMATION: 1618-1210L01 bispecific antibody heavy chain

<400> SEQUENCE: 167

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Tyr Gly
            20                  25                  30

Ser Met Tyr Trp Val Arg Gln Ala Pro Gly Lys Gly Leu Glu Trp Val
        35                  40                  45

Ser Ser Ile Ser Ser Gly Ser Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ser Ser Tyr Tyr Gly Ser Tyr Tyr Ser Ile Asp Tyr Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160
```

-continued

```
Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Asp Lys Thr His Thr Cys Pro Pro Cys Pro Ala Pro Glu Ala Ala Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys Gly Gly Gly Gly Ser Gly Gly Gly Gly Ser Glu Val Gln
    450                 455                 460

Leu Leu Glu Ser Gly Gly Gly Leu Val Gln Pro Gly Gly Ser Leu Arg
465                 470                 475                 480

Leu Ser Cys Ala Ala Ser Gly Phe Asp Phe Glu Ser Tyr Ala Met Ser
                485                 490                 495

Trp Val Arg Gln Ala Pro Gly Lys Gly Leu Glu Trp Val Ser Ala Ile
            500                 505                 510

Ser Gly Ser Gly Gly Ser Thr Tyr Tyr Ala Asp Ser Val Lys Gly Arg
        515                 520                 525

Phe Thr Ile Ser Arg Asp Asn Ser Lys Asn Thr Leu Tyr Leu Gln Met
    530                 535                 540

Asn Ser Leu Arg Ala Glu Asp Thr Ala Val Tyr Tyr Cys Ala Arg Tyr
545                 550                 555                 560

Tyr Gly Gly Tyr Tyr Ser Ala Trp Met Asp Tyr Trp Gly Gln Gly Thr
                565                 570                 575

Leu Val Thr Val Ser Ser Gly Gly Gly Gly Ser Gly Gly Gly Gly Ser
```

```
            580                 585                 590

Gly Gly Gly Gly Ser Asp Ile Gln Met Thr Gln Ser Pro Ser Ser Leu
        595                 600                 605

Ser Ala Ser Val Gly Asp Arg Val Thr Ile Thr Cys Arg Ala Ser Gln
    610                 615                 620

Ser Ile Arg Ser Ala Leu Asn Trp Tyr Gln Gln Lys Pro Gly Lys Ala
625                 630                 635                 640

Pro Lys Leu Leu Ile Tyr Ala Ala Ser Ser Leu Gln Ser Gly Val Pro
                645                 650                 655

Ser Arg Phe Ser Gly Ser Gly Ser Gly Thr Asp Phe Thr Leu Thr Ile
            660                 665                 670

Ser Ser Leu Gln Pro Glu Asp Phe Ala Thr Tyr Tyr Cys Gln Gln Thr
        675                 680                 685

Tyr Gly Tyr Leu His Thr Phe Gly Gln Gly Thr Lys Leu Glu Ile Lys
    690                 695                 700


<210> SEQ ID NO 168
<211> LENGTH: 214
<212> TYPE: PRT
<213> ORGANISM: Artificial Sequence
<220> FEATURE:
<223> OTHER INFORMATION: 1618-1210LO1 bispecific antibody light chain

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Asp Asn Leu Pro
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```